(12) United States Patent
Smith et al.

(10) Patent No.: US 11,479,767 B2
(45) Date of Patent: Oct. 25, 2022

(54) MODIFIED GUIDE RNAS

(71) Applicant: Intellia Therapeutics, Inc., Cambridge, MA (US)

(72) Inventors: Amy Madison Rhoden Smith, Durham, NC (US); David V. Morrissey, Winchester, MA (US); Walter Strapps, Dedham, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 410 days.

(21) Appl. No.: 16/434,512

(22) Filed: Jun. 7, 2019

(65) Prior Publication Data
US 2019/0316121 A1    Oct. 17, 2019

Related U.S. Application Data

(63) Continuation of application No. PCT/US2017/065306, filed on Dec. 8, 2017.

(60) Provisional application No. 62/431,756, filed on Dec. 8, 2016.

(51) Int. Cl.
| | | |
|---|---|---|
| *C07H 21/02* | (2006.01) | |
| *C07H 21/04* | (2006.01) | |
| *C12N 15/11* | (2006.01) | |
| *C12N 9/22* | (2006.01) | |

(52) U.S. Cl.
CPC ............. *C12N 15/11* (2013.01); *C12N 9/22* (2013.01); *C12N 2310/20* (2017.05); *C12N 2310/315* (2013.01); *C12N 2310/344* (2013.01); *C12N 2310/346* (2013.01); *C12N 2320/51* (2013.01)

(58) Field of Classification Search
CPC .......................... C12N 15/113; C12N 2310/20
See application file for complete search history.

(56) References Cited

U.S. PATENT DOCUMENTS

| | | | |
|---|---|---|---|
| 2015/0376586 A1 | 12/2015 | May et al. | |
| 2015/0376628 A1* | 12/2015 | Schoenherr | ........ C12N 15/1031 435/91.4 |

FOREIGN PATENT DOCUMENTS

| | | |
|---|---|---|
| WO | 2014152432 A2 | 9/2014 |
| WO | 2016089433 A1 | 6/2016 |
| WO | 2016164356 A1 | 10/2016 |
| WO | 2017004279 A2 | 1/2017 |
| WO | 2017068377 A1 | 4/2017 |
| WO | 2017136794 A1 | 8/2017 |
| WO | 2017173054 A1 | 10/2017 |

OTHER PUBLICATIONS

Finn, J. D. et al. "A Single Administration of CRISPR/Cas9 Lipid Nanoparticles Achieves Robust and Persistent In Vivi Genome Editing" Cell Reports 22, 2227-2235 (2018).
Briner et al., "Guide RNA Functional Modules Direct Cas9 Activity and Orthogonality", Molecular Cell 56:333-339, 2014.
Hendel, Ayal et al. "Chemically modified guide RNAs enhance CRISPR-Cas genome editing in human primary cells." Nature biotechnology vol. 33,9 (2015): 985-989.
Ran, F Ann et al. "In vivo genome editing using *Staphylococcus aureus* Cas9." Nature vol. 520,7546 (2015): 186-91.
Wang Ming et al., "Efficient delivery of genome-editing proteins using bioreducible lipid nanoparticles", Proceedings National Academy of Sciences PNAS, vol. 113, No. 11, Feb. 29, 2016, p. 2868-2873.
Yin Hao et al., "Therapeutic genome editing by combined viral and non-viral delivery of CRISPR system components in vivo", Nature Biotechnology, vol. 34, No. 3, Feb. 1, 2016, p. 328-333.
Yu, Xin et al. "Improved delivery of Cas9 protein/gRNA complexes using lipofectamine CRISPRMAX." Biotechnology Letters vol. 38,6 (2016): 919-29.
Ryan, et al. "Improving CRISPR-Cas specificity with chemical modifications in single-guide RNAs" Nucleic Acids Research, 2018, 46(2):792-803 (published online Dec. 4, 2017).
International Search Report and Written Opinion for PCT/US2017/065306 dated Apr. 17, 2018.

* cited by examiner

*Primary Examiner* — Amy H Bowman
(74) *Attorney, Agent, or Firm* — McNeill Baur PLLC

(57) ABSTRACT

This disclosure relates to modified single and dual guide RNAs having improved in vitro and in vivo activity in gene editing methods.

27 Claims, 41 Drawing Sheets
Specification includes a Sequence Listing.

25 nM

| | TR000110 | TR000111 | TR000112 | TR000113 | TR000114 | TR000115 | TR000116 | TR000117 | TR000118 | TR000119 | TR000121 | TR000002 |
|---|---|---|---|---|---|---|---|---|---|---|---|---|
| CR003393 | 54.1 ± 5 | 61.2 ± 3.1 | 56.7 ± 5 | 55.9 ± 4 | 53.8 ± 10.7 | 56.3 ± 10 | 52.7 ± 5.8 | 55.5 ± 7 | 40.7 ± 12.9 | 48.5 ± 8.1 | 51.3 ± 11.4 | |
| CR003394 | 57.7 ± 4.7 | 61.5 ± 8.2 | 64.8 ± 6.4 | 65.4 ± 8.9 | 60.1 ± 2.5 | 61.6 ± 4.6 | 57.3 ± 7.2 | 57.8 ± 8.3 | 38.6 ± 7.9 | 50.9 ± 10.3 | 54.8 ± 8.9 | |
| CR003395 | 52.4 ± 2.4 | 62.8 ± 6.8 | 61.1 ± 7.2 | 62.8 ± 11.1 | 55.9 ± 7.6 | 57 ± 4.9 | 53.4 ± 7.1 | 52.5 ± 8.1 | 38.2 ± 7.5 | 49.7 ± 14.4 | 53.1 ± 11.7 | |
| CR003396 | 56 ± 3.9 | 56.4 ± 7.6 | 58.7 ± 7.3 | 58.1 ± 7.3 | 54.7 ± 4.9 | 58.8 ± 5 | 48.9 ± 2.8 | 52.5 ± 9.7 | 34.3 ± 6 | 48.3 ± 10.3 | 52.4 ± 9.5 | |
| CR003398 | 50.8 ± 10.2 | 55.2 ± 8.2 | 62.5 ± 6.9 | 59.7 ± 8.9 | 56.3 ± 3.4 | 61.2 ± 5 | 53 ± 7.1 | 53.8 ± 9.2 | 29.4 ± 9.3 | 52.2 ± 12.2 | 51.9 ± 15.6 | |
| CR003402 | 42.7 ± 4.5 | 53.3 ± 5.4 | 56.9 ± 11 | 57.4 ± 12.1 | 52.8 ± 9.3 | 55.1 ± 8.5 | 46.1 ± 8.4 | 50.5 ± 8.8 | 17.7 ± 6.7 | 45.2 ± 12 | 52.8 ± 11.3 | |
| CR003403 | 45.8 ± 9.9 | 52.7 ± 8.6 | 59.7 ± 13.9 | 54.8 ± 13.7 | 47.2 ± 12.1 | 50.9 ± 8.4 | 43.4 ± 10.3 | 47 ± 13 | 10.5 ± 5.9 | 44.5 ± 15.2 | 46 ± 19.3 | |
| CR000686 | | | | | | | | | | | | 34.5 ± 6.4 |

2.5 nM

| | TR000110 | TR000111 | TR000112 | TR000113 | TR000114 | TR000115 | TR000116 | TR000117 | TR000118 | TR000119 | TR000121 | TR000002 |
|---|---|---|---|---|---|---|---|---|---|---|---|---|
| CR003393 | 41.8 ± 6.2 | 50.4 ± 3.2 | 40.2 ± 4.7 | 43.4 ± 2 | 40.1 ± 4.8 | 43.1 ± 3.9 | 39.1 ± 4.2 | 43 ± 6 | 15.6 ± 3.1 | 34.9 ± 11.6 | 38.6 ± 2.2 | |
| CR003394 | 45.4 ± 4.7 | 49.6 ± 7.9 | 43.9 ± 6.6 | 46.7 ± 5.6 | 40.4 ± 7.5 | 47.2 ± 6.9 | 46.8 ± 3.1 | 43.9 ± 2.4 | 13.7 ± 1.6 | 28.9 ± 4.3 | 35.9 ± 6.2 | |
| CR003395 | 39 ± 10 | 56 ± 5.1 | 42.2 ± 3.5 | 48.2 ± 3.2 | 36 ± 2.8 | 47.4 ± 7.3 | 44.4 ± 5.9 | 41.6 ± 7 | 12 ± 1.4 | 25.8 ± 1 | 31.4 ± 1.8 | |
| CR003396 | 34.8 ± 2.3 | 46.5 ± 0.4 | 42 ± 4.9 | 42.4 ± 1.8 | 32 ± 4 | 44.4 ± 5.5 | 41.1 ± 7.7 | 40.5 ± 5.1 | 20.7 ± 1.2 | 26 ± 1.2 | 42.4 ± 8.9 | |
| CR003398 | 33.6 ± 3.3 | 47 ± 6.8 | 41.9 ± 2.6 | 41.9 ± 1.1 | 37.1 ± 4.1 | 43.2 ± 9.4 | 40.1 ± 3.9 | 42.9 ± 3.6 | 1.4 ± 0.1 | 34.2 ± 2 | 40.7 ± 7.4 | |
| CR003402 | 31.2 ± 4.7 | 46.4 ± 5 | 38.5 ± 2.8 | 40.7 ± 3.5 | 29.9 ± 1.1 | 42.4 ± 6.6 | 31.7 ± 2.9 | 32.8 ± 4.6 | 7 ± 0.8 | 31.3 ± 2.1 | 46.8 ± 3.8 | |
| CR003403 | 28 ± 4.3 | 38.3 ± 3.3 | 37.5 ± 4.4 | 36.4 ± 2.7 | 31.4 ± 4.6 | 34.6 ± 3.7 | 32.9 ± 4 | 35.8 ± 4.2 | 1.4 ± 0.1 | 34.6 ± 6.1 | 40.7 ± 6.6 | |
| CR000686 | | | | | | | | | | | | 21.7 ± 4.9 |

|  | TR000127 | TR000128 | TR000130 | TR000134 | TR000135 | TR000136 | TR000137 | TR000138 | TR000139 | TR000142 | TR000143 | TR000002 |
|---|---|---|---|---|---|---|---|---|---|---|---|---|
| CR003723 | 18 ± 13.8 | 22.8 ± 4.1 | 24 ± 2.6 | 26.9 ± 2.8 | 20.8 ± 5 | 22.2 ± 5.7 | 26.7 ± 5 | 23.6 ± 4.1 | 13.7 ± 2.4 | 22.3 ± 4.4 | 10.8 ± 2.2 | 18.5 ± 1.5 |
| CR003725 | 26.9 ± 1.8 | 29.2 ± 4.2 | 27.9 ± 1.3 | 30.6 ± 3.4 | 26.1 ± 3.8 | 25.9 ± 4.4 | 30 ± 3 | 26.9 ± 2 | 18.5 ± 2.2 | 25.1 ± 0.9 | 23.1 ± 1.7 |  |
| CR003726 | 30.4 ± 1.1 | 31.3 ± 3.2 | 30.6 ± 2.9 | 32 ± 2.2 | 29.8 ± 2.5 | 29.9 ± 2.8 | 32.3 ± 1 | 28.7 ± 2.2 | 20.9 ± 2.4 | 27 ± 1.4 | 23.6 ± 2.3 | 24.9 ± 1.1 |
| CR003727 | 31.6 ± 2.1 | 27 ± 2.7 | 29.6 ± 0.8 | 32.1 ± 1.3 | 26.7 ± 1.2 | 27.2 ± 5.2 | 31 ± 2 | 28.1 ± 0.7 | 19.2 ± 0.7 | 26.7 ± 2.1 | 22.5 ± 1.2 | 25.6 ± 3 |
| CR003728 | 34.6 ± 2.4 | 2.4 ± 0.1 | 34.9 ± 2.6 | 37.7 ± 3.1 | 33.1 ± 2.1 | 33.1 ± 4 | 35.4 ± 0.9 | 32.4 ± 2.9 | 25.8 ± 4.8 | 30.7 ± 2.7 | 28.2 ± 2.2 | 28.6 ± 0.7 |
| CR003729 | 34.8 ± 0.9 | 32.3 ± 1.5 | 33.8 ± 1.1 | 34.8 ± 2.5 | 29.8 ± 1.8 | 31.5 ± 3.6 | 32.6 ± 1.7 | 31 ± 1.9 | 25.4 ± 3.7 | 28.6 ± 0.5 | 25.6 ± 1.1 | 27.8 ± 0.6 |
| CR003734 | 27.5 ± 0.3 | 21.5 ± 1.5 | 29.8 ± 1.6 | 29.5 ± 1.6 | 13.7 ± 2.1 | 14.6 ± 1.2 | 31 ± 2.4 | 28 ± 2.5 | 7 ± 1.1 | 25.5 ± 1.3 | 3.4 ± 0.1 | 22.7 ± 2.8 |
| CR000686 | 23 ± 2.8 | 22.4 ± 3.9 | 23.6 ± 6.2 | 26.4 ± 1 | 22.2 ± 2 | 19.5 ± 1.1 | 24.6 ± 3 | 27.4 ± 2.6 | 12.2 ± 1.7 | 22.9 ± 1.8 | 20.2 ± 1.1 | 22.6 ± 3 |

1 nM

|  | TR000127 | TR000128 | TR000130 | TR000134 | TR000135 | TR000136 | TR000137 | TR000138 | TR000139 | TR000142 | TR000143 | TR000002 |
|---|---|---|---|---|---|---|---|---|---|---|---|---|
| CR003723 | 18.3 ± 14.1 | 16 ± 12.1 | 25.3 ± 0.8 | 22.5 ± 3.4 | 14.3 ± 10.6 | 17.5 ± 2 | 23.1 ± 3.8 | 21 ± 1.4 | 8.8 ± 1.4 | 18.3 ± 0.7 | 8.3 ± 1.5 | 14.6 ± 0.4 |
| CR003725 | 26.9 ± 1.8 | 25.1 ± 4.1 | 25 ± 2.7 | 24.8 ± 2.3 | 23.1 ± 2.8 | 16.2 ± 12.1 | 17.3 ± 13.1 | 22.5 ± 1 | 15.2 ± 1.7 | 22.7 ± 1.5 | 19.7 ± 3.1 |  |
| CR003726 | 16.8 ± 12.9 | 26.4 ± 2 | 23.6 ± 2.6 | 25.2 ± 1.5 | 22.7 ± 3.4 | 20.7 ± 1.5 | 26.6 ± 1.4 | 20.4 ± 0.9 | 13.3 ± 0.3 | 21.6 ± 1.5 | 18.6 ± 0.5 | 17 ± 1 |
| CR003727 | 24.1 ± 3.1 | 20.3 ± 1.4 | 21 ± 1.3 | 23.6 ± 2.6 | 19.7 ± 1.7 | 20.3 ± 1.4 | 15.3 ± 11.3 | 20.2 ± 1.5 | 11.7 ± 1.7 | 20.7 ± 0.7 | 15.1 ± 0.8 | 19.7 ± 4.2 |
| CR003728 | 26.9 ± 0.8 | 2.4 ± 0.1 | 28.2 ± 2.4 | 27.9 ± 0.6 | 26.4 ± 3.2 | 22.9 ± 1.2 | 26.4 ± 1.9 | 24.8 ± 0.5 | 18.8 ± 1.8 | 23.3 ± 1.4 | 20.3 ± 1.1 | 23.4 ± 3.7 |
| CR003729 | 26.3 ± 2.5 | 30.5 ± 4.6 | 28.3 ± 2.7 | 28.6 ± 2 | 25.3 ± 3.1 | 24.6 ± 1.6 | 25 ± 0.3 | 23.7 ± 0.6 | 17.1 ± 1.7 | 21.9 ± 0.5 | 21 ± 2 | 22 ± 2 |
| CR003734 | 18.9 ± 5.3 | 15.2 ± 3 | 21.4 ± 1.7 | 20.1 ± 0.1 | 8.5 ± 1.7 | 7.4 ± 0.9 | 20.4 ± 0.8 | 20.4 ± 1.4 | 3 ± 0.1 | 19.3 ± 0.8 | 2.5 ± 0.3 | 17.3 ± 2.1 |
| CR000686 | 16.2 ± 1 | 17.3 ± 3.4 | 18.3 ± 3.3 | 20.5 ± 5 | 15.4 ± 1.2 | 14.8 ± 3 | 18.9 ± 3.6 | 20.1 ± 1.7 | 7.9 ± 2.3 | 17.5 ± 3.3 | 15.4 ± 1 | 14.1 ± 1.6 |

*Figure 9*

| Guide | Average % Editing | Std. Dev. |
|---|---|---|
| G209 Lot#2 | 44.2 | 4.1 |
| G209 Lot#4 | 47.5 | 5.3 |
| G262 | 52.2 | 4.7 |
| G263 | 60.9 | 3.8 |
| G264 | 48.9 | 5.8 |
| G265 | 44.7 | 11.1 |
| G266 | 47.0 | 7.8 |
| G267 | 58.9 | 3.1 |

\* = Phosphorothioate

End-modified sgRNA
G000209

* = Phosphorothioate

Highly modified sgRNA
G000267

| | Average % Editing | Std. Dev. |
|---|---|---|
| PBS | 0.8370155 | 0.03184162 |
| G211 2 mg/kg | 32.89082 | 8.520595 |
| G211 1 mg/kg | 9.024511 | 1.640143 |
| G211 0.3 mg/kg | 2.762495 | 0.9668095 |
| G282 2 mg/kg | 60.99886 | 3.792423 |
| G282 1 mg/kg | 35.13641 | 6.434229 |
| G282 0.3 mg/kg | 9.812781 | 6.713302 |
| G284 2 mg/kg | 6.007987 | 2.434861 |
| G284 1 mg/kg | 2.413099 | 1.540902 |
| G284 0.3 mg/kg | 1.130903 | 0.3189707 |

| | Average % TTR Reduction | Std. Dev. |
|---|---|---|
| PBS | 100.000 | 20.31276 |
| G211 2 mg/kg | 46.73565 | 14.33137 |
| G211 1 mg/kg | 62.66805 | 10.30656 |
| G211 0.3 mg/kg | 68.51203 | 10.40399 |
| G282 2 mg/kg | 9.890765 | 5.288372 |
| G282 1 mg/kg | 39.58118 | 12.35095 |
| G282 0.3 mg/kg | 64.59702 | 10.51861 |
| G284 2 mg/kg | 67.28742 | 10.217 |
| G284 1 mg/kg | 37.76873 | 19.77835 |
| G284 0.3 mg/kg | 30.4822 | 6.612638 |

| Guide | Dose | Average % Editing |
|---|---|---|
| PBS | | 2.38 |
| G269 | 2 MPK | 28.57 |
| | 1 MPK | 16.21 |
| | 0.3 MPK | 3.54 |
| G283 | 2 MPK | 56.32 |
| | 1 MPK | 39.73 |
| | 0.3 MPK | 8.08 |
| G285 | 2 MPK | 4.80 |
| | 1 MPK | 2.90 |
| | 0.3 MPK | 2.44 | dgRNA
CR000686 + TR000002

*Figure 21B*

| Group | Average % Editing | Std. Dev. |
|---|---|---|
| PBS | 0 | 0 |
| G332 1mpk | 34.14 | 9.575 |
| G332 0.5 mpk | 22.08 | 14.13 |
| G333 1 mpk | 29.28 | 18.53 |
| G333 0.5 mpk | 8.801 | 3.082 |
| G336 1 mpk | 67.92 | 8.609 |
| G336 0.5 mpk | 41.72 | 8.277 |
| G338 1 mpk | 56.25 | 8.561 |
| G338 0.5 mpk | 33.48 | 15.63 |
| G339 1 mpk | 58.36 | 9.444 |
| G339 0.5 mpk | 18.23 | 5.654 |
| G342 1 mpk | 35.12 | 16.84 |
| G342 0.5 mpk | 27.94 | 15.83 |
| G347 1 mpk | 6.073 | 1.825 |
| G347 0.5 mpk | 3.399 | 2.13 |
| G348 1 mpk | 5.464 | 2.171 |
| G348 0.5 mpk | 2.333 | 0.448 |
| G350 1 mpk | 52.66 | 12.88 |
| G350 0.5 mpk | 25.27 | 7.695 |
| G351 1 mpk | 54.94 | 16.24 |
| G351 0.5 mpk | 28.52 | 3.014 |
| G282 1 mpk | 71.08 | 3.789 |
| G282 0.5 mpk | 38.6 | 14.45 |

*Figure 22B*

| Guide | Average % Editing |
|---|---|
| TSS | 0.32 |
| G282 | 52.06 |
| G537 | 35.78 |
| G538 | 7.5 |
| G539 | 33.9 |
| G541 | 39.04 |
| G542 | 38.54 |
| G543 | 2.96 |
| G544 | 38.78 |
| G545 | 43.6 |
| G546 | 19.74 |
| G547 | 36.44 |
| G548 | 12.2 |
| G211-42 | 42.04 |
| G349 | 43.48 |

*Figure 23B*

| GUIDE | EC50 |
|---|---|
| G332 | 11.42 |
| G333 | 13.07 |
| G336 | 8.735 |
| G338 | 11.80 |
| G339 | 8.778 |
| G342 | 11.60 |
| G347 | 26.07 |
| G348 | 83.09 |
| G350 | 10.57 |
| G351 | 8.797 |
| G282 | 10.04 |

*Figure 24C*

SEQUENCE LISTING

<160> NUMBER OF SEQ ID NOS: 360

<210> SEQ ID NO 1
<211> LENGTH: 42
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ccaguccagc gaggcaaagg guuuuagagc uaugcuguuu ug                          42

<210> SEQ ID NO 2
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ccaguccagc gaggcaaagg guuuuagagc uaugcuguuu ug                          42

<210> SEQ ID NO 3
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ccaguccagc gaggcaaagg guuuuagagc uaugcuguuu ug                          42

<210> SEQ ID NO 4
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ccaguccagc gaggcaaagg guuuuagagc uaugcuguuu ug                          42

<210> SEQ ID NO 5
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ccaguccagc gaggcaaagg guuuuagagc uaugcuguuu ug                          42

<210> SEQ ID NO 6
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ccaguccagc gaggcaaagg guuuuagagc uaugcuguuu ug                          42
```

```
<210> SEQ ID NO 7
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ccaguccagc gaggcaaagg guuuuagagc uaugcuguuu ug                         42

<210> SEQ ID NO 8
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ccaguccagc gaggcaaagg guuuuagagc uaugcuguuu ug                         42

<210> SEQ ID NO 9
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ccaguccagc gaggcaaagg guuuuagagc uaugcuguuu ug                         42

<210> SEQ ID NO 10
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ccaguccagc gaggcaaagg guuuuagagc uaugcuguuu ug                         42

<210> SEQ ID NO 11
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ccaguccagc gaggcaaagg guuuuagagc uaugcuguuu ug                         42

<210> SEQ ID NO 12
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 12
ccaguccagc gaggcaaagg guuuuagagc uaugcuguuu ug            42

<210> SEQ ID NO 13
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ccaguccagc gaggcaaagg guuuuagagc uaugcuguuu ug            42

<210> SEQ ID NO 14
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ccaguccagc gaggcaaagg guuuuagagc uaugcuguuu ug            42

<210> SEQ ID NO 15
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ccaguccagc gaggcaaagg ggcgcagagc uaugcuguuu ug            42

<210> SEQ ID NO 16
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ccaguccagc gaggcaaagg guuuuagagc uaugcuggcg cg            42

<210> SEQ ID NO 17
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
ccaguccagc gaggcaaagg ggcgcagagc uaugcuggcg cg            42

<210> SEQ ID NO 18
<211> LENGTH: 42

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ccaguccagc gaggcaaagg guuuuagagc uaugcuguuu ug                        42

<210> SEQ ID NO 19
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
guuuuagagc uaugcuguuu ug                                              22

<210> SEQ ID NO 20
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
guuuuagagc uaugcuguuu ug                                              22

<210> SEQ ID NO 21
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
guuuuagagc uaugcuguuu ug                                              22

<210> SEQ ID NO 22
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
guuuuagagc uaugcuguuu ug                                              22

<210> SEQ ID NO 23
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
```
guuuuagagc uaugcuguuu ug                                              22

<210> SEQ ID NO 24
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
guuuuagagc uaugcuguuu ug                                              22

<210> SEQ ID NO 25
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
guuuuagagc uaugcuguuu ug                                              22

<210> SEQ ID NO 26
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
guuuuagagc uaugcuguuu ug                                              22

<210> SEQ ID NO 27
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
guuuuagagc uaugcuguuu ug                                              22

<210> SEQ ID NO 28
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
guuuuagagc uaugcuguuu ug                                              22

<210> SEQ ID NO 29
<211> LENGTH: 22
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 29
guuuuagagc uaugcuguuu ug                                                    22

<210> SEQ ID NO 30
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
guuuuagagc uaugcuguuu ug                                                    22

<210> SEQ ID NO 31
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
guuuuagagc uaugcuguuu ug                                                    22

<210> SEQ ID NO 32
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ccaguccagc gaggcaaagg guuuuagagc uaugcuguuu ug                              42

<210> SEQ ID NO 33
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
ccaguccagc gaggcaaagg guuuuagagc uaugcuguuu ug                              42

<210> SEQ ID NO 34
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ccaguccagc gaggcaaagg guuuuagagc uaugcuguuu ug                              42

<210> SEQ ID NO 35
```

```
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ccaguccagc gaggcaaagg guuuuagagc uaugcuguuu ug                          42

<210> SEQ ID NO 36
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ccaguccagc gaggcaaagg guuuuagagc uaugcuguuu ug                          42

<210> SEQ ID NO 37
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ccaguccagc gaggcaaagg guuuuagagc uaugcuguuu ug                          42

<210> SEQ ID NO 38
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ccaguccagc gaggcaaagg guuuuagagc uaugcuguuu ug                          42

<210> SEQ ID NO 39
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ccaguccagc gaggcaaagg guuuuagagc uaugcuguuu ug                          42

<210> SEQ ID NO 40
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
```

-continued ccaguccagc gaggcaaagg guuuuagagc uaugcuguuu ug        42

<210> SEQ ID NO 41
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ccaguccagc gaggcaaagg guuuuagagc uaugcuguuu ug        42

<210> SEQ ID NO 42
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ccaguccagc gaggcaaagg guuuuagagc uaugcuguuu ug        42

<210> SEQ ID NO 43
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ccaguccagc gaggcaaagg guuuuagagc uaugcuguuu ug        42

<210> SEQ ID NO 44
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
ccaguccagc gaggcaaagg guuuuagagc uaugcuguuu ug        42

<210> SEQ ID NO 45
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
ccaguccagc gaggcaaagg guuuuagagc uaugcuguuu ug        42

<210> SEQ ID NO 46
<211> LENGTH: 42
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 46
ccaguccagc gaggcaaagg guuuuagagc uaugcuguuu ug         42

<210> SEQ ID NO 47
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
ccaguccagc gaggcaaagg guuuuagagc uaugcuguuu ug         42

<210> SEQ ID NO 48
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ccaguccagc gaggcaaagg gucucagagc uaugcuguuu ug         42

<210> SEQ ID NO 49
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
ccaguccagc gaggcaaagg gcuuuagagc uaugcuguuu ug         42

<210> SEQ ID NO 50
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
ccaguccagc gaggcaaagg gucuuagagc uaugcuguuu ug         42

<210> SEQ ID NO 51
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ccaguccagc gaggcaaagg guucuagagc uaugcuguuu ug         42

-continued

```
<210> SEQ ID NO 52
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ccaguccagc gaggcaaagg guuucagagc uaugcuguuu ug                           42

<210> SEQ ID NO 53
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
guuuuagagc uaugcuguuu ug                                                 22

<210> SEQ ID NO 54
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
guuuuagagc uaugcuguuu ug                                                 22

<210> SEQ ID NO 55
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
guuuuagagc uaugcuguuu ug                                                 22

<210> SEQ ID NO 56
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
guuuuagagc uaugcuguuu ug                                                 22

<210> SEQ ID NO 57
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 57
guuuuagagc uaugcuguuu ug                                               22

<210> SEQ ID NO 58
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
guuuuagagc uaugcuguuu ug                                               22

<210> SEQ ID NO 59
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
guuuuagagc uaugcuguuu ug                                               22

<210> SEQ ID NO 60
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
guuuuagagc uaugcuguuu ug                                               22

<210> SEQ ID NO 61
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
guuuuagagc uaugcuguuu ug                                               22

<210> SEQ ID NO 62
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
guuuuagagc uaugcuguuu ug                                               22

<210> SEQ ID NO 63
<211> LENGTH: 22
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 63
guuuuagagc uaugcuguuu ug                                                    22

<210> SEQ ID NO 64
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
guuuuagagc uaugcuguuu ug                                                    22

<210> SEQ ID NO 65
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
guuuuagagc uaugcuguuu ug                                                    22

<210> SEQ ID NO 66
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
guuuuagagc uaugcuguuu ug                                                    22

<210> SEQ ID NO 67
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
guuuuagagc uaugcuguuu ug                                                    22

<210> SEQ ID NO 68
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
guuuuagagc uaugcuguuu ug                                                    22
```

```
<210> SEQ ID NO 69
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gucucagagc uaugcuguuu ug                                                 22

<210> SEQ ID NO 70
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gcuuuagagc uaugcuguuu ug                                                 22

<210> SEQ ID NO 71
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
gucuuagagc uaugcuguuu ug                                                 22

<210> SEQ ID NO 72
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
guucuagagc uaugcuguuu ug                                                 22

<210> SEQ ID NO 73
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
guuucagagc uaugcuguuu ug                                                 22

<210> SEQ ID NO 74
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 74
uuacagccac gucuacagca guuuuagagc uaugcuguuu ug              42

<210> SEQ ID NO 75
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
uuacagccac gucuacagca guuuuagagc uaugcuguuu ug              42

<210> SEQ ID NO 76
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
uuacagccac gucuacagca guuuuagagc uaugcuguuu ug              42

<210> SEQ ID NO 77
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
uuacagccac gucuacagca guuuuagagc uaugcuguuu ug              42

<210> SEQ ID NO 78
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
uuacagccac gucuacagca guuuuagagc uaugcuguuu ug              42

<210> SEQ ID NO 79
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
uuacagccac gucuacagca guuuuagagc uaugcuguuu ug              42

<210> SEQ ID NO 80
<211> LENGTH: 42
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
uuacagccac gucuacagca guuuuagagc uaugcuguuu ug                          42

<210> SEQ ID NO 81
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
uuacagccac gucuacagca guuuuagagc uaugcuguuu ug                          42

<210> SEQ ID NO 82
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
uuacagccac gucuacagca guuuuagagc uaugcuguuu ug                          42

<210> SEQ ID NO 83
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
uuacagccac gucuacagca guuuuagagc uaugcuguuu ug                          42

<210> SEQ ID NO 84
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
uuacagccac gucuacagca guuuuagagc uaugcuguuu ug                          42

<210> SEQ ID NO 85
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
uuacagccac gucuacagca guuuuagagc uaugcuguuu ug                          42
```

```
<210> SEQ ID NO 86
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
uuacagccac gucuacagca guuuuagagc uaugcuguuu ug                               42

<210> SEQ ID NO 87
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
uuacagccac gucuacagca guuuuagagc uaugcuguuu ug                               42

<210> SEQ ID NO 88
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
uuacagccac gucuacagca guuuuagagc uaugcuguuu ug                               42

<210> SEQ ID NO 89
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
uuacagccac gucuacagca guuuuagagc uaugcuguuu ug                               42

<210> SEQ ID NO 90
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
uuacagccac gucuacagca guuuuagagc uaugcuguuu ug                               42

<210> SEQ ID NO 91
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 91
uuacagccac gcuacagca guuuuagagc uaugcuguuu ug         42

<210> SEQ ID NO 92
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 92
uuacagccac gcuacagca guuuuagagc uaugcuguuu ug         42

<210> SEQ ID NO 93
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 93
uuacagccac gcuacagca guuuuagagc uaugcuguuu ug         42

<210> SEQ ID NO 94
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 94
uuacagccac gcuacagca guuuuagagc uaugcuguuu ug         42

<210> SEQ ID NO 95
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 95
uuacagccac gcuacagca guuuuagagc uaugcuguuu ug         42

<210> SEQ ID NO 96
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 96
uuacagccac gcuacagca guuuuagagc uaugcuguuu ug         42

<210> SEQ ID NO 97
<211> LENGTH: 42

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
uuacagccac gucuacagca guuuuagagc uaugcuguuu ug                          42

<210> SEQ ID NO 98
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
uuacagccac gucuacagca guuuuagagc uaugcuguuu ug                          42

<210> SEQ ID NO 99
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
uuacagccac gucuacagca guuuuagagc uaugcuguuu ug                          42

<210> SEQ ID NO 100
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
uuacagccac gucuacagca guuuuagagc uaugcuguuu ug                          42

<210> SEQ ID NO 101
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
uuacagccac gucuacagca guuuuagagc uaugcuguuu ug                          42

<210> SEQ ID NO 102
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
```
uuacagccac gucuacagca ggcgcagagc uaugcuguuu ug          42

<210> SEQ ID NO 103
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
uuacagccac gucuacagca guuuuagagc uaugcuggcg cg          42

<210> SEQ ID NO 104
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
guuuuagagc uaugcuguuu ug          22

<210> SEQ ID NO 105
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
guuuuagagc uaugcuguuu ug          22

<210> SEQ ID NO 106
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
guuuuagagc uaugcuguuu ug          22

<210> SEQ ID NO 107
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
guuuuagagc uaugcuguuu ug          22

<210> SEQ ID NO 108
<211> LENGTH: 22
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 108
guuuuagagc uaugcuguuu ug                                              22

<210> SEQ ID NO 109
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
guuuuagagc uaugcuguuu ug                                              22

<210> SEQ ID NO 110
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
guuuuagagc uaugcuguuu ug                                              22

<210> SEQ ID NO 111
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
guuuuagagc uaugcuguuu ug                                              22

<210> SEQ ID NO 112
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
guuuuagagc uaugcuguuu ug                                              22

<210> SEQ ID NO 113
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
guuuuagagc uaugcuguuu ug                                              22

<210> SEQ ID NO 114
```

```
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
guuuuagagc uaugcuguuu ug                                              22

<210> SEQ ID NO 115
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
guuuuagagc uaugcuguuu ug                                              22

<210> SEQ ID NO 116
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
guuuuagagc uaugcuguuu ug                                              22

<210> SEQ ID NO 117
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
guuuuagagc uaugcuguuu ug                                              22

<210> SEQ ID NO 118
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
guuuuagagc uaugcuguuu ug                                              22

<210> SEQ ID NO 119
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
```
guuuuagagc uaugcuguuu ug                                    22

<210> SEQ ID NO 120
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
guuuuagagc uaugcuguuu ug                                    22

<210> SEQ ID NO 121
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
guuuuagagc uaugcuguuu ug                                    22

<210> SEQ ID NO 122
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gagcuaugcu guuuug                                           16

<210> SEQ ID NO 123
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gagcuaugcu guuuug                                           16

<210> SEQ ID NO 124
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
guuuuagagc uaugcuguuu ug                                    22

<210> SEQ ID NO 125
<211> LENGTH: 22
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 125
guuuuagagc uaugcuguuu ug                                                22

<210> SEQ ID NO 126
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
guuuuagagc uaugcuguuu ug                                                22

<210> SEQ ID NO 127
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
guuuuagagc uaugcuguuu ug                                                22

<210> SEQ ID NO 128
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
guuuuagagc uaugcuguuu ug                                                22

<210> SEQ ID NO 129
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
guuuuagagc uaugcuguuu ug                                                22

<210> SEQ ID NO 130
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
guuuuagagc uaugcuguuu ug                                                22
```

```
<210> SEQ ID NO 131
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
cagggcucuu gaagaucucc guuuuagagc uaugcuguuu ug                        42

<210> SEQ ID NO 132
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
cagggcucuu gaagaucucc guuuuagagc uaugcuguuu ug                        42

<210> SEQ ID NO 133
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
cagggcucuu gaagaucucc guuuuagagc uaugcuguuu ug                        42

<210> SEQ ID NO 134
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
cagggcucuu gaagaucucc guuuuagagc uaugcuguuu ug                        42

<210> SEQ ID NO 135
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
cagggcucuu gaagaucucc guuuuagagc uaugcuguuu ug                        42

<210> SEQ ID NO 136
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 136
cagggcucuu gaagaucucc guuuuagagc uaugcuguuu ug         42

<210> SEQ ID NO 137
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
cagggcucuu gaagaucucc guuuuagagc uaugcuguuu ug         42

<210> SEQ ID NO 138
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
cagggcucuu gaagaucucc guuuuagagc uaugcuguuu ug         42

<210> SEQ ID NO 139
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
cagggcucuu gaagaucucc guuuuagagc uaugcuguuu ug         42

<210> SEQ ID NO 140
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
cagggcucuu gaagaucucc guuuuagagc uaugcuguuu ug         42

<210> SEQ ID NO 141
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
cagggcucuu gaagaucucc guuuuagagc uaugcuguuu ug         42

<210> SEQ ID NO 142
<211> LENGTH: 42
<212> TYPE: RNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"

<400> SEQUENCE: 142
cagggcucuu gaagaucucc guuuuagagc uaugcuguuu ug              42

<210> SEQ ID NO 143
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
cagggcucuu gaagaucucc guuuuagagc uaugcuguuu ug              42

<210> SEQ ID NO 144
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
cagggcucuu gaagaucucc guuuuagagc uaugcuguuu ug              42

<210> SEQ ID NO 145
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
cagggcucuu gaagaucucc guuuuagagc uaugcuguuu ug              42

<210> SEQ ID NO 146
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
cagggcucuu gaagaucucc guuuuagagc uaugcuguuu ug              42

<210> SEQ ID NO 147
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
cagggcucuu gaagaucucc guuuuagagc uaugcuguuu ug              42
```

```
<210> SEQ ID NO 148
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
cagggcucuu gaagaucucc guuuuagagc uaugcuguuu ug                          42

<210> SEQ ID NO 149
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
cagggcucuu gaagaucucc guuuuagagc uaugcuguuu ug                          42

<210> SEQ ID NO 150
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
cagggcucuu gaagaucucc guuuuagagc uaugcuguuu ug                          42

<210> SEQ ID NO 151
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
cagggcucuu gaagaucucc guuuuagagc uaugcuguuu ug                          42

<210> SEQ ID NO 152
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
cagggcucuu gaagaucucc guuuuagagc uaugcuguuu ug                          42

<210> SEQ ID NO 153
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 153
cagggcucuu gaagaucucc guuuuagagc uaugcuguuu ug                              42

<210> SEQ ID NO 154
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
cagggcucuu gaagaucucc guuuuagagc uaugcuguuu ug                              42

<210> SEQ ID NO 155
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
cagggcucuu gaagaucucc guuuuagagc uaugcuguuu ug                              42

<210> SEQ ID NO 156
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
cagggcucuu gaagaucucc guuuuagagc uaugcuguuu ug                              42

<210> SEQ ID NO 157
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
cagggcucuu gaagaucucc guuuuagagc uaugcuguuu ug                              42

<210> SEQ ID NO 158
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
cagggcucuu gaagaucucc guuuuagagc uaugcuguuu ug                              42

<210> SEQ ID NO 159
<211> LENGTH: 42
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cagggcucuu gaagaucucc ggcgcagagc uaugcuguuu ug                          42

<210> SEQ ID NO 160
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
cagggcucuu gaagaucucc guuuuagagc uaugcuggcg cg                          42

<210> SEQ ID NO 161
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
guuuuagagc uaugcuguuu ug                                                22

<210> SEQ ID NO 162
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
guuuuagagc uaugcuguuu ug                                                22

<210> SEQ ID NO 163
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
guuuuagagc uaugcuguuu ug                                                22

<210> SEQ ID NO 164
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
guuuuagagc uaugcuguuu ug                                                22
```

<210> SEQ ID NO 165
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
guuuuagagc uaugcuguuu ug                                              22

<210> SEQ ID NO 166
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
guuuuagagc uaugcuguuu ug                                              22

<210> SEQ ID NO 167
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
guuuuagagc uaugcuguuu ug                                              22

<210> SEQ ID NO 168
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
guuuuagagc uaugcuguuu ug                                              22

<210> SEQ ID NO 169
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
guuuuagagc uaugcuguuu ug                                              22

<210> SEQ ID NO 170
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 170
guuuuagagc uaugcuguuu ug                                    22

<210> SEQ ID NO 171
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
guuuuagagc uaugcuguuu ug                                    22

<210> SEQ ID NO 172
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
guuuuagagc uaugcuguuu ug                                    22

<210> SEQ ID NO 173
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
guuuuagagc uaugcuguuu ug                                    22

<210> SEQ ID NO 174
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
guuuuagagc uaugcuguuu ug                                    22

<210> SEQ ID NO 175
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
guuuuagagc uaugcuguuu ug                                    22

<210> SEQ ID NO 176
<211> LENGTH: 22

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
guuuuagagc uaugcuguuu ug                                              22

<210> SEQ ID NO 177
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
guuuuagagc uaugcuguuu ug                                              22

<210> SEQ ID NO 178
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
guuuuagagc uaugcuguuu ug                                              22

<210> SEQ ID NO 179
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
guuuuagagc uaugcuguuu ug                                              22

<210> SEQ ID NO 180
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
guuuuagagc uaugcuguuu ug                                              22

<210> SEQ ID NO 181
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
```
guuuuagagc uaugcuguuu ug					22

<210> SEQ ID NO 182
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
guuuuagagc uaugcuguuu ug					22

<210> SEQ ID NO 183
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
guuuuagagc uaugcuguuu ug					22

<210> SEQ ID NO 184
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
guuuuagagc uaugcuguuu ug					22

<210> SEQ ID NO 185
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
guuuuagagc uaugcuguuu ug					22

<210> SEQ ID NO 186
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
guuuuagagc uaugcuguuu ug					22

<210> SEQ ID NO 187
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
guuuuagagc uaugcuguuu ug                                              22

<210> SEQ ID NO 188
<211> LENGTH: 74
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
aacagcauag caaguuaaaa uaaggcuagu ccguuaucaa cuugaaaaag uggcaccgag      60
ucggugcuuu uuuu                                                       74

<210> SEQ ID NO 189
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aacagcauag caaguuaaaa uaaggcuagu ccguuaucaa cuugaaaaag uggcaccgag      60
ucggugcuuu u                                                          71

<210> SEQ ID NO 190
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
aacagcauag caaguuaaaa uaaggcuagu ccguuaucaa cuugaaaaag uggcaccgag      60
ucggugcuuu u                                                          71

<210> SEQ ID NO 191
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
aacagcauag caaguuaaaa uaaggcuagu ccguuaucaa cuugaaaaag uggcaccgag      60
ucggugcuuu u                                                          71

<210> SEQ ID NO 192
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 192
aacagcauag caaguuaaaa uaaggcuagu ccguuaucaa cuugaaaaag uggcaccgag    60
ucggugcuuu u                                                        71

<210> SEQ ID NO 193
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
aacagcauag caaguuaaaa uaaggcuagu ccguuaucaa cuugaaaaag uggcaccgag    60
ucggugcuuu u                                                        71

<210> SEQ ID NO 194
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
aacagcauag caaguuaaaa uaaggcuagu ccguuaucaa cuugaaaaag uggcaccgag    60
ucggugcuuu u                                                        71

<210> SEQ ID NO 195
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
aacagcauag caaguuaaaa uaaggcuagu ccguuaucaa cuugaaaaag uggcaccgag    60
ucggugcuuu u                                                        71

<210> SEQ ID NO 196
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aacagcauag caaguuaaaa uaaggcuagu ccguuaucaa cuugaaaaag uggcaccgag    60
ucggugcuuu u                                                        71

<210> SEQ ID NO 197
<211> LENGTH: 71
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 197
aacagcauag caaguuaaaa uaaggcuagu ccguuaucaa cuugaaaaag uggcaccgag    60
ucggugcuuu u                                                        71

<210> SEQ ID NO 198
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
aacagcauag caaguuaaaa uaaggcuagu ccguuaucaa cuugaaaaag uggcaccgag    60
ucggugcuuu u                                                        71

<210> SEQ ID NO 199
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
aacagcauag caaguuaaaa uaaggcuagu ccguuaucaa cuugaaaaag uggcaccgag    60
ucggugcuuu u                                                        71

<210> SEQ ID NO 200
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
aacagcauag caaguuaaaa uaaggcuagu ccguuaucaa cuugaaaaag uggcaccgag    60
ucggugcuuu u                                                        71

<210> SEQ ID NO 201
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
aacagcauag caaguugcgc uaaggcuagu ccguuaucaa cuugaaaaag uggcaccgag    60
ucggugcuuu u                                                        71

<210> SEQ ID NO 202
<211> LENGTH: 71
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 202
gccagcauag caaguuaaaa uaaggcuagu ccguuaucaa cuugaaaaag uggcaccgag      60
ucggugcuuu u                                                          71

<210> SEQ ID NO 203
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
gccagcauag caaguugcgc uaaggcuagu ccguuaucaa cuugaaaaag uggcaccgag      60
ucggugcuuu u                                                          71

<210> SEQ ID NO 204
<211> LENGTH: 74
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
aacagcauag caaguuaaaa uaaggcuagu ccguuaucaa cuugaaaaag uggcaccgag      60
ucggugcuuu uuuu                                                       74

<210> SEQ ID NO 205
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
aacagcauag caaguuaaaa uaaggcuagu ccguuaucaa cuugaaaaag uggcaccgag      60
ucggugcuuu u                                                          71

<210> SEQ ID NO 206
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aacagcauag caaguuaaaa uaaggcuagu ccguuaucaa cuugaaaaag uggcaccgag      60
ucggugcuuu u                                                          71

<210> SEQ ID NO 207
<211> LENGTH: 71
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 207
aacagcauag caaguuaaaa uaaggcuagu ccguuaucaa cuugaaaaag uggcaccgag      60
ucggugcuuu u                                                          71

<210> SEQ ID NO 208
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
aacagcauag caaguuaaaa uaaggcuagu ccguuaucaa cuugaaaaag uggcaccgag      60
ucggugcuuu u                                                          71

<210> SEQ ID NO 209
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
aacagcauag caaguuaaaa uaaggcuagu ccguuaucaa cuugaaaaag uggcaccgag      60
ucggugcuuu u                                                          71

<210> SEQ ID NO 210
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
aacagcauag caaguuaaaa uaaggcuagu ccguuaucaa cuugaaaaag uggcaccgag      60
ucggugcuuu u                                                          71

<210> SEQ ID NO 211
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
aacagcauag caaguuaaaa uaaggcuagu ccguuaucaa cuugaaaaag uggcaccgag      60
ucggugcuuu u                                                          71

<210> SEQ ID NO 212
<211> LENGTH: 71
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aacagcauag caaguuaaaa uaaggcuagu ccguuaucaa cuugaaaaag uggcaccgag      60
ucggugcuuu u                                                          71

<210> SEQ ID NO 213
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
aacagcauag caaguuaaaa uaaggcuagu ccguuaucaa cuugaaaaag uggcaccgag      60
ucggugcuuu u                                                          71

<210> SEQ ID NO 214
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
aacagcauag caaguuaaaa uaaggcuagu ccguuaucaa cuugaaaaag uggcaccgag      60
ucggugcuuu u                                                          71

<210> SEQ ID NO 215
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
aacagcauag caaguuaaaa uaaggcuagu ccguuaucaa cuugaaaaag uggcaccgag      60
ucggugcuuu u                                                          71

<210> SEQ ID NO 216
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aacagcauag caaguuaaaa uaaggcuagu ccguuaucaa cuugaaaaag uggcaccgag      60
ucggugcuuu u                                                          71

<210> SEQ ID NO 217
<211> LENGTH: 71
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
aacagcauag caaguuaaaa uaaggcuagu ccguuaucaa cuugaaaaag uggcaccgag    60
ucggugcuuu u                                                        71

<210> SEQ ID NO 218
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
aacagcauag caaguuaaaa uaaggcuagu ccguuaucaa cuugaaaaag uggcaccgag    60
ucggugcuuu u                                                        71

<210> SEQ ID NO 219
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
aacagcauag caaguuaaaa uaaggcuagu ccguuaucaa cuugaaaaag uggcaccgag    60
ucggugcuuu u                                                        71

<210> SEQ ID NO 220
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
aacagcauag caaguuaaaa uaaggcuagu ccguuaucaa cuugaaaaag uggcaccgag    60
ucggugcuuu u                                                        71

<210> SEQ ID NO 221
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
aacagcauag caaguuaaaa uaaggcuagu ccguuaucaa cuugaaaaag uggcaccgag    60
ucggugcuuu u                                                        71

<210> SEQ ID NO 222
```

```
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
aacagcauag caaguuaaaa uaaggcuagu ccguuaucaa cuugaaaaag uggcaccgag     60
ucggugcuuu u                                                         71

<210> SEQ ID NO 223
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
aacagcauag caaguugaga uaaggcuagu ccguuaucaa cuugaaaaag uggcaccgag     60
ucggugcuuu u                                                         71

<210> SEQ ID NO 224
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
aacagcauag caaguuaaag uaaggcuagu ccguuaucaa cuugaaaaag uggcaccgag     60
ucggugcuuu u                                                         71

<210> SEQ ID NO 225
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
aacagcauag caaguuaaga uaaggcuagu ccguuaucaa cuugaaaaag uggcaccgag     60
ucggugcuuu u                                                         71

<210> SEQ ID NO 226
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
aacagcauag caaguuagaa uaaggcuagu ccguuaucaa cuugaaaaag uggcaccgag     60
ucggugcuuu u                                                         71
```

```
<210> SEQ ID NO 227
<211> LENGTH: 71
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
aacagcauag caaguugaaa uaaggcuagu ccguuaucaa cuugaaaaag uggcaccgag    60
ucggugcuuu u                                                         71

<210> SEQ ID NO 228
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 228
ccaguccagc gaggcaaagg guuuuagagc uagaaauagc aaguuaaaau aaggcuaguc    60
cguuaucaac uugaaaaagu ggcaccgagu cggugcuuuu                         100

<210> SEQ ID NO 229
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 229
ccaguccagc gaggcaaagg guuuuagagc uagaaauagc aaguuaaaau aaggcuaguc    60
cguuaucaac uugaaaaagu ggcaccgagu cggugcuuuu                         100

<210> SEQ ID NO 230
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
ccaguccagc gaggcaaagg guuuuagagc uagaaauagc aaguuaaaau aaggcuaguc    60
cguuaucaac uugaaaaagu ggcaccgagu cggugcuuuu                         100

<210> SEQ ID NO 231
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 231
ccaguccagc gaggcaaagg guuuuagagc uagaaauagc aaguuaaaau aaggcuaguc    60
cguuaucaac uugaaaaagu ggcaccgagu cggugcuuuu                         100
```

<210> SEQ ID NO 232
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232
ccaguccagc gaggcaaagg guuuuagagc uagaaauagc aaguuaaaau aaggcuaguc    60
cguuaucaac uugaaaaagu ggcaccgagu cggugcuuuu                        100

<210> SEQ ID NO 233
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 233
ccaguccagc gaggcaaagg guuuuagagc uagaaauagc aaguuaaaau aaggcuaguc    60
cguuaucaac uugaaaaagu ggcaccgagu cggugcuuuu                        100

<210> SEQ ID NO 234
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 234
ccaguccagc gaggcaaagg guuuuagagc uagaaauagc aaguuaaaau aaggcuaguc    60
cguuaucaac uugaaaaagu ggcaccgagu cggugcuuuu                        100

<210> SEQ ID NO 235
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
guuuuagagc uagaaauagc aaguuaaaau aaggcuaguc cguuaucaac uugaaaaagu    60
ggcaccgagu cggugcuuuu                                               80

<210> SEQ ID NO 236
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
guuuuagagc uagaaauagc aaguuaaaau aaggcuaguc cguuaucaac uugaaaaagu    60
ggcaccgagu cggugcuuuu                                               80

-continued

<210> SEQ ID NO 237
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
guuuuagagc uagaaauagc aaguuaaaau aaggcuaguc cguuaucaac uugaaaaagu      60
ggcaccgagu cggugcuuuu                                                  80

<210> SEQ ID NO 238
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
guuuuagagc uagaaauagc aaguuaaaau aaggcuaguc cguuaucaac uugaaaaagu      60
ggcaccgagu cggugcuuuu                                                  80

<210> SEQ ID NO 239
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
guuuuagagc uagaaauagc aaguuaaaau aaggcuaguc cguuaucaac uugaaaaagu      60
ggcaccgagu cggugcuuuu                                                  80

<210> SEQ ID NO 240
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
guuuuagagc uagaaauagc aaguuaaaau aaggcuaguc cguuaucaac uugaaaaagu      60
ggcaccgagu cggugcuuuu                                                  80

<210> SEQ ID NO 241
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 241
uuacagccac gucuacagca guuuuagagc uagaaauagc aaguuaaaau aaggcuaguc      60
cguuaucaac uugaaaaagu ggcaccgagu cggugcuuuu                              100

<210> SEQ ID NO 242
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242
uuacagccac gucuacagca guuuuagagc uagaaauagc aaguuaaaau aaggcuaguc        60
cguuaucaac uugaaaaagu ggcaccgagu cggugcuuuu                             100

<210> SEQ ID NO 243
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243
uuacagccac gucuacagca guuuuagagc uagaaauagc aaguuaaaau aaggcuaguc        60
cguuaucaac uugaaaaagu ggcaccgagu cggugcuuuu                             100

<210> SEQ ID NO 244
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244
uuacagccac gucuacagca guuuuagagc uagaaauagc aaguuaaaau aaggcuaguc        60
cguuaucaac uugaaaaagu ggcaccgagu cggugcuuuu                             100

<210> SEQ ID NO 245
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245
uuacagccac gucuacagca guuuuagagc uagaaauagc aaguuaaaau aaggcuaguc        60
cguuaucaac uugaaaaagu ggcaccgagu cggugcuuuu                             100

<210> SEQ ID NO 246
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246
uuacagccac gucuacagca guuuuagagc uagaaauagc aaguuaaaau aaggcuaguc        60
cguuaucaac uugaaaaagu ggcaccgagu cggugcuuuu                        100

<210> SEQ ID NO 247
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 248
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 249
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 249
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 250
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 251
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 252
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 253
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 253
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 254
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 255
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 256
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 256
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 257
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 257
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 258
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 258
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 259
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 260
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 260
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 261
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

```
<400> SEQUENCE: 261
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 262
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 263
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 264
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 265
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
guuuuagagc uagaaauagc aaguuaaaau aaggcuaguc cguuaucaac uugaaaaagu    60
ggcaccgagu cggugcuuuu                                               80

<210> SEQ ID NO 266
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 266
guuuuagagc uagaaauagc aaguuaaaau aaggcuaguc cguuaucaac uugaaaaagu    60
ggcaccgagu cggugcuuuu                                               80

<210> SEQ ID NO 267
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
guuuuagagc uagaaauagc aaguuaaaau aaggcuaguc cguuaucaac uugaaaaagu    60
ggcaccgagu cggugcuuuu                                               80

<210> SEQ ID NO 268
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
guuuuagagc uagaaauagc aaguuaaaau aaggcuaguc cguuaucaac uugaaaaagu    60
ggcaccgagu cggugcuuuu                                               80

<210> SEQ ID NO 269
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
guuuuagagc uagaaauagc aaguuaaaau aaggcuaguc cguuaucaac uugaaaaagu    60
ggcaccgagu cggugcuuuu                                               80

<210> SEQ ID NO 270
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
guuuuagagc uagaaauagc aaguuaaaau aaggcuaguc cguuaucaac uugaaaaagu    60
ggcaccgagu cggugcuuuu                                               80

<210> SEQ ID NO 271
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 271
guuuuagagc uagaaauagc aaguuaaaau aaggcuaguc cguuaucaac uugaaaaagu    60
ggcaccgagu cggugcuuuu                                                80

<210> SEQ ID NO 272
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
guuuuagagc uagaaauagc aaguuaaaau aaggcuaguc cguuaucaac uugaaaaagu    60
ggcaccgagu cggugcuuuu                                                80

<210> SEQ ID NO 273
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
guuuuagagc uagaaauagc aaguuaaaau aaggcuaguc cguuaucaac uugaaaaagu    60
ggcaccgagu cggugcuuuu                                                80

<210> SEQ ID NO 274
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
guuuuagagc uagaaauagc aaguuaaaau aaggcuaguc cguuaucaac uugaaaaagu    60
ggcaccgagu cggugcuuuu                                                80

<210> SEQ ID NO 275
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
guuuuagagc uagaaauagc aaguuaaaau aaggcuaguc cguuaucaac uugaaaaagu    60
ggcaccgagu cggugcuuuu                                                80

<210> SEQ ID NO 276
<211> LENGTH: 80
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 276
guuuuagagc uagaaauagc aaguuaaaau aaggcuaguc cguuaucaac uugaaaaagu    60
ggcaccgagu cggugcuuuu                                                80

<210> SEQ ID NO 277
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
guuuuagagc uagaaauagc aaguuaaaau aaggcuaguc cguuaucaac uugaaaaagu    60
ggcaccgagu cggugcuuuu                                                80

<210> SEQ ID NO 278
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
guuuuagagc uagaaauagc aaguuaaaau aaggcuaguc cguuaucaac uugaaaaagu    60
ggcaccgagu cggugcuuuu                                                80

<210> SEQ ID NO 279
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
guuuuagagc uagaaauagc aaguuaaaau aaggcuaguc cguuaucaac uugaaaaagu    60
ggcaccgagu cggugcuuuu                                                80

<210> SEQ ID NO 280
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
guuuuagagc uagaaauagc aaguuaaaau aaggcuaguc cguuaucaac uugaaaaagu    60
ggcaccgagu cggugcuuuu                                                80

<210> SEQ ID NO 281
<211> LENGTH: 80
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 281
guuuuagagc uagaaauagc aaguuaaaau aaggcuaguc cguuaucaac uugaaaaagu    60
ggcaccgagu cggugcuuuu                                                80

<210> SEQ ID NO 282
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
guuuuagagc uagaaauagc aaguuaaaau aaggcuaguc cguuaucaac uugaaaaagu    60
ggcaccgagu cggugcuuuu                                                80

<210> SEQ ID NO 283
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
guuuuagagc uagaaauagc aaguuaaaau aaggcuaguc cguuaucaac uugaaaaagu    60
ggcaccgagu cggugcuuuu                                                80

<210> SEQ ID NO 284
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
guuuuagagc uagaaauagc aaguuaaaau aaggcuaguc cguuaucaac uugaaaaagu    60
ggcaccgagu cggugcuuuu                                                80

<210> SEQ ID NO 285
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
guuuuagagc uagaaauagc aaguuaaaau aaggcuaguc cguuaucaac uugaaaaagu    60
ggcaccgagu cggugcuuuu                                                80

<210> SEQ ID NO 286
<211> LENGTH: 100
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 286
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 287
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 287
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 288
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 288
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 289
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 289
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 290
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 290
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 291
<211> LENGTH: 100
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 292
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 292
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 293
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 293
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 294
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 294
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 295
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 295
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 296
<211> LENGTH: 100
```

<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 296
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 297
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 297
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 298
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 298
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 299
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 299
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 300
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 300
cagggcucuu gaagaucucc guuuuagagc uagaaauagc aaguuaaaau aaggcuaguc    60
cguuaucaac uugaaaaagu ggcaccgagu cggugcuuuu                        100

<210> SEQ ID NO 301

-continued

```
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 301
cagggcucuu gaagaucucc guuuuagagc uagaaauagc aaguuaaaau aaggcuaguc      60
cguuaucaac uugaaaaagu ggcaccgagu cggugcuuuu                          100

<210> SEQ ID NO 302
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302
cagggcucuu gaagaucucc guuuuagagc uagaaauagc aaguuaaaau aaggcuaguc      60
cguuaucaac uugaaaaagu ggcaccgagu cggugcuuuu                          100

<210> SEQ ID NO 303
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303
cagggcucuu gaagaucucc guuuuagagc uagaaauagc aaguuaaaau aaggcuaguc      60
cguuaucaac uugaaaaagu ggcaccgagu cggugcuuuu                          100

<210> SEQ ID NO 304
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 304
cagggcucuu gaagaucucc guuuuagagc uagaaauagc aaguuaaaau aaggcuaguc      60
cguuaucaac uugaaaaagu ggcaccgagu cggugcuuuu                          100

<210> SEQ ID NO 305
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
cagggcucuu gaagaucucc guuuuagagc uagaaauagc aaguuaaaau aaggcuaguc      60
cguuaucaac uugaaaaagu ggcaccgagu cggugcuuuu                          100
```

<210> SEQ ID NO 306
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 306
cagggcucuu gaagaucucc guuuuagagc uagaaauagc aaguuaaaau aaggcuaguc    60
cguuaucaac uugaaaaagu ggcaccgagu cggugcuuuu                         100

<210> SEQ ID NO 307
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 307
cagggcucuu gaagaucucc guuuuagagc uagaaauagc aaguuaaaau aaggcuaguc    60
cguuaucaac uugaaaaagu ggcaccgagu cggugcuuuu                         100

<210> SEQ ID NO 308
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 308
cagggcucuu gaagaucucc guuuuagagc uagaaauagc aaguuaaaau aaggcuaguc    60
cguuaucaac uugaaaaagu ggcaccgagu cggugcuuuu                         100

<210> SEQ ID NO 309
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
guuuuagagc uagaaauagc aaguuaaaau aaggcuaguc cguuaucaac uugaaaaagu    60
ggcaccgagu cggugcuuuu                                               80

<210> SEQ ID NO 310
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
guuuuagagc uagaaauagc aaguuaaaau aaggcuaguc cguuaucaac uugaaaaagu    60
ggcaccgagu cggugcuuuu                                               80

<210> SEQ ID NO 311
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
guuuuagagc uagaaauagc aaguuaaaau aaggcuaguc cguuaucaac uugaaaaagu    60
ggcaccgagu cggugcuuuu                                                80

<210> SEQ ID NO 312
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
guuuuagagc uagaaauagc aaguuaaaau aaggcuaguc cguuaucaac uugaaaaagu    60
ggcaccgagu cggugcuuuu                                                80

<210> SEQ ID NO 313
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
guuuuagagc uagaaauagc aaguuaaaau aaggcuaguc cguuaucaac uugaaaaagu    60
ggcaccgagu cggugcuuuu                                                80

<210> SEQ ID NO 314
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
guuuuagagc uagaaauagc aaguuaaaau aaggcuaguc cguuaucaac uugaaaaagu    60
ggcaccgagu cggugcuuuu                                                80

<210> SEQ ID NO 315
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
guuuuagagc uagaaauagc aaguuaaaau aaggcuaguc cguuaucaac uugaaaaagu    60
ggcaccgagu cggugcuuuu                                                80

<210> SEQ ID NO 316
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 316
guuuuagagc uagaaauagc aaguuaaaau aaggcuaguc cguuaucaac uugaaaaagu      60
ggcaccgagu cggugcuuuu                                                 80

<210> SEQ ID NO 317
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 317
guuuuagagc uagaaauagc aaguuaaaau aaggcuaguc cguuaucaac uugaaaaagu      60
ggcaccgagu cggugcuuuu                                                 80

<210> SEQ ID NO 318
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 318
guuuuagagc uagaaauagc aaguuaaaau aaggcuaguc cguuaucaac uugaaaaagu      60
ggcaccgagu cggugcuuuu                                                 80

<210> SEQ ID NO 319
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 319
guuuuagagc uagaaauagc aaguuaaaau aaggcuaguc cguuaucaac uugaaaaagu      60
ggcaccgagu cggugcuuuu                                                 80

<210> SEQ ID NO 320
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 320
guuuuagagc uagaaauagc aaguuaaaau aaggcuaguc cguuaucaac uugaaaaagu      60
ggcaccgagu cggugcuuuu                                               80

<210> SEQ ID NO 321
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
guuuuagagc uagaaauagc aaguuaaaau aaggcuaguc cguuaucaac uugaaaaagu    60
ggcaccgagu cggugcuuuu                                               80

<210> SEQ ID NO 322
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
guuuuagagc uagaaauagc aaguuaaaau aaggcuaguc cguuaucaac uugaaaaagu    60
ggcaccgagu cggugcuuuu                                               80

<210> SEQ ID NO 323
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
guuuuagagc uagaaauagc aaguuaaaau aaggcuaguc cguuaucaac uugaaaaagu    60
ggcaccgagu cggugcuuuu                                               80

<210> SEQ ID NO 324
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
guuuuagagc uagaaauagc aaguuaaaau aaggcuaguc cguuaucaac uugaaaaagu    60
ggcaccgagu cggugcuuuu                                               80

<210> SEQ ID NO 325
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
guuuuagagc uagaaauagc aaguuaaaau aaggcuaguc cguuaucaac uugaaaaagu    60

```
ggcaccgagu cggugcuuuu                                              80

<210> SEQ ID NO 326
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
guuuuagagc uagaaauagc aaguuaaaau aaggcuaguc cguuaucaac uugaaaaagu    60
ggcaccgagu cggugcuuuu                                              80

<210> SEQ ID NO 327
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
guuuuagagc uagaaauagc aaguuaaaau aaggcuaguc cguuaucaac uugaaaaagu    60
ggcaccgagu cggugcuuuu                                              80

<210> SEQ ID NO 328
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
guuuuagagc uagaaauagc aaguuaaaau aaggcuaguc cguuaucaac uugaaaaagu    60
ggcaccgagu cggugcuuuu                                              80

<210> SEQ ID NO 329
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
guuuuagagc uagaaauagc aaguuaaaau aaggcuaguc cguuaucaac uugaaaaagu    60
ggcaccgagu cggugcuuuu                                              80

<210> SEQ ID NO 330
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 330
```
cccauacucc uacagcacca guuuuagagc uagaaauagc aaguuaaaau aaggcuaguc    60
cguuaucaac uugaaaaagu ggcaccgagu cggugcuuuu                        100

<210> SEQ ID NO 331
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 331
cccauacucc uacagcacca guuuuagagc uagaaauagc aaguuaaaau aaggcuaguc    60
cguuaucaac uugaaaaagu ggcaccgagu cggugcuuuu                        100

<210> SEQ ID NO 332
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 332
cccauacucc uacagcacca guuuuagagc uagaaauagc aaguuaaaau aaggcuaguc    60
cguuaucaac uugaaaaagu ggcaccgagu cggugcuuuu                        100

<210> SEQ ID NO 333
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 333
agtcaataat cagaatcagc aggt                                         24

<210> SEQ ID NO 334
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 334
gttttgttcc agagtctatc accg                                         24

<210> SEQ ID NO 335
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 335
attaccagct tagcatcctg tgaa                                         24

```
<210> SEQ ID NO 336
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 336
agcacatgag accttctgtt tctc                                              24

<210> SEQ ID NO 337
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 337
agaaggcact tcttctttat ctaaggt                                           27

<210> SEQ ID NO 338
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 338
acacgaataa gagcaaatgg gaac                                              24

<210> SEQ ID NO 339
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 339
acacggttta tagagcaaga acac                                              24

<210> SEQ ID NO 340
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 340
gacataggtg tgaccctcac aatc                                              24

<210> SEQ ID NO 341
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 341
ccaguccagc gaggcaaagg guuuuagagc uagaaauagc aaguuaaaau aaggcuaguc    60
cguuaucaac uugaaaaagu ggcaccgagu cggugcuuuu                        100

<210> SEQ ID NO 342
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 342
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 343
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 343
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 344
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 344
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 345
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 345
uuacagccac gucuacagca guuuuagagc uagaaauagc aaguuaaaau aaggcuaguc    60
cguuaucaac uugaaaaagu ggcaccgagu cggugcuuuu                        100

<210> SEQ ID NO 346
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 346
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 347
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 347
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 348
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 348
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 349
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 349
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 350
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 350
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 351
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 351
uuacagccac gucuacagca guuuuagagc uagaaauagc aaguuaaaau aaggcuaguc    60
cguuaucaac uugaaaaagu ggcaccgagu cggugcuuuu    100

<210> SEQ ID NO 352
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 352
uuacagccac gucuacagca guuuuagagc uagaaauagc aaguuaaaau aaggcuaguc    60
cguuaucaac uugaaaaagu ggcaccgagu cggugcuuuu    100

<210> SEQ ID NO 353
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 353
uuacagccac gucuacagca guuuuagagc uagaaauagc aaguuaaaau aaggcuaguc    60
cguuaucaac uugaaaaagu ggcaccgagu cggugcuuuu    100

<210> SEQ ID NO 354
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(20)
<223> OTHER INFORMATION: n is a, c, g, or u

<400> SEQUENCE: 354
nnnnnnnnnn nnnnnnnnnn guuuuagagc uagaaauagc aaguuaaaau aaggcuaguc    60
cguuaucaac uugaaaaagu ggcaccgagu cggugcuuuu    100

<210> SEQ ID NO 355
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 355
guuuuagagc uagaaauagc aaguuaaaau aaggcuaguc cguuaucaac uugaaaaagu    60
ggcaccgagu cggugcuuuu    80

<210> SEQ ID NO 356
<211> LENGTH: 80

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 356
guuuuagagc uagaaauagc aaguuaaaau aaggcuaguc cguuaucaac uugaaaaagu    60
ggcaccgagu cggugcuuuu                                               80

<210> SEQ ID NO 357
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(20)
<223> OTHER INFORMATION: n is a, c, g, or u

<400> SEQUENCE: 357
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 358
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(3)
<223> OTHER INFORMATION: 2'-O-Me modified nucleotides
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (1)..(20)
<223> OTHER INFORMATION: N = any nucleotide
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (5)..(20)
<223> OTHER INFORMATION: n is a, c, g, or u
<220> FEATURE:
<221> NAME/KEY: modified_base
<222> LOCATION: (29)..(40)
<223> OTHER INFORMATION: 2'-O-Me modified nucleotides
<220> FEATURE:
<221> NAME/KEY: modified_base
<222> LOCATION: (69)..(100)
<223> OTHER INFORMATION: 2'-O-Me modified nucleotides
<220> FEATURE:
<221> NAME/KEY: misc_feature
<222> LOCATION: (97)..(98)
<223> OTHER INFORMATION: Phosphorothioate linkage
<220> FEATURE:
```

```
<221> NAME/KEY: misc_feature
<222> LOCATION: (98)..(99)
<223> OTHER INFORMATION: Phosphorothioate linkage
<220> FEATURE:
<221> NAME/KEY: misc_feature
<222> LOCATION: (99)..(100)
<223> OTHER INFORMATION: Phosphorothioate linkage

<400> SEQUENCE: 358
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 359
<211> LENGTH: 4514
<212> TYPE: RNA
<213> ORGANISM: Artificial Sequence
<220> FEATURE:
<221> NAME/KEY: source
<223> OTHER INFORMATION: /note="Description of Artificial Sequence: mRNA
      transcript"

<400> SEQUENCE: 359
gggucccgca gucggcgucc agcggcucug cuuguucgug ugugugucgu ugcaggccuu    60
auucggaucc auggauaaga aguacucaau cgggcuggau aucggaacua auuccguggg   120
uugggcagug aucacggaug aauacaaagu gccguccaag aaguucaagg uccuggggaa   180
caccgauaga cacagcauca agaaaaaucu caucggagcc cugcuguuug acuccggcga   240
aaccgcagaa gcgacccggc ucaaacguac cgcgaggcga cgcuacaccc ggcggaagaa   300
ucgcaucugc uaucugcaag agaucuuuuc gaacgaaaug gcaaaggucg acgacagcuu   360
cuuccaccgc cuggaagaau cuuuccuggu ggaggaggac aagaagcaug aacggcaucc   420
uaucuuugga aacaucgucg acgaaguggc guaccacgaa aaguacccga ccaucuacca   480
ucugcggaag aaguugguug acucaacuga caaggccgac cucagauuga cuacuuggc    540 ccucgcccau augaucaaau uccgcggaca cuuccugauc gaaggcgauc ugaacccuga   600
uaacuccgac guggauaagc uuuucauuca acuggugcag accacaaacc aacuguucga   660
agaaaaccca aucaaugcua gcggcgucga ugccaaggcc auccuguccg cccggcuguc   720
gaagucgcgg cgccucgaaa accugaucgc acagcugccg ggagagaaaa agaacggacu   780
uuucggcaac uugaucgcuc ucucacuggg acucacuccc aauuucaagu ccaauuuuga   840
ccuggccgag gacgcgaagc ugcaacucuc aaaggacacc uacgacgacg acuuggacaa   900
uuugcuggca caaauuggcg aucaguacgc ggaucuguuc cuugccgcua agaaccuuuc   960
ggacgcaauc uugcugucca auaccugcg cgugaacacc gaaauaacca agcgccgcu   1020 uagcgccucg augauuaagc gguacgacga gcaucaccag gaucacgcgc ugcucaaagc  1080
gcucgugaga cagcaacugc cugaaaagua caaggagauc uucuucgacc aguccaagaa  1140
uggguacgca ggguacaucg auggaggcgc uagccaggaa gaguucuaua aguucaucaa  1200
gccaauccug gaaaagaugg acggaaccga agaacugcug gucaagcuga acaggggagga  1260 ucugcuccgg aaacagagaa ccuuugacaa cggaucccauu ccccaccaga uccaucuggg  1320
ugagcugcac gccaucuugc ggcgccagga ggacuuuuac ccauuccuca aggacaaccg  1380
ggaaaagauc gagaaaauuc ugacguuccg cauccguau acgugggcc cacuggcgcg  1440 cggcaauucg cgcuucgcgu ggaugacuag aaaaucagag gaaccauca cuccuuggaa  1500 uuucgaggaa guguggaua agggagcuuc ggcacaaagc uucaucgaac gaaugaccaa  1560
cuucgacaag aaucucccaa acgagaaggu gcuuccuaag cacagccucc uuuacgaaua  1620
```

-continued

```
cuucacuguc uacaacgaac ugacuaaagu gaaauacguu acugaaggaa ugaggaagcc    1680
ggccuuucug uccggagaac agaagaaagc aauugucgau cugcuguuca agaccaaccg    1740
caaggugacc gucaagcagc uuaaagagga cuacuucaag aagaucgagu guuucgacuc    1800
aguggaaauc agcggggugg aggacagauu caacgcuucg cugggaaccu aucaugaucu    1860
ccugaagauc aucaaggaca aggacuuccu ugacaacgag gagaacgagg acauccugga    1920
agauacgguc cugaccuuga cccuuuucga ggaucgcgag augaucgagg agaggcuuaa    1980
gaccuacgcu caucucuucg acgauaaggu caugaaacaa cucaagcgcc gccgguacac    2040 ugguugggc cgccucuccc gcaagcugau caacggauauu cgcgauaaac agagcgguaa    2100
aacuauccug gauuuccuca aaucggaugg cuucgcuaau cguaacuuca ugcaauugau    2160 ccacgcgac agccugaccu uuaaggagga cauccaaaaa gcacaagugu ccggacaggg    2220
agacucacuc caugaacaca ucgcgaaucu ggccgguucg ccggcgauua gaagggaau    2280 ucugcaaacu gugaaggugg ucgacgcgcu ggugaagguc augggacggc acaaaccgga    2340
gaauaucgug auugaaaugg cccgagaaaa ccagacuacc cagaagggcc agaaaaacuc    2400
ccgcgaaagg augaagcgga ucgaagaagg aaucaaggag cugggcagcc agauccugaa    2460
agagcacccg guggaaaaca cgcagcugca gaacgagaag cucuaccugu acauuuugca    2520
aaauggacgg gacauguacg uggaccaaga gcuggacauc aaucgguugu cugauuacga    2580
cguggaccac aucguuccac aguccuuucu gaaggaugac ucgaucgaua caaggguguu    2640
gacucgcagc gacaagaaca gagggaaguc agauaaugug ccaucggagg aggucgugaa    2700
gaagaugaag aauuacuggc ggcagcuccu gaaugcgaag cugauuaccc agagaaaguu    2760
ugacaaucuc acuaaagccg agcgcggcgg acucucagag cuggauaagg cuggauucau    2820
caaacggcag cuggucgaga cucggcagau uaccaagcac guggcgcaga ucuuggacuc    2880
ccgcaugaac acuaaauacg acgagaacga uaagcucauc cgggaaguga aggugauuac    2940
ccugaaaagc aaacuugugu cggacuuucg gaaggacuuu caguuuuaca agugagaga    3000 aaucaacaac uaccaucacg cgcaugacgc auaccucaac gcuggguucg guaccgcccu    3060
gaucaaaaag uacccuaaac uugaaucgga guuuguguac ggagacuaca ggucuacga    3120 cgugaggaag augauagcca aguccgaaca ggaaaucggg aaagcaacug cgaaauacuu    3180
cuuuuacuca aacaucauga acuuuuucaa gacugaaauu acgcuggcca auggagaaau    3240
caggaagagg ccacugaucg aaacuaacgg agaaacgggc gaaaucgugu gggacaaggg    3300
cagggacuuc gcaacuguuc gcaaagugcu cucuaugccg caagucaaua uugugaagaa    3360
aaccgaagug caaaccggcg gauuuucaaa ggaaucgauc ucccaaaga gaaauagcga    3420 caagcucauu gcacgcaaga agacugggga cccgaagaag uacggaggau cgauucgcc    3480 gacugucgca uacuccgucc ucguggugc caagguggag aagggaaaga gcaaaaagcu    3540
caaauccguc aaagagcugc uggggauuac caucauggaa cgauccucgu ucgagaagaa    3600
cccgauugau uuccucgagg cgaagggcuua caaggaggug aagaaggauc ugaucaucaa    3660 acucccccaag uacucacugu ucgaacugga aaauggucgg aagcgcaugc uggcuucggc    3720
cggagaacuc caaaaaggaa augagcuggc cuugccuagc aauacguca acuuccucua    3780 ucuugcuucg cacuacgaaa aacucaaagg gucaccggaa gauaacgaac agaagcagcu    3840
uuucguggag cagcacaagc auuaucugga ugaaaucauc gaacaaaucu ccagguuuuc    3900
aaagcgcgug auccucgccg acgccaaccu cgacaaaguc cugucggccu acaauaagca    3960
```

| | |
|---|---|
| uagagauaag ccgaucagag aacaggccga gaacauuauc cacuuguuca cccugacuaa | 4020 |
| ccugggagcc ccagccgccu ucaaguacuu cgauacuacu aucgaucgca aaagauacac | 4080 |
| guccaccaag gaaguucugg acgcgacccu gauccaccaa agcaucacug acucuacga | 4140 |
| aacuaggauc gaucugucgc agcugggugg cgauggcggu ggauccgga aaagaagag | 4200 |
| aaagguguaa ugagcuagcc aucacauuua aaagcaucuc agccuaccau gagaauaaga | 4260 |
| gaaagaaaau gaagaucaau agcuuauuca ucucuuuuuc uuuuucguug guguaaagcc | 4320 |
| aacacccugu cuaaaaaaca uaaauuucuu uaaucauuuu gccucuuuuc ucugugcuuc | 4380 |
| aauuaauaaa aaauggaaag aaccucgaga aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaau cuag | 4514 |

<210> SEQ ID NO 360
<211> LENGTH: 4603
<212> TYPE: RNA
<213> ORGANISM: Artificial Sequence
<220> FEATURE:
<221> NAME/KEY: source
<223> OTHER INFORMATION: /note="Description of Artificial Sequence: mRNA transcript"

<400> SEQUENCE: 360

| | |
|---|---|
| ggguccccgca gucggcgucc agcggcucug cuuguucgug ugugugucgu ugcaggccuu | 60 |
| auucggaucc auggauaaga aguacucaau cgggcuggau aucggaacua auuccgugg | 120 |
| uugggcagug aucacggaug aauacaaagu gccguccaag aaguucaagg uccuggggaa | 180 |
| caccgauaga cacagcauca agaaaaaucu caucggagcc cugcuguuug acuccggcga | 240 |
| aaccgcagaa gcgacccggc ucaaacguac cgcgaggcga cgcuacaccc ggcggaagaa | 300 |
| ucgcaucugc uaucugcaag agaucuuuuc gaacgaaaug gcaaaggucg acgacagcuu | 360 |
| cuuccaccgc cuggaagaau cuuuccuggu ggaggaggac aagaagcaug aacggcaucc | 420 |
| uaucuuugga aacaucgucg acgaaguggc guaccacgaa aaguacccga ccaucuacca | 480 |
| ucugcggaag aaguugguug acucaacuga caaggccgac cucagauuga ucuacuggc | 540 |
| ccucgcccau augaucaaau uccgcggaca cuuccugauc gaaggcgauc ugaacccuga | 600 |
| uaacuccgac guggauaagc uuucauuca acuggugcag accuacaacc aacguucga | 660 |
| agaaaaccca aucaaugcua gcggcgucga ugccaaggcc aucugucccg cccggcuguc | 720 |
| gaagucgcgg cgccucgaaa accgaucgc acagcgccg ggagagaaaa agaacggacu | 780 |
| uuucggcaac uugaucgcuc ucucacuggg acucaccccc aauuucaagu ccaauuuga | 840 |
| ccuggccgag gacgcgaagc ugcaacucuc aaaggacacc uacgacgacg acuuggacaa | 900 |
| uuugcuggca caaauuggcg aucaguacgc ggaucuguuc cuugccgcua agaaccuuuc | 960 |
| ggacgcaauc uugcugucc auauccgcg cgugaacacc gaaauaacca agcgccgcu | 1020 |
| uagcgccucg augauuaagc gguacgacga gcauaccag gaucucacgc ugcucaaagc | 1080 |
| gcucgugaga cagcaacugc cugaaaagua caaggagauc uucuucgacc aguccaagaa | 1140 |
| ugggaugcaa ggguacaucg auggaggcgc uagccaggaa gaguucuaua aguucaucaa | 1200 |
| gccaauccug gaaaagaugg acggaaccga agaacugcug gucaagcuga caggaggga | 1260 |
| ucugcuccgg aaacagagaa ccuuugacaa cggauccauu ccccaccaga ucaucuggg | 1320 |
| ugagcugcac gccaucuugc ggcgccagga ggacuuuuac ccauuccuca aggacaaccg | 1380 |
| ggaaaagauc gagaaaauuc ugacguuccg caucccguau uacgugggcc cacuggcgcg | 1440 |

```
cggcaauucg cgcuucgcgu ggaugacuag aaaaucagag gaaaccauca cuccuuggaa    1500
uuucgaggaa guuguggaua agggagcuuc ggcacaaagc uucaucgaac gaaugaccaa    1560
cuucgacaag aaucucccaa acgagaaggu gcuuccuaag cacagccucc uuuacgaaua    1620
cuucacuguc uacaacgaac ugacuaaagu gaaauacguu acugaaggaa ugaggaagcc    1680
ggccuuucug uccggagaac agaagaaagc aauugucgau cugcuguuca agaccaaccg    1740
caaggugacc gucaagcagc uuaaagagga cuacuucaag aagaucgagu guucgacuc     1800 agugaaauc agcggggugg aggacagauu caacgcuucg cugggaaccu aucaugaucu     1860
ccugaagauc aucaaggaca aggacuuccu ugacaacgag gagaacgagg acauccugga    1920
agauaucguc cugaccuuga cccuuuucga ggaucgcgag augaucgagg agaggcuuaa    1980
gaccuacgcu caucucuucg acgauaaggu caugaaacaa cucaagcgcc gccgguacac    2040
ugguuggggc cgccucuccc gcaagcugau caacgguauu cgcgauaaac agagcgguaa    2100
aacuauccug gauuuccuca aaucggaugg cuuucgcuaa cguaacuuca ugcaauugau    2160
ccacgacgac agccugaccu uuaaggagga cauccaaaaa gcacaagugu ccggacaggg    2220
agacucacuc caugaacaca ucgcgaaucu ggccgguucg ccggcgauua agaagggaau    2280
ucugcaaacu gugaaggugg ucgacgagcu ggugaagguc augggacggc acaaaccgga    2340
gaauaucgug auugaaaugg cccgagaaaa ccagacuacc cagaagggcc agaaaaacuc    2400
ccgcgaaagg augaagcgga ucgaagaagg aaucaaggag cugggcagcc agauccugaa    2460
agagcacccg guggaaaaca cgcagcugca gaacgagaag cucuaccgu acuauuugca     2520 aaauggacgg gacauguacg uggaccaaga gcuggacauc aaucgguugu cugauuacga    2580
cguggaccac aucguuccac aguccuuucu gaaggaugac ucgaucgaua caaggguguu    2640
gacucgcagc gacaagaaca gagggaaguc agauaaugug ccaucggagg aggucgugaa    2700
gaagaugaag aauuacuggc ggcagccccu gaaugcgaag cugauucccc agagaaaguu    2760
ugacaaucuc acuaaagccg agcgcggcgg acucucagag cuggauaagg cuggauucau    2820
caaacggcag cuggucgaga cucggcagau uaccaagcac guggcgcaga ucuuggacuc    2880
ccgcaugaac acuaaauacg acgagaacga uaagcucauc cgggaaguga aggugauuac    2940
ccugaaaagc aaacuugugu cggacuuucg gaaggacuuu caguuuuaca aagugagaga    3000
aaucaacaac uaccaucacg cgcaugacgc auaccaaac gcugguggucg uaccgcccu     3060 gaucaaaaag uacccuaaac uugaaucgga guuuguguac ggagacuaca aggucuacga    3120
cgugaggaag augauagcca aguccgaaca ggaaaucggg aaagcaacug cgaaauacuu    3180
cuuuuacuca aacaucauga acuuuuucaa gacugaaauu acgcuggcca auggagaaau    3240
caggaagagg ccacugaucg aaacuaacgg agaaacgggc gaaaucgugu gggacaaggg    3300
cagggacuuc gcaacuguuc gcaaagugcu ucuaugccg caagucaaua uugugaagaa     3360
aaccgaagug caaaccggcg gauuuucaaa ggaaucgauc cucccaaaga gaaauagcga    3420
caagcucauu gcacgcaaga aagacuggga cccgaagaag uacggaggau cgauucgcc     3480 gacugucgca uacuccgucc ucguggugga aagguggag aagggaaaga gcaaaaagcu     3540
caaauccguc aaagagcugc uggggauuac caucaugaa cgauccucgu ucgagaagaa     3600
cccgauugau uccucgaggg cgaaggguua caaggaggug aagaaggauc ugaucaucaa    3660 acucccccaag uacucacugu ucgaacugga aauggcgg aagcgcaugc uggcuucggc     3720
cggagaacuc caaaaaggaa augagcuggc cuugccuagc aaguacguca acuuccucua    3780
```

```
ucuugcuucg cacuacgaaa aacucaaagg gucaccggaa gauaacgaac agaagcagcu   3840
uuucguggag cagcacaagc auuaucugga ugaaaucauc gaacaaaucu ccgaguuuuc   3900
aaagcgcgug auccucgccg acgccaaccu cgacaaaguc cugucggccu acaauaagca   3960
uagagauaag ccgaucagag aacaggccga gaacauuauc cacuuguuca cccugacuaa   4020
ccugggagcc ccagccgccu ucaaguacuu cgauacuacu aucgaucgca aaagauacac   4080
guccaccaag gaaguucugg acgcgacccu gauccaccaa agcaucacug gacucuacga   4140
aacuaggauc gaucugucgc agcugggugg cgauggcucg gcuuacccau acgacgugcc   4200
ugacuacgcc ucgcucggau cgggcucccc caaaaagaaa cggaaggugg acggaucccc   4260
gaaaaagaag agaaaggugg acuccggaug agaauuaugc agucuagcca ucacauuuaa   4320
aagcaucuca gccuaccaug agaauaagag aaagaaaaug aagaucaaua gcuuauucau   4380
cucuuuuucu uuuucguugg uguaaagcca acacccuguc uaaaaaacau aaauuucuuu   4440
aaucauuuug ccucuuuucu cugugcuuca auuaauaaaa aauggaaaga accucgagaa   4500
aaaaaaaaaa aaaaaaaaaa aaaaaaaaaa aaaaaaaaaa aaaaaaaaaa aaaaaaaaaa   4560
aaaaaaaaaa aaaaaaaaaa aaaaaaaaaa aaaaaaaauc uag                    4603
```

MODIFIED GUIDE RNAS

SEQUENCE LISTING

The instant application contains a Sequence Listing which has been submitted electronically in ASCII format and is hereby incorporated by reference in its entirety. Said ASCII copy, created on Jun. 7, 2019, is named 01155-0004-00US_SeqList.txt and is 118,923 bytes in size.

This application is a Continuation of International Application No. PCT/US2017/065306, which was filed on Dec. 8, 2017, and which claims the benefit of priority to U.S. Provisional Application No. 62/431,756, which was filed on Dec. 8, 2016, both of which are incorporated by reference in their entirety.

This disclosure relates to the field of gene editing using CRISPR/Cas systems, a part of the prokaryotic immune system that recognizes and cuts exogenous genetic elements. The CRISPR/Cas system relies on a single nuclease, termed CRISPR-associated protein 9 (Cas9), which induces site-specific breaks in DNA. Cas9 is guided to specific DNA sequences by small RNA molecules termed guide RNA (gRNA). Guide RNA comprises trRNA (also known as tracrRNA) and crisprRNA (crRNA). The trRNA and crRNA may be contained within a single guide RNA (sgRNA) or in two separate RNA molecules of a dual guide RNA (dgRNA). Cas9 in combination with trRNA and crRNA or an sgRNA is termed the Cas9 ribonucleoprotein complex (RNP).

Oligonucleotides, and in particular RNA, are sometimes degraded in cells and in serum by endonuclease or exonuclease cleavage. Improved methods and compositions for preventing such degradation, improving stability of gRNAs and enhancing gene editing efficiency is desired, especially for therapeutic applications.

SUMMARY

In some embodiments, therapeutic genome editing tools are provided comprising modified guide RNAs. The modified guide RNAs described herein may improve the stability of the guide RNA and the guide RNA/Cas9 complex and improve the activity of Cas9 (e.g., SpyCas9 and equivalents) to cleave target DNA. In some embodiments, the guide RNA is an sgRNA. In some embodiments, the guide RNA is a dgRNA. In some embodiments, the guide RNA is a tracrRNA. In some embodiments, the guide RNA is a crRNA.

The guide RNAs described herein comprise at least one modified nucleotide. Modifications may include 2'-O-methyl (2'-O-Me), 2'-O-(2-methoxyethyl) (2'-O-moe), 2'-fluoro (2'-F), phosphorothioate (PS) bond between nucleotides, G-C substitutions, and inverted abasic linkages between nucleotides and equivalents thereof. Embodiments of the invention include:

In some embodiments, a single guide RNA (sgRNA) is encompassed comprising a 5' end modification and one or more modification in one or more of: the upper stem region; the hairpin 1 region; and the hairpin 2 region, wherein the 5' end modification comprises at least two phosphorothioate linkages within the first seven nucleotides at the 5' end of the 5' terminus. In some instances, the modification is a 2'-O-methyl (2'-O-Me) modified nucleotide. In some embodiments, the modification is a 2'-fluoro (2'-F) modified nucleotide.

In some embodiments, the sgRNA comprises modifications at US1 to US12 and/or a modification at H1-1 and/or a modification in H2-1. In some embodiments, the sgRNA comprises modifications at H1-1 to H1-12 and/or H2-1 to H2-15. In some embodiments, the sgRNA comprises one or more modifications in each of the upper stem region, the hairpin 1 region, and the hairpin 2 region. In some embodiments, the sgRNA comprises a modified nucleotide between hairpin 1 and hairpin 2 regions. In some embodiments, the sgRNA comprises a modification in the lower stem region.

In some embodiments, the sgRNA comprises a modification at the 5' terminus and/or the 3' terminus. In some embodiments, the sgRNA comprises a 3' end modification in the 3' terminus. In some embodiments, the sgRNA comprises modifications on at least two of the last four nucleotides at the 3' end of the 3' terminus. In some embodiments, the sgRNA comprises a 5' end modification in the 5' terminus. In some embodiments, the sgRNA comprises modifications on at least two of the first four nucleotides at the 5' end of the 5' terminus. In some embodiments, the sgRNA comprises a 3' end modification in the 3' terminus and a 5' end modification in the 5' terminus. In some embodiments, the sgRNA comprises modifications on at least two of the last four nucleotides at the 3' end of the 3' terminus and on at least two of the first four nucleotides at the 5' end of the 5' terminus. In some instances, these modifications are 2'-O-Me, 2'-F, 2'-O-moe, or phosphorothioate (PS) bonds linking the nucleotides. In some embodiments, the sgRNA comprises PS bonds between at least two of the last four nucleotides at the 3' end of the 3' terminus and/or at least two of the first four nucleotides at the 5' end of the 5' terminus. In some instances, the sgRNA comprises 5' terminus and 3' terminus with more than one modification as described herein, such as, with PS bonds and 2'-O-Me modifications.

In some embodiments, the sgRNA comprises a modification in the bulge region. In some embodiments, 50% of the nucleotides in the bulge region are modified, wherein the modification is 2'-O-Me or 2'-F.

In some embodiments, the sgRNA comprises a modification in the nexus region. In some embodiments, the sgRNA comprises modifications at N15, N16, N17, and/or N18 in the nexus region, wherein the modification is 2'-O-Me or 2'-F. In some instances, N16, N17, and N18 are linked with PS bonds.

In some embodiments, the sgRNA comprises at least the first three nucleotides at the 5' end of the 5' terminus, and the last three nucleotides at the 3' end of the 3' terminus are modified.

In some embodiments, the sgRNA comprises modifications at the 3' terminus and/or 5' terminus. In some instances, the first four nucleotides at the 5' end of the 5' terminus, and the last four nucleotides at the 3' end of the 3' terminus are linked with phosphorothioate (PS) bonds. In some embodiments, the 5' and 3' modification comprises 2'-O-Me or 2'-O-moe. In some embodiments, the 5' and 3' modification comprises 2'-F. In some embodiments, the 5' and/or 3' modification comprises PS bonds linking nucleotides. In some embodiments, the 5' and/or 3' modification comprises one or more of 2'-O-Me, 2'-O-moe, 2'-F, and PS bonds linking nucleotides.

In some embodiments, the sgRNA comprises modifications at the first four nucleotides at the 5' end of the 5' terminus and the last four nucleotides at the 3' end of the 3'terminus. In some instances, these modifications are linking PS bond (i.e., PS bonds that link the first four and last four nucleotides). In some embodiments, the sgRNA further comprises 2'-O-Me modifications at the first three nucleotides at the 5' end of the 5' terminus and the last three nucleotides at the 3' end of the 3' terminus.

In some embodiments, the sgRNA comprises modifications at the first four nucleotides at the 5' end of the 5' terminus and the last four nucleotides at the 3' end of the 3' terminus, wherein the modifications are at least PS bonds linking the four nucleotides, and further wherein the first three nucleotides at the 5' end of the 5' terminus and the last three nucleotides at the 3' end of the 3' terminus comprise 2'-O-Me, 2'-O-moe, or 2'-F modifications.

In some embodiments, the sgRNA comprises modifications LS1, LS6, LS7, LS8, LS11, and LS12, wherein the modification is 2'-O-Me or 2'-F.

In some embodiments, the sgRNA comprises modifications at each of the nucleotides in the bulge region, wherein the modification is 2'-O-Me or 2'-F.

In some embodiments, the sgRNA comprises modifications at each of the nucleotides in the upper stem region, wherein the modification is 2'-O-Me or 2'-F.

In some embodiments, the sgRNA comprises modifications at each of the nucleotides in the hairpin 1 region, wherein the modification is 2'-O-Me or 2'-F.

In some embodiments, the sgRNA comprises modifications at each of the nucleotides in the hairpin 2 region, wherein the modification is 2'-O-Me or 2'-F.

In some embodiments, an sgRNA is encompassed comprising 2'-O-Me modified nucleotides at the following positions:
  a. the first three nucleotides at the 5' end of the 5' terminus;
  b. LS1, LS6, LS7, LS8, LS11, and/or LS12 in the lower stem region;
  c. B1 and/or B2 in the bulge region;
  d. each nucleotide in the upper stem region;
  e. N16, N17, and/or N18 in the nexus region;
  f. each nucleotide in the hairpin 1 region;
  g. each nucleotide in the hairpin 2 region; and
  h. the last four nucleotides at the 3' end of the 3' terminus.

In some embodiments, B3-B6 are modified with 2'-O-Me. In some instances, the sgRNA further comprising three phosphorothioate (PS) bonds linking the first four nucleotides at the 5' end of the 5' terminus and three PS bonds linking the last four nucleotides at the 3' end of the 3' terminus. In some embodiments, the sgRNA comprises 2'-F modifications at LS9 and LS10. In some embodiments, the sgRNA comprises 2'F modifications at N15, N16, N17, and N18. In some embodiments, the sgRNA comprises 2'F modifications at H2-9, H2-10, H2-11, H2-12, H2-13, H2-14, and H2-15. In some embodiments, the sgRNA comprises 2'F modifications at the second to last, third to last, and fourth to last nucleotides at the 3' end of the 3' terminus.

In some embodiments, an sgRNA is encompassed comprising 2'-F modified nucleotides at the following positions:
  a. LS9 and LS10 in the lower stem region;
  b. N15, N16, N17, and N18 in the nexus region; and
  c. H2-9, H2-10, H2-11, H2-12, H2-13, H2-14, and H2-15 in the hairpin 2 region.

In some embodiments, the sgRNA comprises 2'-F modified nucleotides at the second to last, third to last, and fourth to last nucleotides at the 3' terminus. In some embodiments, the sgRNA comprises three phosphorothioate (PS) bonds linking the first four nucleotides at the 5' end of the 5' terminus and three PS bonds linking the last four nucleotides at the 3' end of the 3' terminus. In some embodiments, the sgRNA comprises 2'-O-Me or 2'-F modified nucleotides at the first three nucleotides at the 5' end of the 5' terminus, and 2'-O-Me or 2'-F modified nucleotides at three of the last four nucleotides at the 3' end of the 3' terminus.

In some embodiments, an sgRNA is encompassed comprising
  a. 2'-O-Me modified nucleotides at the first three nucleotides at the 5' end of the 5' terminus;
  b. Optional 2'-O-Me modified nucleotides at LS1 and/or LS6;
  c. 2'-O-Me modified nucleotides at US1-US12;
  d. 2'-O-Me modified nucleotides at H1-1-H1-12;
  e. Optional 2'-O-Me modified nucleotide between Hairpin 1 and Hairpin 2;
  f. 2'-O-Me modified nucleotides at H2-1-H2-15; and
  g. 2'-O-Me modified nucleotides at the last four nucleotides at the 3' end of the 3' terminus; and optionally
further comprising three phosphorothioate (PS) bonds linking the first four nucleotides at the 5' end of the 5' terminus and three PS bonds linking the last four nucleotides at the 3' end of the 3' terminus.

In some embodiments, an sgRNA is encompassed comprising:
  a. 2'-O-Me modified nucleotides at the first three nucleotides at the 5' end of the 5' terminus;
  b. 2'-F modified nucleotides at LS1-LS6;
  c. 2'-O-Me modified nucleotides at US1-US12;
  d. 2'-O-Me modified nucleotides at H1-1-H1-12;
  e. a 2'-O-Me modified nucleotide between Hairpin 1 and Hairpin 2;
  f. 2'-O-Me modified nucleotides at H2-1-H2-15; and
  g. 2'-O-Me modified nucleotides at the last four nucleotides at the 3' end of the 3' terminus; and optionally
further comprising three phosphorothioate (PS) bonds linking the first four nucleotides at the 5' end of the 5' terminus and three PS bonds linking the last four nucleotides at the 3' end of the 3' terminus.

In some embodiments, an sgRNA is encompassed comprising:
  a. 2'-O-Me modified nucleotides at the first three nucleotides at the 5' terminus;
  b. 2'-F modified nucleotides at LS2-LS5;
  c. 2'-O-Me modified nucleotides at LS1 and LS6;
  d. 2'-O-Me modified nucleotides at US1-US12;
  e. 2'-O-Me modified nucleotides at H1-1-H1-12;
  f. a 2'-O-Me modified nucleotide between Hairpin 1 and Hairpin 2;
  g. 2'-O-Me modified nucleotides at H2-1-H2-15; and
  h. 2'-O-Me modified nucleotides at the last four nucleotides at the 3' terminus and optionally
further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:
  a. 2'-O-Me modified nucleotides at the first three nucleotides at the 5' terminus;
  b. 2'-O-Me modified nucleotides at US1-US12;
  c. 2'-O-Me modified nucleotides at LS7, LS8, LS11, and LS12;
  d. 2'-O-Me modified nucleotides at H1-1-H1-12;
  e. a 2'-O-Me modified nucleotide between Hairpin 1 and Hairpin 2;
  f. 2'-O-Me modified nucleotides at H2-1-H2-15; and
  g. 2'-O-Me modified nucleotides at the last four nucleotides at the 3' terminus,
and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:
   a. 2'-O-Me modified nucleotides at the first three nucleotides at the 5' terminus;
   b. 2'-O-Me modified nucleotides at US1-US12;
   c. 2'-O-Me modified nucleotides at LS7, LS8, LS11, and LS12;
   d. 2'-F modified nucleotides at LS9 and LS10;
   e. 2'-O-Me modified nucleotides at H1-1-H1-12;
   f. a 2'-O-Me modified nucleotide between Hairpin 1 and Hairpin 2;
   g. 2'-O-Me modified nucleotides at H2-1-H2-15; and
   h. 2'-O-Me modified nucleotides at the last four nucleotides at the 3' terminus,
and optionally further comprising three phosphorothioate (PS) bonds linking the first four nucleotides at the 5' end of the 5' terminus and three PS bonds linking the last four nucleotides at the 3' end of the 3' terminus.

In some embodiments, an sgRNA is encompassed comprising:
   a. 2'-O-Me modified nucleotides at the first three nucleotides at the 5' terminus;
   b. 2'-O-Me modified nucleotides at US1-US12;
   c. 2'-O-Me modified nucleotides at LS8, LS10, and LS12;
   d. 2'-O-F modified nucleotides at LS7, LS9, and LS11;
   e. 2'-O-Me modified nucleotides at H1-1-H1-12;
   f. a 2'-O-Me modified nucleotide between Hairpin 1 and Hairpin 2;
   g. 2'-O-Me modified nucleotides at H2-1-H2-15; and
   h. 2'-O-Me modified nucleotides at the last four nucleotides at the 3' terminus, and optionally
further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:
   a. 2'-O-Me modified nucleotides at the first three nucleotides at the 5' terminus;
   b. 2'-O-Me modified nucleotides at LS1, LS6, LS7, LS8, LS11, and LS12
   c. 2'-O-Me modified nucleotides at US1-US12;
   d. 2'-O-Me modified nucleotides at H1-1-H1-12;
   e. a 2'-O-Me modified nucleotide between Hairpin 1 and Hairpin 2;
   f. 2'-O-Me modified nucleotides at H2-1-H2-15; and
   g. 2'-O-Me modified nucleotides at the last four nucleotides at the 3' terminus, and optionally
further comprising three phosphorothioate (PS) bonds linking the first four nucleotides at the 5' end of the 5' terminus and three PS bonds linking the last four nucleotides at the 3' end of the 3' terminus In some embodiments, a sgRNA is encompassed comprising:
   a. 2'-O-Me modified nucleotides at the first three nucleotides at the 5' terminus;
   b. 2'-O-Me modified nucleotides at LS1, LS6, LS7, LS8, LS11, and LS12;
   c. 2'-F modified nucleotides at LS9 and LS10;
   d. 2'-O-Me modified nucleotides at US1-US12;
   e. 2'-O-Me modified nucleotides at H1-1-H1-12;
   f. a 2'-O-Me modified nucleotide between Hairpin 1 and Hairpin 2;
   g. 2'-O-Me modified nucleotides at H2-1-H2-15; and
   h. 2'-O-Me modified nucleotides at the last four nucleotides at the 3' terminus, and optionally
further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:
   a. 2'-O-Me modified nucleotides at the first three nucleotides at the 5' end of the 5' terminus;
   b. 2'-O-Me modified nucleotides at US1-US12;
   c. 2'-O-Me modified nucleotides at H1-1-H1-12;
   d. a 2'-O-Me modified nucleotide between Hairpin 1 and Hairpin 2;
   e. 2'-O-Me modified nucleotides at H2-1-H2-8;
   f. 2'-F modified nucleotides at H2-9-H2-15;
   g. 2'-F modified nucleotides at the second from last, third from last, and fourth from last nucleotide at the 3' terminus; and
   h. a 2'-O-Me modified nucleotide at the last nucleotide at the 3' terminus, and optionally
further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:
   a. 2'-O-Me modified nucleotides at the first three nucleotides at the 5' terminus;
   b. 2'-O-Me modified nucleotides at US1-US12;
   c. 2'-O-Me modified nucleotides at H1-2, H1-4, H1-6, H1-8, H1-10, and H1-12;
   d. 2'-F modified nucleotides at H1-1, H1-3, H1-5, H1-7, H1-9, and H1-11;
   e. a 2'-F modified nucleotide between Hairpin 1 and Hairpin 2;
   f. 2'-F modified nucleotides at H2-2, H2-4, H2-6, H2-8, H2-10, H2-12; and H2-14;
   g. 2'-O-Me modified nucleotides at H2-1, H2-3, H2-5, H2-7, H2-9, H2-11; H2-13, and H2-15;
   h. 2'-F modified nucleotides at the second from last, and fourth from last nucleotide at the 3' terminus; and
   i. 2'-O-Me modified nucleotide at the third from last and last nucleotide at the 3' end of the 3' terminus,
and optionally further comprising three phosphorothioate (PS) bonds linking the first four nucleotides at the 5' end of the 5' terminus and three PS bonds linking the last four nucleotides at the 3' end of the 3' terminus.

In some embodiments, a sgRNA is encompassed comprising:
   a. 2'-O-Me modified nucleotides LS8, LS10, LS12, H1-2, H1-4, H1-6, H1-8, H1-10, H1-12, H2-1, H2-3, H2-5, H2-7, H2-9, H2-11, H2-13, and H2-15; and
   b. 2'-F modified nucleotides at LS7, LS9, LS11; H1-1, H1-3, H1-5, H1-7, H1-9, H1-11, H1-13, H2-2, H2-4, H2-6, H2-8, H2-10, H2-12, and H2-14, and optionally
further comprising three phosphorothioate (PS) bonds linking the first four nucleotides at the 5' end of the 5' terminus and three PS bonds linking the last four nucleotides at the 3' end of the 3' terminus; and optionally further comprising:
   c. 2'-O-Me modified nucleotides at the last and third to last nucleotide at the 3' end of the 3' terminus; and/or
   d. 2'-F modified nucleotides at the second to last, fourth to last, and/or last nucleotide at the 3' end of the 3' terminus.

In some embodiments, a sgRNA is encompassed comprising the nucleic acids of any of SEQ ID Nos: 228-353, including the modifications of Table 4. In some embodiments, a sgRNA is encompassed comprising any of SEQ ID Nos: 228-332, including the modifications of Table 4. In some embodiments, an sgRNA is encompassed comprising any of SEQ ID Nos: 235-240, 265-285, and 309-329, including the modifications of Table 4. In some embodiments, an sgRNA is encompassed comprising SEQ ID No: 240. In some embodiments, a sgRNA is encompassed comprising SEQ ID No. 240, including the modifications of Table 4. In some embodiments, a sgRNA is encompassed comprising SEQ ID No: 242. In some embodiments, a sgRNA is encompassed comprising SEQ ID No: 358. In additional embodiments, a sgRNA comprising nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification at each nucleotide of the sgRNA that corresponds to a nucleotide of the reference sequence identifier in Table 4, is identical to or equivalent to the modification shown in the reference sequence identifier in Table 4, optionally further comprising three phosphorothioate (PS) bonds linking the first four nucleotides at the 5' end of the 5' terminus and three PS bonds linking the last four nucleotides at the 3' end of the 3' terminus. In some embodiments, the sgRNA further comprises at least three PS bonds linking the nucleotides in the hairpin 1 region. In some embodiments, the sgRNA further comprises at least three PS bonds linking the nucleotides in the hairpin 2 region. In some embodiments, the sgRNA further comprises at least three PS bonds linking the nucleotides in the upper stem region. In some embodiments, the sgRNA forms a ribonucleoprotein complex with *S. pyogenes* Cas9.

FIGURE LEGENDS

FIG. 4 shows percent editing as measured by NGS of mouse TTR gene following transfection of Neuro2A cells with modified crRNAs and trRNAs together with Cas9 mRNA. Standard deviations follow the value.

Figure 6:
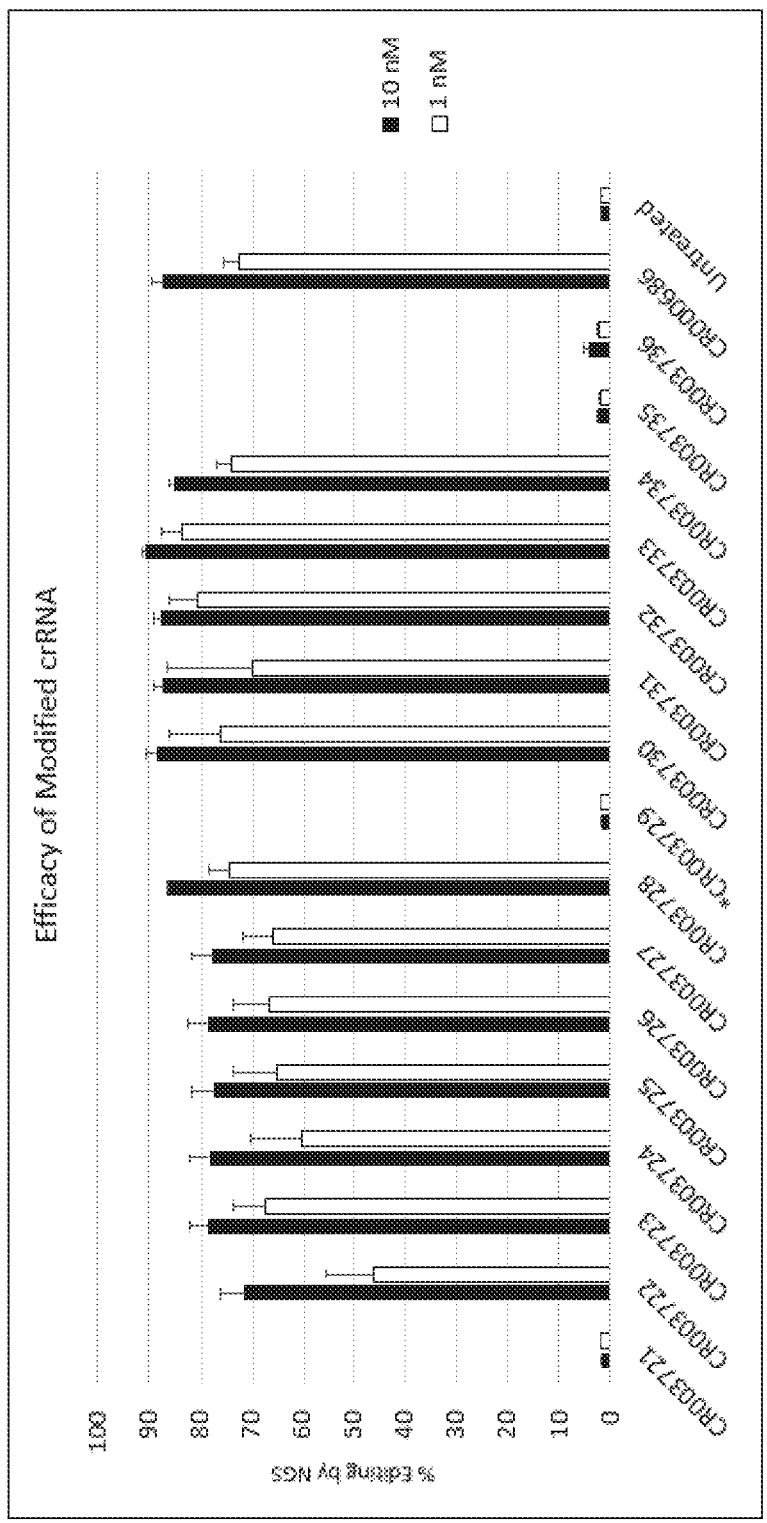

FIG. 6 shows percent editing as measured by NGS of mouse TTR gene following transfection of Neuro2A cells with modified crRNAs and unmodified trRNA (TR000002) together with Cas9 mRNA. The asterisk denotes a dual guide that for technical reasons did not show activity in this experiment. This dual guide was tested again in the experiment represented in FIG. 9, in which it showed editing activity.

Figure 7:
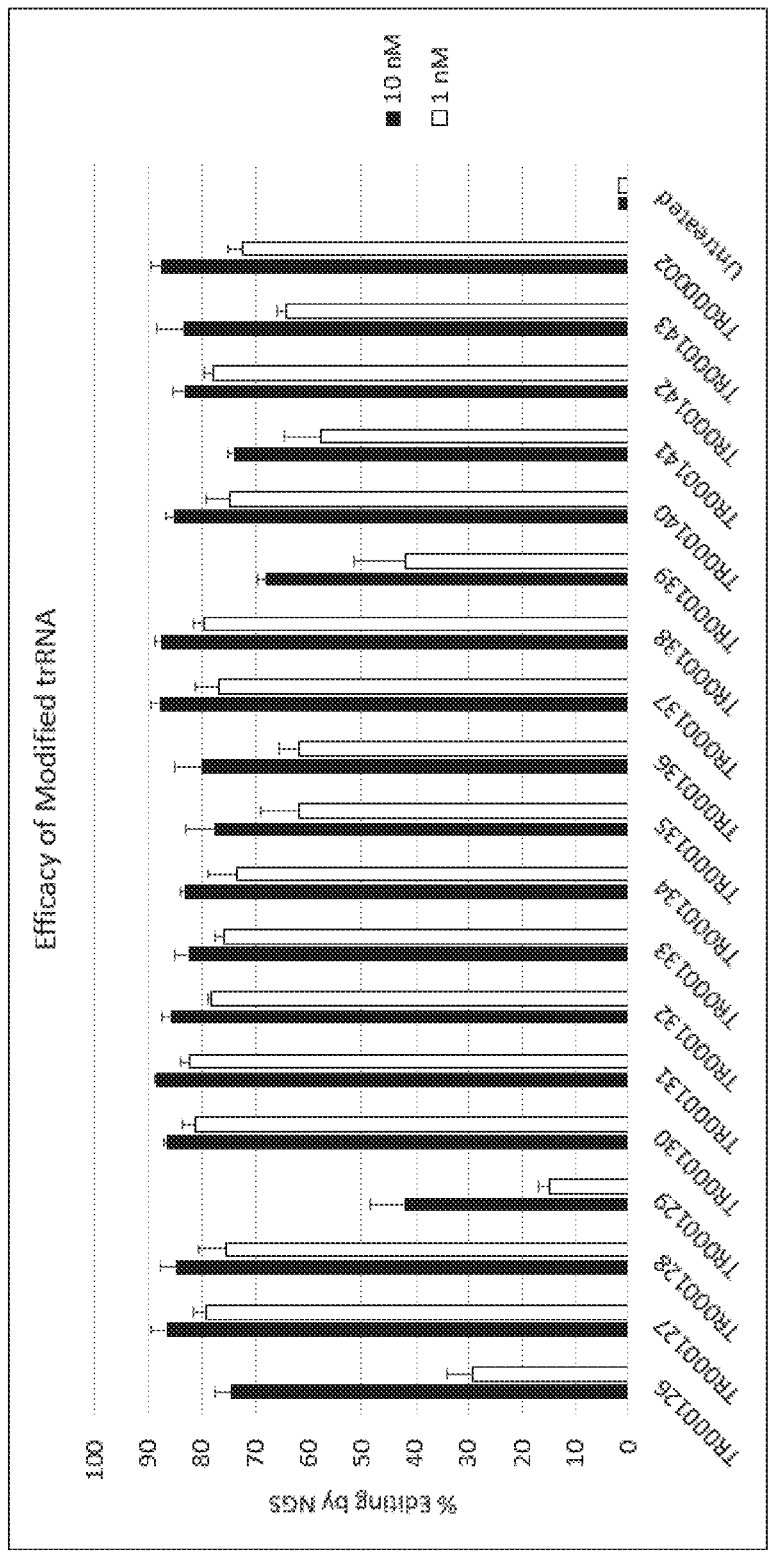

FIG. 7 shows percent editing as measured by NGS of mouse TTR gene following transfection of Neuro2A cells with unmodified crRNA (CR000686) and modified trRNAs together with Cas9 mRNA.

Figure 8:
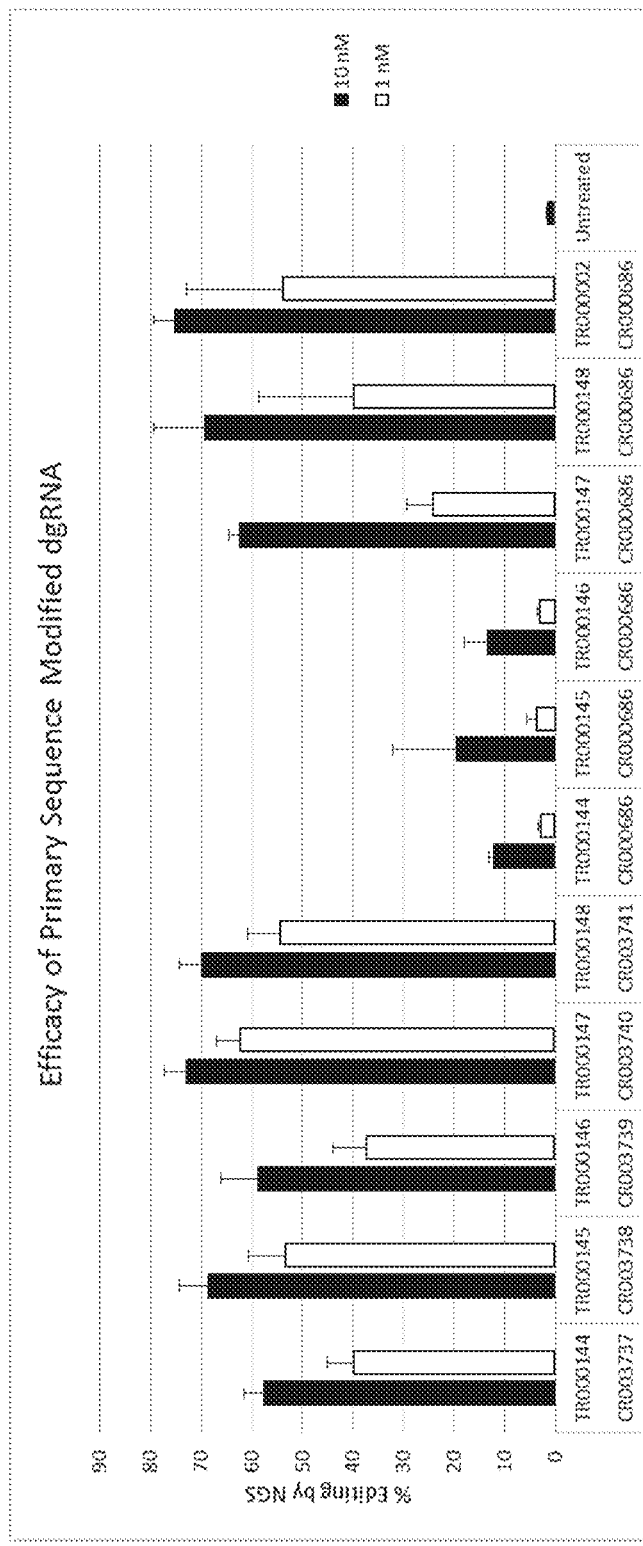

FIG. 8 shows percent editing as measured by NGS of mouse TTR gene following transfection of Neuro2A cells with Cas9 mRNA and crRNA and trRNA pairings with G-C pairings or G-U mismatches not found in the parental sequences.

FIG. 9 shows percent editing as measured by NGS of mouse TTR gene following transfection of Neuro2A cells with modified crRNAs and modified trRNAs together with Cas9 mRNA. Standard deviations follow the value.

Figure 10:
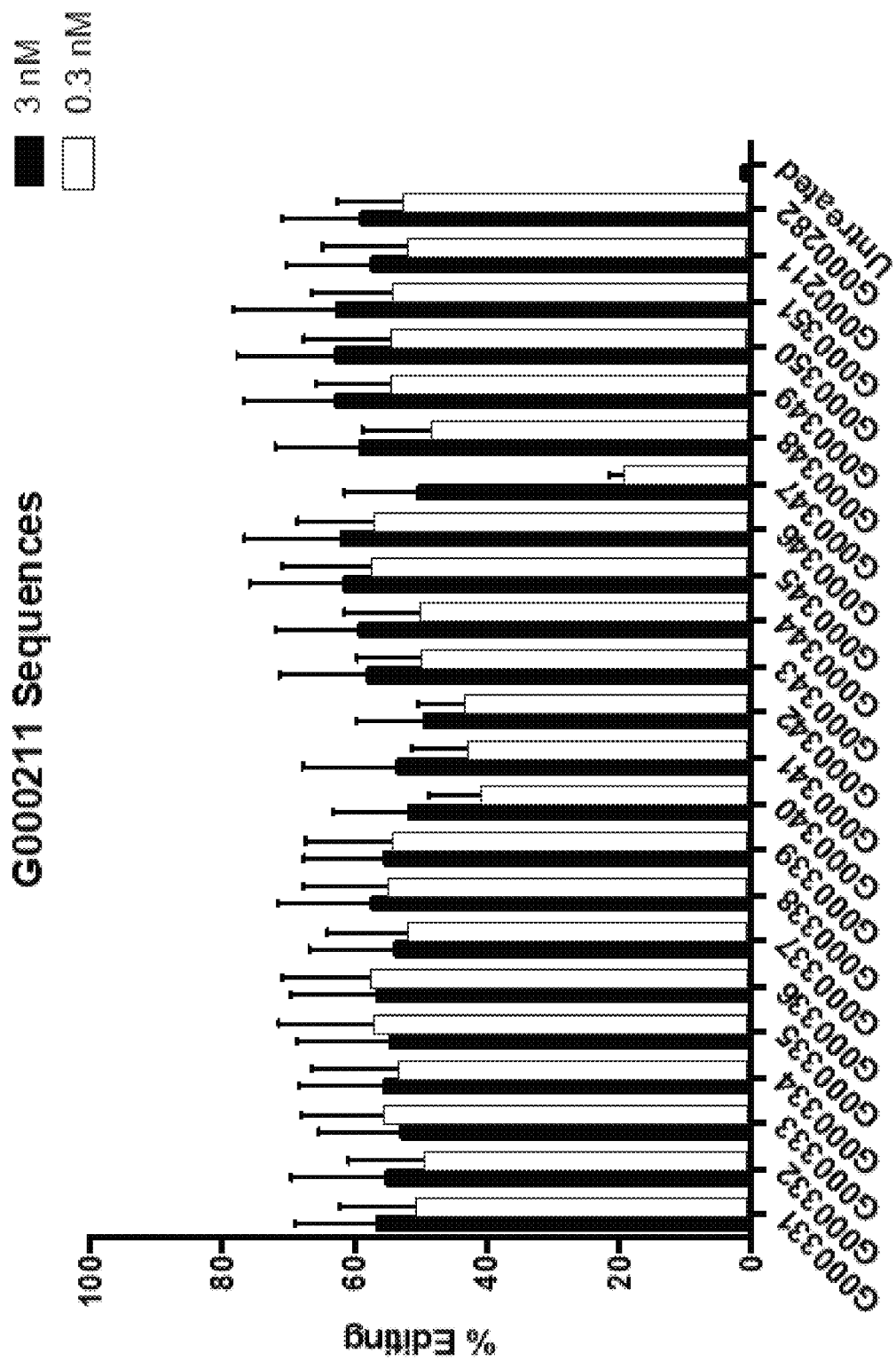

FIG. 10 shows percent editing as measured by NGS of mouse TTR gene following transfection of Neuro2A cells with modified sgRNAs together with Cas9 mRNA.

Figure 11:
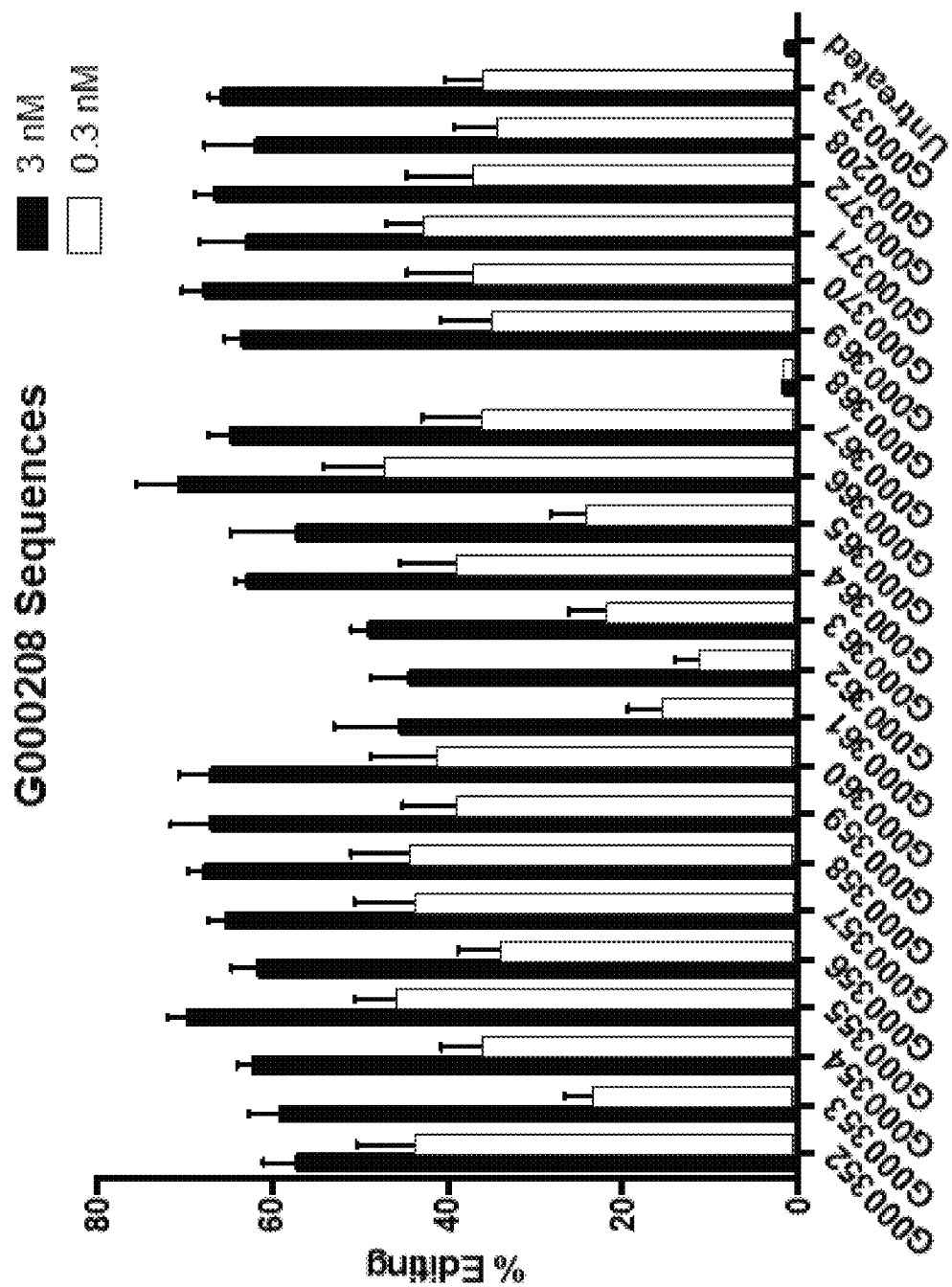

FIG. 11 shows percent editing as measured by NGS of mouse Factor VII (FVII) gene following transfection of Neuro2A cells with modified sgRNAs together with Cas9 mRNA.

Figure 12A:
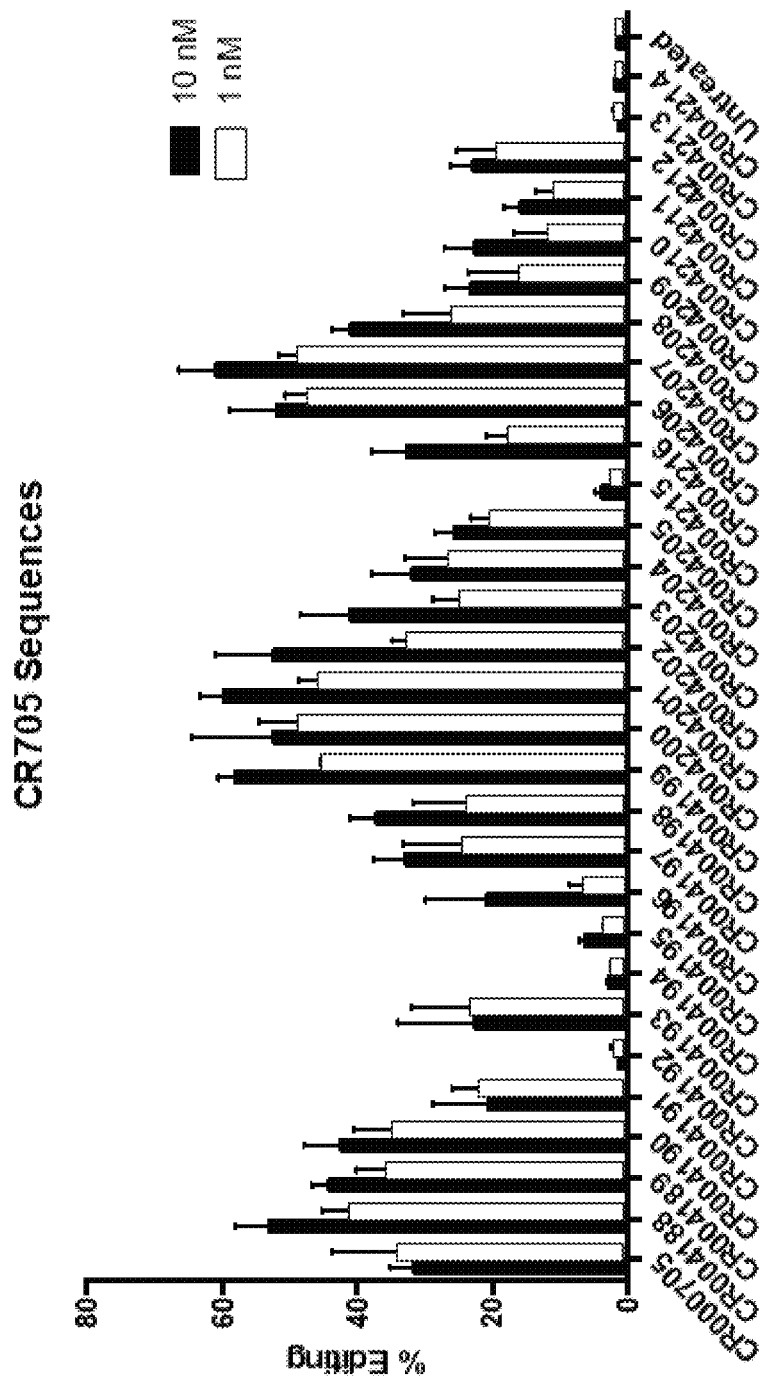
Figure 12B:
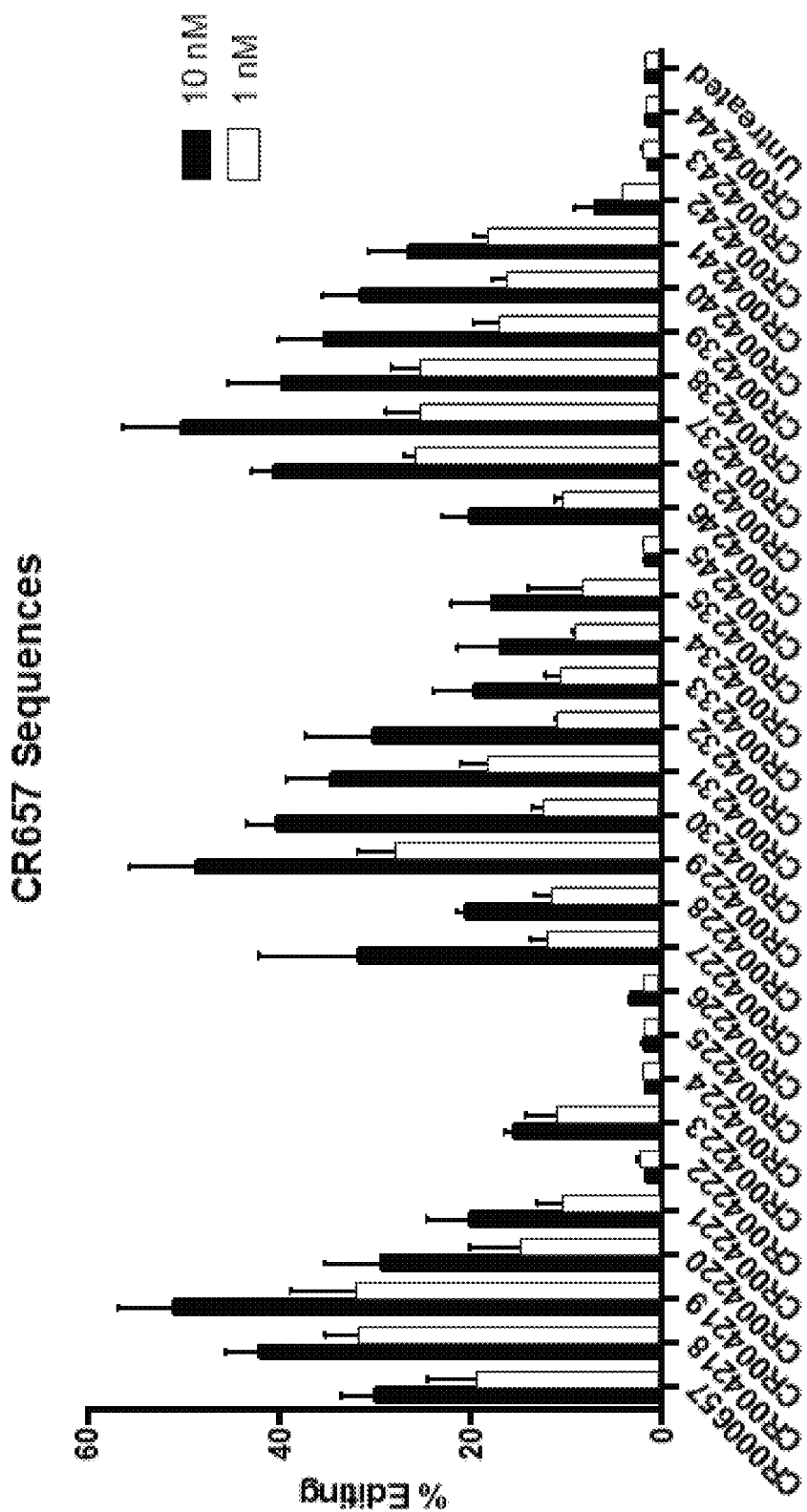

FIGS. 12A and 12B show percent editing as measured by NGS of mouse TTR (FIG. 12A) or FVII (FIG. 12B) following transfection of Neuro2A cells with modified crRNAs and unmodified trRNA together with Cas9 mRNA.

Figure 13A:
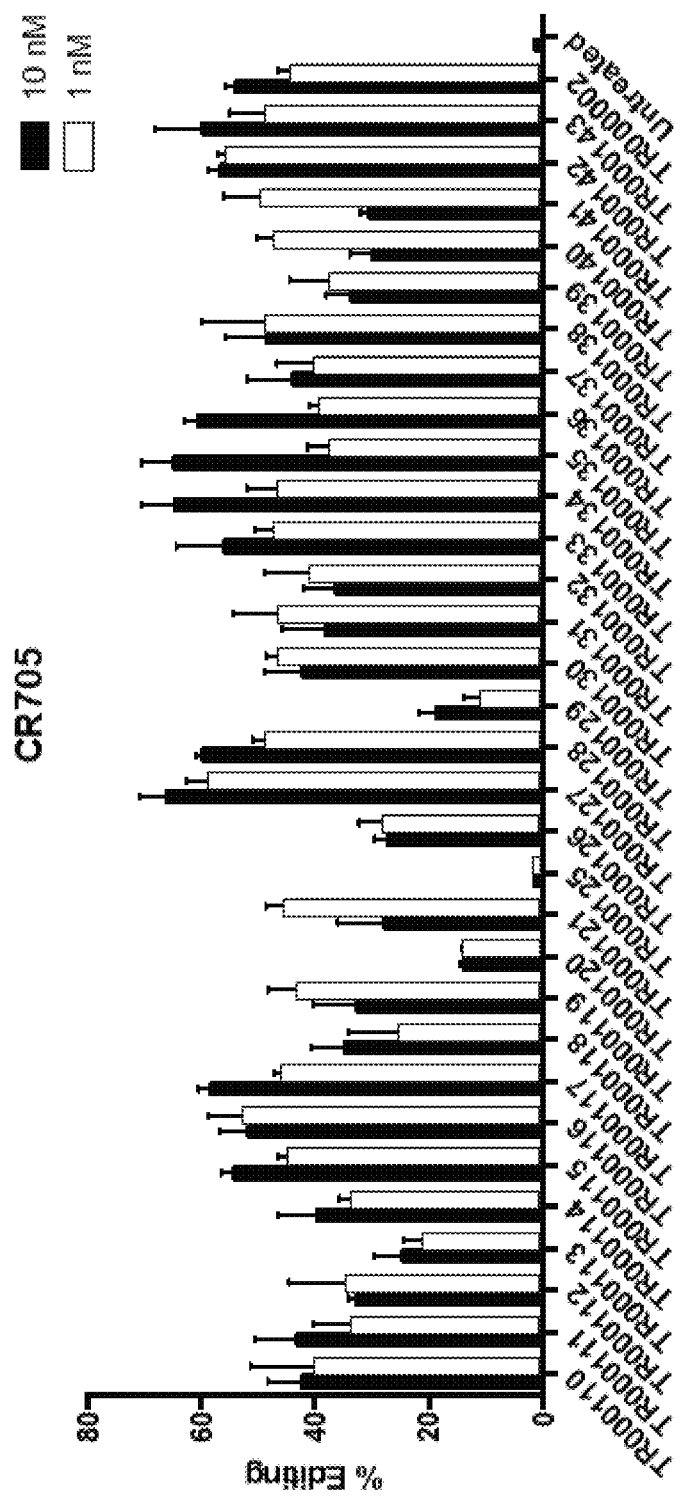
Figure 13B:
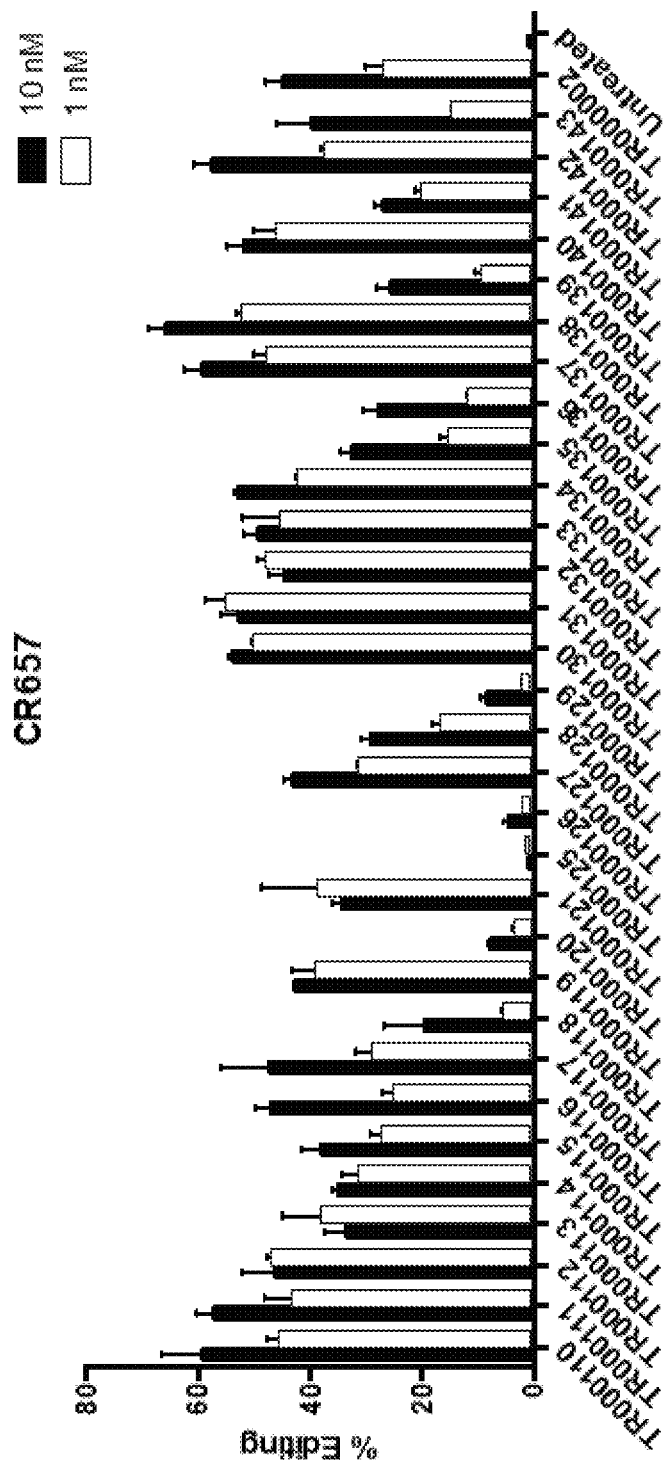
Figure 14A:
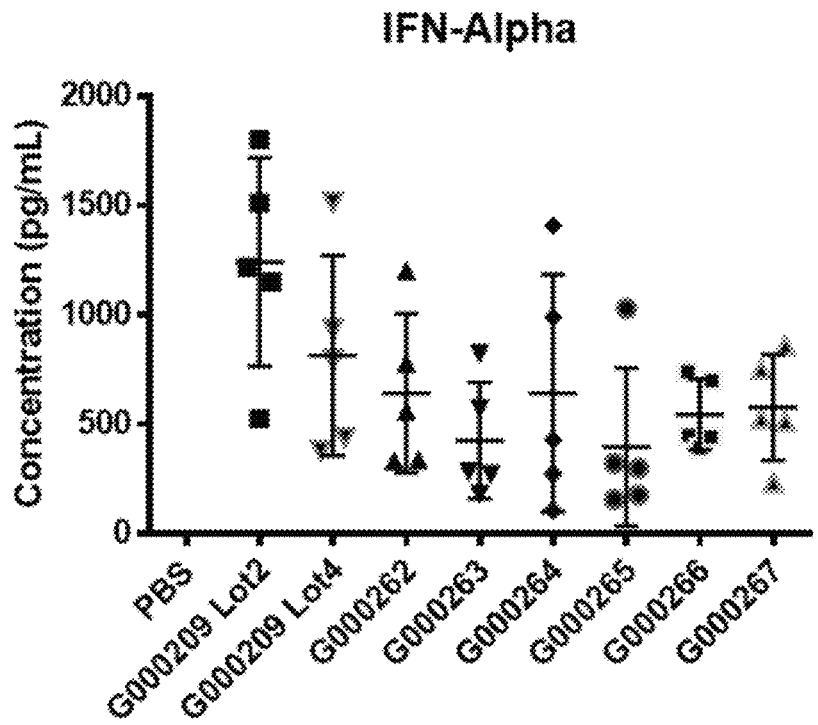
Figure 14B:
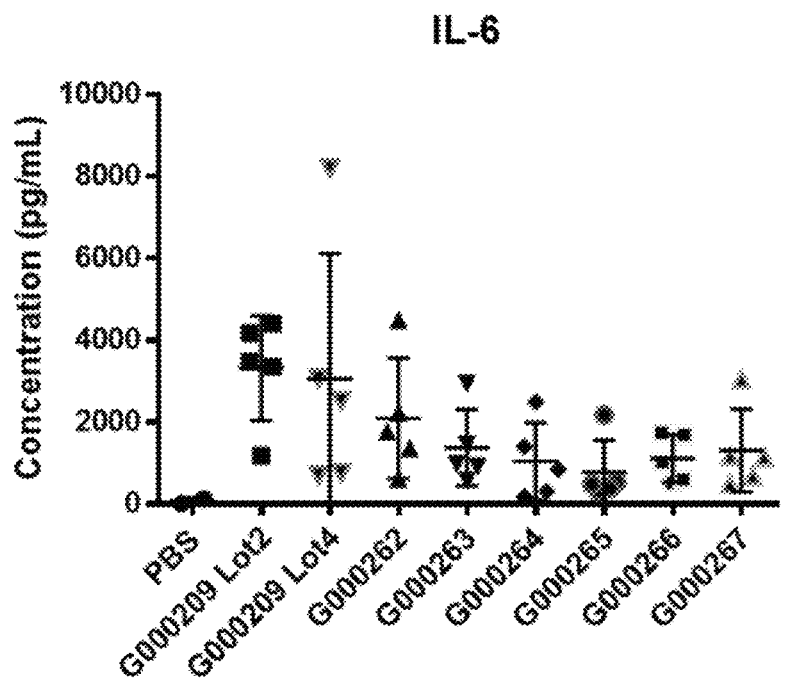
Figure 14C:
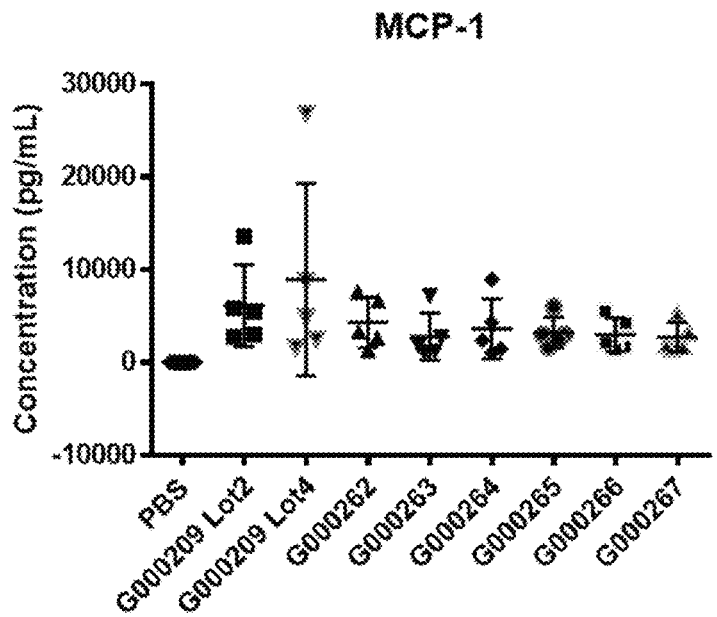
Figure 14D:
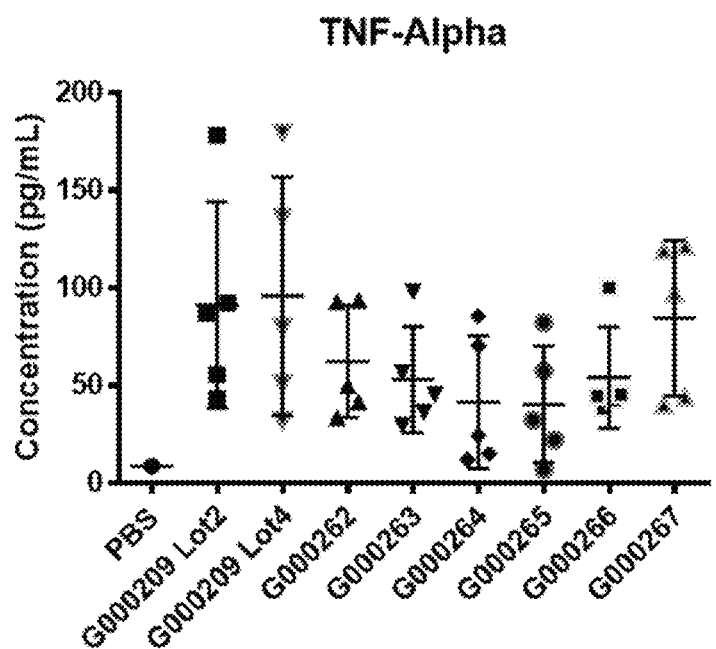

FIGS. 13A and 13B shows percent editing as measured by NGS of mouse TTR (FIG. 13A) or FVII (FIG. 13B) following transfection of Neuro2A cells with modified trRNAs and unmodified crRNA together with Cas9 mRNA.

FIGS. 14A, 14B, 14C, and 14D show interferon alpha (IFN-alpha, 14A), interleukin 6 (IL-6, 14B), monocyte chemotactic protein 1 (MCP-1, 14C), and tumor necrosis factor alpha (TNF-alpha, 14D) levels in serum after in vivo administration of LNPs comprising Cas9 mRNA and sgRNAs.

Figure 15A:
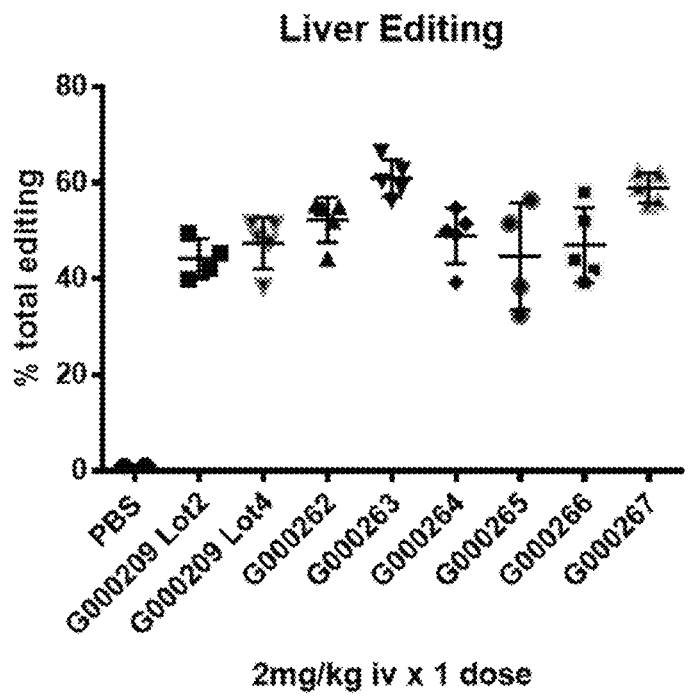
Figure 15B:
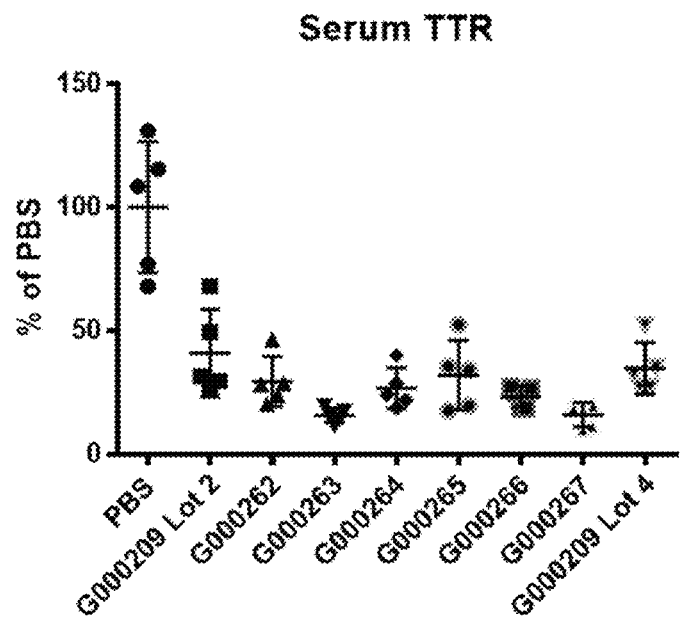
Figures 15C, 15D:
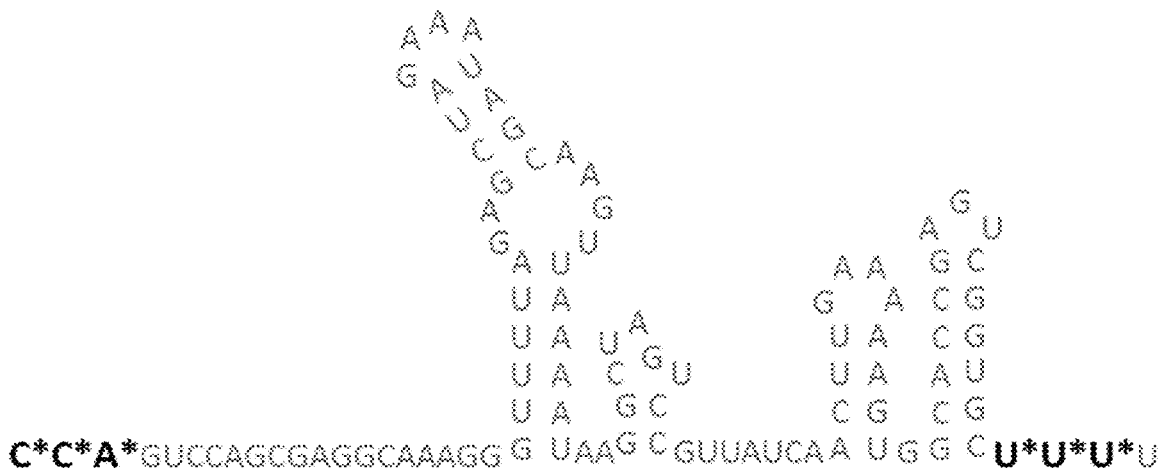
Figure 15E:
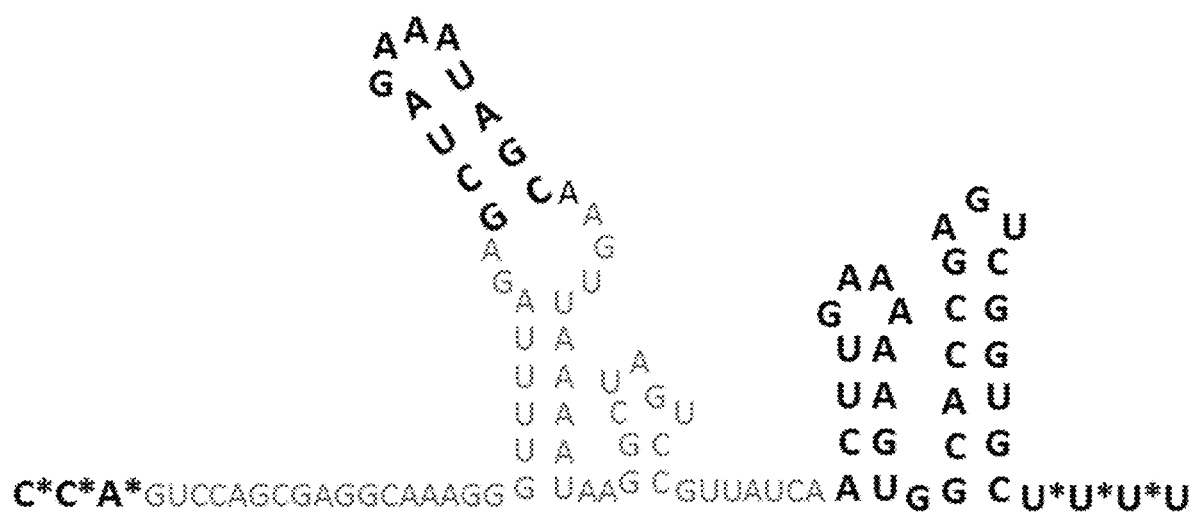
Figure 16A:
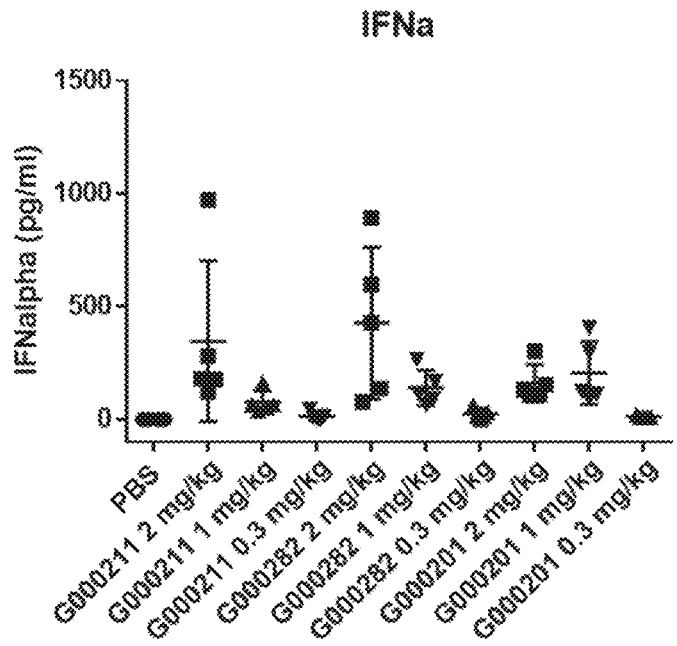
Figure 16B:
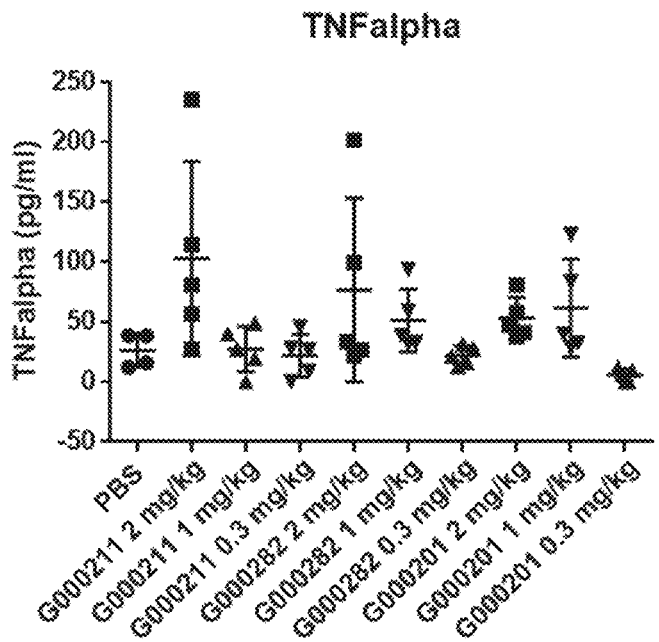
Figure 16C:
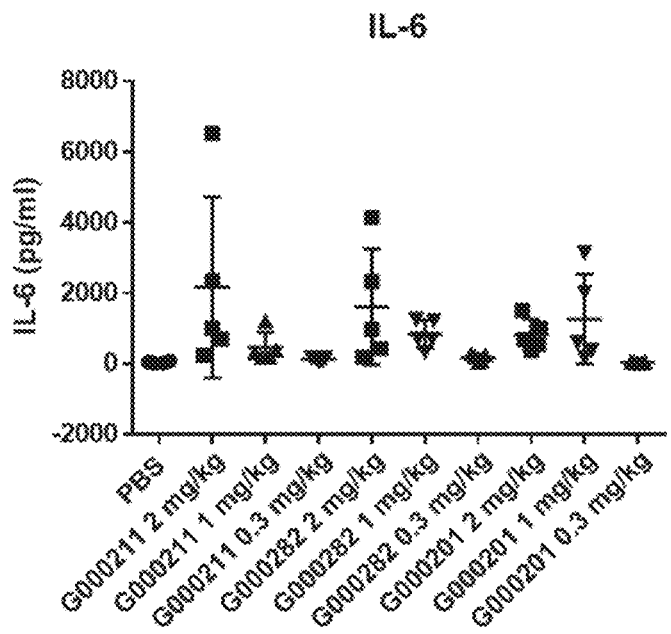
Figure 16D:
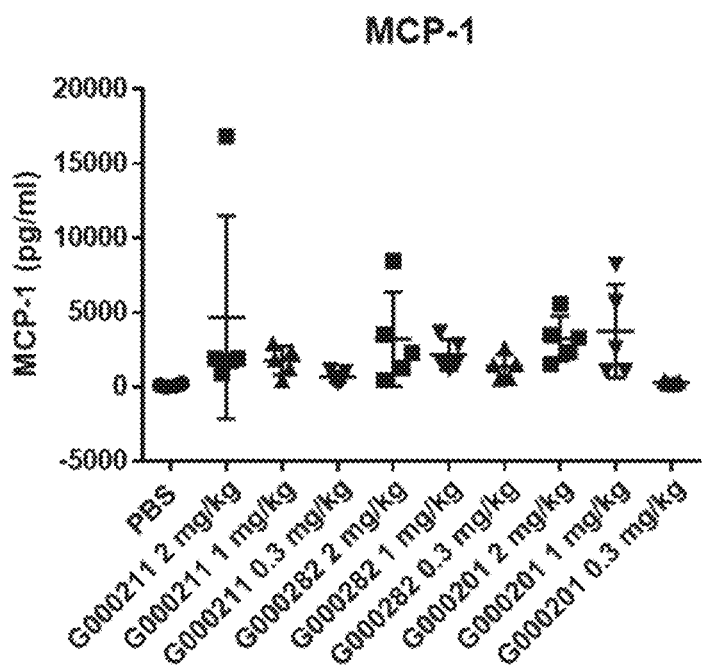

FIGS. 15A, 15B, and 15C show in vivo results following administration of LNPs comprising Cas9 mRNA and sgRNAs. FIG. 15A shows percentage of total editing in liver. FIG. 15B shows serum TTR levels. FIG. 15C shows the mean and standard deviation for the results of FIG. 15A. FIG. 15D summarizes modifications to the G000209 sgRNA (SEQ ID NO: 228). FIG. 15E summarizes modifications to the G000267 sgRNA (SEQ ID NO: 234). In FIGS. 15D and 15E, the nucleotides in bold are 2'-O-Me modified.

FIGS. 16A, 16B, 16C, and 16D show interferon alpha (IFN-alpha, 16A), tumor necrosis factor alpha (TNF-alpha, 16B), interleukin 6 (IL-6, 16C), and monocyte chemotactic protein 1 (MCP-1, 16D) levels in serum after in vivo administration of LNPs comprising Cas9 mRNA and sgRNAs.

Figures 17A, 17B:
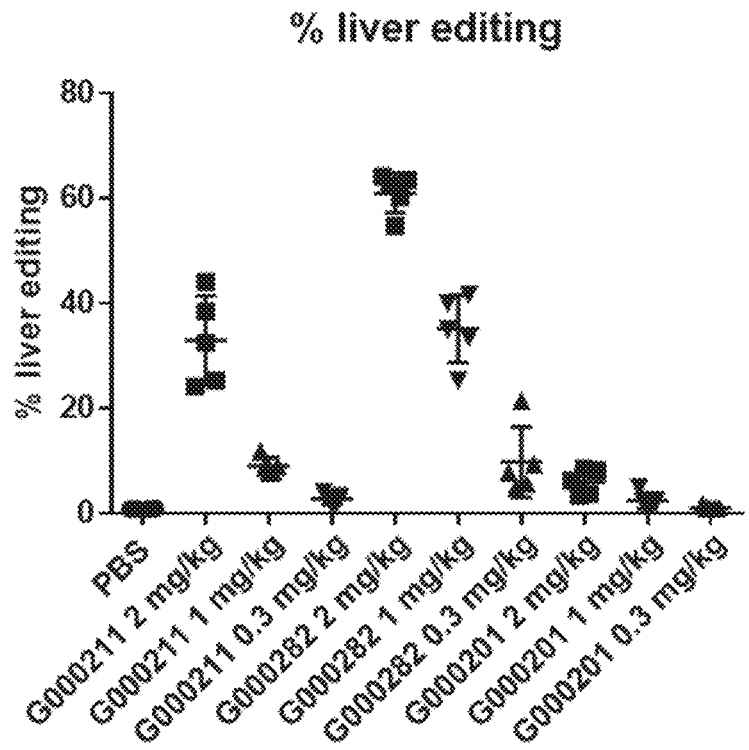
Figures 17C, 17D:
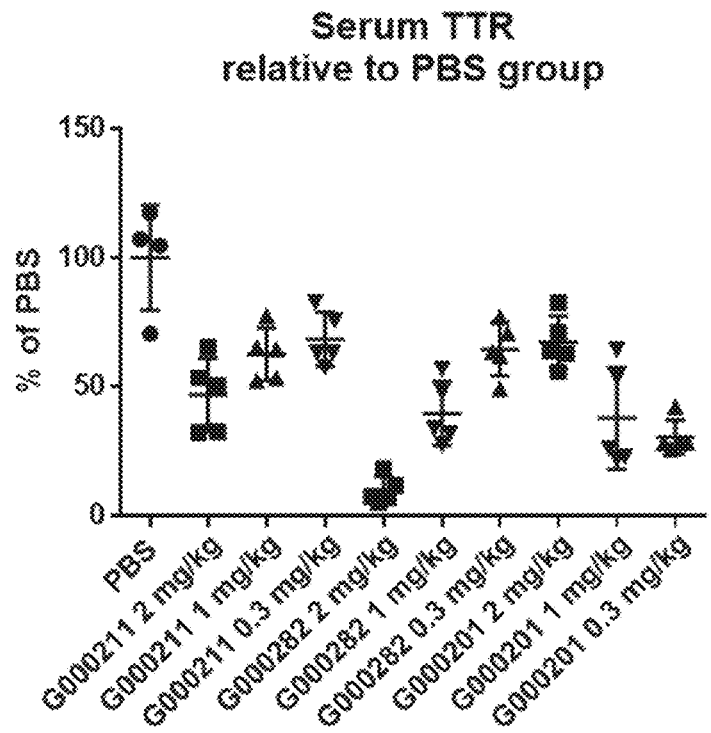

FIGS. 17A, 17B, 17C, and 17D show in vivo results following administration of LNPs comprising Cas9 mRNA and sgRNAs. FIG. 17A shows percentage of total editing in liver. FIG. 17B shows the mean and standard deviation for the results of FIG. 17A. FIG. 17C shows serum TTR levels. FIG. 17D shows the mean and standard deviation for the results of FIG. 17B.

Figure 18A:
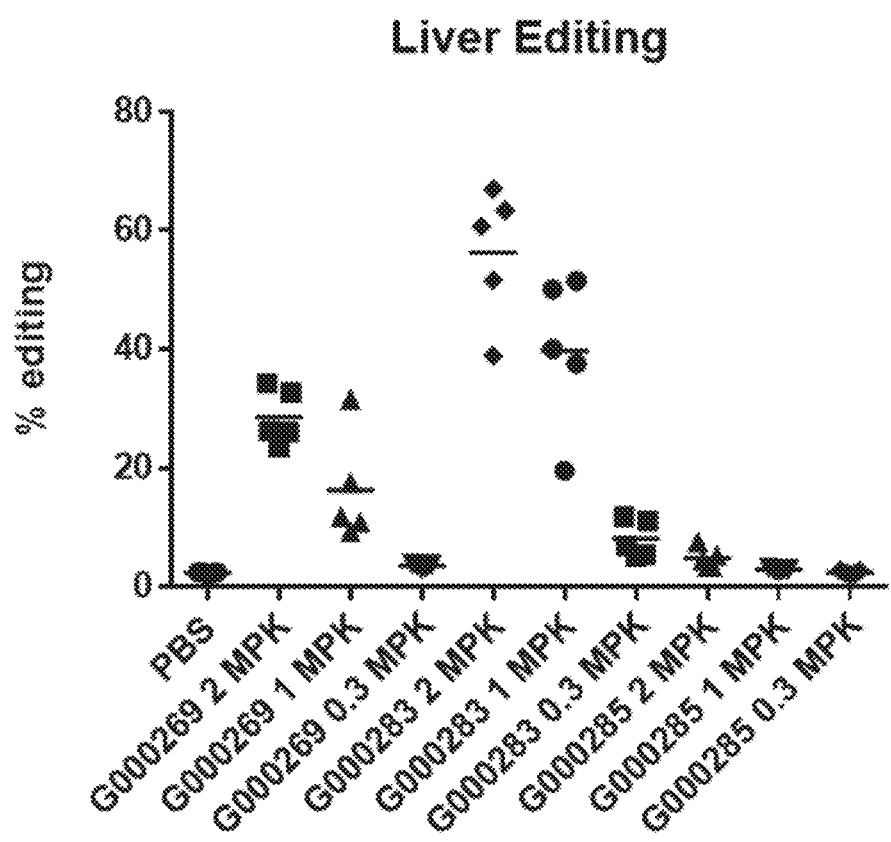
Figures 18B, 18C:
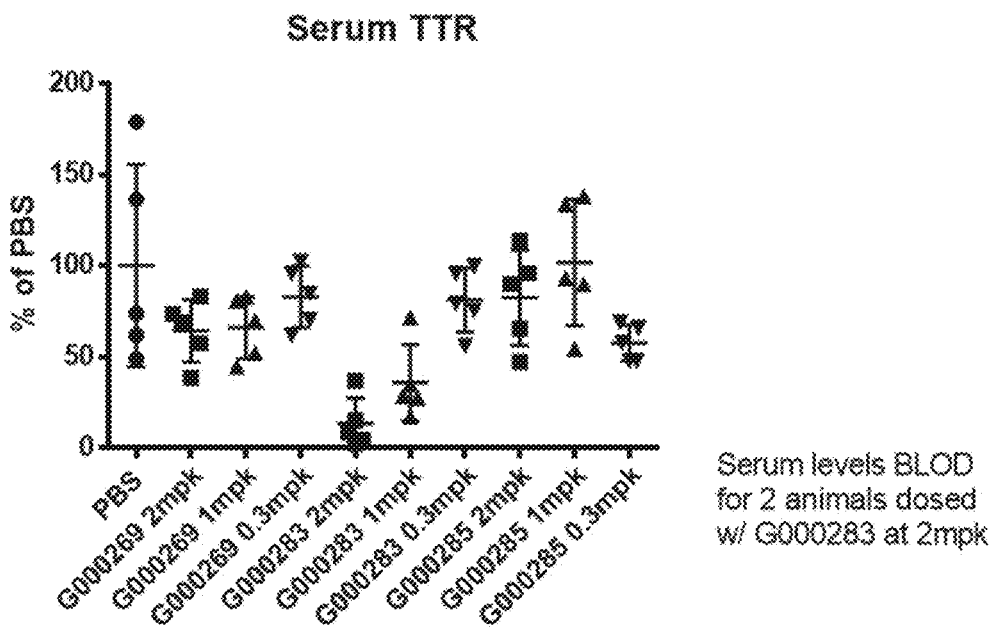
Figure 19A:
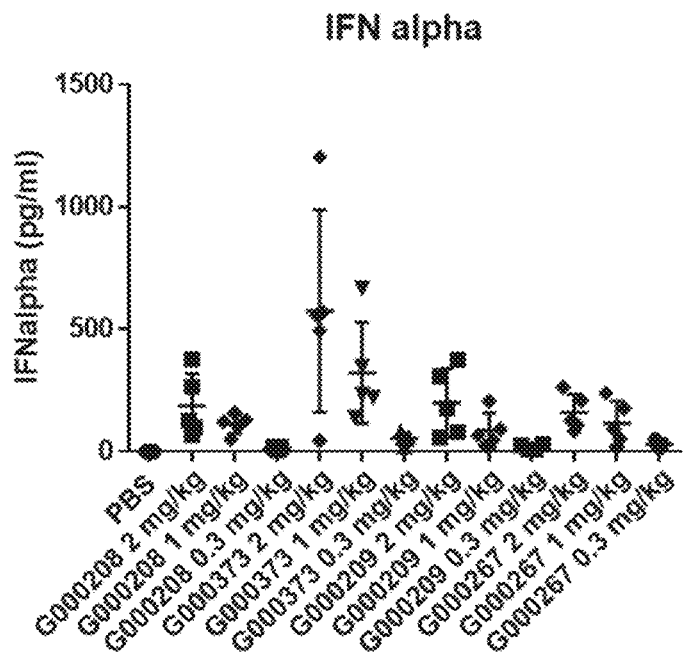
Figure 19B:
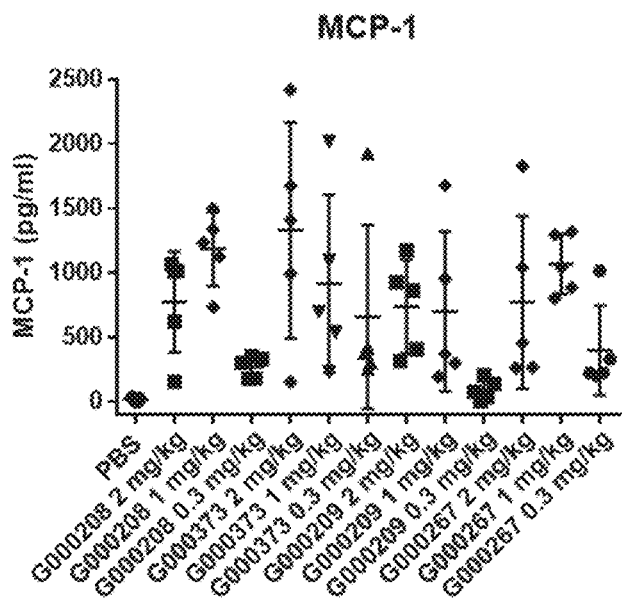
Figure 19C:
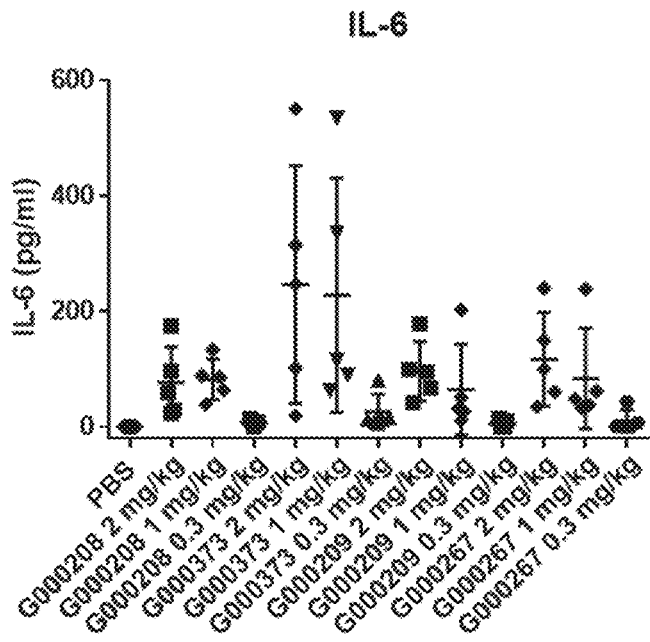
Figure 19D:
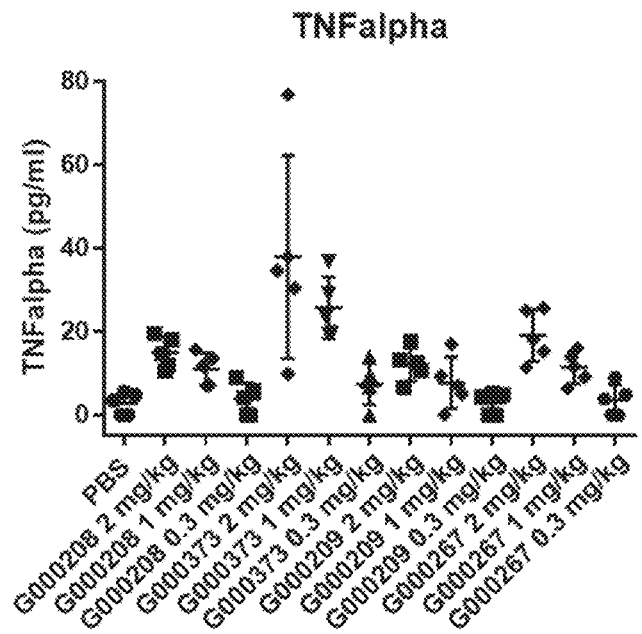

FIGS. 18A, 18B, and 18C show in vivo results following administration of LNPs comprising Cas9 mRNA and sgRNAs. FIG. 18A shows percentage of total editing in liver. FIG. 18B summarizes liver editing data. FIG. 18C shows serum TTR levels. MPK=milligrams per kilogram; BLOD=below level of detection.

FIGS. 19A, 19B, 19C, and 19D show interferon alpha (IFN-alpha, 19A), monocyte chemotactic protein 1 (MCP-1, 19B), interleukin 6 (IL-6, 19C), and tumor necrosis factor alpha (TNF-alpha, 19D) levels in serum after in vivo administration of LNPs comprising Cas9 mRNA and sgRNAs.

Figure 20A:
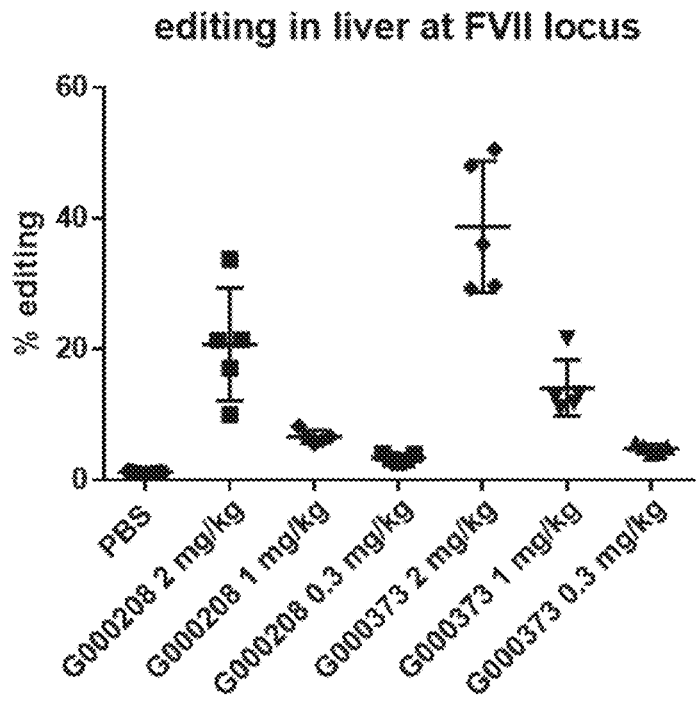
Figure 20B:
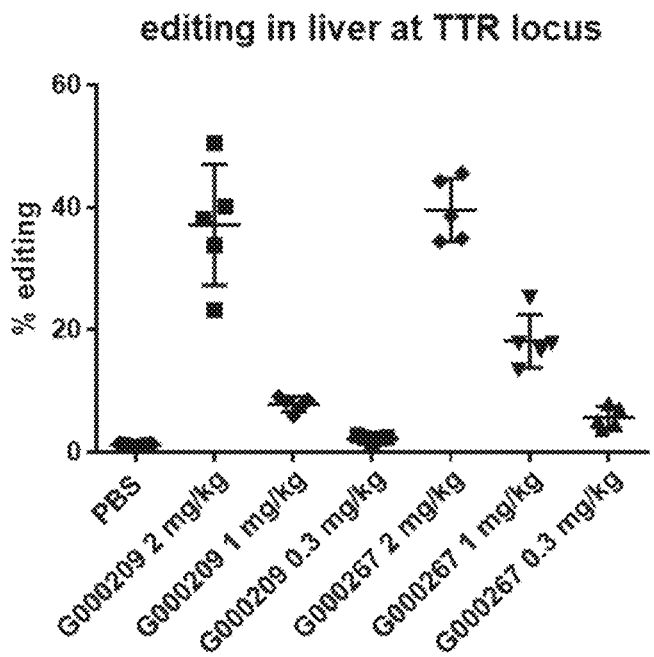

FIGS. 20A and 20B show editing in liver of FVII locus (FIG. 20A) and TTR locus (FIG. 20B) following in vivo administration of LNPs comprising Cas9 mRNA and sgRNAs.

Figure 21A:
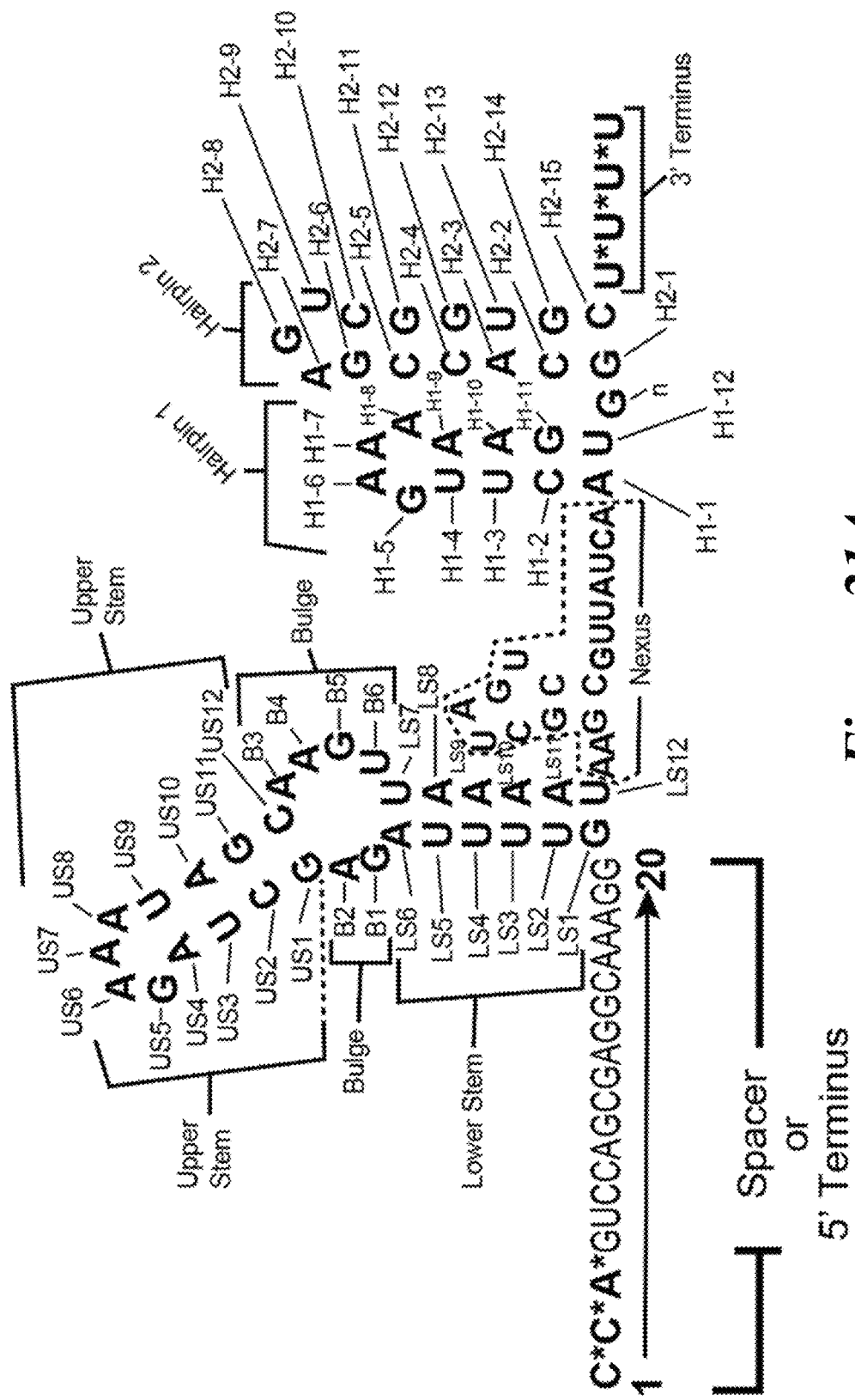
Figure 21B:
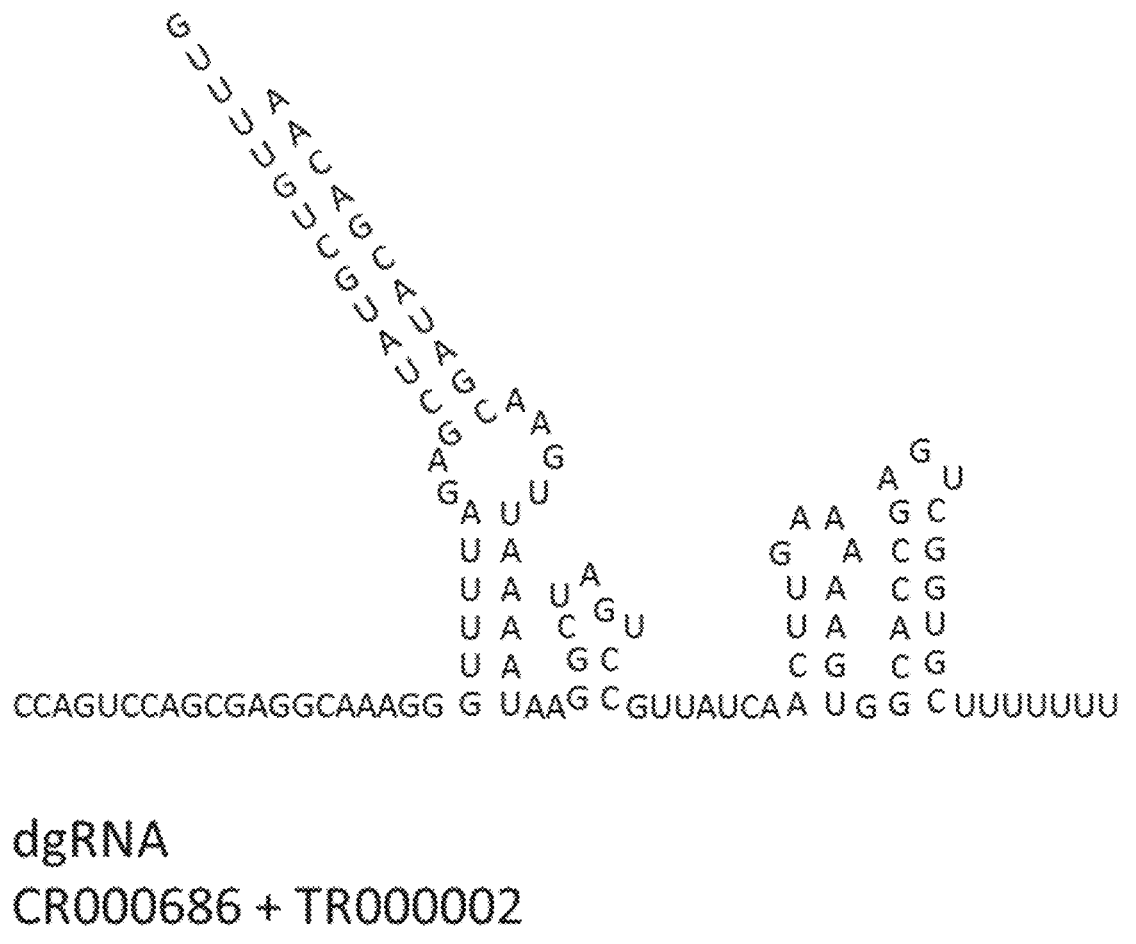
Figure 21C:
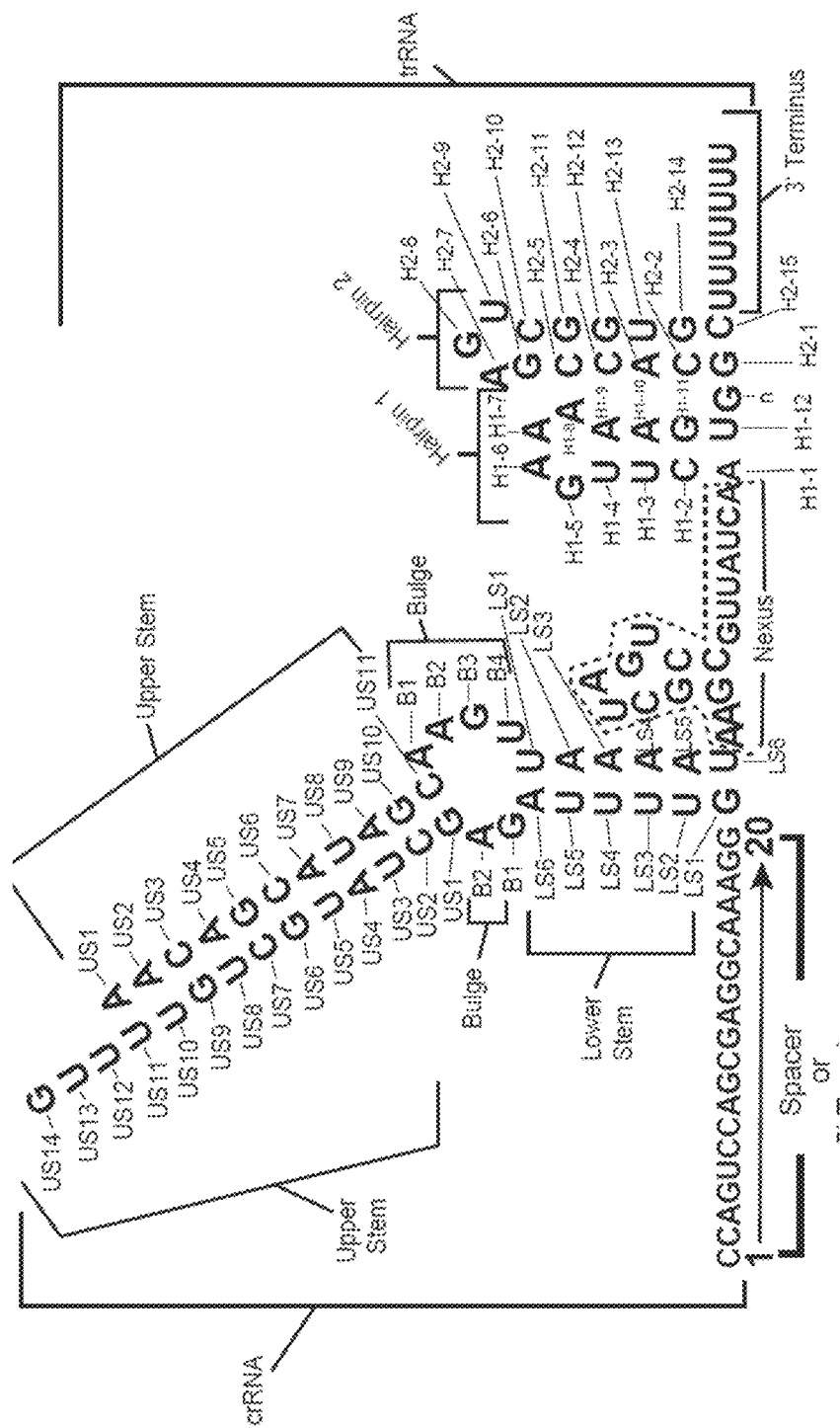

FIGS. 21A, 21B, and 21C show schematics of an annotated sgRNA (SEQ ID NO: 341) (FIG. 21A), non-annotated dgRNA CR000686 (SEQ ID NO: 1) and TR000002 (SEQ ID NO: 188) (FIG. 21B), and annotated dgRNA CR000686 (SEQ ID NO: 1) and TR000002 (SEQ ID NO: 188) (FIG. 21C).

Figure 22A:
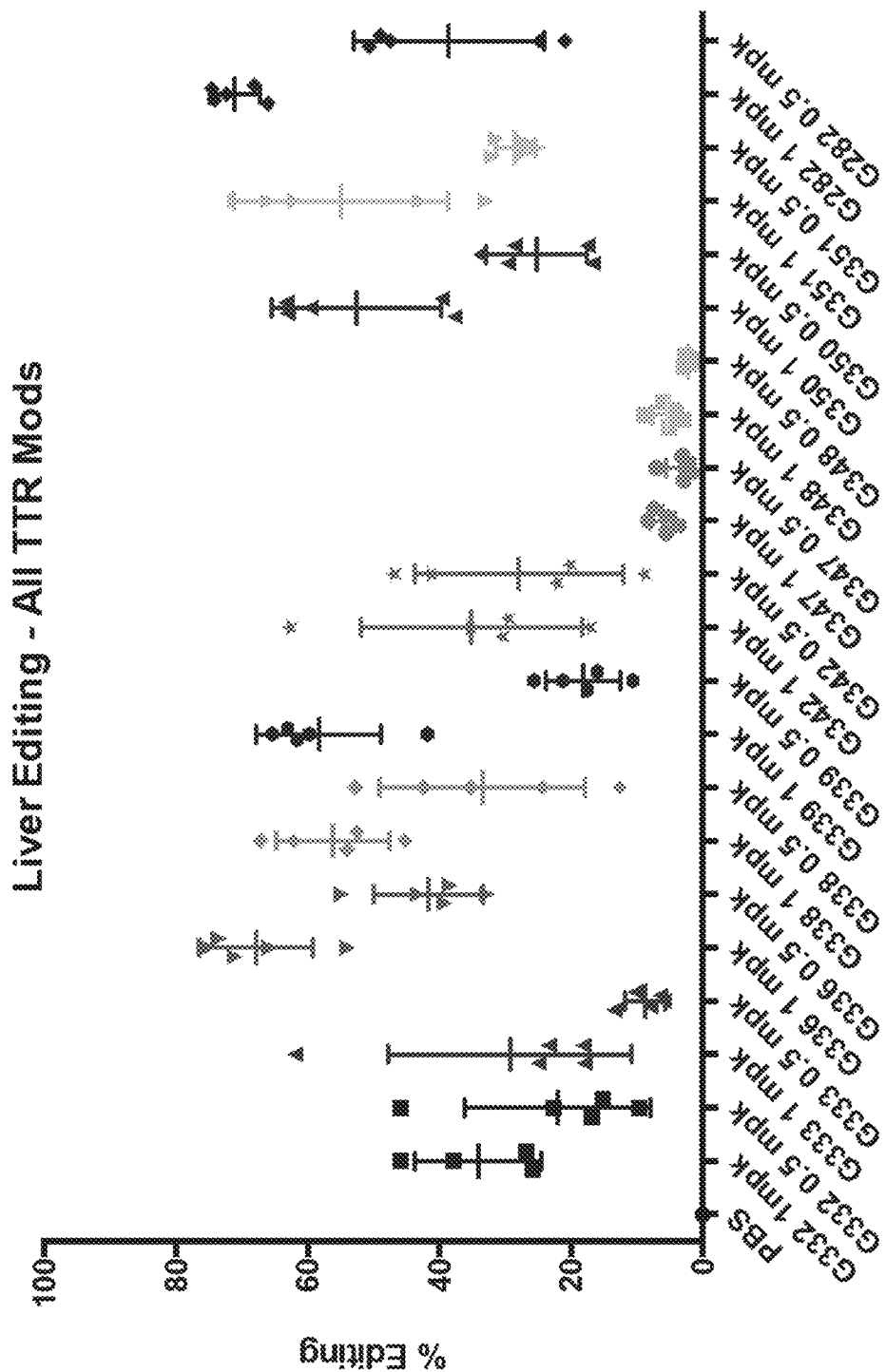
Figure 22C:
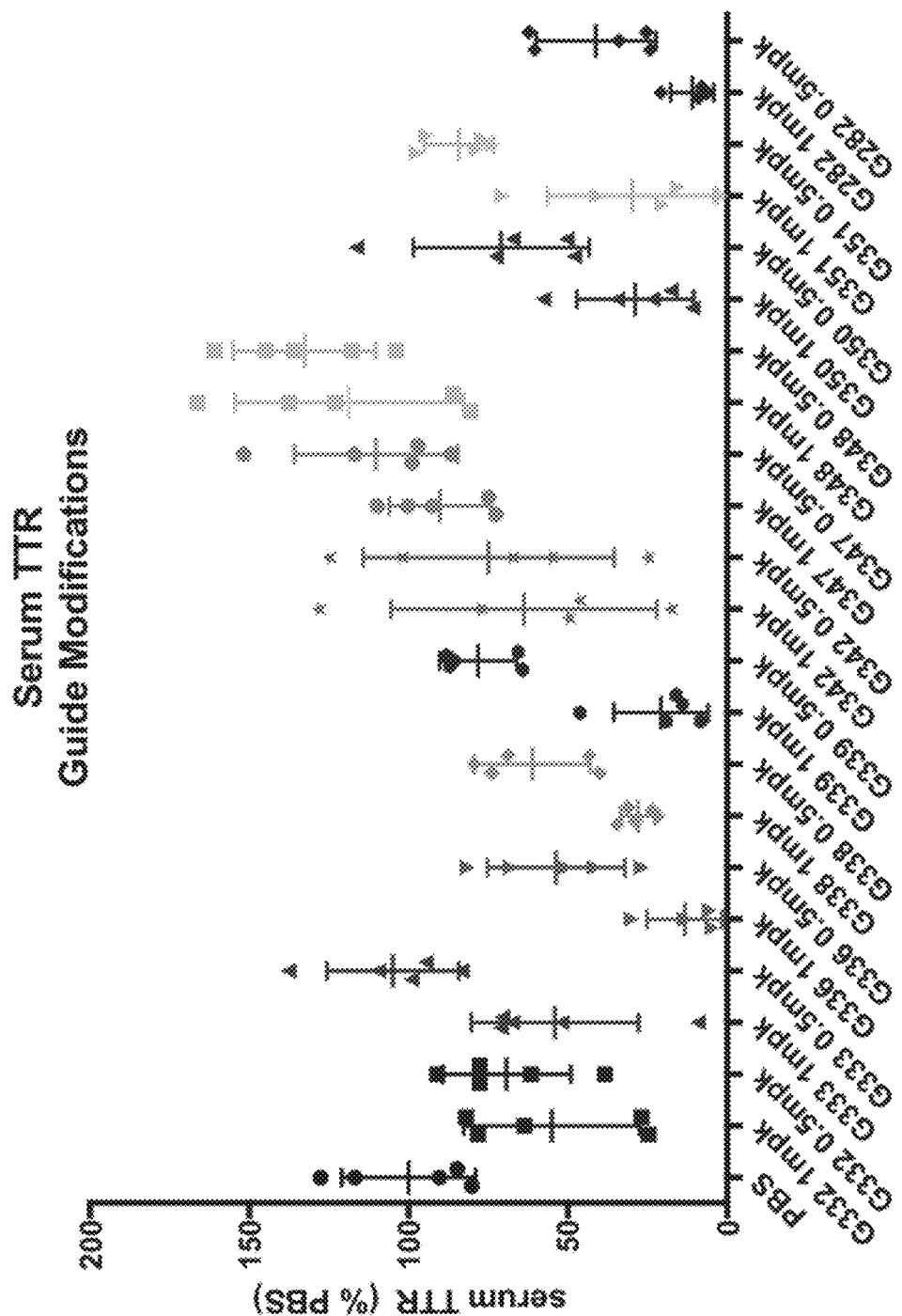

FIGS. 22A, 22B, and 22C show in vivo results following administration of LNPs comprising Cas9 mRNA and sgRNAs. FIG. 22A shows percentage of total editing of TTR locus in liver. FIG. 22B summarizes liver editing data. FIG. 22C shows serum TTR levels.

Figure 23A:
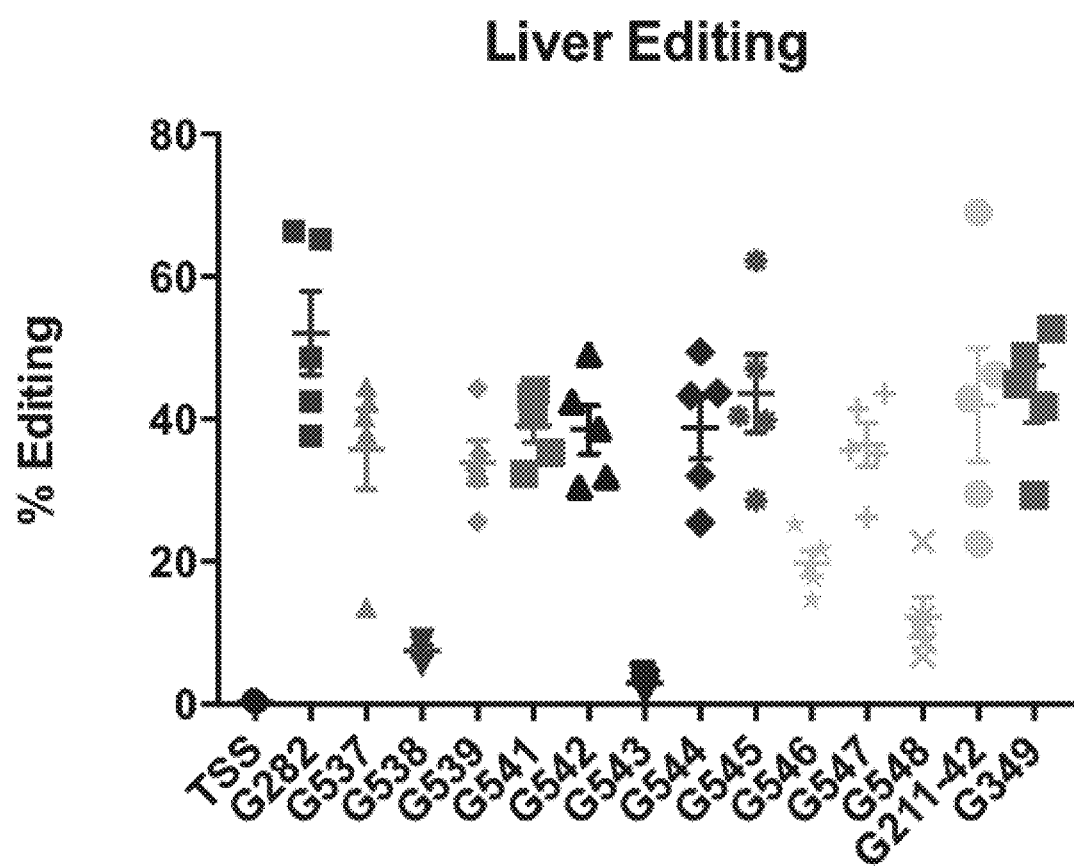
Figure 23C:
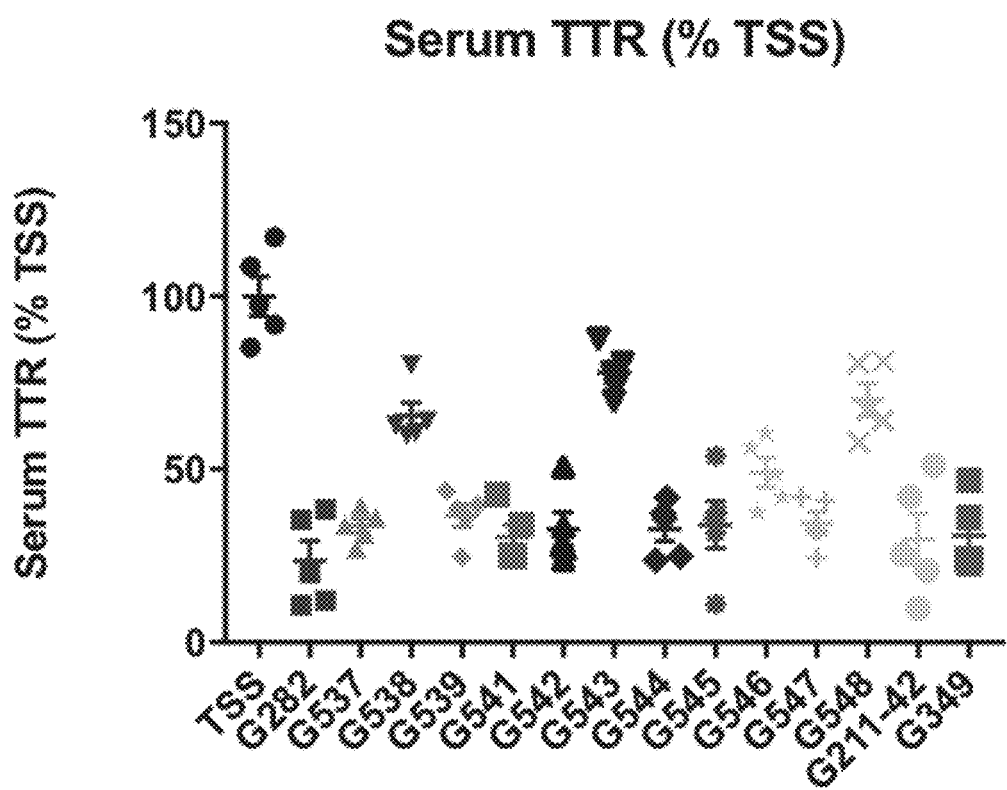

FIGS. 23A, 23B, and 23C show in vivo results following administration of LNPs comprising Cas9 mRNA and sgRNAs. FIG. 23A shows percentage of total editing of TTR locus in liver. FIG. 23B summarizes liver editing data. FIG. 23C shows serum TTR levels.

Figure 24A:
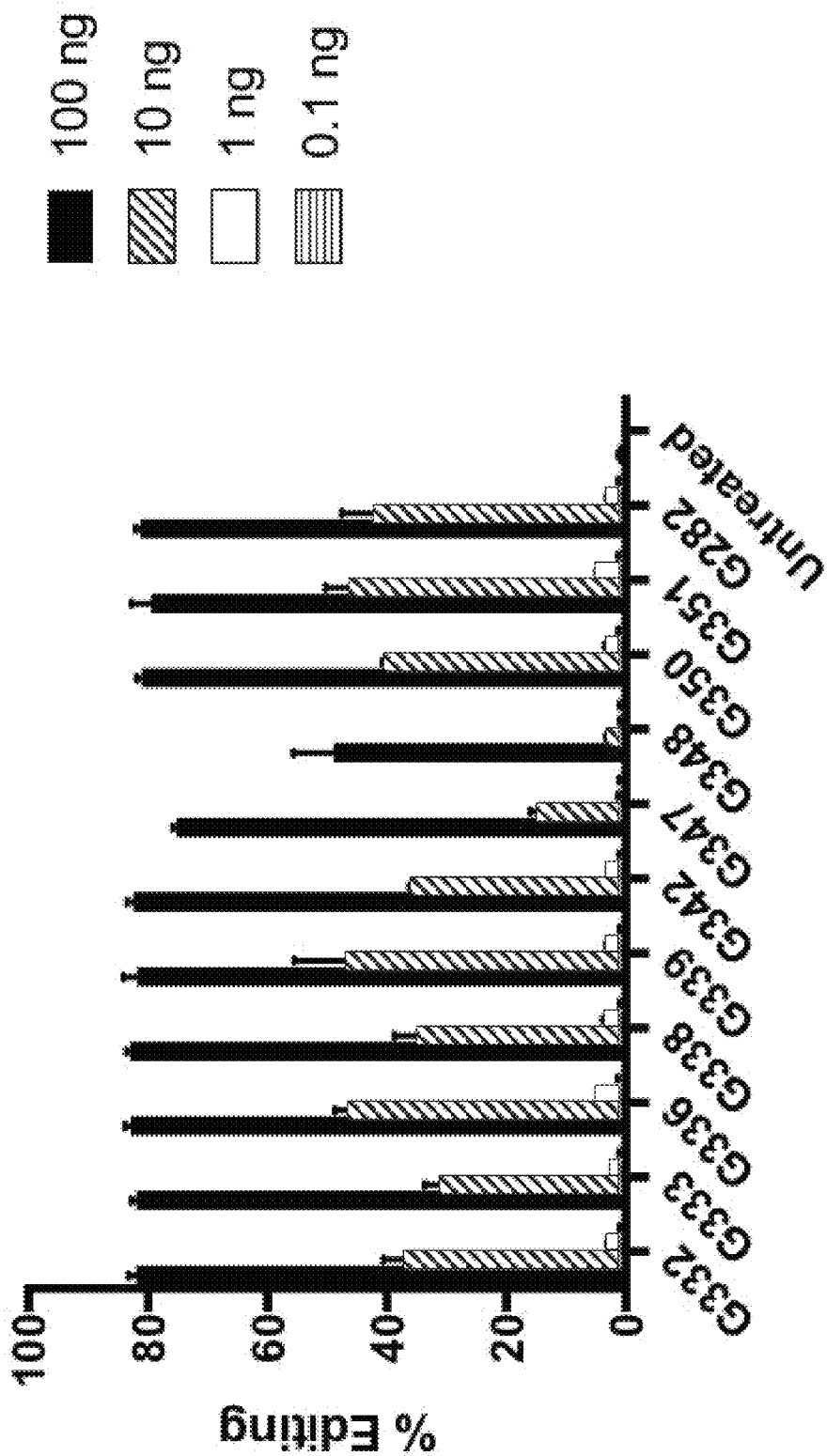
Figure 24B:
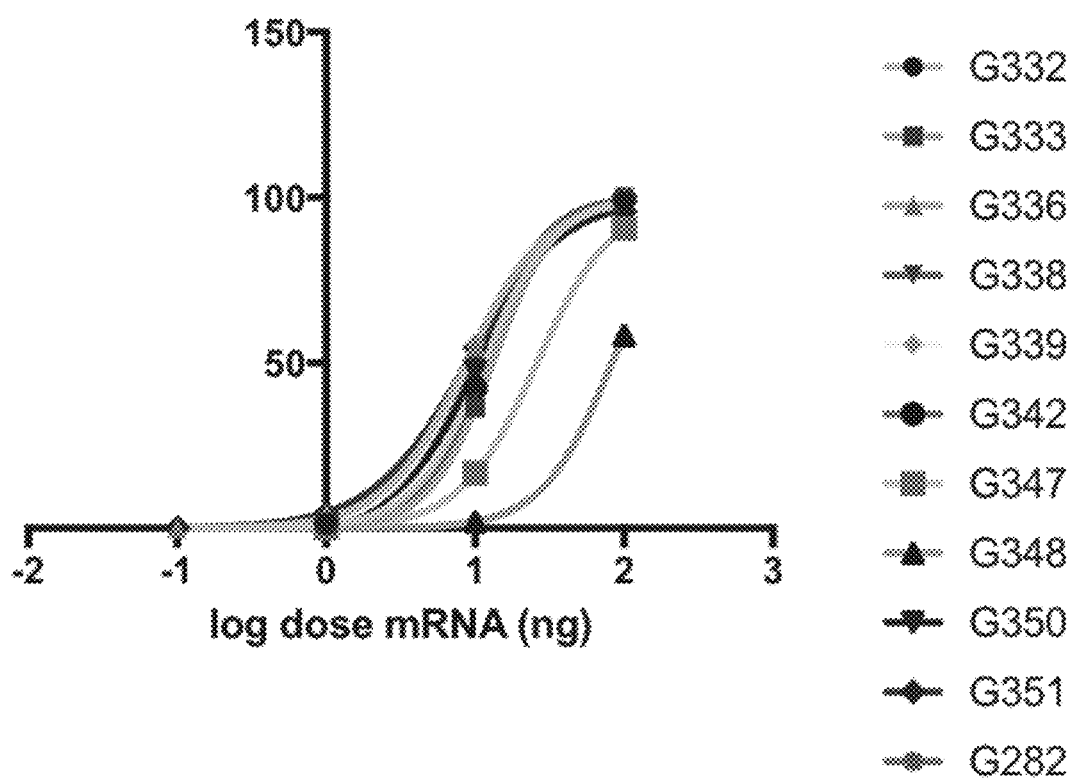

FIGS. 24A, 24B, and 24C show editing in primary mouse hepatocytes following administration of LNPs comprising Cas9 mRNA and sgRNAs. FIG. 24A shows editing percentage of total editing of TTR locus. FIG. 24B shows normalized transforms of editing percentage as a function of mRNA dose used to calculate EC50. FIG. 24C shows EC50 values for the LNPs tested.

DETAILED DESCRIPTION

Provided herein are modified guide RNAs, including dual and single guide RNAs for use in gene editing methods. The modified guides are more stable and show improved in vitro and in vivo efficacy as compared to their non-modified counterparts. Sequences of engineered and tested guide RNAs are shown in Table 4.

TABLE 4

| SEQ ID NO | Name | Alias | Description | Sequence |
|---|---|---|---|---|
| crRNA | | | | |
| 1 | CR000686 | | unmodified | CCAGUCCAGCGAGGCAAAGGGUUUUAGAGCUAUGCUGUUUUG |
| 2 | CR003393 | CR686-1 | upper | CCAGUCCAGCGAGGCAAAGGGUUUUAGAmGmCmUmAmUmGmCmUmGmUmUmUmUmG |
| 3 | CR003394 | CR686-2 | partial upper | CCAGUCCAGCGAGGCAAAGGGUUUUAGAGCUAmUmGmCmUmGmUmUmUmUmG |
| 4 | CR003395 | CR686-3 | partial upper | CCAGUCCAGCGAGGCAAAGGGUUUUAGAGCUAUGCmUmGmUmUmUmUmG |
| 5 | CR003396 | CR686-4 | partial upper | CCAGUCCAGCGAGGCAAAGGGUUUUAGAGCUAUGCUGmUmUmUmUmG |
| 6 | CR003397 | CR686-5 | lower | CCAGUCCAGCGAGGCAAAGGmGmUmUmUmUmAGAGCUAUGCUGUUUUG |
| 7 | CR003398 | CR686-6 | lower walk | CCAGUCCAGCGAGGCAAAGGmGUUUUAGAGCUAUGCUGUUUUG |
| 8 | CR003399 | CR686-7 | lower walk | CCAGUCCAGCGAGGCAAAGGGmUUUUAGAGCUAUGCUGUUUUG |
| 9 | CR003400 | CR686-8 | lower walk | CCAGUCCAGCGAGGCAAAGGGUmUUUAGAGCUAUGCUGUUUUG |
| 10 | CR003401 | CR686-9 | lower walk | CCAGUCCAGCGAGGCAAAGGGUUmUUAGAGCUAUGCUGUUUUG |
| 11 | CR003402 | CR686-10 | lower walk | CCAGUCCAGCGAGGCAAAGGGUUUmUAGAGCUAUGCUGUUUUG |
| 12 | CR003403 | CR686-11 | lower walk | CCAGUCCAGCGAGGCAAAGGGUUUUmAGAGCUAUGCUGUUUUG |
| 13 | CR003404 | CR686-12 | partial lower | CCAGUCCAGCGAGGCAAAGGGmUmUmUmUAGAGCUAUGCUGUUUUG |
| 14 | CR003405 | CR686-13 | partial lower | CCAGUCCAGCGAGGCAAAGGGUmUmUUAGAGCUAUGCUGUUUUG |
| 15 | CR003406 | CR686-GC1 | Lower GC | CCAGUCCAGCGAGGCAAAGGGGCGCAGAGCUAUGCUGUUUUG |
| 16 | CR003407 | CR686-GC3 | Upper GC | CCAGUCCAGCGAGGCAAAGGGUUUUAGAGCUAUGCUGGCGCG |
| 17 | CR003408 | CR686-GC5 | Lower Upper GC | CCAGUCCAGCGAGGCAAAGGGGCGCAGAGCUAUGCUGGCGCG |
| 18 | CR003409 | CR686 all OMe | | mCmCmAmGmUmCmCmAmGmCmGmAmGmGmCmAmAmAmGmGmGmUmUmUmUmAmGmAmGmCmUmAmUmGmCmUmGmUmUmUmUmG |

TABLE 4-continued

| SEQ ID NO | Name | Alias | Description | Sequence |
|---|---|---|---|---|
| 19 | CR003393-mod only | | upper | GUUUUAGAmGmCmUmAmUmGmCmUmGmUmUmUmUmG |
| 20 | CR003394-mod only | | partial upper | GUUUUAGAGCUAmUmGmCmUmGmUmUmUmUmG |
| 21 | CR003395-mod only | | partial upper | GUUUUAGAGCUAUGCmUmGmUmUmUmUmG |
| 22 | CR003396-mod only | | partial upper | GUUUUAGAGCUAUGCUGmUmUmUmUmG |
| 23 | CR003397-mod only | | lower | mGmUmUmUmUmAGAGCUAUGCUGUUUUG |
| 24 | CR003398-mod only | | lower walk | mGUUUUAGAGCUAUGCUGUUUUG |
| 25 | CR003399-mod only | | lower walk | GmUUUUAGAGCUAUGCUGUUUUG |
| 26 | CR003400-mod only | | lower walk | GUmUUUAGAGCUAUGCUGUUUUG |
| 27 | CR003401-mod only | | lower walk | GUUmUUAGAGCUAUGCUGUUUUG |
| 28 | CR003402-mod only | | lower walk | GUUUmUAGAGCUAUGCUGUUUUG |
| 29 | CR003403-mod only | | lower walk | GUUUUmAGAGCUAUGCUGUUUUG |
| 30 | CR003404-mod only | | partial lower | GmUmUmUmUAGAGCUAUGCUGUUUUG |
| 31 | CR003405-mod only | | partial lower | GUmUmUmUUAGAGCUAUGCUGUUUUG |
| 32 | CR003721 | CR686-14 | upper and lower | CCAGUCCAGCGAGGCAAAGGmGUUUmUmAGAmGmCmUmAmUmGmCmUmGmUmUmUmUmG |
| 33 | CR003722 | CR686-15 | lower combo | CCAGUCCAGCGAGGCAAAGGmGUUUmUmAGAGCUAUGCUGUUUUG |
| 34 | CR003723 | CR686-16 | upper, lower combo | CCAGUCCAGCGAGGCAAAGGmGUUUUmUmAGAmGmCmUmAmUmGmCmUmGmUmUmUmUmG |
| 35 | CR003724 | CR686-17 | lower combo | CCAGUCCAGCGAGGCAAAGGmGUUUUmUmAGAGCUAUGCUGUUUUG |
| 36 | CR003725 | CR686-18 | upper, lower combo | CCAGUCCAGCGAGGCAAAGGmGUUUUAGAmGmCmUmAmUmGmCmUmGmUmUmUmUmG |
| 37 | CR003726 | CR686-19 | nexus walk | CCAGUCCAGCGAGGCAAAGGGUUUUAmGAmGmCmUmAmUmGmCmUmGmUmUmUmUmG |
| 38 | CR003727 | CR686-20 | nexus walk | CCAGUCCAGCGAGGCAAAGGGUUUUAGmAmGmCmUmAmUmGmCmUmGmUmUmUmUmG |
| 39 | CR003728 | CR686-21 | nexus walk | CCAGUCCAGCGAGGCAAAGGGUUUUAfGAmGmCmUmAmUmGmCmUmGmUmUmUmUmG |
| 40 | CR003729 | CR686-22 | nexus walk | CCAGUCCAGCGAGGCAAAGGGUUUUAGfAmGmCmUmAmUmGmCmUmGmUmUmUmUmG |
| 41 | CR003730 | CR686-23 | 2'F lower walk | CCAGUCCAGCGAGGCAAAGGGfUUUUAGAmGmCmUmAmUmGmCmUmGmUmUmUmUmG |

TABLE 4-continued

| SEQ ID NO | Name | Alias | Description | Sequence |
|---|---|---|---|---|
| 42 | CR003731 | CR686-24 | 2'F lower walk | CCAGUCCAGCGAGGCAAAGGGUfUUUAGAmGmCmUmAmUmGmCmUmGmUmUmUmG |
| 43 | CR003732 | CR686-25 | 2'F lower walk | CCAGUCCAGCGAGGCAAAGGGUUfUUAGAmGmCmUmAmUmGmCmUmGmUmUmUmG |
| 44 | CR003733 | CR686-26 | 2'F lower walk | CCAGUCCAGCGAGGCAAAGGGUUUfUAGAmGmCmUmAmUmGmCmUmGmUmUmUmG |
| 45 | CR003734 | CR686-27 | 2'F lower combo | CCAGUCCAGCGAGGCAAAGGfGfUfUfUfUfAGAmGmCmUmAmUmGmCmUmGmUmUmUmG |
| 46 | CR003735 | CR686-28 | lower alt | CCAGUCCAGCGAGGCAAAGGfGmUfUmUfUmAGAmGmCmUmAmUmGmCmUmGmUmUmUmG |
| 47 | CR003736 | CR686-29 | lower alt | CCAGUCCAGCGAGGCAAAGGmGfUmUfUmUfAGAmGmCmUmAmUmGmCmUmGmUmUmUmG |
| 48 | CR003737 | CR686-GC6 | Lower GC | CCAGUCCAGCGAGGCAAAGGGUCUCAGAmGmCmUmAmUmGmCmUmGmUmUmUmG |
| 49 | CR003738 | CR686-GC7 | Lower C walk | CCAGUCCAGCGAGGCAAAGGGCUUUAGAmGmCmUmAmUmGmCmUmGmUmUmUmG |
| 50 | CR003739 | CR686-GC8 | Lower C walk | CCAGUCCAGCGAGGCAAAGGGUCUUAGAmGmCmUmAmUmGmCmUmGmUmUmUmG |
| 51 | CR003740 | CR686-GC9 | Lower C walk | CCAGUCCAGCGAGGCAAAGGGUUCUAGAmGmCmUmAmUmGmCmUmGmUmUmUmG |
| 52 | CR003741 | CR686-GC10 | Lower C walk | CCAGUCCAGCGAGGCAAAGGGUUUCAGAmGmCmUmAmUmGmCmUmGmUmUmUmG |
| 53 | CR003721-mod only | CR686-14-mod only | upper and lower | mGUUUmUmAGAmGmCmUmAmUmGmCmUmGmUmUmUmUmG |
| 54 | CR003722-mod only | CR686-15-mod only | lower combo | mGUUUmUmAGAGCUAUGCUGUUUUG |
| 55 | CR003723-mod only | CR686-16-mod only | upper, lower combo | mGUUUUmAGAmGmCmUmAmUmGmCmUmGmUmUmUmUmG |
| 56 | CR003724-mod only | CR686-17-mod only | lower combo | mGUUUUmAGAGCUAUGCUGUUUUG |
| 57 | CR003725-mod only | CR686-18-mod only | upper, lower combo | mGUUUUAGAmGmCmUmAmUmGmCmUmGmUmUmUmUmG |
| 58 | CR003726-mod only | CR686-19-mod only | nexus walk | GUUUUAmGAmGmCmUmAmUmGmCmUmGmUmUmUmUmG |
| 59 | CR003727-mod only | CR686-20-mod only | nexus walk | GUUUUAGmAmGmCmUmAmUmGmCmUmGmUmUmUmUmG |
| 60 | CR003728-mod only | CR686-21-mod only | nexus walk | GUUUUAfGAmGmCmUmAmUmGmCmUmGmUmUmUmUmG |
| 61 | CR003729-mod only | CR686-22-mod only | nexus walk | GUUUUAGfAmGmCmUmAmUmGmCmUmGmUmUmUmUmG |

TABLE 4-continued

| SEQ ID NO | Name | Alias | Description | Sequence |
|---|---|---|---|---|
| 62 | CR003730-mod only | CR686-23-mod only | 2'F lower walk | GfUUUUAGAmGmCmUmAmUmGmCmUmGmUmUmUmUmG |
| 63 | CR003731-mod only | CR686-24-mod only | 2'F lower walk | GUfUUUAGAmGmCmUmAmUmGmCmUmGmUmUmUmUmG |
| 64 | CR003732-mod only | CR686-25-mod only | 2'F lower walk | GUUfUUAGAmGmCmUmAmUmGmCmUmGmUmUmUmUmG |
| 65 | CR003733-mod only | CR686-26-mod only | 2'F lower walk | GUUUfUAGAmGmCmUmAmUmGmCmUmGmUmUmUmUmG |
| 66 | CR003734-mod only | CR686-27-mod only | 2'F lower combo | fGfUfUfUfUfAGAmGmCmUmAmUmGmCmUmGmUmUmUmUmG |
| 67 | CR003735-mod only | CR686-28-mod only | lower alt | fGmUfUmUfUmAGAmGmCmUmAmUmGmCmUmGmUmUmUmUmG |
| 68 | CR003736-mod only | CR686-29-mod only | lower alt | mGfUmUfUmUfAGAmGmCmUmAmUmGmCmUmGmUmUmUmUmG |
| 69 | CR003737-mod only | CR686-GC6-mod only | Lower GC | GUCUCAGAmGmCmUmAmUmGmCmUmGmUmUmUmUmG |
| 70 | CR003738-mod only | CR686-GC7-mod only | Lower C walk | GCUUUAGAmGmCmUmAmUmGmCmUmGmUmUmUmUmG |
| 71 | CR003739-mod only | CR686-GC8-mod only | Lower C walk | GUCUUAGAmGmCmUmAmUmGmCmUmGmUmUmUmUmG |
| 72 | CR003740-mod only | CR686-GC9-mod only | Lower C walk | GUUCUAGAmGmCmUmAmUmGmCmUmGmUmUmUmUmG |
| 73 | CR003741-mod only | CR686-GC10-mod only | Lower C walk | GUUUCAGAmGmCmUmAmUmGmCmUmGmUmUmUmUmG |
| 74 | CR000705 | | unmodified | UUACAGCCACGUCUACAGCAGUUUUAGAGCUAUGCUGUUUUG |
| 75 | CR004188 | CR705-1 | upper | UUACAGCCACGUCUACAGCAGUUUUAGAmGmCmUmAmUmGmCmUmGmUmUmUmUmG |
| 76 | CR004189 | CR705-2 | partial upper | UUACAGCCACGUCUACAGCAGUUUUAGAGCUAmUmGmCmUmGmUmUmUmUmG |
| 77 | CR004190 | CR705-3 | partial upper | UUACAGCCACGUCUACAGCAGUUUUAGAGCUAUGCmUmGmUmUmUmUmG |
| 78 | CR004191 | CR705-4 | partial upper | UUACAGCCACGUCUACAGCAGUUUUAGAGCUAUGCUGmUmUmUmUmG |
| 79 | CR004192 | CR705-5 | lower | UUACAGCCACGUCUACAGCAmGmUmUmUmUmAGAGCUAUGCUGUUUUG |
| 80 | CR004193 | CR705-6 | lower walk | UUACAGCCACGUCUACAGCAmGUUUUAGAGCUAUGCUGUUUUG |
| 81 | CR004194 | CR705-7 | lower walk | UUACAGCCACGUCUACAGCAGmUUUUAGAGCUAUGCUGUUUUG |
| 82 | CR004195 | CR705-8 | lower walk | UUACAGCCACGUCUACAGCAGUmUUUAGAGCUAUGCUGUUUUG |

TABLE 4-continued

| SEQ ID NO | Name | Alias | Description | Sequence |
|---|---|---|---|---|
| 83 | CR004196 | CR705-9 | lower walk | UUACAGCCACGUCUACAGCAGUUmUUAGAGCUAUGCUGUUUUG |
| 84 | CR004197 | CR705-10 | lower walk | UUACAGCCACGUCUACAGCAGUUUmUAGAGCUAUGCUGUUUUG |
| 85 | CR004198 | CR705-11 | lower walk | UUACAGCCACGUCUACAGCAGUUUUmAGAGCUAUGCUGUUUUG |
| 86 | CR004199 | CR705-14 | upper and lower | UUACAGCCACGUCUACAGCAmGUUUmUmAGAmGmCmUmAmUmGmCmUmGmUmUmUmUmG |
| 87 | CR004200 | CR705-15 | lower combo | UUACAGCCACGUCUACAGCAmGUUUmUmAGAGCUAUGCUGUUUUG |
| 88 | CR004201 | CR705-16 | upper, lower combo | UUACAGCCACGUCUACAGCAmGUUUUmAGAmGmCmUmAmUmGmCmUmGmUmUmUmUmG |
| 89 | CR004202 | CR705-17 | lower combo | UUACAGCCACGUCUACAGCAmGUUUUmAGAGCUAUGCUGUUUUG |
| 90 | CR004203 | CR705-18 | upper, lower combo | UUACAGCCACGUCUACAGCAmGUUUUAGAmGmCmUmAmUmGmCmUmGmUmUmUmUmG |
| 91 | CR004204 | CR705-19 | nexus walk | UUACAGCCACGUCUACAGCAGUUUUAmGAmGmCmUmAmUmGmCmUmGmUmUmUmUmG |
| 92 | CR004205 | CR705-20 | nexus walk | UUACAGCCACGUCUACAGCAGUUUUAGmAmGmCmUmAmUmGmCmUmGmUmUmUmUmG |
| 93 | CR004206 | CR705-21 | nexus walk | UUACAGCCACGUCUACAGCAGUUUUAfGAmGmCmUmAmUmGmCmUmGmUmUmUmUmG |
| 94 | CR004207 | CR705-22 | nexus walk | UUACAGCCACGUCUACAGCAGUUUUAGfAmGmCmUmAmUmGmCmUmGmUmUmUmUmG |
| 95 | CR004208 | CR705-23 | 2'F lower walk | UUACAGCCACGUCUACAGCAGfUUUUAGAmGmCmUmAmUmGmCmUmGmUmUmUmUmG |
| 96 | CR004209 | CR705-24 | 2'F lower walk | UUACAGCCACGUCUACAGCAGUfUUUAGAmGmCmUmAmUmGmCmUmGmUmUmUmUmG |
| 97 | CR004210 | CR705-25 | 2'F lower walk | UUACAGCCACGUCUACAGCAGUUfUUAGAmGmCmUmAmUmGmCmUmGmUmUmUmUmG |
| 98 | CR004211 | CR705-26 | 2'F lower walk | UUACAGCCACGUCUACAGCAGUUUfUAGAmGmCmUmAmUmGmCmUmGmUmUmUmUmG |
| 99 | CR004212 | CR705-27 | 2'F lower combo | UUACAGCCACGUCUACAGCAfGfUfUfUfAGAmGmCmUmAmUmGmCmUmGmUmUmUmUmG |
| 100 | CR004213 | CR705-28 | lower alt | UUACAGCCACGUCUACAGCAfGmUfUmUfUmAGAmGmCmUmAmUmGmCmUmGmUmUmUmUmG |
| 101 | CR004214 | CR705-29 | lower alt | UUACAGCCACGUCUACAGCAmGfUmUfUmUfAGAmGmCmUmAmUmGmCmUmGmUmUmUmUmG |
| 102 | CR004215 | CR705-GC1 | Lower GC | UUACAGCCACGUCUACAGCAGGCGCAGAGCUAUGCUGUUUUG |
| 103 | CR004216 | CR705-GC3 | Upper GC | UUACAGCCACGUCUACAGCAGUUUUAGAGCUAUGCUGGCGCG |
| 104 | CR004188-mod only | CR705-1-mod only | upper | GUUUUAGAmGmCmUmAmUmGmCmUmGmUmUmUmUmG |
| 105 | CR004189-mod only | CR705-2-mod only | partial upper | GUUUUAGAGCUAmUmGmCmUmGmUmUmUmUmG |

TABLE 4-continued

| SEQ ID NO | Name | Alias | Description | Sequence |
|---|---|---|---|---|
| 106 | CR004190-mod only | CR705-3-mod only | partial upper | GUUUUAGAGCUAUGCmUmGmUmUmUmUmG |
| 107 | CR004191-mod only | CR705-4-mod only | partial upper | GUUUUAGAGCUAUGCUGmUmUmUmUmG |
| 108 | CR004192-mod only | CR705-5-mod only | lower | mGmUmUmUmUmAGAGCUAUGCUGUUUUG |
| 109 | CR004193-mod only | CR705-6-mod only | lower walk | mGUUUUAGAGCUAUGCUGUUUUG |
| 110 | CR004194-mod only | CR705-7-mod only | lower walk | GmUUUUAGAGCUAUGCUGUUUUG |
| 111 | CR004195-mod only-mod only | CR705-8-mod only | lower walk | GUmUUUAGAGCUAUGCUGUUUUG |
| 112 | CR004196-mod only | CR705-9-mod only | lower walk | GUUmUUAGAGCUAUGCUGUUUUG |
| 113 | CR004197-mod only | CR705-10-mod only | lower walk | GUUUmUAGAGCUAUGCUGUUUUG |
| 114 | CR004198-mod only | CR705-11-mod only | lower walk | GUUUUmAGAGCUAUGCUGUUUUG |
| 115 | CR004199-mod only | CR705-14-mod only | upper and lower | mGUUUmUmAGAmGmCmUmAmUmGmCmUmGmUmUmUmUmG |
| 116 | CR004200-mod only | CR705-15-mod only | lower combo | mGUUUmUmAGAGCUAUGCUGUUUUG |
| 117 | CR004201-mod only | CR705-16-mod only | upper, lower combo | mGUUUUmUmAGAmGmCmUmAmUmGmCmUmGmUmUmUmUmG |
| 118 | CR004202-mod only | CR705-17-mod only | lower combo | mGUUUUmAGAGCUAUGCUGUUUUG |
| 119 | CR004203-mod only | CR705-18-mod only | upper, lower combo | mGUUUUAGAmGmCmUmAmUmGmCmUmGmUmUmUmUmG |
| 120 | CR004204-mod only | CR705-19-mod only | nexus walk | GUUUUAmGAmGmCmUmAmUmGmCmUmGmUmUmUmUmG |
| 121 | CR004205-mod only | CR705-20-mod only | nexus walk | GUUUUAGmAmGmCmUmAmUmGmCmUmGmUmUmUmUmG |
| 122 | CR004206-mod only | CR705-21-mod only | nexus walk | GAmGmCmUmAmUmGmCmUmGmUmUmUmUmG |
| 123 | CR004207-mod only | CR705-22-mod only | nexus walk | GfAmGmCmUmAmUmGmCmUmGmUmUmUmUmG |
| 124 | CR004208-mod only | CR705-23-mod only | 2'F lower walk | GfUUUUAGAmGmCmUmAmUmGmCmUmGmUmUmUmUmG |
| 125 | CR004209-mod only | CR705-24-mod only | 2'F lower walk | GUfUUUAGAmGmCmUmAmUmGmCmUmGmUmUmUmUmG |

TABLE 4-continued

| SEQ ID NO | Name | Alias | Description | Sequence |
|---|---|---|---|---|
| 126 | CR004210-mod only | CR705-25-mod only | 2'F lower walk | GUUfUUAGAmGmCmUmAmUmGmCmUmGmUmUmUmG |
| 127 | CR004211-mod only | CR705-26-mod only | 2'F lower walk | GUUUfUAGAmGmCmUmAmUmGmCmUmGmUmUmUmG |
| 128 | CR004212-mod only | CR705-27-mod only | 2'F lower combo | fGfUfUfUfUfAGAmGmCmUmAmUmGmCmUmGmUmUmUmG |
| 129 | CR004213-mod only | CR705-28-mod only | lower alt | fGmUfUmUfUmAGAmGmCmUmAmUmGmCmUmGmUmUmUmUmG |
| 130 | CR004214-mod only | CR705-29-mod only | lower alt | mGfUmUfUmUfAGAmGmCmUmAmUmGmCmUmGmUmUmUmUmG |
| 131 | CR000657 | | unmodified | CAGGGCUCUUGAAGAUCUCCGUUUUAGAGCUAUGCUGUUUUG |
| 132 | CR004218 | CR657-1 | upper | CAGGGCUCUUGAAGAUCUCCGUUUUAGAmGmCmUmAmUmGmCmUmGmUmUmUmG |
| 133 | CR004219 | CR657-2 | partial upper | CAGGGCUCUUGAAGAUCUCCGUUUUAGAGCUAmUmGmCmUmGmUmUmUmUmG |
| 134 | CR004220 | CR657-3 | partial upper | CAGGGCUCUUGAAGAUCUCCGUUUUAGAGCUAUGCmUmGmUmUmUmUmG |
| 135 | CR004221 | CR657-4 | partial upper | CAGGGCUCUUGAAGAUCUCCGUUUUAGAGCUAUGCUGmUmUmUmUmG |
| 136 | CR004222 | CR657-5 | lower | CAGGGCUCUUGAAGAUCUCCmGmUmUmUmUmAGAGCUAUGCUGUUUUG |
| 137 | CR004223 | CR657-6 | lower walk | CAGGGCUCUUGAAGAUCUCCmGUUUUAGAGCUAUGCUGUUUUG |
| 138 | CR004224 | CR657-7 | lower walk | CAGGGCUCUUGAAGAUCUCCGmUUUUAGAGCUAUGCUGUUUUG |
| 139 | CR004225 | CR657-8 | lower walk | CAGGGCUCUUGAAGAUCUCCGUmUUUAGAGCUAUGCUGUUUUG |
| 140 | CR004226 | CR657-9 | lower walk | CAGGGCUCUUGAAGAUCUCCGUUmUUAGAGCUAUGCUGUUUUG |
| 141 | CR004227 | CR657-10 | lower walk | CAGGGCUCUUGAAGAUCUCCGUUUmUAGAGCUAUGCUGUUUUG |
| 142 | CR004228 | CR657-11 | lower walk | CAGGGCUCUUGAAGAUCUCCGUUUUmAGAGCUAUGCUGUUUUG |
| 143 | CR004229 | CR657-14 | upper and lower | CAGGGCUCUUGAAGAUCUCCmGUUUmUmAGAmGmCmUmAmUmGmCmUmGmUmUmUmUmG |
| 144 | CR004230 | CR657-15 | lower combo | CAGGGCUCUUGAAGAUCUCCmGUUUmUmAGAGCUAUGCUGUUUUG |
| 145 | CR004231 | CR657-16 | upper, lower combo | CAGGGCUCUUGAAGAUCUCCmGUUUmUmAGAmGmCmUmAmUmGmCmUmUmGmUmUmUmUmG |
| 146 | CR004232 | CR657-17 | lower combo | CAGGGCUCUUGAAGAUCUCCmGUUUUmAGAGCUAUGCUGUUUUG |
| 147 | CR004233 | CR657-18 | upper, lower combo | CAGGGCUCUUGAAGAUCUCCmGUUUUAGAmGmCmUmAmUmGmCmUmmGmUmUmUmUmG |

TABLE 4-continued

| SEQ ID NO | Name | Alias | Description | Sequence |
|---|---|---|---|---|
| 148 | CR004234 | CR657-19 | nexus walk | CAGGGCUCUUGAAGAUCUCCGUUUUAmGAmGmCmUmAmUmGmCmUmGmUmUmUmG |
| 149 | CR004235 | CR657-20 | nexus walk | CAGGGCUCUUGAAGAUCUCCGUUUUAGmAmGmCmUmAmUmGmCmUmGmUmUmUmG |
| 150 | CR004236 | CR657-21 | nexus walk | CAGGGCUCUUGAAGAUCUCCGUUUUAfGAmGmCmUmAmUmGmCmUmGmUmUmUmG |
| 151 | CR004237 | CR657-22 | nexus walk | CAGGGCUCUUGAAGAUCUCCGUUUUAGfAmGmCmUmAmUmGmCmUmGmUmUmUmG |
| 152 | CR004238 | CR657-23 | 2'F lower walk | CAGGGCUCUUGAAGAUCUCCGfUUUUAGAmGmCmUmAmUmGmCmUmGmUmUmUmG |
| 153 | CR004239 | CR657-24 | 2'F lower walk | CAGGGCUCUUGAAGAUCUCCGUfUUUAGAmGmCmUmAmUmGmCmUmGmUmUmUmG |
| 154 | CR004240 | CR657-25 | 2'F lower walk | CAGGGCUCUUGAAGAUCUCCGUUfUUAGAmGmCmUmAmUmGmCmUmGmUmUmUmG |
| 155 | CR004241 | CR657-26 | 2'F lower walk | CAGGGCUCUUGAAGAUCUCCGUUUfUAGAmGmCmUmAmUmGmCmUmGmUmUmUmG |
| 156 | CR004242 | CR657-27 | 2'F lower combo | CAGGGCUCUUGAAGAUCUCCfGfUfUfUfUfAGAmGmCmUmAmUmGmCmUmGmUmUmUmG |
| 157 | CR004243 | CR657-28 | lower alt | CAGGGCUCUUGAAGAUCUCCfGmUfUmUfUmAGAmGmCmUmAmUmGmCmUmGmUmUmUmG |
| 158 | CR004244 | CR657-29 | lower alt | CAGGGCUCUUGAAGAUCUCCmGfUmUfUmUfAGAmGmCmUmAmUmGmCmUmGmUmUmUmG |
| 159 | CR004245 | CR657-GC1 | Lower GC | CAGGGCUCUUGAAGAUCUCCGGCGCAGAGCUAUGCUGUUUUG |
| 160 | CR004246 | CR657-GC3 | Upper GC | CAGGGCUCUUGAAGAUCUCCGUUUUAGAGCUAUGCUGGCGCG |
| 161 | CR004218-mod only | CR657-1-mod only | upper | GUUUUAGAmGmCmUmAmUmGmCmUmGmUmUmUmG |
| 162 | CR004219-mod only | CR657-2-mod only | partial upper | GUUUUAGAGCUAmUmGmCmUmGmUmUmUmG |
| 163 | CR004220-mod only | CR657-3-mod only | partial upper | GUUUUAGAGCUAUGCmUmGmUmUmUmG |
| 164 | CR004221-mod only | CR657-4-mod only | partial upper | GUUUUAGAGCUAUGCUGmUmUmUmG |
| 165 | CR004222-mod only | CR657-5-mod only | lower | mGmUmUmUmUmAGAGCUAUGCUGUUUUG |
| 166 | CR004223-mod only | CR657-6-mod only | lower walk | mGUUUUAGAGCUAUGCUGUUUUG |
| 167 | CR004224-mod only | CR657-7-mod only | lower walk | GmUUUUAGAGCUAUGCUGUUUUG |
| 168 | CR004225-mod only | CR657-8-mod only | lower walk | GUmUUUAGAGCUAUGCUGUUUUG |
| 169 | CR004226-mod only | CR657-9-mod only | lower walk | GUUmUUAGAGCUAUGCUGUUUUG |
| 170 | CR004227-mod only | CR657-10-mod only | lower walk | GUUUmUAGAGCUAUGCUGUUUUG |

TABLE 4-continued

| SEQ ID NO | Name | Alias | Description | Sequence |
|---|---|---|---|---|
| 171 | CR004228-mod only | CR657-11-mod only | lower walk | GUUUUmAGAGCUAUGCUGUUUUG |
| 172 | CR004229-mod only | CR657-14-mod only | upper and lower | mGUUUmUmAGAmGmCmUmAmUmGmCmUmGmUmUmUmUmG |
| 173 | CR004230-mod only | CR657-15-mod only | lower combo | mGUUUmUmAGAGCUAUGCUGUUUUG |
| 174 | CR004231-mod only | CR657-16-mod only | upper, lower combo | mGUUUUmAGAmGmCmUmAmUmGmCmUmGmUmUmUmUmG |
| 175 | CR004232-mod only | CR657-17-mod only | lower combo | mGUUUUmAGAGCUAUGCUGUUUUG |
| 176 | CR004233-mod only | CR657-18-mod only | upper, lower combo | mGUUUUAGAmGmCmUmAmUmGmCmUmGmUmUmUmUmG |
| 177 | CR004234-mod only | CR657-19-mod only | nexus walk | GUUUUAmGAmGmCmUmAmUmGmCmUmGmUmUmUmUmG |
| 178 | CR004235-mod only | CR657-20-mod only | nexus walk | GUUUUAGmAmGmCmUmAmUmGmCmUmGmUmUmUmUmG |
| 179 | CR004236-mod only | CR657-21-mod only | nexus walk | GUUUUAfGAmGmCmUmAmUmGmCmUmGmUmUmUmUmG |
| 180 | CR004237-mod only | CR657-22-mod only | nexus walk | GUUUUAGfAmGmCmUmAmUmGmCmUmGmUmUmUmUmG |
| 181 | CR004238-mod only | CR657-23-mod only | 2'F lower walk | GfUUUUAGAmGmCmUmAmUmGmCmUmGmUmUmUmUmG |
| 182 | CR004239-mod only | CR657-24-mod only | 2'F lower walk | GUfUUUAGAmGmCmUmAmUmGmCmUmGmUmUmUmUmG |
| 183 | CR004240-mod only | CR657-25-mod only | 2'F lower walk | GUUfUUAGAmGmCmUmAmUmGmCmUmGmUmUmUmUmG |
| 184 | CR004241-mod only | CR657-26-mod only | 2'F lower walk | GUUUfUAGAmGmCmUmAmUmGmCmUmGmUmUmUmUmG |
| 185 | CR004242-mod only | CR657-27-mod only | 2'F lower combo | fGfUfUfUfAGAmGmCmUmAmUmGmCmUmGmUmUmUmUmG |
| 186 | CR004243-mod only | CR657-28-mod only | lower alt | fGmUfUmUfUmAGAmGmCmUmAmUmGmCmUmGmUmUmUmUmG |
| 187 | CR004244-mod only | CR657-29-mod only | lower alt | mGfUmUfUmUfAGAmGmCmUmAmUmGmCmUmGmUmUmUmUmG | trRNA

| 188 | TR000002 | | unmodified | AACAGCAUAGCAAGUUAAAAUAAGGCUAGUCCGUUAUCAACUUGAAAAAGUGGCACCGAGUCGGUGCUUUUUUU |

TABLE 4-continued

| SEQ ID NO | Name | Alias | Description | Sequence |
|---|---|---|---|---|
| 189 | TR000110 | TR2-v2-1 | shortened tail | AACAGCAUAGCAAGUUAAAAUAAGGCUAGUCCGUUAUCAACUUGAAAAAGUGGCACCGAGUCGGUGCUUUU |
| 190 | TR000111 | TR2-v2-2 | Upper, hairpins | mAmAmCmAmGmCmAmUmAmGmCAAGUUAAAAUAAGGCUAGUCCGUUAUCAmCmUmUmGmAmAmAmAmGmUmGmCmAmCmCmGmAmGmUmCmGmGmUmGmCmUmUmUmU |
| 191 | TR000112 | TR2-v2-3 | upper only | mAmAmCmAmGmCmAmUmAmGmCAAGUUAAAAUAAGGCUAGUCCGUUAUCAACUUGAAAAAGUGGCACCGAGUCGGUGCUUUU |
| 192 | TR000113 | TR2-v2-4 | hairpin 1 | AACAGCAUAGCAAGUUAAAAUAAGGCUAGUCCGUUAUCAmAmCmUmUmGmAmAmAmAmGmUmGGCACCGAGUCGGUGCUUUU |
| 193 | TR000114 | TR2-v2-5 | hairpin 2 | AACAGCAUAGCAAGUUAAAAUAAGGCUAGUCCGUUAUCAACUUGAAAAAGUGmCmAmCmCmGmAmGmUmCmGmGmUmGmCmUmUmUmU |
| 194 | TR000115 | TR2-v2-6 | upper, hairpin 2 | mAmAmCmAmGmCmAmUmAmGmCAAGUUAAAAUAAGGCUAGUCCGUUAUCAACUUGAAAAAGUGmCmAmCmCmGmAmGmUmCmGmGmUmGmCmUmUmUmU |
| 195 | TR000116 | TR2-v2-7 | both hairpins | AACAGCAUAGCAAGUUAAAAUAAGGCUAGUCCGUUAUCAmAmCmUmUmGmAmAmAmAmGmUmGmGmCmAmCmCmGmAmGmUmCmGmGmUmGmCmUmUmUmU |
| 196 | TR000117 | TR2-v2-8 | lower walk | AACAGCAUAGCAAGUmUmAAAAUAAGGCUAGUCCGUUAUCAACUUGAAAAAGUGGCACCGAGUCGGUGCUUUU |
| 197 | TR000118 | TR2-v2-9 | lower walk | AACAGCAUAGCAAGUUAmAmAAUAAGGCUAGUCCGUUAUCAACUUGAAAAAGUGGCACCGAGUCGGUGCUUUU |
| 198 | TR000119 | TR2-v2-10 | lower walk | AACAGCAUAGCAAGUUAAAmAmUAAGGCUAGUCCGUUAUCAACUUGAAAAAGUGGCACCGAGUCGGUGCUUUU |
| 199 | TR000120 | TR2-v2-11 | partial nexus | AACAGCAUAGCAAGUUAAAAUAAGGCUAGUCCGmUmUmAUCAACUUGAAAAAGUGGCACCGAGUCGGUGCUUUU |
| 200 | TR000121 | TR2-v2-12 | partial nexus | AACAGCAUAGCAAGUUAAAAUAAGGCUAGUCCGUUAmUmCmAACUUGAAAAAGUGGCACCGAGUCGGUGCUUUU |
| 201 | TR000122 | TR2-GC1 | Lower GC | AACAGCAUAGCAAGUUGCGCUAAGGCUAGUCCGUUAUCAACUUGAAAAAGUGGCACCGAGUCGGUGCUUUU |
| 202 | TR000123 | TR2-GC3 | upper GC | GCCAGCAUAGCAAGUUAAAAUAAGGCUAGUCCGUUAUCAACUUGAAAAAGUGGCACCGAGUCGGUGCUUUU |
| 203 | TR000124 | TR2-GC5 | Lower Upper GC | GCCAGCAUAGCAAGUUGCGCUAAGGCUAGUCCGUUAUCAACUUGAAAAAGUGGCACCGAGUCGGUGCUUUU |
| 204 | TR000125 | TR2 all OMe | | mAmAmCmAmGmCmAmUmAmGmCmAmAmGmUmUmAmAmAmAmUmAmAmGmGmCmUmAmGmUmCmCmGmUmUmAmUmCmAmAmCmUmUmGmAmAmAmAmAmGmUmGmGmCmAmCmCmGmAmGmUmCmGmGmUmGmCmUmUmUmUmU |
| 205 | TR000126 | TR2-v2-13 | lower | mAmAmCmAmGmCmAmUmAmGmCAAGUmUmAmAmAmAmUAAGGCUAGUCCGUUAUCAmAmCmUmUmGmAmAmAmAmAmGmUmGmGmCmAmCmCmGmAmGmUmCmGmGmUmGmCmUmUmUmU |
| 206 | TR000127 | TR2-v2-14 | lower | mAmAmCmAmGmCmAmUmAmGmCAAGUmUmAAAmAmUAAGGCUAGUCCGUUAUCAmAmCmUmUmGmAmAmAmAmAmGmUmGmGmCmAmCmCmGmAmGmUmCmGmGmUmGmCmUmUmUmU |
| 207 | TR000128 | TR2-v2-15 | lower | mAmAmCmAmGmCmAmUmAmGmCAAGUmUmAfAfAmAmUAAGGCUAGUCCGUUAUCAmAmCmUmUmGmAmAmAmAmAmGmUmGmGmCmAmCmCmGmAmGmUmCmGmGmUmGmCmUmUmUmU |
| 208 | TR000129 | TR2-v2-16 | lower alt | mAmAmCmAmGmCmAmUmAmGmCAAGUmUfAmAfAmAfUAAGGCUAGUCCGUUAUCAmAmCmUmUmGmAmAmAmAmAmGmUmGmGmCmAmCmCmGmAmGmUmCmGmGmUmGmCmUmUmUmU |
| 209 | TR000130 | TR2-v2-17 | lower alt | mAmAmCmAmGmCmAmUmAmGmCAAGUmUfAmAfAmAfAmUAAGGCUAGUCCGUUAUCAmAmCmUmUmGmAmAmAmAmAmGmUmGmGmCmAmCmCmGmAmGmUmCmGmGmUmGmCmUmUmUmU |

TABLE 4-continued

| SEQ ID NO | Name | Alias | Description | Sequence |
|---|---|---|---|---|
| 210 | TR000131 | TR2-v2-18 | nexus walk | mAmAmCmAmGmCmAmUmAmGmCAAGUUAAAAUAAGGCUAGUCCGUUAUCmAmAmCmUmUmGmAmAmAmAmAmGmUmGmGmCmAmCmCmGmAmGmUmCmGmGmUmGmCmUmUmU |
| 211 | TR000132 | TR2-v2-19 | nexus walk | mAmAmCmAmGmCmAmUmAmGmCAAGUUAAAAUAAGGCUAGUCCGUUAUmCmAmCmUmUmGmAmAmAmAmAmGmUmGmGmCmAmCmCmGmAmGmUmCmGmGmUmGmCmUmUmU |
| 212 | TR000133 | TR2-v2-20 | nexus walk | mAmAmCmAmGmCmAmUmAmGmCAAGUUAAAAUAAGGCUAGUCCGUUAmUCmAmCmUmUmGmAmAmAmAmAmGmUmGmGmCmAmCmCmGmAmGmUmCmGmGmUmGmCmUmUmU |
| 213 | TR000134 | TR2-v2-21 | nexus walk | mAmAmCmAmGmCmAmUmAmGmCAAGUUAAAAUAAGGCUAGUCCGUUmAUCmAmCmUmUmGmAmAmAmAmAmGmUmGmGmCmAmCmCmGmAmGmUmCmGmGmUmGmCmUmUmU |
| 214 | TR000135 | TR2-v2-22 | nexus walk | mAmAmCmAmGmCmAmUmAmGmCAAGUUAAAAUAAGGCUAGUCCGUmUAUCmAmAmCmUmUmGmAmAmAmAmAmGmUmGmGmCmAmCmCmGmAmGmUmCmGmGmUmGmCmUmUmU |
| 215 | TR000136 | TR2-v2-23 | nexus walk | mAmAmCmAmGmCmAmUmAmGmCAAGUUAAAAUAAGGCUAGUCCGmUUAUCmAmAmCmUmUmGmAmAmAmAmAmGmUmGmGmCmAmCmCmGmAmGmUmCmGmGmUmGmCmUmUmU |
| 216 | TR000137 | TR2-v2-24 | nexus walk | mAmAmCmAmGmCmAmUmAmGmCAAGUUAAAAUAAGGCUAGUCCGUUAUfCfAmAmCmUmUmGmAmAmAmAmAmGmUmGmGmCmAmCmCmGmAmGmUmCmGmGmUmGmCmUmUmU |
| 217 | TR000138 | TR2-v2-25 | nexus walk | mAmAmCmAmGmCmAmUmAmGmCAAGUUAAAAUAAGGCUAGUCCGUUfAfUCmAmAmCmUmUmGmAmAmAmAmAmGmUmGmGmCmAmCmCmGmAmGmUmCmGmGmUmGmCmUmUmU |
| 218 | TR000139 | TR2-v2-26 | nexus walk | mAmAmCmAmGmCmAmUmAmGmCAAGUUAAAAUAAGGCUAGUCCGfUfUAUCmAmAmCmUmUmGmAmAmAmAmAmGmUmGmGmCmAmCmCmGmAmGmUmCmGmGmUmGmCmUmUmU |
| 219 | TR000140 | TR2-v2-27 | nexus walk | mAmAmCmAmGmCmAmUmAmGmCAAGUUAAAAUAAmGmGmCUAGUCCGUUAUCmAmCmUmUmGmAmAmAmAmAmGmUmGmGmCmAmCmCmGmAmGmUmCmGmGmUmGmCmUmUmU |
| 220 | TR000141 | TR2-v2-28 | nexus walk | mAmAmCmAmGmCmAmUmAmGmCAAGUUAAAAUAAGGCUAGUmCmCmGUUAUCmAmCmUmUmGmAmAmAmAmAmGmUmGmGmCmAmCmCmGmAmGmUmCmGmGmUmGmCmUmUmU |
| 221 | TR000142 | TR2-v2-29 | bulge walk | mAmAmCmAmGmCmAmUmAmGmCmAmAGUUAAAAUAAGGCUAGUCCGUUAUCmAmAmCmUmUmGmAmAmAmAmAmGmUmGmGmCmAmCmCmGmAmGmUmCmGmGmUmGmCmUmUmU |
| 222 | TR000143 | TR2-v2-30 | bulge walk | mAmAmCmAmGmCmAmUmAmGmCAAmGmUUAAAAUAAGGCUAGUCCGUUAUCmAmAmCmUmUmGmAmAmAmAmAmGmUmGmGmCmAmCmCmGmAmGmUmCmGmGmUmGmCmUmUmU |
| 223 | TR000144 | TR2-GC6 | Lower GC walk | AACAGCAUAGCAAGUUGAGAUAAGGCUAGUCCGUUAUCAACUUGAAAAAGUGGCACCGAGUCGGUGCUUUU |
| 224 | TR000145 | TR2-GC7 | Lower GC walk | AACAGCAUAGCAAGUUAAAGUAAGGCUAGUCCGUUAUCAACUUGAAAAAGUGGCACCGAGUCGGUGCUUUU |
| 225 | TR000146 | TR2-GC8 | Lower GC walk | AACAGCAUAGCAAGUUAAGAUAAGGCUAGUCCGUUAUCAACUUGAAAAAGUGGCACCGAGUCGGUGCUUUU |
| 226 | TR000147 | TR2-GC9 | Lower GC walk | AACAGCAUAGCAAGUUAGAAUAAGGCUAGUCCGUUAUCAACUUGAAAAAGUGGCACCGAGUCGGUGCUUUU |
| 227 | TR000148 | TR2-GC10 | Lower GC walk | AACAGCAUAGCAAGUUGAAAUAAGGCUAGUCCGUUAUCAACUUGAAAAAGUGGCACCGAGUCGGUGCUUUU |
| sgRNA | | | | |
| 228 | G000209 | | | mC*mC*mA*GUCCAGCGAGGCAAAGGGUUUUAGAGCUAGAAAUAGCAAGUUAAAAUAAGGCUAGUCCGUUAUCAACUUGAAAAAGUGGCACCGAGUCGGUGCmU*mU*U |
| 229 | G000262 | G209-1 | hairpin 2 | mC*mC*mA*GUCCAGCGAGGCAAAGGGUUUUAGAGCUAGAAAUAGCAAGUUAAAAUAAGGCUAGUCCGUUAUCAACUUGAAAAAGUmGmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 230 | G000263 | G209-2 | hairpins | mC*mC*mA*GUCCAGCGAGGCAAAGGGUUUUAGAGCUAGAAAUAGCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 231 | G000264 | G209-3 | tetra-loop | mC*mC*mA*GUCCAGCGAGGCAAAGGGUUUUAGAGCUAmGmAmAmAUAGCAAGUUAAAAUAAGGCUAGUCCGUUAUCAACUUGAAAAAGUGGCACCGAGUCGGUGCmU*mU*mU*U |
| 232 | G000265 | G209-4 | upper | mC*mC*mA*GUCCAGCGAGGCAAAGGGUUUUAGAmGmCmUmAGAAAmUmAmGmCAAGUUAAAAUAAGGCUAGUCCGUUAUCAACUUGAAAAAGUGGCACCGAGUCGGUGCmU*mU*mU*U |
| 233 | G000266 | G209-5 | upper and loop | mC*mC*mA*GUCCAGCGAGGCAAAGGGUUUUAGAmGmCmUmAmGmAmAmAmUmAmGmCAAGUUAAAAUAAGGCUAGUCCGUUAUCAACUUGAAAAGUGGCACCGAGUCGGUGCmU*mU*mU*U |
| 234 | G000267 | G209-6 | upper, loop, hairpins | mC*mC*mA*GUCCAGCGAGGCAAAGGGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 235 | G000262-mod only | G209-1-mod only | hairpin 2 | GUUUUAGAGCUAGAAAUAGCAAGUUAAAAUAAGGCUAGUCCGUUAUCAACUUGAAAAAGUmGmGmCmAmCmCmGmAmGmUmCmGmGmUmGmCmU*mU*mU*mU |
| 236 | G000263-mod only | G209-2-mod only | hairpins | GUUUUAGAGCUAGAAAUAGCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 237 | G000264-mod only | G209-3-mod only | tetra-loop | GUUUUAGAGCUAmGmAmAmAUAGCAAGUUAAAAUAAGGCUAGUCCGUUAUCAACUUGAAAAAGUGGCACCGAGUCGGUGCmU*mU*mU*U |
| 238 | G000265-mod only | G209-4-mod only | upper | GUUUUAGAmGmCmUmAGAAAmUmAmGmCAAGUUAAAAUAAGGCUAGUCCGUUAUCAACUUGAAAAAGUGGCACCGAGUCGGUGCmU*mU*mU*U |
| 239 | G000266-mod only | G209-5-mod only | upper and loop | GUUUUAGAmGmCmUmAmGmAmAmAmUmAmGmCAAGUUAAAAUAAGGCUAGUCCGUUAUCAACUUGAAAAAGUGGCACCGAGUCGGUGCmU*mU*mU*U |
| 240 | G000267-mod only | G209-6-mod only | upper, loop, hairpins | GUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 241 | G000211 | | end mod | mU*mU*mA*CAGCCACGUCUACAGCAGUUUUAGAGCUAGAAAUAGCAAGUUAAAAUAAGGCUAGUCCGUUAUCAACUUGAAAAAGUGGCACCGAGUCGGUGCmU*mU*mU*U |
| 242 | G000282 | | mod6 | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 243 | G000201 | | unmod | UUACAGCCACGUCUACAGCAGUUUUAGAGCUAGAAAUAGCAAGUUAAAAUAAGGCUAGUCCGUUAUCAACUUGAAAAAGUGGCACCGAGUCGGUGCUUUU |
| 244 | G000331 | G211-7 | lower cr | mU*mU*mA*CAGCCACGUCUACAGCAmGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 245 | G000332 | G211-8 | lower cr | mU*mU*mA*CAGCCACGUCUACAGCAfGfUfUfUfUfAGAmGmCmUmAmGmAmAmAmUmAmGmCAAGUUAAAAUAAGGCUAGUCCGUUAUCAmCmUmUmGmAmAmAmAmGmUmGmGmCmAmCmCmGmAmGmUmCmGmGmUmGmCmU*mU*mU*mU |
| 246 | G000333 | G211-9 | lower cr | mU*mU*mA*CAGCCACGUCUACAGCAmGfUfUfUfUmAGAmGmCmUmAmGmAmAmAmUmAmGmCAAGUUAAAAUAAGGCUAGUCCGUUAUCAmCmUmUmGmAmAmAmAmGmUmGmGmCmAmCmCmGmAmGmUmCmGmGmUmGmCmU*mU*mU*mU |
| 247 | G000334 | G211-10 | lower tr | mU*mU*mA*CAGCCACGUCUACAGCAGUUUUAGAmGmCmUmAmGmAmAmAmUmAmGmCAAGUmUmAmAAAmUAAGGCUAGUCCGUUAUCAmA |

TABLE 4-continued

| SEQ ID NO | Name | Alias | Description | Sequence |
|---|---|---|---|---|
| | | | | mCmUmUmGmAmAmAmAmAmGmUmGmGmCmAmCmCmGmAmGmUm CmGmGmUmGmCmU*mU*mU*mU |
| 248 | G000335 | G211-11 | lower tr | mU*mU*mA*CAGCCACGUCUACAGCAGUUUUAGAmGmCmUmAmGmA mAmAmUmAmGmCAAGUmUmAfAfAmAmUAAGGCUAGUCCGUUAUCA mAmCmUmGmAmAmAmAmAmGmUmGmGmCmAmCmCmGmAmGmU mCmGmGmUmGmCmU*mU*mU*mU |
| 249 | G000336 | G211-12 | lower tr | mU*mU*mA*CAGCCACGUCUACAGCAGUUUUAGAmGmCmUmAmGmA mAmAmUmAmGmCAAGUfUmAfAmAfAmAmUAAGGCUAGUCCGUUAUCA mAmCmUmGmAmAmAmAmAmGmUmGmGmCmAmCmCmGmAmGmUmC mGmGmUmGmCmU*mU*mU*mU |
| 250 | G000337 | G211-13 | lower all | mU*mU*mA*CAGCCACGUCUACAGCAmGUUUUmAGAmGmCmUmAmG mAmAmAmUmAmGmCAAGUmUmAAAmAmUAAGGCUAGUCCGUUAUCA mAmCmUmGmAmAmAmAmAmGmUmGmGmCmAmCmCmGmAmG mUmCmGmGmUmGmCmU*mU*mU*mU |
| 251 | G000338 | G211-14 | lower all | mU*mU*mA*CAGCCACGUCUACAGCAmGUUUUmAGAmGmCmUmAmG mAmAmAmUmAmGmCAAGUmUmAfAfAmAmUAAGGCUAGUCCGUUAU CAmAmCmUmGmAmAmAmAmAmGmUmGmGmCmAmCmCmGmAm GmUmCmGmGmUmGmCmU*mU*mU*mU |
| 252 | G000339 | G211-15 | lower all | mU*mU*mA*CAGCCACGUCUACAGCAmGUUUUmAGAmGmCmUmAmG mAmAmAmUmAmGmCAAGUfUmAfAmAfAmAmUAAGGCUAGUCCGUUAU CAmAmCmUmGmAmAmAmAmAmGmUmGmGmCmAmCmCmGmAm GmUmCmGmGmUmGmCmU*mU*mU*mU |
| 253 | G000340 | G211-16 | lower all | mU*mU*mA*CAGCCACGUCUACAGCAfGfUfUfUfUfAGAmGmCmU mAmGmAmAmAmUmAmGmCAAGUmUmAAAmAmUAAGGCUAGUCCGUU AUCAmAmCmUmGmAmAmAmAmAmGmUmGmGmCmAmCmCmGmAmG mUmCmGmGmUmGmCmU*mU*mU*mU |
| 254 | G000341 | G211-17 | lower all | mU*mU*mA*CAGCCACGUCUACAGCAfGfUfUfUfUfAGAmGmCmU mAmGmAmAmAmUmAmGmCAAGUmUmAfAfAmAmUAAGGCUAGUCCG UUAUCAmAmCmUmGmAmAmAmAmAmGmUmGmGmCmAmCmCmGmA mGmUmCmGmGmUmGmCmU*mU*mU*mU |
| 255 | G000342 | G211-18 | lower all | mU*mU*mA*CAGCCACGUCUACAGCAfGfUfUfUfUfAGAmGmCmU mAmGmAmAmAmUmAmGmCAAGUfUmAfAmAfAmAmUAAGGCUAGUCCG UUAUCAmAmCmUmGmAmAmAmAmAmGmUmGmGmCmAmCmCmGmA mGmUmCmGmGmUmGmCmU*mU*mU*mU |
| 256 | G000343 | G211-19 | Bulge cr | mU*mU*mA*CAGCCACGUCUACAGCAGUUUAmGmAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUmC mGmGmUmGmCmU*mU*mU*mU |
| 257 | G000344 | G211-20 | Bulge tr | mU*mU*mA*CAGCCACGUCUACAGCAGUUUUAGAmGmCmUmAmGmA mAmAmUmAmGmCmAmAmGmUUAAAAUAAGGCUAGUCCGUUAUCAmA mCmUmUmGmAmAmAmAmAmGmUmGmGmCmAmCmCmGmAmGmUm CmGmGmUmGmCmU*mU*mU*mU |
| 258 | G000345 | G211-21 | nexus | mU*mU*mA*CAGCCACGUCUACAGCAGUUUUAGAmGmCmUmAmGmA mAmAmUmAmGmCAAGUUAAAAUAAGGCUAGUCCGUUfAfUfCfAmA mCmUmUmGmAmAmAmAmAmGmUmGmGmCmAmCmCmGmAmGmUmCmG mGmUmGmCmU*mU*mU*mU |
| 259 | G000346 | G211-22 | nexus | mU*mU*mA*CAGCCACGUCUACAGCAGUUUUAGAmGmCmUmAmGmA mAmAmUmAmGmCAAGUUAAAAUAAGGCUAGUCCGUUAmUmCmAmAm CmUmUmGmAmAmAmAmAmGmUmGmGmCmAmCmCmGmAmGmUmC mGmGmUmGmCmU*mU*mU*mU |
| 260 | G000347 | G211-23 | lower all | mU*mU*mA*CAGCCACGUCUACAGCAfGfUfUfUfUfAmGmAmGmC mUmAmGmAmAmAmUmAmGmCmAmAmGmUmUmAfAfAmAmUAAGGCU AGUCCGUUAmUmCmAmAmCmUmUmGmAmAmAmAmAmGmUmGmGmCm AmCmCmGmAmGmUmCmGmGmUmGmCmU*mU*mU*mU |
| 261 | G000348 | G211-24 | no PS | mUmUmACAGCCACGUCUACAGCAGUUUUAGAmGmCmUmAmGmAmAm AmUmAmGmCAAGUUAAAAUAAGGCUAGUCCGUUAUCAmAmCmUmUm GmAmAmAmAmAmGmUmGmGmCmAmCmCmGmAmGmUmCmGmGm UmGmCmUmUmUmU |
| 262 | G000349 | G211-25 | 2 OMe PS | mU*mU*ACAGCCACGUCUACAGCAGUUUUAGAmGmCmUmAmGmAmA mGmAmAmAmAmAmGmUmGmGmCmAmCmCmGmAmGmUmCmGmG mUmGmCmU*mU*mU |

TABLE 4-continued

| SEQ ID NO | Name | Alias | Description | Sequence |
|---|---|---|---|---|
| 263 | G000350 | G211-26 | 2'F hairpin | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGfUfCfGfGfUfGfCfU*fU*fU*mU |
| 264 | G000351 | G211-27 | Alt hairpin | mU*mU*mA*CAGCCACGUCUACAGCAGUUUUAGAmGmCmUmAmGmAmAmAmUmAmGmCAAGUUAAAAUAAGGCUAGUCCGUUAUCAfUmUfGmAfAmAfAmUfGmUfGmGfCmAfCmCfGmAfGmUfCmGfGmUfGmCfU*mU*fU*mU |
| 265 | G000331-mod only | G211-7-mod only | lower cr | mGUUUUmAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 266 | G000332-mod only | G211-8-mod only | lower cr | fGfUfUfUfUfAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 267 | G000333-mod only | G211-9-mod only | lower cr | mGfUfUfUmAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 268 | G000334-mod only | G211-10-mod only | lower tr | GUUUUAGAmGmCmUmAmGmAmAmAmUmAmGmCAAGUmUmAAAmAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 269 | G000335-mod only | G211-11-mod only | lower tr | GUUUUAGAmGmCmUmAmGmAmAmAmUmAmGmCAAGUmUmAfAfAmAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 270 | G000336-mod only | G211-12-mod only | lower tr | GUUUUAGAmGmCmUmAmGmAmAmAmUmAmGmCAAGUfUmAfAmAfAmUAAGGCUAGUCCGUUAUCAmAmCmUmUmGmAmAmAmAmGmU |
| 271 | G000337-mod only | G211-13-mod only all | lower | mGUUUUmAGAmGmCmUmAmGmAmAmAmUmAmGmCAAGUmUmAAAmAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 272 | G000338-mod only | G211-14-mod only all | lower | mGUUUUmAGAmGmCmUmAmGmAmAmAmUmAmGmCAAGUmUmAfAfAmAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 273 | G000339-mod only | G211-15-mod only all | lower | mGUUUUmAGAmGmCmUmAmGmAmAmAmUmAmGmCAAGUfUmAfAmAfAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 274 | G000340-mod only | G211-16-mod only all | lower | fGfUfUfUfUfAGAmGmCmUmAmGmAmAmAmUmAmGmCAAGUmUmAAAmAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 275 | G000341-mod only | G211-17-mod only all | lower | fGfUfUfUfUfAGAmGmCmUmAmGmAmAmAmUmAmGmCAAGUmUmAfAfAmAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 276 | G000342-mod only | G211-18-mod only all | lower | fGfUfUfUfUfAGAmGmCmUmAmGmAmAmAmUmAmGmCAAGUfUmAfAmAfAmUAAGGCUAGUCCGUUAUCAmAmCmUmUmGmAmAmAmAmGmUmGmGmCmAmCmCmGmAmGmUmCmGmGmUmGmCmU*mU*mU*mU |
| 277 | G000343-mod only | G211-19-mod only | Bulge cr | GUUUUAmGmAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 278 | G000344-mod only | G211-20-mod only | Bulge tr | GUUUUAGAmGmCmUmAmGmAmAmAmUmAmGmCmAmAmGmUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 279 | G000345-mod only | G211-21-mod only | nexus | GUUUUAGAmGmCmUmAmGmAmAmAmUmAmGmCAAGUUAAAAUAAGGCUAGUCCGUUfAfUfCfAmAmCmUmUmGmAmAmAmAmGmUmGmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 280 | G000346-mod only | G211-22-mod only | nexus | GUUUUAGAmGmCmUmAmGmAmAmAmUmAmGmCAAGUUAAAAUAAG GCUAGUCCGUUAmUmCmAmAmCmUmUmGmAmAmAmAmAmGmUmG mGmCmAmCmCmGmAmGmUmCmGmGmUmGmCmU*mU*mU*mU |
| 281 | G000347-mod only | G211-23-mod only | lower all | fGfUfUfUfUfAmGmAmGmCmUmAmGmAmAmAmUmAmGmCmAmAmG mUmUmAfAfAmUAAGGCUAGUCCGUUAmUmCmAmAmCmUmUmG mAmAmAmAmGmUmGmGmCmAmCmCmGmAmGmUmCmGmGmU mGmCmU*mU*mU*mU |
| 282 | G000348-mod only | G211-24-mod only | no PS | GUUUUAGAmGmCmUmAmGmAmAmAmUmAmGmCAAGUUAAAAUAAG GCUAGUCCGUUAUCAmAmCmUmUmGmAmAmAmAmAmGmUmGmGm CmAmCmCmGmAmGmUmCmGmGmUmGmCmUmUmUmU |
| 283 | G000349-mod only | G211-25-mod only | 2 OMe PS | GUUUUAGAmGmCmUmAmGmAmAmAmUmAmGmCAAGUUAAAAUAAG GCUAGUCCGUUAUCAmAmCmUmUmGmAmAmAmAmAmGmUmGmGm CmAmCmCmGmAmGmUmCmGmGmUmGmCmCmUmU*mU*mU |
| 284 | G000350-mod only | G211-26-mod only | 2'F hairpin | GUUUUAGAmGmCmUmAmGmAmAmAmUmAmGmCAAGUUAAAAUAAG GCUAGUCCGUUAUCAmAmCmUmUmGmAmAmAmAmAmGmUmGmGm CmAmCmCmGmAmGfUfCfGfGfUfGfCfU*fU*fU*mU |
| 285 | G000351-mod only | G211-27-mod only | Alt hairpin | GUUUUAGAmGmCmUmAmGmAmAmAmUmAmGmCAAGUUAAAAUAAG GCUAGUCCGUUAUCAfAmCfUmUfGmAfAmAfAmAfGmUfGmGfCm AfCmCfGmAfGmUfCmGfGmUfGmCfU*mU*fU*mU |
| 286 | G000208 | | end mod | mC*mA*mG*GGCUCUUGAAGAUCUCCGUUUUAGAGCUAGAAAUAGC AAGUUAAAAUAAGGCUAGUCCGUUAUCAACUUGAAAAAGUGGCACC GAGUCGGUGCmU*mU*mU*U |
| 287 | G000373 | | mod6 | mC*mA*mG*GGCUCUUGAAGAUCUCCGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGmUmCmG mGmUmGmCmU*mU*mU*mU |
| 288 | G000352 | G208-7 | lower cr | mC*mA*mG*GGCUCUUGAAGAUCUCCmGUUUUmAGAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUmC mGmGmUmGmCmU*mU*mU*mU |
| 289 | G000353 | G208-8 | lower cr | mC*mA*mG*GGCUCUUGAAGAUCUCCfGfUfUfUfUfAGAmGmCmU mAmGmAmAmAmUmAmGmCAAGUUAAAAUAAGGCUAGUCCGUUAUCA mAmCmUmUmGmAmAmAmAmAmGmUmGmGmCmAmCmCmGmAmGmUmC mGmGmUmGmCmU*mU*mU*mU |
| 290 | G000354 | G208-9 | lower cr | mC*mA*mG*GGCUCUUGAAGAUCUCCmGfUfUfUfUmAGAmGmCmU mAmGmAmAmAmUmAmGmCAAGUUAAAAUAAGGCUAGUCCGUUAUCA mAmCmUmUmGmAmAmAmAmAmGmUmGmGmCmAmCmCmGmAmGmU mCmGmGmUmGmCmU*mU*mU*mU |
| 291 | G000355 | G208-10 | lower tr | mC*mA*mG*GGCUCUUGAAGAUCUCCGUUUUAGAmGmCmUmAmGmA mAmAmUmAmGmCAAGUmUmAAAmUAAGGCUAGUCCGUUAUCAmA mCmUmUmGmAmAmAmAmAmGmUmGmGmCmAmCmCmGmAmGmU mCmGmGmUmGmCmU*mU*mU*mU |
| 292 | G000356 | G208-11 | lower tr | mC*mA*mG*GGCUCUUGAAGAUCUCCGUUUUAGAmGmCmUmAmGmA mAmAmUmAmGmCAAGUmUmAfAfAmUAAGGCUAGUCCGUUAUCA mAmCmUmUmGmAmAmAmAmAmGmUmGmGmCmAmCmCmGmAmGm UmCmGmGmUmGmCmU*mU*mU*mU |
| 293 | G000357 | G208-12 | lower tr | mC*mA*mG*GGCUCUUGAAGAUCUCCGUUUUAGAmGmCmUmAmGmA mAmAmUmAmGmCAAGUfUmAfAmAfAmUAAGGCUAGUCCGUUAUCA mAmCmUmUmGmAmAmAmAmAmGmUmGmGmCmAmCmCmGmAmGm UmCmGmGmUmGmCmU*mU*mU*mU |
| 294 | G000358 | G208-13 | lower all | mC*mA*mG*GGCUCUUGAAGAUCUCCmGUUUUmAGAmGmCmUmAmG mAmAmAmUmAmGmCAAGUmUmAAAmUAAGGCUAGUCCGUUAUCA mAmCmUmUmGmAmAmAmAmAmGmUmGmGmCmAmCmCmGmAmG mUmCmGmGmUmGmCmU*mU*mU*mU |
| 295 | G000359 | G208-14 | lower all | mC*mA*mG*GGCUCUUGAAGAUCUCCmGUUUUmAGAmGmCmUmAmG mAmAmAmUmAmGmCAAGUmUmAfAfAmUAAGGCUAGUCCGUUAU CAmAmCmUmUmGmAmAmAmAmAmGmUmGmGmCmAmCmCmGmAm GmUmCmGmGmUmGmCmU*mU*mU*mU |

TABLE 4-continued

| SEQ ID NO | Name | Alias | Description | Sequence |
|---|---|---|---|---|
| 296 | G000360 | G208-15 | lower all | mC*mA*mG*GGCUCUUGAAGAUCUCCmGUUUUmAGAmGmCmUmAmG mAmAmAmUmAmGmCAAGUfUmAfAmAfAmUAAGGCUAGUCCGUUAU CAmAmCmUmUmGmAmAmAmAmAmGmUmGmGmCmAmCmCmGmAm GmUmCmGmGmUmGmCmU*mU*mU*mU |
| 297 | G000361 | G208-16 | lower all | mC*mA*mG*GGCUCUUGAAGAUCUCCfGfUfUfUfUfAGAmGmCmU mAmGmAmAmAmUmAmGmCAAGUmUmAAAmAmUAAGGCUAGUCCGUU AUCAmAmCmUmUmGmAmAmAmAmAmGmUmGmGmCmAmCmCmGmAm GmUmCmGmGmUmGmCmU*mU*mU*mU |
| 298 | G000362 | G208-17 | lower all | mC*mA*mG*GGCUCUUGAAGAUCUCCfGfUfUfUfUfAGAmGmCmU mAmGmAmAmAmUmAmGmCAAGUmUmAfAfAmAfAmUAAGGCUAGUCCG UUAUCAmAmCmUmUmGmAmAmAmAmAmGmUmGmGmCmAmCmCmGmA mGmUmCmGmGmUmGmCmU*mU*mU*mU |
| 299 | G000363 | G208-18 | lower all | mC*mA*mG*GGCUCUUGAAGAUCUCCfGfUfUfUfUfAGAmGmCmU mAmGmAmAmAmUmAmGmCAAGUfUmAfAmAfAmUAAGGCUAGUCCG UUAUCAmAmCmUmUmGmAmAmAmAmAmGmUmGmGmCmAmCmCmGmA mGmUmCmGmGmUmGmCmU*mU*mU*mU |
| 300 | G000364 | G208-19 | Bulge cr | mC*mA*mG*GGCUCUUGAAGAUCUCCGUUUUmAmGmAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUmC mGmGmUmGmCmU*mU*mU*mU |
| 301 | G000365 | G208-20 | Bulge tr | mC*mA*mG*GGCUCUUGAAGAUCUCCGUUUUAGAmGmCmUmAmGmA mAmAmUmAmGmCmAmAmGmUUAAAAUAAGGCUAGUCCGUUAUCAmA mCmUmUmGmAmAmAmAmAmGmUmGmGmCmAmCmCmGmAmGmU mCmGmGmUmGmCmU*mU*mU*mU |
| 302 | G000366 | G208-21 | nexus | mC*mA*mG*GGCUCUUGAAGAUCUCCGUUUUAGAmGmCmUmAmGmA mAmAmUmAmGmCAAGUUAAAAUAAGGCUAGUCCGUUfAfUfCfAmA mCmUmUmGmAmAmAmAmAmGmUmGmGmCmAmCmCmGmAmGmUmC mGmGmUmGmCmU*mU*mU*mU |
| 303 | G000367 | G208-22 | nexus | mC*mA*mG*GGCUCUUGAAGAUCUCCGUUUUAGAmGmCmUmAmGmA mAmAmUmAmGmCAAGUUAAAAUAAGGCUAGUCCGUUAmUmCmAmAm CmUmUmGmAmAmAmAmAmGmUmGmGmCmAmCmCmGmAmGmUm CmGmGmUmGmCmU*mU*mU*mU |
| 304 | G000368 | G208-23 | lower all | mC*mA*mG*GGCUCUUGAAGAUCUCCfGfUfUfUfUfAmGmAmGmC mUmAmGmAmAmAmUmAmGmCmAmAmGmUmUmAfAfAmAmUAAGGCU AGUCCGUUAmUmCmAmAmCmUmUmGmAmAmAmAmAmGmUmGmGmC mAmCmCmGmAmGmUmCmGmGmUmGmCmU*mU*mU*mU |
| 305 | G000369 | G208-24 | no PS | mCmAmGGGCUCUUGAAGAUCUCCGUUUUAGAmGmCmUmAmGmAmA mAmUmAmGmCAAGUUAAAAUAAGGCUAGUCCGUUAUCAmAmCmUmU mGmAmAmAmAmAmGmUmGmGmCmAmCmCmGmAmGmUmCmGmG mUmGmCmUmUmU |
| 306 | G000370 | G208-25 | 2 OMe PS | mC*mAG*GGCUCUUGAAGAUCUCCGUUUUAGAmGmCmUmAmGmAmA mAmUmAmGmCAAGUUAAAAUAAGGCUAGUCCGUUAUCAmAmCmUmU mGmAmAmAmAmAmGmUmGmGmCmAmCmCmGmAmGmUmCmGmG mUmGmCmUmU*mU*mU |
| 307 | G000371 | G208-26 | 2'F hairpin | mC*mA*mG*GGCUCUUGAAGAUCUCCGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGfUfCfGfGfU fGfCfU*fU*fU*mU |
| 308 | G000372 | G208-27 | Alt hairpin | mC*mA*mG*GGCUCUUGAAGAUCUCCGUUUUAGAmGmCmUmAmGmA mAmAmUmAmGmCAAGUUAAAAUAAGGCUAGUCCGUUAUCAfAmCfU mUfGmAfAmAfAmAfGmUfGmGfCmAfCmCfGmAfGmUfCmGfGmU fGmCfU*mU*fU*mU |
| 309 | G000352-mod only | G208-7-mod only | lower cr | mGUUUUmAGAmGmCmUmAmGmAmAmAmUmAmGmCAAGUUAAAAU AAGGCUAGUCCGUUAUCAmAmCmUmUmGmAmAmAmAmAmGmUmG mGmCmAmCmCmGmAmGmUmCmGmGmUmGmCmU*mU*mU*mU |
| 310 | G000353-mod only | G208-8-mod only | lower cr | fGfUfUfUfUfAGAmGmCmUmAmGmAmAmAmUmAmGmCAAGUUAAA AAGGCUAGUCCGUUAUCAmAmCmUmUmGmAmAmAmAmAmGmUmG AUmGmCmAmCmCmGmAmGmUmCmGmGmUmGmCmU*mU*mU*mU |
| 311 | G000354-mod only | G208-9-mod only | lower cr | mGfUfUfUfUmAGAmGmCmUmAmGmAmAmAmUmAmGmCAAGUUAAA AUAAGGCUAGUCCGUUAUCAmAmCmUmUmGmAmAmAmAmAmGmUm GmGmCmAmCmCmGmAmGmUmCmGmGmUmGmCmU*mU*mU*mU |

TABLE 4-continued

| SEQ ID NO | Name | Alias | Description | Sequence |
|---|---|---|---|---|
| 312 | G000355-mod only | G208-10-mod only | lower tr | GUUUUAGAmGmCmUmAmGmAmAmAmUmAmGmCAAGUmUmAAAmAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 313 | G000356-mod only | G208-11-mod only | lower tr | GUUUUAGAmGmCmUmAmGmAmAmAmUmAmGmCAAGUmUmAfAfAmAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 314 | G000357-mod only | G208-12-mod only | lower tr | GUUUUAGAmGmCmUmAmGmAmAmAmUmAmGmCAAGUfUmAfAmAfAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 315 | G000358-mod only | G208-13-mod only | lower all | mGUUUUmAGAmGmCmUmAmGmAmAmAmUmAmGmCAAGUmUmAAAmAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 316 | G000359-mod only | G208-14-mod only | lower all | mGUUUUmAGAmGmCmUmAmGmAmAmAmUmAmGmCAAGUmUmAfAfAmAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 317 | G000360-mod only | G208-15-mod only | lower all | mGUUUUmAGAmGmCmUmAmGmAmAmAmUmAmGmCAAGUfUmAfAmAfAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 318 | G000361-mod only | G208-16-mod only | lower all | fGfUfUfUfUfAGAmGmCmUmAmGmAmAmAmUmAmGmCAAGUmUmAAAmAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 319 | G000362-mod only | G208-17-mod only | lower all | fGfUfUfUfUfAGAmGmCmUmAmGmAmAmAmUmAmGmCAAGUmUmAfAfAmAmUAAGGCUAGUCCGUUAUCAmCmUmUmGmAmAmAmAmAmGmmGmUmGmGmCmAmCmCmGmAmGmUmCmGmGmUmGmGmCmU*mU*mU*mU |
| 320 | G000363-mod only | G208-18-mod only | lower all | fGfUfUfUfUfAGAmGmCmUmAmGmAmAmAmUmAmGmCAAGUfUmAfAmAfAmUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 321 | G000364-mod only | G208-19-Bulge mod only | cr | GUUUUAmGmAmGmCmUmAmGmAmAmAmUmAmGmCAAGUUAAAAUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 322 | G000365-mod only | G208-20-Bulge mod only | tr | GUUUUAGAmGmCmUmAmGmAmAmAmUmAmGmCmAmAmGmUUAAAAUAAGGCUAGUCCGUUAUCAmCmUmUmGmAmAmAmAmAmGmUmGmGmCmAmCmCmGmAmGmUmCmGmGmUmGmGmCmU*mU*mU*mU |
| 323 | G000366-mod only | G208-21-nexus mod only | | GUUUUAGAmGmCmUmAmGmAmAmAmUmAmGmCAAGUUAAAAUAAGGCUAGUCCGUUfAfUfCfAmAmCmUmUmGmAmAmAmAmAmGmUmGmGmCmAmCmCmGmAmGmUmCmGmGmUmGmGmCmU*mU*mU*mU |
| 324 | G000367-mod only | G208-22-nexus mod only | | GUUUUAGAmGmCmUmAmGmAmAmAmUmAmGmCAAGUUAAAAUAAGGCUAGUCCGUUAmUmCmAmCmUmUmGmAmAmAmAmAmGmUmGmGmCmAmCmCmGmAmGmUmCmGmGmUmGmGmCmU*mU*mU*mU |
| 325 | G000368-mod only | G208-23-mod only | lower all | fGfUfUfUfUfAmGmAmGmCmUmAmGmAmAmAmUmAmGmCmAmAmGmUmUmAfAfAmAmUAAGGCUAGUCCGUUAmUmCmAmAmCmUmUmGmAmAmAmAmAmGmUmGmGmCmAmCmCmGmAmGmUmCmGmGmUmCmGmGmUmGmGmCmU*mU*mU*mU |
| 326 | G000369-mod only | G208-24-no PS mod only | | GUUUUAGAmGmCmUmAmGmAmAmAmUmAmGmCAAGUUAAAAUAAGGCUAGUCCGUUAUCAmCmUmUmGmAmAmAmAmAmGmUmGmGmCmAmCmCmGmAmGmUmCmGmGmUmGmGmCmUmUmUmU |
| 327 | G000370-mod only | G208-25-2 OMe PS mod only | | GUUUUAGAmGmCmUmAmGmAmAmAmUmAmGmCAAGUUAAAAUAAGGCUAGUCCGUUAUCAmCmUmUmGmAmAmAmAmAmGmUmGmGmCmAmCmCmGmAmGmUmCmGmGmUmGmGmCmUmU*mU*mU |
| 328 | G000371-mod only | G208-26-2'F mod only | hairpin | GUUUUAGAmGmCmUmAmGmAmAmAmUmAmGmCAAGUUAAAAUAAGGCUAGUCCGUUAUCAmCmUmUmGmAmAmAmAmAmGmUmGmGmCmAmCmCmGmAmGfUfCfGfUfGfCfU*fU*fU*mU |

TABLE 4-continued

| SEQ ID NO | Name | Alias | Description | Sequence |
|---|---|---|---|---|
| 329 | G000372-mod only | G208-27-mod only | Alt hairpin | GUUUUAGAmGmCmUmAmGmAmAmAmUmAmGmCAAGUUAAAAUAAG GCUAGUCCGUUAUCAfAmCfUmUfGmAfAmAfAmAfGmUfGmGfCm AfCmCfGmAfGmUfCmGfGmUfGmCfU*mU*fU*mU |
| 330 | G000269 | | end mod | mC*mC*mC*AUACUCCUACAGCACCAGUUUUAGAGCUAGAAAUAGC AAGUUAAAAUAAGGCUAGUCCGUUAUCAACUUGAAAAAGUGGCACC GAGUCGGUGCmU*mU*mU*U |
| 331 | G000283 | | mod6 | mC*mC*mC*AUACUCCUACAGCACCAGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGmUmCmGm GmUmGmCmU*mU*mU*mU |
| 332 | G000285 | | unmod | CCCAUACUCCUACAGCACCAGUUUUAGAGCUAGAAAUAGCAAGUUA AAAUAAGGCUAGUCCGUUAUCAACUUGAAAAAGUGGCACCGAGUCG GUGCUUUU |
| 342 | G000537 | G211-33 | 5'end 3xOMePS | mU*mU*mA*CAGCCACGUCUACAGCAGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGmUmCm GmGmUmGmCmUmUmU |
| 343 | G000538 | G211-34 | 3'end 3xOMePS | mUmUmACAGCCACGUCUACAGCAGUUUUAGAmGmCmUmAmGmAmA mAmUmAmGmCAAGUUAAAAUAAGGCUAGUCCGUUAUCAmAmCmUm UmGmAmAmAmAmAmGmUmGmGmCmAmCmCmGmAmGmUmCmG mGmUmGmCmU*mU*mU*mU |
| 344 | G000539 | G211-35 | 5xOMePS | mU*mU*mA*mC*mA*GCCACGUCUACAGCAGUUUUAGAmGmCmUmA mGmAmAmAmUmAmGmCAAGUUAAAAUAAGGCUAGUCCGUUAUCAm AmCmUmUmGmAmAmAmAmAmGmUmGmGmCmAmCmCmGmAmGm UmCmGmGmUmG*mC*mU*mU*mU*mU |
| 345 | G000541 | G211-37 | 3xOMePS + 2PS | mU*mU*mA*C*A*GCCACGUCUACAGCAGUUUUAGAmGmCmUmAmG mAmAmAmUmAmGmCAAGUUAAAAUAAGGCUAGUCCGUUAUCAmAmC mUmGmAmAmAmAmAmGmUmGmGmCmAmCmCmGmAmGmUmCm GmGmUmG*mC*mU*mU*mU*mU |
| 346 | G000542 | G211-38 | 3xOMePS + 7PS | mU*mU*mA*C*A*G*C*C*A*C*GUCUACAGCAGUUUUAGAmGmCm UmAmGmAmAmAmUmAmGmCAAGUUAAAAUAAGGCUAGUCCGUUAUC AmAmCmUmUmGmAmAmAmAmAmGmUmGmGmCmAmCmCmGmAmG mU*mC*mG*mG*mU*mG*mC*mU*mU*mU*mU |
| 347 | G000543 | G211-39 | invd abasic | (invd)UUACAGCCACGUCUACAGCAGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmGmAmGmUmCmG mGmUmGmCmUmUmUmU(invd) |
| 348 | G000544 | G211-40 | invd abasic + 3xOMePS | (invd)mU*mU*mA*CAGCCACGUCUACAGCAGUUUUAGAmGmCmU mAmGmAmAmAmUmAmGmCAAGUUAAAAUAAGGCUAGUCCGUUAUCA mCmUmUmGmAmAmAmAmAmGmUmGmGmCmAmCmCmGmAmGmC UmCmGmGmUmGmCmU*mU*mU*mU(invd) |
| 349 | G000564 | G211-42 | 3xMOE-PS | moeU*moeU*moeA*CAGCCACGUCUACAGCAGUUUUAGAmGmCmU mAmGmAmAmAmUmAmGmCAAGUUAAAAUAAGGCUAGUCCGUUAUCA mAmCmUmUmGmAmAmAmAmAmGmUmGmGmCmAmCmCmGmAmGmUmC mGmGmUmGmCmoeU*moeU*moeU*mU |
| 350 | G000545 | G211-43 | US loop PS | mU*mU*mA*CAGCCACGUCUACAGCAGUUUUAGAmGmCmUmA*mG* mA*mA*mA*mUmAmGmCAAGUUAAAAUAAGGCUAGUCCGUUAUCAm AmCmUmUmGmAmAmAmAmAmGmUmGmGmCmAmCmCmGmAmGm UmCmGmGmUmGmCmU*mU*mU*mU |
| 351 | G000546 | G211-44 | H1 loop PS | mU*mU*mA*CAGCCACGUCUACAGCAGUUUUAGAmGmCmUmAmGmA mAmAmUmAmGmCAAGUUAAAAUAAGGCUAGUCCGUUAUCAmAmCmU mU*mG*mA*mA*mA*mAmAmGmUmGmGmCmAmCmCmGmAmGmU mCmGmGmUmGmCmU*mU*mU*mU |
| 352 | G000547 | G211-45 | H2 loop PS | mU*mU*mA*CAGCCACGUCUACAGCAGUUUUAGAmGmCmUmAmGmA mAmAmUmAmGmCAAGUUAAAAUAAGGCUAGUCCGUUAUCAmAmCmU mUmGmAmAmAmAmAmGmUmGmGmCmAmCmCmG*mA*mG*mU* mCmGmGmUmGmCmU*mU*mU*mU |
| 353 | G000548 | G211-46 | all loops PS | mU*mU*mA*CAGCCACGUCUACAGCAGUUUUAGAmGmCmUmA*mG* mA*mA*mA*mUmAmGmCAAGUUAAAAUAAGGCUAGUCCGUUAUCAm AmCmU*mG*mA*mA*mA*mAmAmGmUmGmGmCmAmCmCmG* mA*mG*mU*mCmGmGmUmGmCmU*mU*mU*mU |

TABLE 4-continued

| SEQ ID NO | Name | Alias | Description | Sequence |
|---|---|---|---|---|
| 354 | | | Mod6 (with modifications not shown in sequence listing) | mN*mN*mN*NNNNNNNNNNNNNNNNNGUUUUAGAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUm CmGmGmUmGmCmU*mU*mU*mU N = any nucleotide |
| 355 | | | Invariable region only | GUUUUAGAGCUAGAAAUAGCAAGUUAAAAUAAGGCUAGUCCGUUAU CAACUUGAAAAAGUGGCACCGAGUCGGUGCUUUU |
| 356 | | | Mod6 pattern; invariable region only | GUUUUAGAmGmCmUmAmGmAmAmAmUmAmGmCAAGUUAAAAUAA GGCUAGUCCGUUAUCAmAmCmUmUmGmAmAmAmAmAmGmUmGmG mCmAmCmCmGmAmGmUmCmGmGmUmGmCmU*mU*mU*mU |
| 357 | | | Variable and invariable region | NNNNNNNNNNNNNNNNNNNNGUUUUAGAGCUAGAAAUAGCAAGUUA AAAUAAGGCUAGUCCGUUAUCAACUUGAAAAAGUGGCACCGAGUCG GUGCUUUU |
| 358 | | | Mod6 with modifications shown in sequence listing | mN*mN*mN*NNNNNNNNNNNNNNNNNGUUUUAGAmGmCmUmAmG mAmAmAmUmAmGmCAAGUUAAAAUAAGGCUAGUCCGUUAUCAmAmC mUmUmGmAmAmAmAmAmGmUmGmGmCmAmCmCmGmAmGmUm CmGmGmUmGmCmU*mU*mU*mU N = any nucleotide |

"Guide RNA" and "gRNA" are used herein interchangeably to refer collectively to either an sgRNA, a trRNA (also known as tracrRNA), or a crRNA (also known as a CRISPR RNA). The crRNA and trRNA may be associated on one RNA molecule (single guide RNA [sgRNA]) or in two separate RNA molecules (dual guide RNA [dgRNA]). "Guide RNA" or "gRNA" refers to each type.

The trRNA sequences may be naturally-occurring, or the trRNA sequence may include modifications or variations compared to naturally-occurring sequences.

"Editing efficiency" or "editing percentage" or "percent editing" as used herein is the total number of sequence reads with insertions or deletions of nucleotides into the target region of interest over the total number of sequence reads following cleavage by a Cas RNP.

"Hairpin" as used herein describes a loop of nucleic acids that is created when a nucleic acid strand folds and forms base pairs with another section of the same strand. A hairpin may form a structure that comprises a loop or a U-shape. In some embodiments, a hairpin may be comprised of a RNA loop. Hairpins can be formed with two complementary sequences in a single nucleic acid molecule bind together, with a folding or wrinkling of the molecule. In some embodiments, hairpins comprise stem or stem loop structures.

"Regions" as used herein describes conserved groups of nucleic acids. Regions may also be referred to as "modules" or "domains." Regions of a gRNA may perform particular functions, e.g., in directing endonuclease activity of the RNP, for example as described in Briner A E et al., *Molecular Cell* 56: 333-339 (2014). Regions of a gRNA are described in Tables 1-3.

"Ribonucleoprotein" (RNP) or "RNP complex" as used herein describes a gRNA, for example, together with a nuclease, such as a Cas protein. In some embodiments, the RNP comprises Cas9 and gRNA.

"Stem loop" as used herein describes a secondary structure of nucleotides that form a base-paired "stem" that ends in a loop of unpaired nucleic acids. A stem may be formed when two regions of the same nucleic acid strand are at least partially complementary in sequence when read in opposite directions. "Loop" as used herein describes a region of nucleotides that do not base pair (i.e., are not complementary) that may cap a stem. A "tetraloop" describes a loop of 4 nucleotides. As used herein, the upper stem of a sgRNA may comprise a tetraloop.

In certain embodiments involving dgRNA, a "stem" region as used herein describes a secondary structure of nucleotides that forms a base-paired region between certain regions of a crRNA and trRNA (e.g., the lower and upper stem regions of each RNA). The "stem" region of a dgRNA may also be referred to in the art as a "flagpole" region.

"Treatment" as used herein covers any administration or application of a therapeutic for disease in a subject, and includes inhibiting the disease, arresting its development, relieving one or more symptoms of the disease, curing the disease, or preventing reoccurrence of one or more symptoms of the disease.

1. Types of Modifications

A. 2'-O-methyl Modifications

Modified sugars are believed to control the puckering of nucleotide sugar rings, a physical property that influences oligonucleotide binding affinity for complementary strands, duplex formation, and interaction with nucleases. Substitutions on sugar rings can therefore alter the confirmation and puckering of these sugars. For example, 2'-O-methyl (2'-O-Me) modifications can increase binding affinity and nuclease stability of oligonucleotides, though as shown in the Examples, the effect of any modification at a given position in an oligonucleotide needs to be empirically determined.

The terms "mA," "mC," "mU," or "mG" may be used to denote a nucleotide that has been modified with 2'-O-Me.

Modification of a ribonucleotide as 2'-O-methyl ribonucleotide can be depicted as follows:

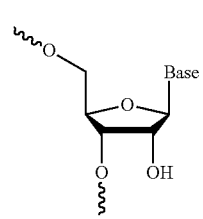

RNA

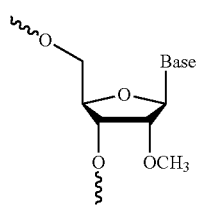

2'-O-Me

B. 2'-O-(2-methoxyethyl) Modifications

In some embodiments, the modification may be 2'-O-(2-methoxyethyl) (2'-O-moe). Modification of a ribonucleotide as a 2'-O-moe ribonucleotide can be depicted as follows:

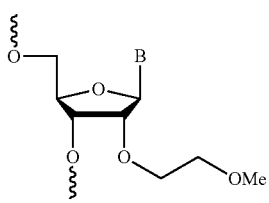

MOE

The terms "moeA," "moeC," "moeU," or "moeG" may be used to denote a nucleotide that has been modified with 2'-O-moe.

C. 2'-fluoro Modifications

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fU," or "fG" may be used to denote a nucleotide that has been substituted with 2'-F.

Substitution of 2'-F can be depicted as follows:

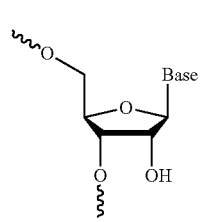

Natural composition of RNA

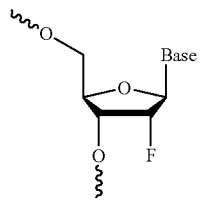

2'F-RNA

2'F substitution

D. Phosphorothioate Modifications

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond. Similarly, the terms "fA*," "fC*," "fU*," or "fG*" may be used to denote a nucleotide that has been substituted with 2'-F and that is linked to the next (e.g., 3') nucleotide with a PS bond. Equivalents of a PS linkage or bond are encompassed by embodiments described herein.

The diagram below shows the substitution of S- into a nonbridging phosphate oxygen, generating a PS bond in lieu of a phosphodiester bond:

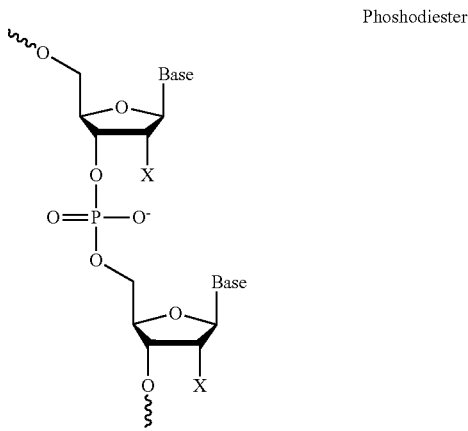

Phoshodiester

Natural phosphodiester linkage of RNA

Phosphorothioate (PS)

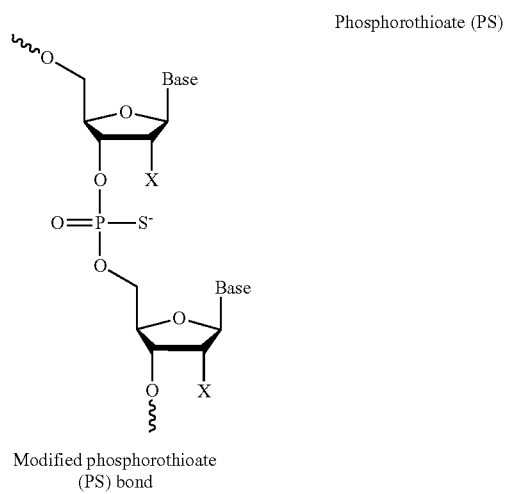

Modified phosphorothioate
(PS) bond

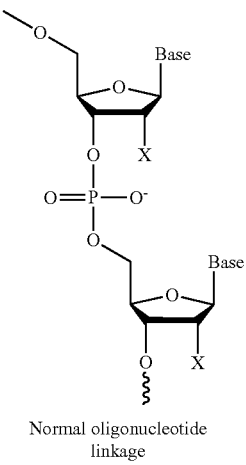

Normal oligonucleotide
linkage

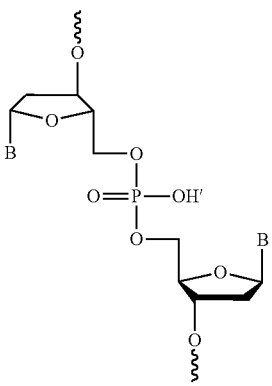

Inverted oligonucleotide
linkage

E. G-C Substitutions

In some embodiments, gRNAs are modified with sequence substitutions that do not comprise chemical modifications. In some embodiments, modified gRNAs are engineered with G-C pairings (e.g., in lower and/or upper stem regions) that are not found in the parental gRNA sequence. In some embodiments, modified gRNAs are engineered with G-U mismatches ("GU wobbles" or mismatch pairings) that are not found in the parental gRNA sequence.

F. Inverted Abasic Modifications

Abasic nucleotides refer to those which lack nitrogenous bases. The figure below depicts an oligonucleotide with an abasic (also known as apurinic) site that lacks a base:

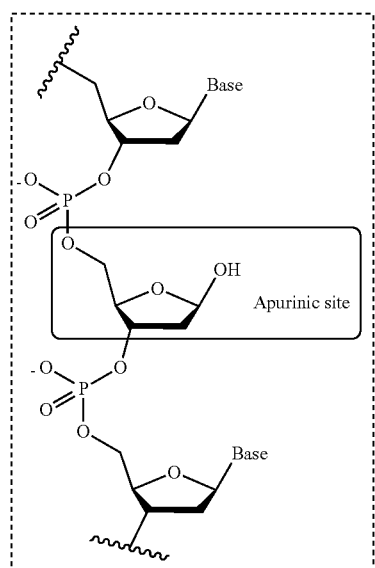

Inverted bases refer to those with linkages that are inverted from the normal 5' to 3' linkage (i.e., either a 5' to 5' linkage or a 3' to 3' linkage). For example:

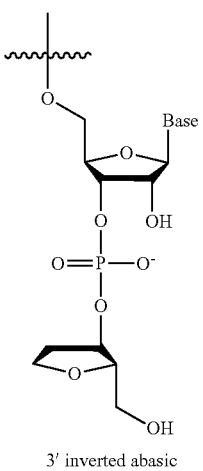

3' inverted abasic

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap. In this application, the terms "invd" indicates an inverted abasic nucleotide linkage.

The above modifications and their equivalents are included within the scope of the embodiments described herein.

2. Guide RNA Compositions

Compositions comprising guide RNA are encompassed. In some embodiments, the guide RNA comprises a trRNA. In some embodiments, the guide RNA comprises a crRNA. In some embodiments, the guide RNA comprises a crRNA and trRNA. In some embodiments, the guide RNA comprises a crRNA and trRNA on one RNA molecule as a sgRNA. In some embodiments, the guide RNA comprises a crRNA and trRNA on two RNA molecules as a dgRNA. In a dgRNA, the two RNA molecules may associate via base pairing.

In some embodiments, the guide RNA comprises a 5' terminus region. In some embodiments, the guide RNA does not comprise a 5' terminus region. In some embodiments, the 5' terminus region comprises a "spacer" region as described in Briner A E et al., *Molecular Cell* 56: 333-339 (2014) for sgRNA (but applicable herein to all guide RNAs). In some embodiments, the 5' terminus region comprises a 5' end modification. A 5' terminus region with or without a spacer region may be associated with a crRNA, trRNA, sgRNA and/or dgRNA. The spacer region is also sometimes referred to herein, and by others, as a "guide region," "guide domain" or "targeting domain." A "target sequence" as used herein refers to a sequence of nucleic acid to which the guide region/domain directs a nuclease for cleavage. In some embodiments, a spyCas9 protein may be directed by a guide region/domain to a target sequence of a target nucleic acid molecule by the nucleotides present in the spacer region. In some embodiments, the guide RNA does not comprise a spacer region.

In some embodiments, the guide RNAs described herein comprise or consist of any of the sequences shown in Table 4. Note, however, that where a sequence shows a guide/spacer region, it should be recognized that the composition may comprise this region or not. Further, guide RNAs are encompassed that comprise the modifications of any of the sequences shown in Table 4, and identified therein by SEQ ID No. That is, the nucleotides may be the same or different, but the modification pattern shown may be the same or similar to a modification pattern of a guide sequence of Table 4. A modification pattern includes the relative position and identity of modifications of the gRNA or a region of the gRNA (e.g. 5' terminus region, lower stem region, bulge region, upper stem region, nexus region, hairpin 1 region, hairpin 2 region, 3' terminus region). In some embodiments, the modification pattern contains at least 50%, 55%, 60%, 70%, 75%, 80%, 85%, 90%, 95%, 96%, 97%, 98%, and 99% of the modifications of any one of the sequences shown in the sequence column of Table 4, or over one or more regions of the sequence. In some embodiments, the modification pattern is at least 50%, 55%, 60%, 70%, 75%, 80%, 85%, 90%, 95%, 96%, 97%, 98%, and 99% identical to the modification pattern of any one of the sequences shown in the sequence column of Table 4. In some embodiments, the modification pattern is at least 50%, 55%, 60%, 70%, 75%, 80%, 85%, 90%, 95%, 96%, 97%, 98%, and 99% identical over one or more regions of the sequence shown in Table 4, e.g., a 5' terminus region, lower stem region, bulge region, upper stem region, nexus region, hairpin 1 region, hairpin 2 region, and/or 3' terminus region. For example, in some embodiments, a guide RNA is encompassed wherein the modification pattern is least 50%, 55%, 60%, 70%, 75%, 80%, 85%, 90%, 95%, 96%, 97%, 98%, and 99% identical to the modification pattern of a sequence over the 5' terminus region. In some embodiments, a guide RNA is encompassed wherein the modification pattern is least 50%, 55%, 60%, 70%, 75%, 80%, 85%, 90%, 95%, 96%, 97%, 98%, and 99% identical over the lower stem. In some embodiments, a guide RNA is encompassed wherein the modification pattern is least 50%, 55%, 60%, 70%, 75%, 80%, 85%, 90%, 95%, 96%, 97%, 98%, and 99% identical over the bulge. In some embodiments, a guide RNA is encompassed wherein the modification pattern is least 50%, 55%, 60%, 70%, 75%, 80%, 85%, 90%, 95%, 96%, 97%, 98%, and 99% identical over the upper stem. In some embodiments, a guide RNA is encompassed wherein the modification pattern is least 50%, 55%, 60%, 70%, 75%, 80%, 85%, 90%, 95%, 96%, 97%, 98%, and 99% identical over the nexus. In some embodiments, a guide RNA is encompassed wherein the modification pattern is least 50%, 55%, 60%, 70%, 75%, 80%, 85%, 90%, 95%, 96%, 97%, 98%, and 99% identical over the hairpin 1. In some embodiments, a guide RNA is encompassed wherein the modification pattern is least 50%, 55%, 60%, 70%, 75%, 80%, 85%, 90%, 95%, 96%, 97%, 98%, and 99% identical over the hairpin 2. In some embodiments, a guide RNA is encompassed wherein the modification pattern is least 50%, 55%, 60%, 70%, 75%, 80%, 85%, 90%, 95%, 96%, 97%, 98%, and 99% identical over the 3' terminus. In some embodiments, the modification pattern differs from the modification pattern of a sequence of Table 4, or a region (e.g. 5' terminus, lower stem, bulge, upper stem, nexus, hairpin 1, hairpin 2, 3' terminus) of such a sequence, at 0, 1, 2, 3, 4, 5, or 6 nucleotides. In some embodiments, the gRNA comprises modifications that differ from the modifications of a sequence of Table 4, at 0, 1, 2, 3, 4, 5, or 6 nucleotides. In some embodiments, the gRNA comprises modifications that differ from modifications of a region (e.g. 5' terminus, lower stem, bulge, upper stem, nexus, hairpin 1, hairpin 2, 3' terminus) of a sequence of Table 4, at 0, 1, 2, 3, 4, 5, or 6 nucleotides.

In some embodiments, the gRNA comprises a 2'-O-methyl (2'-O-Me) modified nucleotide. In some embodiments, the gRNA comprises a 2'-O-(2-methoxyethyl) (2'-O-moe) modified nucleotide. In some embodiments, the gRNA comprises a 2'-fluoro (2'-F) modified nucleotide. In some embodiments, the gRNA comprises a phosphorothioate (PS) bond between nucleotides.

In some embodiments, the gRNA comprises a 5' end modification, a 3' end modification, or 5' and 3' end modifications. In some embodiments, the 5' end modification comprises a phosphorothioate (PS) bond between nucleotides. In some embodiments, the 5' end modification comprises a 2'-O-methyl (2'-O-Me), 2'-O-(2-methoxyethyl) (2'-O-moe), and/or 2'-fluoro (2'-F) modified nucleotide. In some embodiments, the 5' end modification comprises at least one phosphorothioate (PS) bond and one or more of a 2'-O-methyl (2'-O-Me), 2'-O-(2-methoxyethyl) (2'-O-moe), and/or 2'-fluoro (2'-F) modified nucleotide. The end modification may comprise a phosphorothioate (PS), 2'-O-methyl (2'-O-Me), 2'-O-(2-methoxyethyl) (2'-O-moe), and/or 2'-fluoro (2'-F) modification. Equivalent end modifications are also encompassed by embodiments described herein. In some embodiments, the gRNA comprises an end modification in combination with a modification of one or more regions of the gRNA.

A. Compositions of sgRNAs

In some embodiments, the compositions and methods of the invention comprise gRNA comprising a crRNA and trRNA that direct a nuclease such as Cas9 to a target DNA sequence. In some embodiments, the gRNAs described herein may be associated on one RNA molecule (single guide RNA or sgRNA).

In some embodiments, the invention comprises a sgRNA comprising or consisting of any one of the sequences described in SEQ ID Nos: 228-332.

In some embodiments, a sgRNA comprising any one of the modified sequences of SEQ ID Nos: 235-240, 265-285, and 309-329 is provided. In some embodiments, a sgRNA comprising any one of the modified sequences of SEQ ID Nos: 235-240, 265-285, and 309-329, wherein the sgRNA further comprises a 5' "spacer" sequence ("guide sequence") that is complementary to a target sequence, and directs a Cas9 to its target for cleavage is encompassed. In some instances, the invention comprises sgRNA comprising nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification pattern is identical to the modification pattern shown in the reference sequence identifier.

1. Domains of sgRNAs

Briner A E et al., *Molecular Cell* 56:333-339 (2014) describes functional domains of sgRNAs, referred to herein as "domains", including the "spacer" domain responsible for targeting, the "lower stem", the "bulge", "upper stem" (which may include a tetraloop), the "nexus", and the "hairpin 1" and "hairpin 2" domains. See, Briner et al. at page 334, FIG. 1A.

Table 1 and FIG. 21A provide a description of the domains of a sgRNA as used herein. In Table 1, the "n" between regions represents a variable number of nucleotides, for example, from 0 to 1, 2, 3, 4, 5, 6, 7, 8, 9, 10, 11, 12, 13, 14, 15, 16, 17, 18, 19, 20, or more. In some embodiments, n equals 0. In some embodiments, n equals 1.

TABLE 1

| Regions of sgRNA (linear view, 5' to 3') | | | | | | | | |
|---|---|---|---|---|---|---|---|---|
| | LS1-6 | | B1-2 | | US1-12 | | B3-6 | |
| 5' terminus (n) | lower stem | n | bulge | n | upper stem | n | bulge | n |
| LS7-12 | N1-18 | | H1-1 thru H1-12 | | H2-1 thru H2-15 | | | |
| lower stem | n | nexus | n | hairpin 1 | n | hairpin 2 | | 3' terminus | a) 5' Terminus Region

In some embodiments, the sgRNA comprises nucleotides at the 5' terminus as shown in Table 1. In some embodiments, the 5' terminus of the sgRNA comprises a spacer or guide region that functions to direct a Cas protein to a target nucleotide sequence. In some embodiments, the 5' terminus does not comprise a spacer or guide region. In some embodiments, the 5' terminus comprises a spacer and additional nucleotides that do not function to direct a Cas protein to a target nucleotide region.

In some embodiments, the guide region comprises the first 1-10, 11, 12, 13, 14, 15, 16, 17, 18, 19, or 20 nucleotides at the 5' end of the sgRNA. In some embodiments, the guide region comprises 20 nucleotides. In some embodiments, the guide region may comprise 5, 6, 7, 8, 9, 10, 11, 12, 13, 14, 15, 16, 17, 18, 19, 20, 21, 22, 23, 24, or 25 or more nucleotides. In some embodiments, the guide region may comprise 17 nucleotides. In some embodiments, the guide region may comprise 18 nucleotides. In some embodiments, the guide region may comprise 19 nucleotides.

In some embodiments, the selection of the guide region is determined based on target sequences within the gene of interest for editing. For example, in some embodiments, the sgRNA comprises a guide region that is complementary to target sequences of a gene of interest.

In some embodiments, the target sequence in the gene of interest may be complementary to the guide region of the sgRNA. In some embodiments, the degree of complementarity or identity between a guide region of a sgRNA and its corresponding target sequence in the gene of interest may be about 50%, 55%, 60%, 65%, 70%, 75%, 80%, 85%, 90%, 95%, 96%, 97%, 98%, 99%, or 100%. In some embodiments, the guide region of a sgRNA and the target region of a gene of interest may be 100% complementary or identical. In other embodiments, the guide region of a sgRNA and the target region of a gene of interest may contain at least one mismatch. For example, the guide region of a sgRNA and the target sequence of a gene of interest may contain 1, 2, 3, 4, 5, 6, 7, 8, 9, or 10 mismatches, where the total length of the target sequence is at least about 17, 18, 19, 20 or more base pairs. In some embodiments, the guide region of a sgRNA and the target region of a gene of interest may contain 1-6 mismatches where the guide sequence comprises at least about 17, 18, 19, 20 or more nucleotides. In some embodiments, the guide region of a sgRNA and the target region of a gene of interest may contain 1, 2, 3, 4, 5, or 6 mismatches where the guide sequence comprises about 20 nucleotides. The 5' terminus may comprise nucleotides that are not considered guide regions (i.e., do not function to direct a cas9 protein to a target nucleic acid).

b) Lower Stem

In some embodiments, the sgRNA comprises a lower stem (LS) region that when viewed linearly, is separated by a bulge and upper stem regions. See Table 1.

In some embodiments, the lower stem regions comprise 1-12 nucleotides, e.g. in one embodiment the lower stem regions comprise LS1-LS12. In some embodiments, the lower stem region comprises fewer nucleotides than shown in Table 1 and FIG. 21A. In some embodiments, the lower stem region comprises more nucleotides than shown in Table 1 and FIG. 21A. When the lower stem region comprises fewer or more nucleotides than shown in the schematic of Table 1 and FIG. 21A, the modification pattern, as will be apparent to the skilled artisan, should be maintained.

In some embodiments, the lower stem region has nucleotides that are complementary in nucleic acid sequence when read in opposite directions. In some embodiments, the complementarity in nucleic acid sequence of lower stem leads to a secondary structure of a stem in the sgRNA (e.g., the regions may base pair with one another). In some embodiments, the lower stem regions may not be perfectly complimentary to each other when read in opposite directions.

c) Bulge

In some embodiments, the sgRNA comprises a bulge region comprising six nucleotides, B1-B6. When viewed linearly, the bulge region is separated into two regions. See Table 1. In some embodiments, the bulge region comprises six nucleotides, wherein the first two nucleotides are followed by an upper stem region, followed by the last four nucleotides of the bulge. In some embodiments, the bulge region comprises fewer nucleotides than shown in Table 1 and FIG. 21A. In some embodiments, the bulge region comprises more nucleotides than shown in Table 1 and FIG. 21A. When the bulge region comprises fewer or more nucleotides than shown in the schematic of Table 1 and FIG. 21A, the modification pattern, as will be apparent to the skilled artisan, should be maintained.

In some embodiments, the presence of a bulge results in a directional kink between the upper and lower stem modules in a sgRNA.

d) Upper Stem

In some embodiments, the sgRNA comprises an upper stem region comprising 12 nucleotides. In some embodiments, the upper stem region comprises a loop sequence. In some instances, the loop is a tetraloop (loop consisting of four nucleotides).

In some embodiments, the upper stem region comprises fewer nucleotides than shown in Table 1 and FIG. 21A. In some embodiments, the upper stem region comprises more nucleotides than shown in Table 1 and FIG. 21A. When the upper stem region comprises fewer or more nucleotides than shown in the schematic of Table 1 and FIG. 21A, the modification pattern, as will be apparent to the skilled artisan, should be maintained.

In some embodiments, the upper stem region has nucleotides that are complementary in nucleic acid sequence when read in opposite directions. In some embodiments, the complementarity in nucleic acid sequence of upper stem leads to a secondary structure of a stem in the sgRNA (e.g., the regions may base pair with one another). In some embodiments, the upper stem regions may not be perfectly complimentary to each other when read in opposite directions.

e) Nexus

In some embodiments, the sgRNA comprises a nexus region that is located between the lower stem region and the hairpin 1 region. In some embodiments, the nexus comprises 18 nucleotides. In some embodiments, the nexus region comprises nucleotides N1 through N18 as shown in Table 1 and FIG. 21A.

In some embodiments, the nexus region comprises fewer nucleotides than shown in Table 1 and FIG. 21A. In some embodiments, the nexus region comprises more nucleotides than shown in Table 1 and FIG. 21A. When the nexus region comprises fewer or more nucleotides than shown in the schematic of Table 1 and FIG. 21A, the modification pattern, as will be apparent to the skilled artisan, should be maintained.

In some embodiments, the nexus region has nucleotides that are complementary in nucleic acid sequence when read in opposite directions. In some embodiments, the complementarity in nucleic acid sequence leads to a secondary structure of a stem and/or stem loop in the sgRNA (e.g., certain nucleotides in the nexus region may base pair with one another). In some embodiments, the nexus regions may not be perfectly complimentary to each other when read in opposite directions.

f) Hairpin

In some embodiments, the sgRNA comprises one or more hairpin regions. In some embodiments, the hairpin region is downstream of (e.g., 3' to) the nexus region. In some embodiments, the region of nucleotides immediately downstream of the nexus region is termed "hairpin 1" or "H1". In some embodiments, the region of nucleotides 3' to hairpin 1 is termed "hairpin 2" or "H2". In some embodiments, the hairpin region comprises hairpin 1 and hairpin 2. In some embodiments, the sgRNA comprises only hairpin 1 or hairpin 2.

In some embodiments, the hairpin 1 region comprises 12 nucleic acids immediately downstream of the nexus region. In some embodiments, the hairpin 1 region comprises nucleotides H1-1 through H1-12 as shown in Table 1 and FIG. 21A.

In some embodiments, the hairpin 2 region comprises 15 nucleic acids downstream of the hairpin 1 region. In some embodiments, the hairpin 2 region comprises nucleotides H2-1 through H2-15 as shown in Table 1 and FIG. 21A.

In some embodiments, one or more nucleotides is present between the hairpin 1 and the hairpin 2 regions. The one or more nucleotides between the hairpin 1 and hairpin 2 region may be modified or unmodified. In some embodiments, hairpin 1 and hairpin 2 are separated by one nucleotide. In some embodiments, the hairpin regions comprise fewer nucleotides than shown in Table 1 and FIG. 21A. In some embodiments, the hairpin regions comprise more nucleotides than shown in Table 1 and FIG. 21A. When a hairpin region comprises fewer or more nucleotides than shown in the schematic of Table 1 and FIG. 21A, the modification pattern, as will be apparent to the skilled artisan, should be maintained.

In some embodiments, a hairpin region has nucleotides that are complementary in nucleic acid sequence when read in opposite directions. In some embodiments, the hairpin regions may not be perfectly complimentary to each other when read in opposite directions (e.g., the top or loop of the hairpin comprises unpaired nucleotides).

In some embodiments, the sgRNA comprises replacement of hairpin 1 with nucleotides "n", wherein "n" is an integer between 1 and 50, 40, 30, 20, 15, 10, 5, 4, 3, and 2. In some embodiments, the hairpin 1 region of a sgRNA is replaced by 2 nucleotides.

g) 3' Terminus Region

In some embodiments, the sgRNA comprises nucleotides after the hairpin region(s). In some embodiments, the 3' terminus region comprises 1, 2, 3, 4, 5, 6, 7, 8, 9, 10, 15 or 20 or more nucleotides, e.g. that are not associated with the secondary structure of a hairpin. In some embodiments, the 3' terminus region comprises 1, 2, 3, or 4 nucleotides that are not associated with the secondary structure of a hairpin. In some embodiments, the 3' terminus region comprises 4 nucleotides that are not associated with the secondary structure of a hairpin. In some embodiments, the 3' terminus region comprises 1, 2, or 3 nucleotides that are not associated with the secondary structure of a hairpin.

2. Modifications of sgRNAs

In some embodiments, the invention comprises a sgRNA comprising one or more modifications within one or more of the following regions: the nucleotides at the 5' terminus; the lower stem region; the bulge region; the upper stem region; the nexus region; the hairpin 1 region; the hairpin 2 region; and the nucleotides at the 3' terminus.

In some embodiments, the modification comprises a 2'-O-methyl (2'-O-Me) modified nucleotide. In some embodiments, the modification comprises a 2'-O-(2-methoxyethyl) (2'-O-moe) modified nucleotide. In some embodiments, the modification comprises a 2'-fluoro (2'-F) modified nucleotide. In some embodiments, the modification comprises a phosphorothioate (PS) bond between nucleotides.

In some embodiments, the sgRNA comprises modifications at 1, 2, 3, or 4 of the first 4 nucleotides at its 5' end. In some embodiments, the first three or four nucleotides at the 5' terminus, and the last three or four nucleotides at the 3' terminus are modified. In some embodiments, the first four nucleotides at the 5' terminus, and the last four nucleotides at the 3' terminus are linked with phosphorothioate (PS) bonds. In some embodiments, the modification comprises 2'-O-Me. In some embodiments, the modification comprises 2'-F. In some embodiments, the modification comprises 2'-O-moe.

In some embodiments, the sgRNA comprises modifications at 1, 2, 3, or 4 of the first 4 nucleotides at the 5' end. In some embodiments, the sgRNA comprises modifications at 1, 2, 3, or 4 of the first 4 nucleotides at the 3' end. In some embodiments, the first four nucleotides at the 5' terminus and the last four nucleotides at the 3' terminus are linked with a PS bond, and the first three nucleotides at the 5' terminus and the last three nucleotides at the 3' terminus comprise 2'-O-Me or 2'-O-moe modifications.

In some embodiments, the first four nucleotides at the 5' terminus and the last four nucleotides at the 3' terminus are linked with a PS bond, and the first three nucleotides at the 5' terminus and the last three nucleotides at the 3' terminus comprise 2'-F modifications.

In some embodiments, a sgRNA is provided wherein LS1, LS6, LS7, LS8, LS11, and LS12 are modified with 2'-O-Me. In some embodiments, each of the nucleotides in the bulge region of the sgRNA are modified with 2'-O-Me. In some embodiments, each of the nucleotides in the upper stem region of the sgRNA are modified with 2'-O-Me. In some embodiments, N16, N17, and N18 in the nexus region of the sgRNA are modified with 2'-O-Me. In some embodiments, each of the nucleotides in the hairpin 1 region of the sgRNA are modified with 2'-O-Me. In some embodiments, each of the nucleotides in the hairpin 2 region of the sgRNA are modified with 2'-O-Me.

In some embodiments, the sgRNA comprises 2'-O-Me modified nucleotides at the following nucleotides: the first three nucleotides at the 5' terminus; LS1, LS6, LS7, LS8, LS11, and LS12; B1 and B2 in the bulge region; each of the nucleotides in the upper stem region of the sgRNA; N16, N17, and N18 in the nexus region; each of the nucleotides in the hairpin 1 region; each of the nucleotides in the hairpin 2 region; and last four nucleotides at the 3' terminus.

In some embodiments, the sgRNA further comprises three phosphorothioate (PS) bonds linking the first four nucleotides at the 5' terminus and three PS bonds linking the last four nucleotides at the 3' terminus. In some embodiments, the sgRNA further comprises 2'-O-Me or 2'-F modified nucleic acids at the first three nucleotides at the 5' terminus, and 2'-O-Me or 2'-F modified nucleic acids at the last four nucleotides at the 3' terminus. In some embodiments, LS9 and LS10 are modified with 2'-F. In some embodiments, N15, N16, N17, and N18 are modified with 2'-F. In some embodiments, H2-9, H2-10, H2-11, H2-12, H2-13, HS-14, and H2-15 are modified with 2'-F. In some embodiments, the second to last, third to last, and fourth to last nucleotides at the 3' terminus are modified with 2'-F In some embodiments, a single guide RNA (sgRNA) is provided comprising 2'-F modified nucleic acids at the following nucleotides: LS9 and LS10 in the lower stem region; N15, N16, N17, and N18 in the nexus region; and H2-9, H2-10, H2-11, H2-12, H2-13, HS-14, and H2-15 in the hairpin 2 region. In some embodiments, the sgRNA further comprises 2'-F modified nucleotides at the second to last, third to last, and fourth to last nucleotides at the 3' terminus. In some embodiments, the sgRNA further comprises three phosphorothioate (PS) bonds linking the first four nucleotides at the 5' terminus and three PS bonds linking the last four nucleotides at the 3' terminus. In some embodiments, the sgRNA further comprises 2'-O-Me or 2'-F modified nucleic acids at the first three nucleotides at the 5' terminus, and 2'-O-Me or 2'-F modified nucleic acids at three of the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at LS1 and LS6; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-F modified nucleotides at LS1-LS6; 2'-O-Me modified nucleotides at US1-US12; 2'-O-Me modified nucleotides at H1-1-H1-12; a 2'-O-Me modified nucleotide at "n" between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-F modified nucleotides at LS2-LS5; 2'-O-Me modified nucleotides at LS1 and LS6; 2'-O-Me modified nucleotides at US1-US12; 2'-O-Me modified nucleotides at H1-1-H1-12; a 2'-O-Me modified nucleotide at "n" between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at LS7, LS8, LS11, and LS12; 2'-O-Me modified nucleotides at H1-1-H1-12; a 2'-O-Me modified nucleotide at "n" between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at LS8, LS10, and LS12; 2'-O-F modified nucleotides at LS7, LS9, and LS11; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at LS1, LS6, LS7, LS8, LS11, and LS12; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at LS1, LS6, LS7, LS8, LS11, and LS12; 2'-F modified nucleotides at LS9 and LS10; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-15; and 2'-O-Me modified nucleotides at the last four nucleotides at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at H1-1-H1-12; a 2'-O-Me modified nucleotide between Hairpin 1 and Hairpin 2; 2'-O-Me modified nucleotides at H2-1-H2-8; 2'-F modified nucleotides at H2-9-H2-15; 2'-F modified nucleotides at the second from last, third from last, and fourth from last nucleotide at the 3' terminus; and a 2'-O-Me modified nucleotide at the last nucleotide at the 3' terminus. In some embodiments, the sgRNA further comprises three phosphorothioate (PS) bonds linking the first four nucleotides at the 5' terminus and three PS bonds linking the last four nucleotides at the 3' terminus.

In some embodiments, a single guide RNA (sgRNA) is provided comprising 2'-O-Me modified nucleotides at the first three nucleotides at the 5' terminus; 2'-O-Me modified nucleotides at US1-US12; 2'-O-Me modified nucleotides at H1-2, H1-4, H1-6, H1-8, H1-10, and H1-12; 2'-F modified nucleotides at H1-1, H1-3, H1-5, H1-7, H1-9, and H1-11; a 2'-F modified nucleotide between Hairpin 1 and Hairpin 2; 2'-F modified nucleotides at H2-2, H2-4, H2-6, H2-8, H2-10, H2-12; and H2-14; 2'-O-Me modified nucleotides at H2-1, H2-3, H2-5, H2-7, H2-9, H2-11; H2-13, and H2-15; 2'-F modified nucleotides at the second from last, and fourth from last nucleotide at the 3' terminus; and 2'-O-Me modified nucleotide at the third from last, and last nucleotide at the 3' terminus. In some embodiments, the sgRNA further comprises three phosphorothioate (PS) bonds linking the first four nucleotides at the 5' terminus and three PS bonds linking the last four nucleotides at the 3' terminus.

Disclosed herein, in some embodiments, is a single guide RNA (sgRNA) comprising 2'-O-Me modifications at nucleotides LS8, LS10, LS12, H1-2, H1-4, H1-6, H1-8, H1-10, H1-12, H2-1, H2-3, H2-5, H2-7, H2-9, H2-11, H2-13, and H2-15; and 2'-F modifications at LS7, LS9, LS11; H1-1, H1-3, H1-5, H1-7, H1-9, H1-11, H1-13, H2-2, H2-4, H2-6, H2-8, H2-10, H2-12, and H2-14. In some embodiments, the sgRNA further comprises three phosphorothioate (PS) bonds linking the first four nucleotides at the 5' terminus and three PS bonds linking the last four nucleotides at the 3' terminus. In some embodiments, the sgRNA further comprises 2'-O-Me modified nucleotides at the last and third to last nucleotide at the 3' terminus; and 2'-F modified nucleotides at the second to last and third to last nucleotide at the 3' terminus.

Disclosed herein, in some embodiments, is a sgRNA comprising the nucleic acids of any one of SEQ ID Nos: 228-232. Disclosed herein, in some embodiments, is a sgRNA comprising the nucleic acids of any one of SEQ ID Nos: 235-240, 265-285, and 309-329. Disclosed herein, in some embodiments, is a sgRNA comprises nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification pattern is identical to the modification pattern shown in the reference sequence identifier. In some embodiments, the sgRNA further comprises three phosphorothioate (PS) bonds linking the first four nucleotides at the 5' terminus and three PS bonds linking the last four nucleotides at the 3' terminus.

In some embodiments, a sgRNA comprising a 5' end modification and one or more modifications in one or more of: the upper stem region; the hairpin 1 region; and the hairpin 2 region is provided, wherein the 5' end modification comprises at least two phosphorothioate linkages within the first seven nucleotides of the 5' terminus.

In some embodiments, a sgRNA comprising a 5' end modification and one or more modifications in one or more of: the upper stem region; the hairpin 1 region; and the hairpin 2 region is provided, wherein the 5' end modification comprises one or more phosphorothioate linkages at the 5' end of the RNA. In some embodiments, one or more phorphorothioate bonds link the 5' terminal nucleotides.

In some embodiments, a sgRNA comprising a 5' end modification and one or more modifications in one or more of: the upper stem region; the hairpin 1 region; and the hairpin 2 region is provided, wherein the 5' end modification comprises one or more phosphorothioate linkages within the first seven nucleotides of the 5' terminus.

In some embodiments, a sgRNA comprising any one of the modified sgRNA sequences of SEQ ID Nos: 228-332 is provided.

In some embodiments, a sgRNA comprising or consisting of any one of the modified sgRNA sequences of SEQ ID Nos: 235-240, 265-285, and 309-329 is provided.

In some embodiments, the invention comprises a sgRNA comprising any one of the modified sequences of SEQ ID Nos: 235-240, 265-285, and 309-329, wherein the sgRNA further comprises a 5' spacer sequence that is at least partially complementary to a target sequence, and directs a Cas9 to its target for cleavage.

In some embodiments, the invention comprises a sgRNA comprising nucleotides having at least 99, 98, 97, 96, 95, 94, 93, 92, 91, 90, 85, 80, 75, or 70% identity to the nucleotides of any one of SEQ ID Nos: 235-240, 265-285, and 309-329, wherein the modification pattern is identical to the modification pattern shown in the reference sequence identifier. That is, the nucleotides A, U, C, and G may differ by 99, 98, 97, 96, 95, 94, 93, 92, 91, 90, 85, 80, 75, or 70% compared to what is shown in in the sequences, but the modification remains unchanged.

In some embodiments, the invention comprises a sgRNA comprising one or more modifications within one or more of the following regions: the nucleotides at the 5' terminus; the lower stem region; the bulge region; the upper stem region; the; the nexus region; the hairpin 1 region; the hairpin 2 region; and the nucleotides at the 3' terminus.

In some embodiments, the modification comprises a 2'-O-methyl (2'-O-Me) modified nucleotide. In some embodiments, the modification comprises a 2'-fluoro (2'-F) modified nucleotide. In some embodiments, the modification comprises a phosphorothioate (PS) bond between nucleotides. In some embodiments, the modification comprises an inverted abasic nucleotide.

In some embodiments, a sgRNA is provided comprising 2'-O-Me modified nucleotides at: the first three nucleotides in the 5' terminus; LS1, LS6, LS7, LS8, LS11, and LS12 in the lower stem; B1 and B2 in the bulge region; each of the nucleotides in the upper stem region; N16, N17, and N18 in the nexus region; each of the nucleotides in the hairpin 1 region; one nucleotide between hairpin 1 and hairpin 2; each of the nucleotides in the hairpin 2 region; and the last four nucleotides at the 3' terminus. In one embodiment, the sgRNA further comprises three PS bonds between the first four nucleotides at the 5' terminus and three PS bonds between the last four nucleotides at the 3' terminus.

In some embodiments, a sgRNA is provided comprising 2'-O-Me modified nucleotides at: the first three nucleotides in the 5' terminus; LS1, LS6, LS7, LS8, LS11, and LS12 in the lower stem; B1-B6 in the bulge region; each of the nucleotides in the upper stem region; N16, N17, and N18 in the nexus region; each of the nucleotides in the hairpin 1 region; one nucleotide between hairpin 1 and hairpin 2; each of the nucleotides in the hairpin 2 region; and the last four nucleotides at the 3' terminus. In one embodiment, the sgRNA further comprises three PS bonds between the first four nucleotides at the 5' terminus and three PS bonds between the last four nucleotides at the 3' terminus.

In some embodiments, a sgRNA is provided comprising 2'-F modified nucleotides at: LS9 and LS10 in the lower stem; 15-N18 in the nexus region; H2-9-HS-15 in the hairpin 2 region; and the second to last, third to last, and fourth to last nucleotide in the 3' terminus region.

In some embodiments, a sgRNA is provided comprising 2'-F modified nucleotides at: each nucleotide in the lower stem; 15-N18 in the nexus region; H2-9-HS-15 in the hairpin 2 region; and the second to last, third to last, and fourth to last nucleotide in the 3' terminus region.

In some embodiments, a single guide RNA (sgRNA) is provided comprising 2'-O-Me modified nucleotides at LS8, LS10, LS12, H1-2, H1-4, H1-6, H1-8, H1-10, H1-12, H2-1, H2-3, H2-5, H2-7, H2-9, H2-11, H2-13, H2-15, and the last and third to last nucleotides at the 3' terminus; and 2'-F modifications at LS7, LS9, LS11; H1-1, H1-3, H1-5, H1-7, H1-9, H1-11, H1-13, H2-2, H2-4, H2-6, H2-8, H2-10, H2-12, H2-14, and the second to last and fourth to last nucleotide at the 3' terminus.

Each of the following embodiments are encompassed:

Embodiment 01

A single guide RNA (sgRNA) comprising one or more modifications in one or more of the following regions:
a. the 5' terminus;
b. the lower stem region;
c. the bulge region;
d. the upper stem region;
e. the nexus region;
f. the hairpin 1 region;
g. the hairpin 2 region; and
h. the 3' terminus.

Embodiment 02

The sgRNA of embodiment 1, wherein the modification comprises a 2'-O-methyl (2'-O-Me) modified nucleotide.

Embodiment 03

The sgRNA of embodiment 1, wherein the modification comprises a 2'-fluoro (2'-F) modified nucleotide.

Embodiment 04

The sgRNA of embodiment 1, wherein the modification comprises a phosphorothioate (PS) bond between nucleotides.

Embodiment 05

The sgRNA of any one of embodiments 1-3, wherein the first three or four nucleotides at the 5' terminus, and the last three or four nucleotides at the 3' terminus are modified.

Embodiment 06

The sgRNA of any one of embodiments 1-5, wherein the first four nucleotides at the 5' terminus, and the last four nucleotides at the 3' terminus are linked with phosphorothioate (PS) bonds.

Embodiment 07

The sgRNA of embodiment 5, wherein the modification comprises 2'-O-Me.

Embodiment 08

The sgRNA of embodiment 5, wherein the modification comprises 2'-F.

Embodiment 09

The sgRNA of any one of embodiments 1-7, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-O-Me modifications.

Embodiment 10

The sgRNA of any one of embodiments 1-8, wherein the first four nucleotides at the 5' terminus and the last four nucleotides at the 3' terminus are linked with a PS bond, and wherein the first three nucleotides at the 5' terminus and the last three nucleotides at the 3' terminus comprise 2'-F modifications.

Embodiment 11

The sgRNA of any one of embodiments 1-10, wherein LS1, LS6, LS7, LS8, LS11, and LS12 are modified with 2'-O-Me.

Embodiment 12

The sgRNA of any one of embodiments 1-11, wherein each of the nucleotides in the bulge region are modified with 2'-O-Me.

Embodiment 13

The sgRNA of any one of embodiments 1-12, wherein each of the nucleotides in the upper stem region are modified with 2'-O-Me.

Embodiment 14

The sgRNA of any one of embodiments 1-13, wherein N16, N17, and N18 in the nexus region are modified with 2'-O-Me.

Embodiment 15

The sgRNA of any one of embodiments 1-14, wherein each of the nucleotides in the hairpin 1 region are modified with 2'-O-Me.

Embodiment 16

The sgRNA of any one of embodiments 1-15, wherein each of the nucleotides in the hairpin 2 region are modified with 2'-O-Me.

Embodiment 17

A single guide RNA (sgRNA) comprising 2'-O-Me modified nucleic acids at the following nucleotides:
a. the first three nucleotides at the 5' terminus;
b. LS1, LS6, LS7, LS8, LS11, and LS12 in the lower stem region;
c. B1 and B2 in the bulge region;
d. each nucleotide in the upper stem region;
e. N16, N17, and N18 in the nexus region;
f. each nucleotide in the hairpin 1 region;
g. each nucleotide in the hairpin 2 region; and
h. the last four nucleotides at the 3' terminus.

Embodiment 18

The sgRNA of embodiment 17, wherein B3-B6 are modified with 2'-O-Me.

Embodiment 19

The sgRNA of embodiment 17, further comprising three phosphorothioate (PS) bonds linking the first four nucleotides at the 5' terminus and three PS bonds linking the last four nucleotides at the 3' terminus.

Embodiment 20

The sgRNA of any one of embodiments 1-10, wherein LS9 and LS10 are modified with 2'-F.

Embodiment 21

The sgRNA of any one of embodiments 1-10 and 20, wherein N15, N16, N17, and N18 are modified with 2'-F.

Embodiment 22

The sgRNA of any one of embodiments 1-10 and 20-21, wherein H2-9, H2-10, H2-11, H2-12, H2-13, H2-14, and H2-15 are modified with 2'-F.

Embodiment 23

The sgRNA of any one of embodiments 1-10 and 21-22, wherein the second to last, third to last, and fourth to last nucleotides at the 3' terminus are modified with 2'-F.

Embodiment 24

A single guide RNA (sgRNA) comprising 2'-F modified nucleotides at the following positions:
a. LS9 and LS10 in the lower stem region;
b. N15, N16, N17, and N18 in the nexus region; and
c. H2-9, H2-10, H2-11, H2-12, H2-13, H2-14, and H2-15 in the hairpin 2 region.

Embodiment 25

The sgRNA of embodiment 24, further comprising 2'-F modified nucleotides at the second to last, third to last, and fourth to last nucleotides at the 3' terminus.

Embodiment 26

The sgRNA of any one of embodiments 24 or 25, further comprising three phosphorothioate (PS) bonds linking the first four nucleotides at the 5' terminus and three PS bonds linking the last four nucleotides at the 3' terminus.

Embodiment 27

The sgRNA of any one of embodiments 24-26, further comprising 2'-O-Me or 2'-F modified nucleotides at the first three nucleotides at the 5' terminus, and 2'-O-Me or 2'-F modified nucleotides at the three of the last four nucleotides at the 3' terminus.

Embodiment 28

A single guide RNA (sgRNA) comprising
a. 2'-O-Me modified nucleotides at the first three nucleotides at the 5' terminus;
b. 2'-O-Me modified nucleotides at LS1 and LS6;
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus.

Embodiment 29

The sgRNA of embodiment 28 further comprising three phosphorothioate (PS) bonds linking the first four nucleotides at the 5' terminus and three PS bonds linking the last four nucleotides at the 3' terminus.

Embodiment 30

A single guide RNA (sgRNA) comprising
a. 2'-O-Me modified nucleotides at the first three nucleotides at the 5' terminus;
b. 2'-F modified nucleotides at LS1-LS6;
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;

f. 2'-O-Me modified nucleotides at H2-1-H2-15; and
g. 2'-O-Me modified nucleotides at the last four nucleotides at the 3' terminus.

Embodiment 31

The sgRNA of embodiment 30 further comprising three phosphorothioate (PS) bonds linking the first four nucleotides at the 5' terminus and three PS bonds linking the last four nucleotides at the 3' terminus.

Embodiment 32

A single guide RNA (sgRNA) comprising
a. 2'-O-Me modified nucleotides at the first three nucleotides at the 5' terminus;
b. 2'-F modified nucleotides at LS2-LS5;
c. 2'-O-Me modified nucleotides at LS1 and LS6;
d. 2'-O-Me modified nucleotides at US1-US12;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 33

The sgRNA of embodiment 32 further comprising three phosphorothioate (PS) bonds linking the first four nucleotides at the 5' terminus and three PS bonds linking the last four nucleotides at the 3' terminus.

Embodiment 34

A single guide RNA (sgRNA) comprising
a. 2'-O-Me modified nucleotides at the first three nucleotides at the 5' terminus;
b. 2'-O-Me modified nucleotides at US1-US12;
c. 2'-O-Me modified nucleotides at LS7, LS8, LS11, and LS12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus.

Embodiment 35

The sgRNA of embodiment 34 further comprising three phosphorothioate (PS) bonds linking the first four nucleotides at the 5' terminus and three PS bonds linking the last four nucleotides at the 3' terminus.

Embodiment 36

A single guide RNA (sgRNA) comprising
a. 2'-O-Me modified nucleotides at the first three nucleotides at the 5' terminus;
b. 2'-O-Me modified nucleotides at US1-US12;
c. 2'-O-Me modified nucleotides at LS7, LS8, LS11, and LS12;
d. 2'-F modified nucleotides at LS9 and LS10;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 37

The sgRNA of embodiment 36 further comprising three phosphorothioate (PS) bonds linking the first four nucleotides at the 5' terminus and three PS bonds linking the last four nucleotides at the 3' terminus.

Embodiment 38

A single guide RNA (sgRNA) comprising
a. 2'-O-Me modified nucleotides at the first three nucleotides at the 5' terminus;
b. 2'-O-Me modified nucleotides at US1-US12;
c. 2'-O-Me modified nucleotides at LS8, LS10, and LS12;
d. 2'-O-F modified nucleotides at LS7, LS9, and LS11;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and
h. 2'-O-Me modified nucleotides at the last four nucleotides at the 3' terminus.

Embodiment 39

The sgRNA of embodiment 32 further comprising three phosphorothioate (PS) bonds linking the first four nucleotides at the 5' terminus and three PS bonds linking the last four nucleotides at the 3' terminus.

Embodiment 40

A single guide RNA (sgRNA) comprising
a. 2'-O-Me modified nucleotides at the first three nucleotides at the 5' terminus;
b. 2'-O-Me modified nucleotides at LS1, LS6, LS7, LS8, LS11, and LS12
c. 2'-O-Me modified nucleotides at US1-US12;
d. 2'-O-Me modified nucleotides at H1-1-H1-12;
e. a 2'-O-Me modified nucleotide between Hairpin 1 and Hairpin 2;
f. 2'-O-Me modified nucleotides at H2-1-H2-15; and
g. 2'-O-Me modified nucleotides at the last four nucleotides at the 3' terminus.

Embodiment 41

The sgRNA of embodiment 40 further comprising three phosphorothioate (PS) bonds linking the first four nucleotides at the 5' terminus and three PS bonds linking the last four nucleotides at the 3' terminus Embodiment 42. A single guide RNA (sgRNA) comprising
a. 2'-O-Me modified nucleotides at the first three nucleotides at the 5' terminus;
b. 2'-O-Me modified nucleotides at LS1, LS6, LS7, LS8, LS11, and LS12;
c. 2'-F modified nucleotides at LS9 and LS10;
d. 2'-O-Me modified nucleotides at US1-US12;
e. 2'-O-Me modified nucleotides at H1-1-H1-12;
f. a 2'-O-Me modified nucleotide between Hairpin 1 and Hairpin 2;
g. 2'-O-Me modified nucleotides at H2-1-H2-15; and h. 2'-O-Me modified nucleotides at the last four nucleotides at the 3' terminus.

Embodiment 43

The sgRNA of embodiment 43 further comprising three phosphorothioate (PS) bonds linking the first four nucleotides at the 5' terminus and three PS bonds linking the last four nucleotides at the 3' terminus.

Embodiment 44

A single guide RNA (sgRNA) comprising
a. 2'-O-Me modified nucleotides at the first three nucleotides at the 5' terminus;
b. 2'-O-Me modified nucleotides at US1-US12;
c. 2'-O-Me modified nucleotides at H1-1-H1-12;
d. a 2'-O-Me modified nucleotide between Hairpin 1 and Hairpin 2;
e. 2'-O-Me modified nucleotides at H2-1-H2-8;
f. 2'-F modified nucleotides at H2-9-H2-15;
g. 2'-F modified nucleotides at the second from last, third from last, and fourth from last nucleotide at the 3' terminus; and
h. a 2'-O-Me modified nucleotide at the last nucleotide at the 3' terminus.

Embodiment 45

The sgRNA of embodiment 44 further comprising three phosphorothioate (PS) bonds linking the first four nucleotides at the 5' terminus and three PS bonds linking the last four nucleotides at the 3' terminus.

Embodiment 46

A single guide RNA (sgRNA) comprising
a. 2'-O-Me modified nucleotides at the first three nucleotides at the 5' terminus;
b. 2'-O-Me modified nucleotides at US1-US12;
c. 2'-O-Me modified nucleotides at H1-2, H1-4, H1-6, H1-8, H1-10, and H1-12;
d. 2'-F modified nucleotides at H1-1, H1-3, H1-5, H1-7, H1-9, and H1-11;
e. a 2'-F modified nucleotide between Hairpin 1 and Hairpin 2;
f. 2'-F modified nucleotides at H2-2, H2-4, H2-6, H2-8, H2-10, H2-12; and H2-14;
g. 2'-O-Me modified nucleotides at H2-1, H2-3, H2-5, H2-7, H2-9, H2-11; H2-13, and H2-15;
h. 2'-F modified nucleotides at the second from last, and fourth from last nucleotide at the 3' terminus; and
i. 2'-O-Me modified nucleotide at the third from last, and last nucleotide at the 3' terminus.

Embodiment 47

The sgRNA of embodiment 46 further comprising three phosphorothioate (PS) bonds linking the first four nucleotides at the 5' terminus and three PS bonds linking the last four nucleotides at the 3' terminus.

Embodiment 48

A single guide RNA (sgRNA) comprising
a. 2'-O-Me modified nucleotides LS8, LS10, LS12, H1-2, H1-4, H1-6, H1-8, H1-10, H1-12, H2-1, H2-3, H2-5, H2-7, H2-9, H2-11, H2-13, and H2-15; and
b. 2'-F modified nucleotides at LS7, LS9, LS11; H1-1, H1-3, H1-5, H1-7, H1-9, H1-11, H1-13, H2-2, H2-4, H2-6, H2-8, H2-10, H2-12, and H2-14.

Embodiment 49

The sgRNA of embodiment 48, further comprising three phosphorothioate (PS) bonds linking the first four nucleotides at the 5' terminus and three PS bonds linking the last four nucleotides at the 3' terminus.

Embodiment 50

The sgRNA of any one of embodiments 48-49, further comprising
a. 2'-O-Me modified nucleotides at the last and third to last nucleotide at the 3' terminus; and
b. 2'-F modified nucleotides at the second to last and third to last nucleotide at the 3' terminus.

Embodiment 51

A sgRNA comprising the nucleic acids of any one of SEQ ID Nos: 228-332.

Embodiment 52

A sgRNA comprising the nucleic acids of any one of SEQ ID Nos: 235-240, 265-285, and 309-329.

Embodiment 53

A sgRNA comprising nucleic acids having at least 99, 98, 97, 96, 95, 94, 93, 92, 91, 90, 85, 80, 75, or 70% identity to the nucleic acids of any one of SEQ ID Nos: 235-240, 265-285, and 309-329, wherein the modification pattern is identical to the modification pattern shown in the reference sequence identifier.

Embodiment 54

The sgRNA of any one of embodiments 51-53, further comprising three phosphorothioate (PS) bonds linking the first four nucleotides at the 5' terminus and three PS bonds linking the last four nucleotides at the 3' terminus.

B. Compositions of dgRNAs

In some embodiments, the compositions and methods of the invention comprise gRNA comprising a crRNA and trRNA that direct a nuclease such as Cas9 to a target DNA sequence. In some embodiments, the gRNAs are associated, but on two separate RNA molecules (dual guide RNA or dgRNA).

Table 2 and FIG. 21C provides a description of domains of a crRNA as used herein. The 5' terminus region may comprise a spacer region at or near the 5' terminus of the crRNA and functions to direct a Cas9 to a target region in the DNA, e.g., as described herein. In Table 2, the "n" between regions represents a variable number of nucleotides, for example, from 0 to 1, 2, 3, 4, 5, 6, 7, 8, 9, 10, 11, 12, 13, 14, 15, 16, 17, 18, 19, 20, or more. In some embodiments, n equals 0. Any of the dgRNAs described herein may include an "n" between any domain.

Table 3 and FIG. 21C provide a description of domains of a trRNA as used herein. In Table 3, the "n" between regions represents a variable number of nucleotides, for example, from 0 to 1, 2, 3, 4, 5, 6, 7, 8, 9, 10, 11, 12, 13, 14, 15, 16, 17, 18, 19, 20, or more. In some embodiments, n equals 0. Any of the dgRNAs described herein may include an "n" between any domain.

1. Domains of dgRNAs

As described in Briner 2014, dgRNAs can be developed based on specific functional domains, referred to herein as "domains", including the spacer responsible for targeting, the lower stem, the bulge, the upper stem, the nexus, and the hairpin domains. In dgRNAs, the crRNA comprises some components of the gRNA and the trRNA comprises some components of the gRNA.

Regions of crRNAs are provided in Table 2 and FIG. 21C. Regions of trRNAs are provided in Table 3 and FIG. 21C. FIG. 21C shows a schematic of an exemplary dgRNA.

TABLE 2

| Regions of crRNA (linear view, 5' to 3') | | | | | | |
|---|---|---|---|---|---|---|
| | LS1-6 | | B1-2 | | US1-14 | |
| 5' terminus (n) | lower stem | n | bulge | n | upper stem | 3' terminus |

TABLE 3

| Regions of trRNA (linear view, 5' to 3') | | | | | | | | | | | |
|---|---|---|---|---|---|---|---|---|---|---|---|
| | US1-11 | | B1-4 | | LS1-6 | | N1-18 | | H1-1 thru H1-12 | | H2-1 thru H2-15 |
| 5' terminus (n) | upper stem | n | bulge | n | lower stem | n | nexus | n | hairpin 1 | n | hairpin 2 | 3' terminus | a) 5' Terminus Region

In some embodiments, the dgRNA comprises nucleotides at the 5' terminus of the crRNA and trRNA as shown in Tables 2-3 and FIG. 21C.

In some embodiments, the 5' terminus of the crRNA comprises a spacer or guide region that functions to direct a Cas protein to a target nucleotide sequence. In some embodiments, the 5' terminus does not comprise a spacer or guide region. In some embodiments, the 5' terminus comprises a spacer and additional nucleotides that do not function to direct a Cas protein to a target nucleotide region.

In some embodiments, the guide region comprises the first 1-10, 11, 12, 13, 14, 15, 16, 17, 18, 19, or 20 nucleotides at the 5' end of the crRNA. In some embodiments, the guide region comprises 20 nucleotides. In some embodiments, the guide region may comprise 5, 6, 7, 8, 9, 10, 11, 12, 13, 14, 15, 16, 17, 18, 19, 20, 21, 22, 23, 24, or 25 or more nucleotides. In some embodiments, the guide region may comprise 17 nucleotides. In some embodiments, the guide region may comprise 18 nucleotides. In some embodiments, the guide region may comprise 19 nucleotides.

In some embodiments, the selection of the guide region is determined based on target sequences within the gene of interest for editing. For example, in some embodiments, the crRNA comprises a guide region that is complementary to target sequences of a gene of interest.

In some embodiments, the target sequence in the gene of interest may be complementary to the guide region of the crRNA. In some embodiments, the degree of complementarity or identity between a guide region of a crRNA and its corresponding target sequence in the gene of interest may be about 50%, 55%, 60%, 65%, 70%, 75%, 80%, 85%, 90%, 95%, 96%, 97%, 98%, 99%, or 100%. In some embodiments, the guide region of a crRNA and the target region of a gene of interest may be 100% complementary or identical. In other embodiments, the guide region of a crRNA and the target region of a gene of interest may contain at least one mismatch. For example, the guide region of a crRNA and the target sequence of a gene of interest may contain 1, 2, 3, 4, 5, 6, 7, 8, 9, or 10 mismatches, where the total length of the target sequence is at least about 17, 18, 19, 20 or more base pairs. In some embodiments, the guide region of a crRNA and the target region of a gene of interest may contain 1-6 mismatches where the guide sequence comprises at least about 17, 18, 19, 20 or more nucleotides. In some embodiments, the guide region of a crRNA and the target region of a gene of interest may contain 1, 2, 3, 4, 5, or 6 mismatches where the guide sequence comprises about 20 nucleotides.

In some embodiments, the trRNA comprises a 5' terminus. In some embodiments, the trRNA comprises a 5' terminus which forms, in part, the upper stem of a dgRNA. The 5' terminus of the trRNA is not complementary to a region of the target gene.

b) Lower Stem

In some embodiments, the dgRNA comprises a lower stem (LS) region. The lower stem region comprises a crRNA lower stem region and a trRNA lower stem region that associate as depicted in FIG. 21C. In some embodiments, the lower stem region of the crRNA is at least partially complementary to the lower stem region of the trRNA. In some embodiments, the lower stem region of the crRNA is fully complementary to the lower stem region of the trRNA.

In some embodiments, the lower stem region of the crRNA and trRNA each comprise 6 nucleotides. In some embodiments, the lower stem region of the crRNA and trRNA each comprise fewer nucleotides than shown in Tables 2 and 3 and FIG. 21C. In some embodiments, the lower stem region comprises more nucleotides than shown in Tables 2 and 3 and FIG. 21C. When the lower stem region comprises fewer or more nucleotides than shown in the schematic of Tables 2 and 3 and FIG. 21C, the modification patterns, as will be apparent to the skilled artisan, are maintained. In some embodiments, the number of nucleotides in the lower stem of the crRNA differs from the number of nucleotides in the lower stem of the trRNA.

c) Bulge

In some embodiments, the dgRNA comprises a bulge (B) region. In some embodiments, the crRNA comprises one bulge region and the trRNA comprises one bulge region. In some embodiments, each bulge region comprises 1-4 nucleotides. In some embodiments, the bulge region of the crRNA comprises two nucleotides, and the bulge region of the trRNA comprises four nucleotides.

In some embodiments, the crRNA bulge region is located between the lower stem region and the upper stem region of the crRNA. In some embodiments, the bulge region of the crRNA comprises two nucleotides. In some embodiments, the bulge region of the crRNA comprises nucleotides B1 and B2 as shown Table 2 and FIG. 21C.

In some embodiments, the trRNA bulge region is located between the upper stem region and the lower stem region of the trRNA. In some embodiments, the bulge region of the trRNA comprises four nucleotides. In some embodiments, the bulge region of the trRNA comprises nucleotides B1 through B4 as shown Table 3 and FIG. 21C.

In some embodiments, the presence of a bulge results in a directional kink between the upper and lower stems modules in a dgRNA. The crRNA bulge and trRNA bulge may be partially complementary. The crRNA bulge and trRNA bulge may have no complementary.

In some embodiments, the bulge regions of the crRNA and trRNA comprise more nucleotides than shown in Tables 2 and 3 and FIG. 21C. When the bulge region comprises fewer or more nucleotides than shown in the schematic of Tables 2 and 3 and FIG. 21C, the modification patterns, as will be apparent to the skilled artisan, are maintained. In some embodiments, the number of nucleotides in the bulge of the crRNA differs from the number of nucleotides in the bulge of the trRNA.

d) Upper Stem

In some embodiments, the dgRNA comprises an upper stem (US) region. The upper stem region comprises a crRNA upper stem region and a trRNA upper stem region that associate as depicted in FIG. 21C. In some embodiments, the upper stem region of the crRNA is at least partially complementary to the upper stem region of the trRNA. In some embodiments, the upper stem region of the crRNA is fully complementary to the upper stem region of the trRNA.

In some embodiments, the upper stem region of the crRNA comprises fourteen nucleotides. In some embodiments, the upper stem region of the trRNA comprises eleven nucleotides. In some embodiments, the upper stem regions of the crRNA and trRNA each comprise fewer nucleotides than shown in Tables 2 and 3 and FIG. 21C. In some embodiments, the upper stem regions of the crRNA and trRNA comprise more nucleotides than shown in Tables 2 and 3 and FIG. 21C. When the upper stem region comprises fewer or more nucleotides than shown in the schematic of Tables 2 and 3 and FIG. 21C, the modification patterns, as will be apparent to the skilled artisan, are maintained.

In some embodiments, the upper stem of the crRNA comprises nucleotides US1 through US14 as shown in Table 2 and FIG. 21C.

In some embodiments, the upper stem of the trRNA comprises nucleotides US1 through US11 as shown in Table 3 and FIG. 21C.

e) Nexus

In some embodiments, the dgRNA comprises a trRNA comprising a nexus region. In some embodiments, the nexus is between the lower stem region and the hairpin 1 region of the trRNA. In some embodiments, the nexus is located immediately downstream of the lower stem of the trRNA. In some embodiments, the nexus comprises eighteen nucleotides. In some embodiments, the nexus region of the trRNA comprises nucleotides N1-N18 as shown in Table 3 and FIG. 21C. In some embodiments, the nexus comprises fewer nucleotides than shown in Table 3 and FIG. 21C. In some embodiments, the nexus region of the trRNA comprises more nucleotides than shown in Table 3 and FIG. 21C. When the nexus region comprises fewer or more nucleotides than shown in Table 3 and FIG. 21C, the modification patterns, as will be apparent to the skilled artisan, are maintained.

In some embodiments, the nexus region has nucleotides that are complementary in nucleic acid sequence when read in opposite directions. In some embodiments, the complementarity in nucleic acid sequence leads to a secondary structure of a stem and/or stem loop in the sgRNA (e.g., certain nucleotides in the nexus region may base pair with one another). In some embodiments, the nexus regions may not be perfectly complimentary to each other when read in opposite directions.

f) Hairpin

In some embodiments, the hairpin region of the trRNA is downstream of the nexus region. In some embodiments, the region of nucleotides immediately downstream of the nexus region is termed "hairpin 1." In some embodiments, the region of nucleotides immediately downstream of the hairpin 1 region is termed "hairpin 2." In some embodiments, the hairpin region comprises hairpin 1 and hairpin 2. In some instances, hairpin 1 and hairpin 2 are separated by one or more nucleotide "n." In some embodiments, n=1. In some embodiments, the trRNA comprises only hairpin 1 or hairpin 2.

Replacement of the hairpin 1 region of a trRNA with 2 nucleotides has been shown to allow editing activity of a Cas RNP (see US20150376586, FIG. 16). In some embodiments, the trRNA comprises replacement of hairpin 1 with nucleotides "n", wherein "n" is an integer between 1 and 50, 40, 30, 20, 15, 10, 5, 4, 3, and 2. In some embodiments, the hairpin 1 region of a trRNA is replaced by 2 nucleotides.

In some embodiments, hairpin 1 of the trRNA comprises twelve nucleotides immediately downstream of the nexus region. In some embodiments, the hairpin 1 region of the trRNA comprises nucleotides H1-1 through H1-12 as shown in Table 3 and FIG. 21C.

In some embodiments, non-hairpin nucleotides are present between the hairpin 1 and the hairpin 2 regions of the trRNA. In some embodiments, one to two non-hairpin nucleotides reside between hairpin 1 and hairpin 2.

In some embodiments, hairpin 2 of the trRNA comprises fifteen nucleotides after (3' to) hairpin 1. In some embodiments, the hairpin 2 region of the trRNA comprises nucleotides H2-1 through H2-15 as shown in Table 3 and FIG. 21C. In some embodiments, the hairpin 2 region of the trRNA comprises nucleotides H2-1 through H2-15 as shown in Table 3, and the "n" between hairpin 1 and hairpin 2 is 1 or 2.

In some embodiments, a hairpin region of the trRNA comprises more nucleotides than shown in Table 3 and FIG. 21C. When a hairpin region comprises fewer or more nucleotides than shown in Table 3 and FIG. 21C, the modification patterns, as will be apparent to the skilled artisan, are maintained.

In some embodiments, a hairpin region has nucleotides that are complementary in nucleic acid sequence when read in opposite directions. In some embodiments, the hairpin regions may not be perfectly complimentary to each other when read in opposite directions (e.g., the top or loop of the hairpin comprises unpaired nucleotides).

In some embodiments, the trRNA comprises replacement of hairpin 1 with nucleotides "n", wherein "n" is an integer between 1 and 50, 40, 30, 20, 15, 10, 5, 4, 3, and 2. In some embodiments, the hairpin 1 region of a trRNA is replaced by 2 nucleotides.

g) 3' Terminus

In some embodiments, the dgRNA comprises a trRNA comprising a 3' terminus region comprising additional nucleotides after (3' to) the hairpin region(s). In some embodiments, the 3' terminus region comprises 1, 2, 3, 4, 5, 6, 7, 8, 9, 10, 15 or 20 or more nucleotides that are not associated with the secondary structure of a hairpin. In some embodiments, the 3' terminus region comprises 1, 2, 3, or 4 nucleotides that are not associated with the secondary structure of a hairpin. In some embodiments, the 3' terminus region comprises 4 nucleotides that are not associated with the secondary structure of a hairpin. In some embodiments, the 3' terminus region comprises 1, 2, or 3 nucleotides that are not associated with the secondary structure of a hairpin.

2. Modifications of dgRNAs

In some embodiments, a dgRNA comprises a modified crRNA and an unmodified trRNA. In some embodiments, a dgRNA comprises an unmodified crRNA and a modified trRNA. In some embodiments, both the crRNA and trRNA of a dgRNA comprise modifications.

In some embodiments, the gRNAs described herein are in two separate RNA molecules (dual guide or dgRNA). See, Tables 2, 3, and FIG. 21C.

In some embodiments, the invention comprises a dgRNA comprising or consisting of a) any one of the crRNA sequences of SEQ ID Nos: 1-187; and b) any one of the trRNA sequences described in SEQ ID Nos: 188-227.

In some embodiments, a dgRNA comprising any one of the modified crRNA sequences of 1-187 is provided.

In some embodiments, a dgRNA comprising any one of the modified trRNA sequences of 188-227 is provided.

In some embodiments, a dgRNA comprising any one of the modified crRNA sequences of SEQ ID Nos: 19-31, 53-73, and 104-130 is provided. In some embodiments, the invention comprises a dgRNA comprising any one of the modified sequences of SEQ ID Nos: 19-31, 53-73, and 104-130, wherein the crRNA further comprises a 5' spacer sequence that is at least partially complementary to a target sequence, and directs a Cas9 to its target for cleavage.

In some embodiments, the invention comprises a crRNA comprising any one of the sequences described in SEQ ID Nos: 1-187. In some embodiments, the invention comprises a crRNA comprising or consisting of any one of the sequences described in SEQ ID Nos: 19-31, 53-73, and 104-130. In some embodiments, the invention comprises a crRNA comprising any one of the sequences described in SEQ ID Nos: 19-31, 53-73, and 104-130 and a spacer region.

In some embodiments, the invention comprises a trRNA comprising or consisting of any one of the sequences described in SEQ ID Nos:188-277.

In some embodiments, the invention comprises a crRNA comprising nucleotides having at least 99, 98, 97, 96, 95, 94, 93, 92, 91, 90, 85, 80, 75, or 70% identity to the nucleotides of any one of SEQ ID Nos: 1-187, wherein the modification pattern is identical to the modification pattern shown in the reference sequence identifier. That is, the nucleotides A, U, C, and G may differ by 99, 98, 97, 96, 95, 94, 93, 92, 91, 90, 85, 80, 75, or 70% compared to what is shown in in the sequences, but the modification remains unchanged.

In some embodiments, the invention comprises a trRNA comprising nucleotides having at least 99, 98, 97, 96, 95, 94, 93, 92, 91, 90, 85, 80, 75, or 70% identity to the nucleotides of any one of SEQ ID Nos: 188-277, wherein the modification pattern is identical to the modification pattern shown in the reference sequence identifier. That is, the nucleotides A, U, C, and G may differ by 99, 98, 97, 96, 95, 94, 93, 92, 91, 90, 85, 80, 75, or 70% compared to what is shown in the sequences, but the modification on each nucleotide remains unchanged.

3. crRNAs, trRNAs, and dgRNAs with Modifications

In some embodiments, the crRNA comprises one or more modified nucleotides within one or more of the 5' terminus, lower stem, bulge, upper stem, and 3' terminus.

In some embodiments, the modification comprises 2'-O-Me.

In some embodiments, the modification comprises 2'-F.

In some embodiments, the modification comprises a phosphorothioate (PS) bond linking one or more nucleotides. In some embodiments, the modification is three PS bonds linking the first four nucleotides at the 5' terminus and three PS bonds linking the last four nucleotides at the 3' terminus.

In some embodiments, the modification comprises an inverted abasic nucleotide.

In some embodiments, a crRNA is provided comprising 2'-O-Me modified nucleotides at each nucleotide in the upper stem. In some embodiments, US-1 through US-14 of the crRNA are each modified with 2'-O-Me. In some embodiments, LS1 and LS6 of the crRNA are modified with 2'-O-Me. In some embodiments, LS5 of the crRNA is modified with 2'-O-Me.

In some embodiments, a crRNA comprising 2'-O-Me modified nucleotides at each of the nucleotides in the upper stem, and LS1 and LS6 in the lower stem is provided. In some embodiments, the crRNA further comprises one or more 2'-O-Me or 2'-O-moe modified nucleotides in the 5' and/or 3' terminus region, e.g. in a 5' and/or 3' end modification.

In some embodiments, a crRNA comprising 2'-O-Me modified nucleotides at each of the nucleotides in the upper stem, LS1, LS5, and LS6 in the lower stem is provided. In some embodiments, the crRNA further comprises one or more 2'-O-Me or 2'-O-moe modified nucleotides in the 5' and/or 3' terminus region, e.g. in a 5' and/or 3' end modification.

In some embodiments, the invention comprises a crRNA comprising 2'-F modified nucleotides at LS1, LS2, and LS6 in the lower stem. In some embodiments, the crRNA further comprises 2'-F modified nucleotides at each of B1 and B2 in the bulge region. In some embodiments, the invention comprises a crRNA comprising 2'-F modified nucleotides at LS1, LS2, and LS6 in the lower stem, and at each of B1 and B2 in the bulge region. In some embodiments, the crRNA further comprises one or more 2'-O-Me or 2'-O-moe modified nucleotides in the 5' and/or 3' terminus region, e.g. in a 5' and/or 3' end modification.

In some embodiments, the crRNA comprises 2'-O-Me modified nucleotides at nucleotides LS1 and LS6 in the lower stem region; each of the nucleic acids in the bulge region; and each of the nucleic acids in the upper stem region. In some embodiments, the LS5 nucleotide of the crRNA is also modified with 2'-O-Me. In some embodiments, LS2, LS3, and LS4 of the crRNA are not modified. In some embodiments, the crRNA further comprises one or more 2'-O-Me or 2'-O-moe modified nucleotides in the 5' and/or 3' terminus region, e.g. in a 5' and/or 3' end modification.

In some embodiments, the crRNA comprises 2'-fluoro (2'-F) modified nucleotides at LS1, LS2, and LS6 in the lower stem region, and each of the nucleotides in the bulge region. In some embodiments, the crRNA comprises 2'-fluoro (2'-F) modified nucleotides at LS1, LS2, and LS6 in the lower stem region, and at B2 and B2 in the bulge region. In some embodiments, the crRNA comprises 2'-fluoro (2'-F) modified nucleotides at LS1-LS6 in the lower stem region, and each of the nucleotides in the bulge region. In some embodiments, the crRNA further comprises one or more 2'-O-Me or 2'-O-moe modified nucleotides in the 5' and/or 3' terminus region, e.g. in a 5' and/or 3' end modification.

In some embodiments, the invention comprises a trRNA comprising one or more modified nucleotides within one or more of the following regions: the 5' terminus, the upper stem region; the bulge region; the lower stem region; the nexus region; the hairpin 1 region; the intervening region between the hairpin 1 and hairpin 2 regions; the hairpin 2 region; and the 3' terminus region.

In some embodiments, the modification comprises 2'-O-Me.

In some embodiments, the modification comprises 2'-F.

In some embodiments, the modification comprises a phosphorothioate (PS) bond linking one or more nucleotides. In some embodiments, the modification is three PS bonds linking the first four nucleotides at the 5' terminus and three PS bonds linking the last four nucleotides at the 3' terminus.

In some embodiments, the modification comprises an inverted abasic nucleotide.

In some embodiments, the trRNA comprises 2'-O-Me modified nucleotides at each nucleic acid in the upper stem; B1 and B2 in the bulge region; LS1 and LS2 in the lower stem region; N3, N4, N5, N15, N16, N17, and N18 in the nexus region; each nucleotide in the hairpin 1 region; one nucleotide between the hairpin 1 and hairpin 2 region; and each nucleotide in the hairpin 2 region. In some embodiments, the trRNA further comprises one or more 2'-O-Me or 2'-O-moe modified nucleotides in the 5' and/or 3' terminus region, e.g. in a 5' and/or 3' end modification.

In some embodiments, the trRNA comprises 2'-O-Me modified nucleotides at each nucleic acid in the upper stem; each nucleotide in the bulge region; LS1, LS2, LS5, and LS6 in the lower stem region; N3-N5, N10-N18 in the nexus region; each nucleotide in the hairpin 1 region; one nucleotide between the hairpin 1 and hairpin 2 region; and each nucleotide in the hairpin 2 region. In some embodiments, the crRNA further comprises one or more 2'-O-Me or 2'-O-moe modified nucleotides in the 5' and/or 3' terminus region, e.g. in a 5' and/or 3' end modification.

In some embodiments, the trRNA comprises 2'-F modified nucleotides at N15 through N18 in the nexus region. In some embodiments, the trRNA further comprises one or more 2'-F modified nucleotides in the 5' and/or 3' terminus region, e.g. in a 5' and/or 3' end modification.

In some embodiments, the trRNA comprises 2'-F modified nucleotides at LS4 and LS5 in the lower stem region, and N13-N18 in the nexus region. In some embodiments, the trRNA further comprises one or more 2'-F modified nucleotides in the 5' and/or 3' terminus region, e.g. in a 5' and/or 3' end modification.

In some embodiments, the trRNA comprises 2'-F modified nucleotides at LS1, LS3, and LS5 in the lower stem, and 2'-O-Me modified nucleotides at LS2, LS4, and LS6 in the lower stem.

Disclosed herein, in some embodiments, is a crispr RNA (crRNA) comprising one or more modifications within one or more of the following regions: the first five nucleotides at the 5' terminus; the lower stem region; the bulge region; the upper stem region; and the last five nucleotides at the 3' terminus. In some embodiments, the modification comprises a 2'-O-methyl (2'-O-Me) modified nucleotide. In some embodiments, the modification comprises a 2'-fluoro (2'-F) modified nucleotide. In some embodiments, the modification comprises a phosphorothioate (PS) bond between nucleotides. In some embodiments, the first three nucleotides at the 5' terminus, and the last three nucleotides at the 3' terminus are modified. In some embodiments, the first four nucleotides at the 5' terminus, and the last four nucleotides at the 3' terminus are linked with phosphorothioate (PS) bonds. In some embodiments, the modification comprises 2'-O-Me. In some embodiments, the modification comprises 2'-F. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-O-Me modifications. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-F modifications. In some embodiments, LS1 and LS6 are modified with 2'-O-Me. In some embodiments, each of the nucleotides in the upper stem region are modified with 2'-O-Me.

In some embodiments, the invention comprises a crispr RNA (crRNA) comprising 2'-O-Me modified nucleic acids at the following nucleotides: LS1 and LS6 in the lower stem region; and each nucleotide in the upper stem region. In some embodiments, the crRNA further comprises three phosphorothioate (PS) bonds linking the first four nucleotides at the 5' terminus and three PS bonds linking the last four nucleotides at the 3' terminus. In some embodiments, the crRNA further comprises 2'-O-Me or 2'-F modified nucleic acids at the first three nucleotides at the 5' terminus, and 2'-O-Me or 2'-F modified nucleic acids at the last three nucleotides at the 3' terminus. In some embodiments, LS1, LS2, and LS6 are modified with 2'-F. In some embodiments, each nucleotide in the bulge region is modified with 2'-F.

Disclosed herein, in some embodiments, is a crispr RNA (crRNA) comprising 2'-F modified nucleic acids at the following nucleotides: LS1, LS2, and LS6 in the lower stem region; and each nucleotide in the bulge region. In some embodiments, the crRNA further comprises three phosphorothioate (PS) bonds linking the first four nucleotides at the 5' terminus and three PS bonds linking the last four nucleotides at the 3' terminus. In some embodiments, the crRNA further comprises 2'-O-Me or 2'-F modified nucleic acids at the first three nucleotides at the 5' terminus, and 2'-O-Me or 2'-F modified nucleic acids at the last three nucleotides at the 3' terminus.

In some embodiments, a crRNA comprising the nucleic acids of any one of SEQ ID Nos: 1-187 is provided. In some embodiments, a crRNA comprising the nucleic acids of any one of SEQ ID Nos: 19-31, 53-73, 104-130, and 161-187 is provided. In some embodiments, a crRNA comprising nucleic acids having at least 99, 98, 97, 96, 95, 94, 93, 92, 91, 90, 85, 80, 75, or 70% identity to the nucleic acids of any one of SEQ ID Nos: 19-31, 53-73, 104-130, and 161-187, wherein the modification pattern is identical to the modification pattern shown in the reference sequence identifier, is provided. In some embodiments, the crRNA further comprises three phosphorothioate (PS) bonds linking the first four nucleotides at the 5' terminus and three PS bonds linking the last four nucleotides at the 3' terminus.

Also encompassed is a tracr RNA (trRNA) comprising one or more modifications within one or more of the following regions: the first five nucleotides at the 5' terminus; the upper stem region; the bulge region; the lower stem region; the nexus region; the hairpin 1 region; the hairpin 2 region; and the last five nucleotides at the 3' terminus. In some embodiments, the modification comprises a 2'-O-methyl (2'-O-Me) modified nucleotide. In some embodiments, the modification comprises a 2'-fluoro (2'-F) modified nucleotide. In some embodiments, the modification comprises a phosphorothioate (PS) bond between nucleotides. In some embodiments, the first four nucleotides at the 5' terminus, and the last four nucleotides at the 3' terminus are linked with phosphorothioate (PS) bonds. In some embodiments, the first three nucleotides at the 5' terminus, and the last three nucleotides at the 3' terminus are modified. In some embodiments, the modification comprises 2'-O-Me. In some embodiments, the modification comprises 2'-F. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-O-Me modifications. In some embodiments, the first four nucleotides at the 5' terminus and the last four nucleotides at the 3' terminus are linked with a PS bond, and wherein the first three nucleotides at the 5' terminus and the last three nucleotides at the 3' terminus comprise 2'-F modifications. In some embodiments, each nucleotide in the upper stem region is modified with 2'-O-Me. In some embodiments, B1 and B2 within the bulge region are modified with 2'-O-Me. In some embodiments, N3, N4, N5, N15, N16, N17, and N18 in the nexus region are modified with 2'-O-Me. In some embodiments, each nucleotide in the hairpin 1 region is modified with 2'-O-Me. In some embodiments, each nucleotide in the hairpin 2 region is modified with 2'-O-Me.

In some embodiments, the invention comprises a tracr RNA (trRNA) comprising 2'-O-Me modified nucleic acids at the following nucleotides: each nucleotide in the upper stem; B1 and B2 within the bulge region; N3, N4, N5, N15, N16, N17, and N18 in the nexus region; each nucleotide in the hairpin 1 region; and each nucleotide in the hairpin 2 region. In some embodiments, the trRNA further comprises three phosphorothioate (PS) bonds linking the first four nucleotides at the 5' terminus and three PS bonds linking the last four nucleotides at the 3' terminus. In some embodiments, the trRNA further comprises 2'-O-Me or 2'-F modified nucleotides at the first three nucleotides at the 5' terminus, and 2'-O-Me or 2'-F modified nucleic acids at the last three nucleotides at the 3' terminus. In some embodiments, N15, N16, N17, and N18 are modified with 2'-F. In some embodiments, LS1, LS3, and LS5 are modified with 2'-F, and LS2, LS4, and LS6 are modified with 2'-O-Me. In some embodiments, the trRNA further comprises three phosphorothioate (PS) bonds linking the first four nucleotides at the 5' terminus and three PS bonds linking the last four nucleotides at the 3' terminus. In some embodiments, the trRNA further comprises 2'-O-Me or 2'-F modified nucleic acids at the first three nucleotides at the 5' terminus, and 2'-O-Me or 2'-F modified nucleic acids at the last three nucleotides at the 3' terminus.

In some embodiments, a trRNA comprising the nucleic acids of any one of SEQ ID Nos: 188-227 is provided. In some embodiments, a trRNA comprising nucleic acids having at least 99, 98, 97, 96, 95, 94, 93, 92, 91, 90, 85, 80, 75, or 70% identity to the nucleic acids of any one of SEQ ID Nos: 188-227, wherein the modification pattern is identical to the modification pattern shown in the reference sequence identifier, is provided. In some embodiments, the trRNA further comprises three phosphorothioate (PS) bonds linking the first four nucleotides at the 5' terminus and three PS bonds linking the last four nucleotides at the 3' terminus.

In some instances, a dual guide comprising a crRNA and a trRNA is provided, wherein the crRNA comprises the nucleic acids of any one of SEQ ID Nos: 1-187, and wherein the trRNA comprises the nucleic acids of any one of SEQ ID Nos: 188-227.

A dual guide comprising a crRNA disclosed herein and a trRNA disclosed herein is encompassed, as is a dual guide comprising a crRNA disclosed herein and an unmodified trRNA. In some embodiments, a dual guide comprising an unmodified crRNA and a modified trRNA disclosed herein is provided.

In some embodiments, and of the following are encompassed:

Embodiment 55

A crispr RNA (crRNA) comprising one or more modifications within one or more of the following regions:
a. the first five nucleotides at the 5' terminus;
b. the lower stem region;
c. the bulge region;
d. the upper stem region; and
e. the last five nucleotides at the 3' terminus.

Embodiment 56

The crRNA of embodiment 55, wherein the modification comprises a 2'-O-methyl (2'-O-Me) modified nucleotide.

Embodiment 57

The crRNA of embodiment 55, wherein the modification comprises a 2'-fluoro (2'-F) modified nucleotide.

Embodiment 58

The crRNA of embodiment 55, wherein the modification comprises a phosphorothioate (PS) bond between nucleotides.

Embodiment 59

The crRNA of any one of embodiments 55-58, wherein the first three nucleotides at the 5' terminus and the last three nucleotides at the 3' terminus are modified.

Embodiment 60

The crRNA of any one of embodiments 55-58, wherein the first four nucleotides at the 5' terminus, and the last four nucleotides at the 3' terminus are linked with phosphorothioate (PS) bonds.

Embodiment 61

The crRNA of embodiment 59, wherein the modification comprises 2'-O-Me.

Embodiment 62

The crRNA of embodiment 59, wherein the modification comprises 2'-F.

Embodiment 63

The crRNA of any one of embodiments 55-62, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-O-Me modifications.

Embodiment 64

The crRNA of any one of embodiments 55-62, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-F modifications.

Embodiment 65

The crRNA of any one of embodiments 55-60, wherein LS1 and LS6 are modified with 2'-O-Me.

Embodiment 66

The crRNA of any one of embodiments 55-60 and 65, wherein each of the nucleotides in the upper stem region are modified with 2'-O-Me.

Embodiment 67

A crispr RNA (crRNA) comprising 2'-O-Me modified nucleotides at:
a. LS1 and LS6 in the lower stem region; and
b. each nucleotide in the upper stem region.

Embodiment 68

The crRNA of embodiment 67, further comprising three phosphorothioate (PS) bonds linking the first four nucleotides at the 5' terminus and three PS bonds linking the last four nucleotides at the 3' terminus.

Embodiment 69

The crRNA of embodiment 67 or 68, further comprising 2'-O-Me or 2'-F modified nucleotides at the first three nucleotides at the 5' terminus, and 2'-O-Me or 2'-F modified nucleotides at the last three nucleotides at the 3' terminus.

Embodiment 70

The crRNA of any of embodiments 55-60, wherein LS1, LS2, and LS6 are modified with 2'-F.

Embodiment 71

The crRNA of any of embodiments 55-60 and 70, wherein each nucleotide in the bulge region is modified with 2'-F.

Embodiment 72

A crispr RNA (crRNA) comprising 2'-F modified nucleotides at:
a. LS1, LS2, and LS6 in the lower stem region; and
b. each nucleotide in the bulge region.

Embodiment 73

The crRNA of any one of embodiments 70-72, further comprising three phosphorothioate (PS) bonds linking the first four nucleotides at the 5' terminus and three PS bonds linking the last four nucleotides at the 3' terminus.

Embodiment 74

The crRNA of embodiment 72 or 73, further comprising 2'-O-Me or 2'-F modified nucleotides at the first three nucleotides at the 5' terminus, and 2'-O-Me or 2'-F modified nucleotides at the last three nucleotides at the 3' terminus.

Embodiment 75

A crRNA comprising the nucleic acids of any one of SEQ ID Nos: 1-187.

Embodiment 76

A crRNA comprising the nucleic acids of any one of SEQ ID Nos: 19-31, 53-73, 104-130, and 161-187.

Embodiment 77

A crRNA comprising nucleic acids having at least 99, 98, 97, 96, 95, 94, 93, 92, 91, 90, 85, 80, 75, or 70% identity to the nucleic acids of any one of SEQ ID Nos: 19-31, 53-73, 104-130, and 161-187, wherein the modification pattern is identical to the modification pattern shown in the reference sequence identifier.

Embodiment 78

The crRNA of any one of embodiments 75-77, further comprising three phosphorothioate (PS) bonds linking the first four nucleotides at the 5' terminus and three PS bonds linking the last four nucleotides at the 3' terminus.

Embodiment 79

A tracr RNA (trRNA) comprising one or more modifications within one or more of the following regions:
a. the first five nucleotides at the 5' terminus;
b. the upper stem region;
c. the bulge region;
d. the lower stem region;
e. the nexus region;
f. the hairpin 1 region;
g. the hairpin 2 region; and
h. the last five nucleotides at the 3' terminus.

Embodiment 80

The trRNA of embodiment 79, wherein the modification comprises a 2'-O-methyl (2'-O-Me) modified nucleotide.

Embodiment 81

The trRNA of embodiment 79, wherein the modification comprises a 2'-fluoro (2'-F) modified nucleotide.

Embodiment 82

The trRNA of embodiment 79, wherein the modification comprises a phosphorothioate (PS) bond between nucleotides.

Embodiment 83

The trRNA of any one of embodiments 79-82, wherein the first four nucleotides at the 5' terminus, and the last four nucleotides at the 3' terminus are linked with phosphorothioate (PS) bonds.

Embodiment 84

The trRNA of any one of embodiments 79-82, wherein the first three nucleotides at the 5' terminus, and the last three nucleotides at the 3' terminus are modified.

Embodiment 85

The trRNA of embodiment 84, wherein the modification comprises 2'-O-Me.

Embodiment 86

The trRNA of embodiment 84, wherein the modification comprises 2'-F.

Embodiment 87

The trRNA of any one of embodiments 79-86, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-O-Me modifications.

Embodiment 88

The trRNA of any one of embodiments 79-86, wherein the first four nucleotides at the 5' terminus and the last four nucleotides at the 3'terminus are linked with a PS bond, and wherein the first three nucleotides at the 5' terminus and the last three nucleotides at the 3' terminus comprise 2'-F modifications.

Embodiment 89

The trRNA of any one of embodiments 79-84, wherein each nucleotide in the upper stem region is modified with 2'-O-Me.

Embodiment 90

The trRNA of any one of embodiments 79-84 and 89, wherein B1 and B2 within the bulge region are modified with 2'-O-Me.

Embodiment 91

The trRNA of any one of embodiments 79-84 and 89-90, wherein N3, N4, N5, N15, N16, N17, and N18 in the nexus region are modified with 2'-O-Me.

Embodiment 92

The trRNA of any one of embodiments 79-84 and 89-91, wherein each nucleotide in the hairpin 1 region is modified with 2'-O-Me.

Embodiment 93

The trRNA of any one of embodiments 79-84 and 89-92, wherein each nucleotide in the hairpin 2 region is modified with 2'-O-Me.

Embodiment 94

A tracr RNA (trRNA) comprising 2'-O-Me modified nucleotides at:
a. each nucleotide in the upper stem;
b. B1 and B2 within the bulge region;
c. N3, N4, N5, N15, N16, N17, and N18 in the nexus region;
d. each nucleotide in the hairpin 1 region; and
e. each nucleotide in the hairpin 2 region.

Embodiment 95

The trRNA of embodiment 94, further comprising three phosphorothioate (PS) bonds linking the first four nucleotides at the 5' terminus and three PS bonds linking the last four nucleotides at the 3' terminus.

Embodiment 96

The crRNA of embodiment 94 or 95, further comprising 2'-O-Me or 2'-F modified nucleotides at the first three nucleotides at the 5' terminus, and 2'-O-Me or 2'-F modified nucleic acids at the last three nucleotides at the 3' terminus.

Embodiment 97

The trRNA of any of embodiments 79-84, wherein N15, N16, N17, and N18 are modified with 2'-F.

Embodiment 98

The trRNA of any of embodiments 79-84 and 97, wherein LS1, LS3, and LS5 are modified with 2'-F, and LS2, LS4, and LS6 are modified with 2'-O-Me.

Embodiment 99

The trRNA of any one of embodiments 87-98, further comprising three phosphorothioate (PS) bonds linking the first four nucleotides at the 5' terminus and three PS bonds linking the last four nucleotides at the 3' terminus.

Embodiment 100

The trRNA of embodiment 98 or 99, further comprising 2'-O-Me or 2'-F modified nucleotides at the first three nucleotides at the 5' terminus, and 2'-O-Me or 2'-F modified nucleotides at the last three nucleotides at the 3' terminus.

Embodiment 101

A trRNA comprising the nucleic acids of any one of SEQ ID Nos: 188-227.

Embodiment 102

A trRNA comprising nucleic acids having at least 99, 98, 97, 96, 95, 94, 93, 92, 91, 90, 85, 80, 75, or 70% identity to the nucleic acids of any one of SEQ ID Nos: 188-227, wherein the modification pattern is identical to the modification pattern shown in the reference sequence identifier.

Embodiment 103

The trRNA of any one of embodiments 101-102, further comprising three phosphorothioate (PS) bonds linking the first four nucleotides at the 5' terminus and three PS bonds linking the last four nucleotides at the 3' terminus.

Embodiment 104

A dual guide comprising a crRNA and a trRNA, wherein the crRNA comprises the nucleotides of any one of SEQ ID Nos: 1-187, and wherein the trRNA comprises the nucleic acids of any one of SEQ ID Nos: 188-227.

Embodiment 105

A dual guide comprising a crRNA of any one of embodiments 55-78 and a trRNA of any one of embodiments 79-103.

Embodiment 106

A dual guide comprising a crRNA of any one of embodiments 55-78 and an unmodified trRNA.

Embodiment 107

A dual guide comprising an unmodified crRNA and a trRNA of any one of embodiments 79-103.

C. Modifications to Terminal Nucleotides

In some embodiments, the 5' or 3' terminal nucleotides of any of the guide RNAs described herein are modified. In some embodiments, the terminal (i.e., last) 1, 2, 3, 4, 5, 6, or 7 nucleotides in 3' terminus region of guide RNA, including, for example, the sgRNA, the dgRNA, the crRNA, trRNA, or both crRNA and trRNA are modified. In some embodiments, the terminal (i.e., last) 1, 2, 3, 4, 5, 6, or 7 nucleotides in 3' terminus region of guide RNA comprise more than one modification. In some embodiments, at least one of the terminal (i.e., last) 1, 2, 3, 4, 5, 6, or 7 nucleotides at the 3' terminus region are modified. In some embodiments, at least two of the terminal (i.e., last) 1, 2, 3, 4, 5, 6, or 7 nucleotides in 3' terminus region are modified. In some embodiments, at least three of the terminal (i.e., last) 1, 2, 3, 4, 5, 6, or 7 nucleotides in 3' terminus region are modified. some embodiments, the modification comprises a PS linkage.

In some embodiments, the 5' end of the 5' terminus region is modified, for example, the first 1, 2, 3, 4, 5, 6, or 7 nucleotides of the sgRNA, the dgRNA, crRNA, trRNA, or both crRNA and trRNA are modified. In some embodiments, the first 1, 2, 3, 4, 5, 6, or 7 nucleotides in 3' terminus region of guide RNA comprise more than one modification. In some embodiments, at least one of the terminal (i.e., first) 1, 2, 3, 4, 5, 6, or 7 nucleotides at the 5' end are modified. In some embodiments, at least two of the terminal 1, 2, 3, 4, 5, 6, or 7 nucleotides at the 5' end are modified. In some embodiments, at least three of the terminal 1, 2, 3, 4, 5, 6, or 7 nucleotides at the 5' end are modified. some embodiments, the modification comprises a PS linkage.

In some embodiments, both the 5' and 3' termini (e.g., ends) of the guide RNA, e.g., sgRNA, dgRNA, crRNA, trRNA, or both crRNA and trRNA are modified. In some embodiments, only the 5' terminus of the guide RNA, e.g., sgRNA, dgRNA, crRNA, trRNA, or both crRNA and trRNA is modified. In some embodiments, only the 3' terminus of the guide RNA, e.g., sgRNA, dgRNA, crRNA, trRNA, or both crRNA and trRNA is modified.

In some embodiments, the gRNA comprises modifications at 1, 2, 3, 4, 5, 6, or 7 of the first 7 nucleotides at a 5' end of the gRNA. In some embodiments, the gRNA comprises modifications at 1, 2, 3, 4, 5, 6, or 7 of the 7 terminal nucleotides at a 3' end. In some embodiments, 2, 3, or 4 of the first 4 nucleotides at the 5' end, and/or 2, 3, or 4 of the terminal 4 nucleotides at the 3' end are modified. In some embodiments, 2, 3, or 4 of the first 4 nucleotides at the 5' end are linked with phosphorothioate (PS) bonds.

In some embodiments, the modification to the 5' terminus and/or 3' terminus comprises a 2'-O-methyl (2'-O-Me) or 2'-O-(2-methoxyethyl) (2'-O-moe) modification to a nucleotide. In some embodiments, the modification comprises a 2'-fluoro (2'-F) modification to a nucleotide. In some embodiments, the modification comprises a phosphorothioate (PS) linkage between nucleotides. In some embodiments, the modification comprises an inverted abasic nucleotide. In some embodiments, the modification comprises a more than one modification selected from 2'-O-Me, 2'-O-moe, 2'-fluoro (2'-F), a phosphorothioate (PS) linkage between nucleotides, and an inverted abasic nucleotide. In some embodiments, an equivalent modification is encompassed.

In some embodiments, the guide RNA, e.g., sgRNA, dgRNA, crRNA, trRNA, or both crRNA and trRNA comprises one or more phosphorothioate (PS) linkages between the first one, two, three, four, five, six, or seven nucleotides at the 5' terminus. In some embodiments, the guide RNA, e.g., sgRNA, dgRNA, crRNA, trRNA, or both crRNA and trRNA comprises one or more PS linkages between the last one, two, three, four, five, six, or seven nucleotides at the 3' terminus. In some embodiments, the guide RNA, e.g., sgRNA, dgRNA, crRNA, trRNA, or both crRNA and trRNA comprises one or more PS linkages between the last one, two, three, four, five, six, or seven nucleotides at both the 5' terminus and the 3' terminus. In some embodiments, in addition to PS linkages, the 5' and 3' terminal nucleotides may comprise 2'-O-Me, 2'-O-moe, or 2'-F modified nucleotides.

In some embodiments, the guide RNA, e.g., sgRNA, dgRNA, crRNA, trRNA, or both crRNA and trRNA comprises modified nucleotides at the 5' and 3' terminus, and modified nucleotides in one or more other regions described in Tables 1-3 and FIG. 21A or 21C.

In some embodiments, the crRNA, trRNA, or both crRNA and trRNA comprises modified nucleotides that are not at the 5' or 3' ends. Specific patterns of modifications are described below and in Table 4.

3. Delivery of gRNAs and Cas Protein

In some embodiments, in addition to the at least one gRNA, the compositions provided herein further comprise a nuclease. In some embodiments, the nuclease is a Cas protein. In some embodiments, the gRNA together with a Cas protein is called a Cas RNP. In some embodiments, the Cas protein is from the Type-II CRISPR/Cas system. In some embodiments, the Cas protein is Cas9. In some embodiments, the Cas9 protein is a wild type Cas9. In some embodiments, the Cas9 protein is derived from the *Streptococcus pyogenes* Cas9 protein, e.g., a *S. pyogenes* Cas9. In some embodiments, the Cas9 protein is not derived from *S. pyogenes*, but functions in the same way as *S. pyogenes* Cas9 such that gRNA that is specific to *S. pyogenes* Cas9 will direct the non-*S. pyogenes* Cas9 to its target site. In some embodiments, the Cas induces a double strand break in target DNA. Equivalents of *S. pyogenes* Cas9 protein are encompassed by the embodiments described herein.

Cas9 encompasses modified and variants thereof. Modified versions of Cas9 having one catalytic domain, either RuvC or HNH, that is inactive are termed "nickases." Nickases cut only one strand on the target DNA, thus creating a single-strand break. A single-strand break may also be known as a "nick." In some embodiments, the compositions and methods comprise nickases. In some embodiments, the compositions and methods comprise a nickase Cas9 that induces a nick rather than a double strand break in the target DNA.

In some embodiments, the Cas protein may be modified to contain only one functional nuclease domain. For example, the Cas protein may be modified such that one of the nuclease domains is mutated or fully or partially deleted to reduce its nucleic acid cleavage activity. In some embodiments, a nickase Cas is used having a RuvC domain with reduced activity. In some embodiments, a nickase Cas is used having an inactive RuvC domain. In some embodiments, a nickase Cas is used having an HNH domain with reduced activity. In some embodiments, a nickase Cas is used having an inactive HNH domain.

In some embodiments, a conserved amino acid within a Cas protein nuclease domain is substituted to reduce or alter nuclease activity. In some embodiments, a Cas protein may comprise an amino acid substitution in the RuvC or RuvC-like nuclease domain. Exemplary amino acid substitutions in the RuvC or RuvC-like nuclease domain include D10A (based on the S. pyogenes Cas9 protein). In some embodiments, the Cas protein may comprise an amino acid substitution in the HNH or HNH-like nuclease domain. Exemplary amino acid substitutions in the HNH or HNH-like nuclease domain include E762A, H840A, N863A, H983A, and D986A (based on the S. pyogenes Cas9 protein).

In some embodiments, the RNP complex described herein comprises a nickase and a pair of guide RNAs that are complementary to the sense and antisense strands of the target sequence, respectively. In this embodiment, the guide RNAs direct the nickase to a target sequence and introduce a double stranded break (DSB) by generating a nick on opposite strands of the target sequence (i.e., double nicking). In some embodiments, use of double nicking may improve specificity and reduce off-target effects. In some embodiments, a nickase Cas is used together with two separate guide RNAs targeting opposite strands of DNA to produce a double nick in the target DNA. In some embodiments, a nickase Cas is used together with two separate guide RNAs that are selected to be in close proximity to produce a double nick in the target DNA.

In some embodiments, chimeric Cas proteins are used, where one domain or region of the protein is replaced by a portion of a different protein. In some embodiments, a Cas nuclease domain may be replaced with a domain from a different nuclease such as Fok1. In some embodiments, a Cas protein may be a modified nuclease.

In some embodiments, the Cas protein comprises a fusion protein comprising a catalytically inactive Cas9 linked to a heterologous functional domain (see, e.g., WO2014152432). In some embodiments, the catalytically inactive Cas9 is from S. pyogenes. In some embodiments, the catalytically inactive Cas9 comprises mutations that inactivate the Cas9. In some embodiments, the heterologous functional domain is a domain that modifies gene expression, histones, or DNA. In some embodiments, the heterologous functional domain is a transcriptional activation domain or a transcriptional repressor domain.

A. PAM

In some embodiments, the target sequence may be adjacent to the PAM. In some embodiments, the PAM may be adjacent to or within 1, 2, 3, or 4, nucleotides of the 3' end of the target sequence. The length and the sequence of the PAM may depend on the Cas protein used. For example, the PAM may be selected from a consensus or a particular PAM sequence for a specific Cas9 protein or Cas9 ortholog, including those disclosed in FIG. 1 of Ran et al., Nature 520:186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG, NAG, NGA, NGAG, NGCG, NNGRRT, TTN, NGGNG, NG, NAAAAN, NNAAAAW, NNNNACA, GNNNCNNA, and NNNNGATT (wherein N is defined as any nucleotide, and W is defined as either A or T, and R is defined as either A or G). In some embodiments, the PAM sequence may be NGG. In some embodiments, the PAM sequence may be NGGNG. In some embodiments, the PAM sequence may be NNAAAAW.

B. Delivery of Modified gRNA

Lipid nanoparticles (LNPs) are a well-known means for delivery of nucleotide and protein cargo, and may be used for delivery of the gRNA, mRNA, Cas9, and RNPs disclosed herein. In some embodiments, the LNPs deliver nucleic acid, protein, or nucleic acid together with protein.

In some embodiments, the invention comprises a method for delivering any one of the gRNAs disclosed herein to a subject, wherein the gRNA is associated with an LNP. In some embodiments, the gRNA/LNP is also associated with a Cas9 or an mRNA encoding Cas9.

In some embodiments, the invention comprises a composition comprising any one of the gRNAs disclosed and an LNP. In some embodiments, the composition further comprises a Cas9 or an mRNA encoding Cas9.

In some embodiments, the LNPs comprise cationic lipids. In some embodiments, the LNPs comprise (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)-butanoyl)oxy)-2-((((3-(diethylamino)propoxy)carbonyl)oxy)methyl)propyl (9Z, 12Z)-octadeca-9,12-dienoate). In some embodiments, the LNPs comprise molar ratios of a cationic lipid amine to RNA phosphate (N:P) of about 4.5.

In some embodiments, LNPs associated with the gRNAs disclosed herein are for use in preparing a medicament for treating a disease or disorder.

Electroporation is a well-known means for delivery of cargo, and any electroporation methodology may be used for delivery of any one of the gRNAs disclosed herein. In some embodiments, electroporation may be used to deliver any one of the gRNAs disclosed herein and Cas9 or an mRNA encoding Cas9.

In some embodiments, the invention comprises a method for delivering any one of the gRNAs disclosed herein to an ex vivo cell, wherein the gRNA is associated with an LNP or not associated with an LNP. In some embodiments, the gRNA/LNP or gRNA is also associated with a Cas9 or an mRNA encoding Cas9.

4. Methods of Gene Modulation

In some embodiments, the invention comprises a pharmaceutical formulation comprising any one of the gRNAs disclosed herein together with a pharmaceutically acceptable carrier. In some embodiments, the invention comprises a pharmaceutical formulation comprising any one of the gRNAs disclosed herein and an LNP together with a pharmaceutically acceptable carrier. In some embodiments, the invention comprises a pharmaceutical formulation comprising any one of the gRNAs disclosed herein, a Cas9 protein or an mRNA encoding a Cas9 protein, and a LNP together with a pharmaceutically acceptable carrier. In some embodiments, the pharmaceutical formulation is for use in preparing a medicament for treating a disease or disorder. In some embodiments, the invention comprises a method of treating a human patient comprising administering any one of the gRNAs or pharmaceutical formulations described herein.

In some embodiments, the invention comprises a method or use of modifying a target DNA comprising, administering or delivering a Cas protein or Cas mRNA and any one or more of the gRNAs disclosed herein.

In some embodiments, the invention comprises a method or use for modulation of a target gene comprising, administering or delivering a Cas protein or Cas mRNA and any one or more of the gRNAs disclosed herein. In some embodiments, the modulation is editing of the target gene. In some embodiments, the modulation is a change in expression of the protein encoded by the target gene.

In some embodiments, the method or use results in gene editing. In some embodiments, the method or use results in a double-stranded break within the target gene. In some embodiments, the method or use results in formation of indel mutations during non-homologous end joining of the DSB. In some embodiments, the method or use results in an insertion or deletion of nucleotides in a target gene. In some embodiments, the insertion or deletion of nucleotides in a target gene leads to a frameshift mutation or premature stop codon that results in a non-functional protein. In some embodiments, the insertion or deletion of nucleotides in a target gene leads to a knockdown or elimination of target gene expression. In some embodiments, the method or use comprises homology directed repair of a DSB. In some embodiments, the method or use further comprises delivering to the cell a template, wherein at least a part of the template incorporates into a target DNA at or near a double strand break site induced by the Cas protein.

In some embodiments, the method or use results in gene modulation. In some embodiments, the gene modulation is an increase or decrease in gene expression, a change in methylation state of DNA, or modification of a histone subunit. In some embodiments, the method or use results in increased or decreased expression of the protein encoded by the target gene.

In some embodiments, any of the gRNAs disclosed herein may be useful in preparing a medicament for treating a disease or disorder.

A. Measures of Gene Modulation

The efficacy of modified gRNAs can be tested in vitro and in vivo. In some embodiments, the invention comprises one or more of the gRNAs disclosed herein, wherein the gRNA results in gene modulation when provided to a cell together with Cas9. In some embodiments, the efficacy of gRNA can be measured in in vitro or in vivo assays.

1. In Vitro Measurement of Cas Efficacy

In some embodiments, the activity of a Cas RNP comprising a modified sgRNA is compared to the activity of a Cas RNP comprising an unmodified sgRNA.

In some embodiments, the activity of a Cas RNP comprising a dgRNA comprising a modified trRNA is compared to the activity of a Cas RNP comprising a dgRNA comprising an unmodified trRNA.

In some embodiments, the activity of a Cas RNP comprising a dgRNA comprising a modified crRNA is compared to the activity of a Cas RNP comprising a dgRNA comprising an unmodified crRNA.

In some embodiments, the activity of a Cas RNP comprising a dgRNA comprising a modified crRNA and a modified trRNA is compared to the activity of a Cas RNP comprising an unmodified crRNA and an unmodified trRNA.

In some embodiments, the efficiency of a gRNA in increasing or decreasing target protein expression is determined by measuring the amount of target protein. In some embodiments, the invention comprises any one of the gRNAs described herein, wherein the gRNA increases or decreases the amount of protein produced from the targeted gene. In some embodiments, the invention comprises a method of modulating protein expression comprising administering any one of the gRNAs disclosed herein to a subject, wherein the gRNA directs Cas9 to the gene encoding the target protein, and the target protein expression is increased or decreased as compared to a gRNA control that does not target Cas9 to that gene.

In some embodiments, the efficiency of editing with specific gRNAs is determined by the editing present at the target location in the genome following delivery of Cas9 and the gRNA (either sgRNA or dgRNA comprising a crRNA and trRNA). In some embodiments, the efficiency of editing with specific gRNAs is measured by next-generation sequencing. In some embodiments, the editing percentage of the target region of interest is determined. In some embodiments, the total number of sequence reads with insertions or deletions of nucleotides into the target region of interest over the total number of sequence reads is measured following delivery of a gRNA and Cas9. In some embodiments, the invention comprises a method of increasing the efficiency of gene editing comprising, administering or delivering any one of the modified gRNAs described herein to a cell, wherein the percentage of gene editing is increased as compared to a control gRNA that is not similarly modified.

In some embodiments, the efficiency of editing with specific gRNAs is measured by the presence of insertions or deletions of nucleotides introduced by successful gene editing. In some embodiments, the invention comprises a method of creating insertions or deletions of nucleotides in genes comprising, administering or delivering any one of the modified gRNAs described herein to a cell, wherein the nucleotides are inserted or deleted as compared to a control gRNA that is not similarly modified. In some embodiments, activity of a Cas9 and gRNAs is tested in biochemical assays. In some embodiments, activity of a Cas9 and gRNAs is tested in a cell-free cleavage assay. In some embodiments, activity of a Cas9 and gRNAs is tested in Neuro2A cells.

In some embodiments, Cas 9 and sgRNA or dgRNA comprising modified crRNA and/or trRNA shows similar, greater, or reduced activity compared to the unmodified sgRNA or dgRNA comprising unmodified crRNA and trRNA. In some embodiments, Cas9 and modified sgRNA or dgRNA comprising modified crRNA and/or trRNA shows enhanced activity compared to the unmodified sgRNA or dgRNA comprising unmodified crRNA and trRNA.

2. In Vivo Measurement of Cas Efficacy

In some embodiments, the activity of modified gRNAs is measured after in vivo dosing of LNPs comprising modified gRNAs and Cas protein or mRNA encoding Cas protein.

In some embodiments, in vivo efficacy of a gRNA or composition provided herein is determined by editing efficacy measured in DNA extracted from tissue (e.g., liver tissue) after administration of gRNA and Cas9.

3. In Vivo Measurement of Immune System Activation

Modifications to gRNA as disclosed herein may reduce the subject's immune response to in vivo dosing of gRNAs. In some embodiments, activation of the subject's immune response is measured by serum concentrations of cytokine(s) following in vivo dosing of sgRNA or dgRNA comprising trRNA and crRNA together with Cas9 mRNA or protein (e.g., formulated in a LNP). In some embodiments, the cytokine is interferon-alpha (IFN-alpha), interleukin 6 (IL-6), monocyte chemotactic protein 1 (MCP-1), and/or tumor necrosis factor alpha (TNF-alpha). In some embodiments, the invention comprises a method of reducing a subject's immune response to delivery of a gRNA comprising, administering any one of the gRNAs disclosed herein, wherein the gRNA produces a reduced response by the subject's immune system following administration. In some embodiments, the invention comprises a method of reducing activation of the subject's immune system following administration as compared to a control gRNA that is not similarly modified.

In some embodiments, administration of Cas RNP or Cas9 mRNA together with the modified gRNA (e.g., sgRNA or dgRNA) produces lower serum concentration(s) of immune cytokines compared to administration of unmodified sgRNA. In some embodiments, the invention comprises a method of reducing a subject's serum concentration of immune cytokines comprising, administering any one of the gRNAs disclosed herein, wherein the gRNA produces a lower concentration of immune cytokines in a subject's serum as compared to a control gRNA that is not similarly modified.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Examples

The following examples are provided to illustrate certain disclosed embodiments and are not to be construed as limiting the scope of this disclosure in any way.

Example 1—Materials and Methods

A. Synthetic Guide RNA (gRNA)

gRNA in both dual (dgRNA, i.e., crRNA and trRNA) and single guide (sgRNA) format were chemically synthesized by commercial vendors with modified nucleotides and linkages as provided in Table 4.

B. In Vitro Transcription ("IVT") of Cas9 mRNA

Capped and polyadenylated Cas9 mRNA containing N1-methyl pseudo-U was generated by in vitro transcription using a linearized plasmid DNA template and T7 RNA polymerase. Plasmid DNA containing a T7 promoter and a 100 nucleotide (nt) poly(A/T) region was linearized by XbaI and obtained from a commercial manufacturer. The IVT reaction to generate Cas9 modified mRNA was incubated at 37° C. for 4 hours in the following conditions: 50 ng/μL linearized plasmid; 2 mM each of GTP, ATP, CTP, and N1-methyl pseudo-UTP (Trilink); 10 mM ARCA (Trilink); 5 U/pt T7 RNA polymerase (NEB); 1 U/pt Murine RNase inhibitor (NEB); 0.004 U/μL Inorganic $E.$ $coli$ pyrophosphatase (NEB); and 1× reaction buffer. After the 4 hr incubation, TURBO DNase (ThermoFisher) was added to a final concentration of 0.01 U/4, and the reaction was incubated for an additional 30 minutes to remove the DNA template. The Cas9 mRNA was purified from enzyme and nucleotides using standard protocols, including silica binding columns such as a MegaClear Transcription Clean-up kit (ThermoFisher) or precipitation steps using LiCl followed by EtOH with NaOAc. The transcript concentration was determined by measuring the light absorbance at 260 nm (Nanodrop), and the transcript was analyzed by capillary electrophoresis by Bioanlayzer (Agilent).

C. Cas9 mRNA and gRNA Transfections in Neuro2A Cells

The mouse cell line Neuro2A was cultured in DMEM media supplemented with 10% fetal bovine serum and was plated at a density of 15,000 cells/well in a 96-well plate 24 hours prior to transfection. On the day of transfection, the media was aspirated from cells and replaced with fresh media. Lipofectamine-2000 (Invitrogen) was diluted 1:50 (v/v) in Opti-MEM (Invitrogen). Cas9 mRNA and single guide RNA were diluted separately in Opti-MEM. For the dual guide format, crRNA and trRNA were diluted together in 1:1 molar ratio in Opti-MEM. Both Cas9 mRNA and gRNA were mixed separately 1:1 (v/v) with diluted Lipofectamine-2000, producing two lipoplexes. After 5 minutes of incubation, lipoplexes were added in succession to cells, for a final concentration of 100 ng Cas9 mRNA/well and 0.4 μL total lipofection reagent. Guides were tested at two dose levels for each experiment, including 25 nM and 2.5 nM, 16.7 nM and 1.67 nM, 10 nM and 1 nM, 8.3 nM and 0.83 nM, and 3 nM and 0.3 nM. For dual guide, this concentration includes equimolar amounts of crRNA and trRNA, such that, for example, 25 nM crRNA and 25 nM trRNA produce 25 nM total dual guide. Cells were lysed 24 hours post transfection, and lysates were used directly in the PCR reaction that was analyzed for editing by NGS.

```
Cas9 mRNA with 1xNLS (SEQ ID NO: 359):
GGGUCCCGCAGUCGGCGUCCAGCGGCUCUGCUUGUUCGUGUGUGUGUCGUUGCAGGCCU

UAUUCGGAUCCAUGGAUAAGAAGUACUCAAUCGGGCUGGAUAUCGGAACUAAUUC

CGUGGGUUGGGCAGUGAUCACGGAUGAAUACAAAGUGCCGUCCAAGAAGUUCAAGGU

CCUGGGGAACACCGAUAGACACAGCAUCAAGAAAAAUCUCAUCGGAGCCCUGCUGUU

UGACUCCGGCGAAACCGCAGAAGCGACCCGGCUCAAACGUACCGCGAGGCGACGCUA

CACCCGGCGGAAGAAUCGCAUCUGCUAUCUGCAAGAGAUCUUUUCGAACGAAAUGGC

AAAGGUCGACGACAGCUUCUUCCACCGCCUGGAAGAAUCUUUCCUGGUGGAGGAGGA

CAAGAAGCAUGAACGGCAUCCUAUCUUUGGAAACAUCGUCGACGAAGUGGCGUACCA

CGAAAAGUACCCGACCAUCUACCAUCUGCGGAAGAAGUUGGUUGACUCAACUGACAA
```

-continued

GGCCGACCUCAGAUUGAUCUACUUGGCCCUCGCCCAUAUGAUCAAAUUCCGCGGACA

CUUCCUGAUCGAAGGCGAUCUGAACCCUGAUAACUCCGACGUGGAUAAGCUUUUCAU

UCAACUGGUGCAGACCUACAACCAACUGUUCGAAGAAAACCCAAUCAAUGCUAGCGG

CGUCGAUGCCAAGGCCAUCCUGUCCGCCCGGCUGUCGAAGUCGCGGCGCCUCGAAAA

CCUGAUCGCACAGCUGCCGGGAGAGAAAAAGAACGGACUUUUCGGCAACUUGAUCGC

UCUCUCACUGGGACUCACUCCCAAUUUCAAGUCCAAUUUUGACCUGGCCGAGGACGC

GAAGCUGCAACUCUCAAAGGACACCUACGACGACGACUUGGACAAUUUGCUGGCACA

AAUUGGCGAUCAGUACGCGGAUCUGUUCCUUGCCGCUAAGAACCUUUCGGACGCAAU

CUUGCUGUCCGAUAUCCUGCGCGUGAACACCGAAAUAACCAAAGCGCCGCUUAGCGC

CUCGAUGAUUAAGCGGUACGACGAGCAUCACCAGGAUCUCACGCUGCUCAAAGCGCU

CGUGAGACAGCAACUGCCUGAAAAGUACAAGGAGAUCUUCUUCGACCAGUCCAAGAA

UGGGUACGCAGGGUACAUCGAUGGAGGCGCUAGCCAGGAAGAGUUCUAUAAGUUCAU

CAAGCCAAUCCUGGAAAAGAUGGACGGAACCGAAGAACUGCUGGUCAAGCUGAACAG

GGAGGAUCUGCUCCGGAAACAGAGAACCUUUGACAACGGAUCCAUUCCCCACCAGAU

CCAUCUGGGUGAGCUGCACGCCAUCUUGCGGCGCCAGGAGGACUUUUACCCAUUCCU

CAAGGACAACCGGGAAAAGAUCGAGAAAAUUCUGACGUUCCGCAUCCCGUAUUACGU

GGGCCCACUGGCGCGCGGCAAUUCGCGCUUCGCGUGGAUGACUAGAAAAUCAGAGGA

AACCAUCACUCCUUGGAAUUUCGAGGAAGUUGUGGAUAAGGGAGCUUCGGCACAAAG

CUUCAUCGAACGAAUGACCAACUUCGACAAGAAUCUCCCAAACGAGAAGGUGCUUCC

UAAGCACAGCCUCCUUUACGAAUACUUCACUGUCUACAACGAACUGACUAAAGUGAA

AUACGUUACUGAAGGAAUGAGGAAGCCGGCCUUUCUGUCCGGAGAACAGAAGAAAGC

AAUUGUCGAUCUGCUGUUCAAGACCAACCGCAAGGUGACCGUCAAGCAGCUUAAAGA

GGACUACUUCAAGAAGAUCGAGUGUUUCGACUCAGUGGAAAUCAGCGGGGUGGAGGA

CAGAUUCAACGCUUCGCUGGGAACCUAUCAUGAUCUCCUGAAGAUCAUCAAGGACAA

GGACUUCCUUGACAACGAGGAGAACGAGGACAUCCUGGAAGAUAUCGUCCUGACCUU

GACCCUUUUCGAGGAUCGCGAGAUGAUCGAGGAGAGGCUUAAGACCUACGCUCAUCU

CUUCGACGAUAAGGUCAUGAAACAACUCAAGCGCCGCCGGUACACUGGUUGGGGCCG

CCUCUCCCGCAAGCUGAUCAACGGUAUUCGCGAUAAACAGAGCGGUAAAACUAUCCU

GGAUUUCCUCAAAUCGGAUGGCUUCGCUAAUCGUAACUUCAUGCAAUUGAUCCACGA

CGACAGCCUGACCUUUAAGGAGGACAUCCAAAAAGCACAAGUGUCCGGACAGGGAGA

CUCACUCCAUGAACACAUCGCGAAUCUGGCCGGUUCGCCGGCGAUUAAGAAGGGAAU

UCUGCAAACUGUGAAGGUGGUCGACGAGCUGGUGAAGGUCAUGGGACGGCACAAACC

GGAGAAUAUCGUGAUUGAAAUGGCCCGAGAAAACCAGACUACCCAGAAGGGCCAGAA

AAACUCCCGCGAAAGGAUGAAGCGGAUCGAAGAAGGAAUCAAGGAGCUGGGCAGCCA

GAUCCUGAAAGAGCACCCGGUGGAAAACACGCAGCUGCAGAACGAGAAGCUCUACCU

GUACUAUUUGCAAAAUGGACGGGACAUGUACGUGGACCAAGAGCUGGACAUCAAUCG

GUUGUCUGAUUACGACGUGGACCACAUCGUUCCACAGUCCUUUCUGAAGGAUGACUC

GAUCGAUAACAAGGUGUUGACUCGCAGCGACAAGAACAGAGGGAAGUCAGAUAAUGU

GCCAUCGGAGGAGGUCGUGAAGAAGAUGAAGAAUUACUGGCGGCAGCUCCUGAAUGC

GAAGCUGAUUACCCAGAGAAAGUUUGACAAUCUCACUAAAGCCGAGCGCGGCGGACU

-continued

```
CUCAGAGCUGGAUAAGGCUGGAUUCAUCAAACGGCAGCUGGUCGAGACUCGGCAGAU

UACCAAGCACGUGGCGCAGAUCUUGGACUCCCGCAUGAACACUAAAUACGACGAGAA

CGAUAAGCUCAUCCGGGAAGUGAAGGUGAUUACCCUGAAAAGCAAACUUGUGUCGGA

CUUUCGGAAGGACUUUCAGUUUUACAAAGUGAGAGAAAUCAACAACUACCAUCACGC

GCAUGACGCAUACCUCAACGCUGUGGUCGGUACCGCCCUGAUCAAAAAGUACCCUAA

ACUUGAAUCGGAGUUUGUGUACGGAGACUACAAGGUCUACGACGUGAGGAAGAUGAU

AGCCAAGUCCGAACAGGAAAUCGGGAAAGCAACUGCGAAAUACUUCUUUUACUCAAA

CAUCAUGAACUUUUUCAAGACUGAAAUUACGCUGGCCAAUGGAGAAAUCAGGAAGAG

GCCACUGAUCGAAACUAACGGAGAAACGGGCGAAAUCGUGUGGGACAAGGGCAGGGA

CUUCGCAACUGUUCGCAAAGUGCUCUCUAUGCCGCAAGUCAAUAUUGUGAAGAAAAC

CGAAGUGCAAACCGGCGGAUUUUCAAAGGAAUCGAUCCUCCCAAAGAGAAAUAGCGA

CAAGCUCAUUGCACGCAAGAAAGACUGGGACCCGAAGAAGUACGGAGGAUUCGAUUC

GCCGACUGUCGCAUACUCCGUCCUCGUGGUGGCCAAGGUGGAGAAGGGAAAGAGCAA

AAAGCUCAAAUCCGUCAAAGAGCUGCUGGGGAUUACCAUCAUGGAACGAUCCUCGUU

CGAGAAGAACCCGAUUGAUUUCCUCGAGGCGAAGGGUUACAAGGAGGUGAAGAAGGA

UCUGAUCAUCAAACUCCCCAAGUACUCACUGUUCGAACUGGAAAAUGGUCGGAAGCG

CAUGCUGGCUUCGGCCGGAGAACUCCAAAAAGGAAAUGAGCUGGCCUUGCCUAGCAA

GUACGUCAACUUCCUCUAUCUUGCUUCGCACUACGAAAAACUCAAAGGGUCACCGGA

AGAUAACGAACAGAAGCAGCUUUUCGUGGAGCAGCACAAGCAUUAUCUGGAUGAAAU

CAUCGAACAAAUCUCCGAGUUUUCAAAGCGCGUGAUCCUCGCCGACGCCAACCUCGA

CAAAGUCCUGUCGGCCUACAAUAAGCAUAGAGAUAAGCCGAUCAGAGAACAGGCCGA

GAACAUUAUCCACUUGUUCACCCUGACUAACCUGGGAGCCCCAGCCGCCUUCAAGUA

CUUCGAUACUACUAUCGAUCGCAAAAGAUACACGUCCACCAAGGAAGUUCUGGACGC

GACCCUGAUCCACCAAAGCAUCACUGGACUCUACGAAACUAGGAUCGAUCUGUCGCA

GCUGGGUGGCGAUGGCGGUGGAUCUCCGAAAAAGAAGAGAAAGGUGUAAUGAGCUAG

CCAUCACAUUUAAAAGCAUCUCAGCCUACCAUGAGAAUAAGAGAAAGAAAAUGAAGA

UCAAUAGCUUAUUCAUCUCUUUUUCUUUUUCGUUGGUGUAAAGCCAACACCCUGUCU

AAAAAACAUAAAUUUCUUUAAUCAUUUUGCCUCUUUUCUCUGUGCUUCAAUUAAUAA

AAAAUGGAAAGAACCUCGAGAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

AAAAAAUCUAG

Cas9 mRNA with 2xNLS and HA tag (SEQ ID NO: 360):
GGGUCCCGCAGUCGGCGUCCAGCGGCUCUGCUUGUUCGUGUGUGUGUCGUUGCAGGC

CUUAUUCGGAUCCAUGGAUAAGAAGUACUCAAUCGGGCUGGAUAUCGGAACUAAUUC

CGUGGGUUGGGCAGUGAUCACGGAUGAAUACAAAGUGCCGUCCAAGAAGUUCAAGGU

CCUGGGGAACACCGAUAGACACAGCAUCAAGAAAAAUCUCAUCGGAGCCCUGCUGUU

UGACUCCGGCGAAACCGCAGAAGCGACCCGGCUCAAACGUACCGCGAGGCGACGCUA

CACCCGGCGGAAGAAUCGCAUCUGCUAUCUGCAAGAGAUCUUUUCGAACGAAAUGGC

AAAGGUCGACGACAGCUUCUUCCACCGCCUGGAAGAAUCUUUCCUGGUGGAGGAGGA

CAAGAAGCAUGAACGGCAUCCUAUCUUUGGAAACAUCGUCGACGAAGUGGCGUACCA

CGAAAAGUACCCGACCAUCUACCAUCUGCGGAAGAAGUUGGUUGACUCAACUGACAA
```

-continued

```
GGCCGACCUCAGAUUGAUCUACUUGGCCCUCGCCCAUAUGAUCAAAUUCCGCGGACA
CUUCCUGAUCGAAGGCGAUCUGAACCCUGAUAACUCCGACGUGGAUAAGCUUUUCAU
UCAACUGGUGCAGACCUACAACCAACUGUUCGAAGAAACCCAAUCAAUGCUAGCGG
CGUCGAUGCCAAGGCCAUCCUGUCCGCCCGGCUGUCGAAGUCGCGGCGCCUCGAAAA
CCUGAUCGCACAGCUGCCGGGAGAGAAAAAGAACGGACUUUUCGGCAACUUGAUCGC
UCUCUCACUGGGACUCACUCCCAAUUUCAAGUCCAAUUUUGACCUGGCCGAGGACGC
GAAGCUGCAACUCUCAAAGGACACCUACGACGACGACUUGGACAAUUUGCUGGCACA
AAUUGGCGAUCAGUACGCGGAUCUGUUCCUUGCCGCUAAGAACCUUUCGGACGCAAU
CUUGCUGUCCGAUAUCCUGCGCGUGAACACCGAAAUAACCAAAGCGCCGCUUAGCGC
CUCGAUGAUUAAGCGGUACGACGAGCAUCACCAGGAUCUCACGCUGCUCAAAGCGCU
CGUGAGACAGCAACUGCCUGAAAAGUACAAGGAGAUCUUCUUCGACCAGUCCAAGAA
UGGGUACGCAGGGUACAUCGAUGGAGGCGCUAGCCAGGAAGAGUUCUAUAAGUUCAU
CAAGCCAAUCCUGGAAAAGAUGGACGGAACCGAAGAACUGCUGGUCAAGCUGAACAG
GGAGGAUCUGCUCCGGAAACAGAGAACCUUUGACAACGGAUCCAUUCCCCACCAGAU
CCAUCUGGGUGAGCUGCACGCCAUCUUGCGGCGCCAGGAGGACUUUUACCCAUUCCU
CAAGGACAACCGGGAAAAGAUCGAGAAAAUUCUGACGUUCCGCAUCCCGUAUUACGU
GGGCCCACUGGCGCGCGGCAAUUCGCGCUUCGCGUGGAUGACUAGAAAAUCAGAGGA
AACCAUCACUCCUUGGAAUUUCGAGGAAGUUGUGGAUAAGGGAGCUUCGGCACAAAG
CUUCAUCGAACGAAUGACCAACUUCGACAAGAAUCUCCCAAACGAGAAGGUGCUUCC
UAAGCACAGCCUCCUUUACGAAUACUUCACUGUCUACAACGAACUGACUAAAGUGAA
AUACGUUACUGAAGGAAUGAGGAAGCCGGCCUUUCUGUCCGGAGAACAGAAGAAAGC
AAUUGUCGAUCUGCUGUUCAAGACCAACCGCAAGGUGACCGUCAAGCAGCUUAAAGA
GGACUACUUCAAGAAGAUCGAGUGUUUCGACUCAGUGGAAAUCAGCGGGGUGGAGGA
CAGAUUCAACGCUUCGCUGGGAACCUAUCAUGAUCUCCUGAAGAUCAUCAAGGACAA
GGACUUCCUUGACAACGAGGAGAACGAGGACAUCCUGGAAGAUAUCGUCCUGACCUU
GACCCUUUUCGAGGAUCGCGAGAUGAUCGAGGAGAGGCUUAAGACCUACGCUCAUCU
CUUCGACGAUAAGGUCAUGAAACAACUCAAGCGCCGCCGGUACACUGGUUGGGGCCG
CCUCUCCCGCAAGCUGAUCAACGGUAUUCGCGAUAAACAGAGCGGUAAAACUAUCCU
GGAUUUCCUCAAAUCGGAUGGCUUCGCUAAUCGUAACUUCAUGCAAUUGAUCCACGA
CGACAGCCUGACCUUUAAGGAGGACAUCCAAAAAGCACAAGUGUCCGGACAGGGAGA
CUCACUCCAUGAACACAUCGCGAAUCUGGCCGGUUCGCCGGCGAUUAAGAAGGGAAU
UCUGCAAACUGUGAAGGUGGUCGACGAGCUGGUGAAGGUCAUGGGACGGCACAAACC
GGAGAAUAUCGUGAUUGAAAUGGCCCGAGAAAACCAGACUACCCAGAAGGGCCAGAA
AAACUCCCGCGAAAGGAUGAAGCGGAUCGAAGAAGGAAUCAAGGAGCUGGGCAGCCA
GAUCCUGAAAGAGCACCCGGUGGAAAAACACGCAGCUGCAGAACGAGAAGCUCUACCU
GUACUAUUUGCAAAAUGGACGGGACAUGUACGUGGACCAAGAGCUGGACAUCAAUCG
GUUGUCUGAUUACGACGUGGACCACAUCGUUCCACAGUCCUUUCUGAAGGAUGACUC
GAUCGAUAACAAGGUGUUGACUCGCAGCGACAAGAACAGAGGGAAGUCAGAUAAUGU
GCCAUCGGAGGAGGUCGUGAAGAAGAUGAAGAAUUACUGGCGGCAGCUCCUGAAUGC
GAAGCUGAUUACCCAGAGAAAGUUUGACAAUCUCACUAAAGCCGAGCGCGGCGGACU
CUCAGAGCUGGAUAAGGCUGGAUUCAUCAAACGGCAGCUGGUCGAGACUCGGCAGAU
```

-continued

```
UACCAAGCACGUGGCGCAGAUCUUGGACUCCCGCAUGAACACUAAAUACGACGAGAA

CGAUAAGCUCAUCCGGGAAGUGAAGGUGAUUACCCUGAAAAGCAAACUUGUGUCGGA

CUUUCGGAAGGACUUUCAGUUUUACAAAGUGAGAGAAAUCAACAACUACCAUCACGC

GCAUGACGCAUACCUCAACGCUGUGGUCGGUACCGCCCUGAUCAAAAAGUACCCUAA

ACUUGAAUCGGAGUUUGUGUACGGAGACUACAAGGUCUACGACGUGAGGAAGAUGAU

AGCCAAGUCCGAACAGGAAAUCGGGAAAGCAACUGCGAAAUACUUCUUUUACUCAAA

CAUCAUGAACUUUUUCAAGACUGAAAUUACGCUGGCCAAUGGAGAAAUCAGGAAGAG

GCCACUGAUCGAAACUAACGGAGAAACGGGCGAAAUCGUGUGGGACAAGGGCAGGGA

CUUCGCAACUGUUCGCAAAGUGCUCUCUAUGCCGCAAGUCAAUAUUGUGAAGAAAAC

CGAAGUGCAAACCGGCGGAUUUUCAAAGGAAUCGAUCCUCCCAAAGAGAAAUAGCGA

CAAGCUCAUUGCACGCAAGAAAGACUGGGACCCGAAGAAGUACGGAGGAUUCGAUUC

GCCGACUGUCGCAUACUCCGUCCUCGUGGUGGCCAAGGUGGAGAAGGGAAAGAGCAA

AAAGCUCAAAUCCGUCAAAGAGCUGCUGGGGAUUACCAUCAUGGAACGAUCCUCGUU

CGAGAAGAACCCGAUUGAUUUCCUCGAGGCGAAGGGUUACAAGGAGGUGAAGAAGGA

UCUGAUCAUCAAACUCCCCAAGUACUCACUGUUCGAACUGGAAAAUGGUCGGAAGCG

CAUGCUGGCUUCGGCCGGAGAACUCCAAAAAGGAAAUGAGCUGGCCUUGCCUAGCAA

GUACGUCAACUUCCUCUAUCUUGCUUCGCACUACGAAAAACUCAAAGGGUCACCGGA

AGAUAACGAACAGAAGCAGCUUUUCGUGGAGCAGCACAAGCAUUAUCUGGAUGAAAU

CAUCGAACAAAUCUCCGAGUUUUCAAAGCGCGUGAUCCUCGCCGACGCCAACCUCGA

CAAAGUCCUGUCGGCCUACAAUAAGCAUAGAGAUAAGCCGAUCAGAGAACAGGCCGA

GAACAUUAUCCACUUGUUCACCCUGACUAACCUGGGAGCCCCAGCCGCCUUCAAGUA

CUUCGAUACUACUAUCGAUCGCAAAAGAUACACGUCCACCAAGGAAGUUCUGGACGC

GACCCUGAUCCACCAAAGCAUCACUGGACUCUACGAAACUAGGAUCGAUCUGUCGCA

GCUGGGUGGCGAUGGCUCGGCUUACCCAUACGACGUGCCUGACUACGCCUCGCUCGG

AUCGGGCUCCCCCAAAAAGAAACGGAAGGUGGACGGAUCCCCGAAAAAGAAGAGAAA

GGUGGACUCCGGAUGAGAAUUAUGCAGUCUAGCCAUCACAUUUAAAAGCAUCUCAGC

CUACCAUGAGAAUAAGAGAAAGAAAAUGAAGAUCAAUAGCUUAUUCAUCUCUUUUUC

UUUUUCGUUGGUGUAAAGCCAACACCCUGUCUAAAAAACAUAAAUUUCUUUAAUCAU

UUUGCCUCUUUUCUCUGUGCUUCAAUUAAUAAAAAAUGGAAAGAACCUCGAGAAAAA

AAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAUCUAG
```

D. Primary Liver Hepatocytes

Primary mouse liver hepatocytes (PMH) (Gibco) were cultured per the manufacturer's protocol (Invitrogen, protocol Nov. 28, 2012). In brief, the cells were thawed and resuspended in hepatocyte thawing medium with supplements (Gibco, Cat. CM7000) followed by centrifugation at 100 g for 10 minutes. The supernatant was discarded and the pelleted cells resuspended in hepatocyte plating medium plus supplement pack (Invitrogen, Cat. A1217601 and CM3000). Cells were counted and plated on Bio-coat collagen I coated 96-well plates (ThermoFisher, Cat. 877272) at a density of 15,000 cells/well and incubated for 5 hours at 37° C. and 5% CO2 atmosphere to allow for monolayer formation. After 5 hours, the plating media was removed and replaced with supplemented hepatocyte culture medium (Invitrogen, Cat. A1217601 and CM4000) containing LNP formulated Cas9 mRNA and guide RNA plus 3% mouse serum. LNPs were diluted from a starting dose level of 100 ng Cas9 mRNA and approximately 30 nM guide RNA per well, carrying out serial dilutions down to 0.1 ng mRNA and 0.03 nM guide per well. Cells were incubated for approximately 48 hours at 37° C. and 5% $CO_2$ atmosphere before cell lysis and NGS analysis as described herein.

E. Lipid Nanoparticle ("LNP") Formulation

LNPs were formulated with a cationic lipid amine to RNA phosphate (N:P) molar ratio of about 4.5. The lipid nanoparticle components were dissolved in 100% ethanol with the following molar ratios: 45 mol-% (12.7 mM) cationic lipid (e.g., (9Z,12Z)-3-((4,4-bis(octyloxy)butanoyl)oxy)-2-(((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate); 44 mol-% (12.4 mM) helper lipid (e.g., cholesterol); 9 mol-% (2.53 mM) neutral lipid (e.g., DSPC); and 2 mol-% (0.563 mM) PEG (e.g., PEG2k-DMG). The RNA cargo were prepared in 25 mM sodium acetate buffer, pH 4.5, resulting in a concentration of RNA cargo of approximately 0.45 mg/mL.

The LNPs were formed by microfluidic mixing of the lipid and RNA solutions using a Precision Nanosystems NanoAssemblr™ Benchtop Instrument, according to the manufacturer's protocol. A 2:1 ratio of aqueous to organic solvent was maintained during mixing using differential flow rates.

LNP Formulation Procedure A:

After mixing, the LNPs were collected, diluted in phosphate buffered saline (PBS, approximately 1:1), and then mixed 1:1 with water. Then they were buffer-exchanged into 1×TSS (50 mM Tris, 45 mM NaCl, 5% sucrose at pH 7.5) on PD-10 columns (GE Healthcare), using manufacturer's protocol. The LNPs were concentrated using 10 kDa Amicon spin filter (centrifugation at 4000 g at 4° C.) to achieve the desired concentration. The resulting mixture was then filtered using a 0.2 μm sterile filter. The resulting filtrate was stored at −80° C.

F. Next-Generation Sequencing ("NGS") and Analysis for On-Target Cleavage Efficiency To quantitatively determine the efficiency of editing at the target location in the genome, deep sequencing was utilized to identify the presence of insertions and deletions introduced by gene editing.

PCR primers were designed around the target site (e.g., TTR, FVII), and the genomic area of interest was amplified. Primer sequences are provided below in Table 5.

TABLE 5

| Guide | Gene | Forward Primer (5'-3') | SEQ ID | Reverse Primer (5'-3') | SEQ ID |
|---|---|---|---|---|---|
| For experiments with guides based on CR000686/G000209 targeting domains | TTR | AGTCAATAATCAGAATCAGCAGGT | 333 | AGAAGGCACTTCTTCTTTATCTAAGGGT | 337 |
| For experiments with guides based on CR000705/G000211 targeting domains | TTR | GTTTTGTTCCAGAGTCTATCACCG | 334 | ACACGAATAAGAGCAAATGGGAAC | 338 |
| For experiments with guides based on G000269/G000285 targeting domains | TTR | ATTACCAGCTTAGCATCCTGTGAA | 335 | ACACGGTTTATAGAGCAAGAACAC | 339 |
| For experiments with guides based on CR000657/G000208 targeting domains | FVII | AGCACATGAGACCTTCTGTTTCTC | 336 | GACATAGGTGTGACCCTCACAATC | 340 | remaining buffer was exchanged into PBS (100-fold excess of sample volume), overnight at 4° C. under gentle stirring using a 10 kDa Slide-a-Lyzer™ G2 Dialysis Cassette (ThermoFisher Scientific). The LNPs were concentrated using 10 kDa Amicon spin filter (centrifugation at 4000 g at 4° C.) to achieve the desired concentration. The resulting mixture was then filtered using a 0.2 μm sterile filter. The resulting filtrate was stored at 2-8° C.

LNP Formulation Procedure B:

After mixing, the LNPs were collected, diluted in 50 mM Tris at pH 7.5 (approximately 1:1), and then LNPs were exchanged into 50 mM Tris at pH 7.5 (100-fold excess of sample volume), overnight at 4° C. under gentle stirring using a 10 kDa Slide-a-Lyzer™ G2 Dialysis Cassette (ThermoFisher Scientific). The LNPs were concentrated using 10 kDa Amicon spin filter (centrifugation at 4000 g at 4° C.) to achieve twice the desired concentration. These concentrated LNPs were mixed 1:1 with 50 mM Tris, 90 mM NaCl, 10% sucrose at pH 7.5 (2×TSS). The resulting mixture was then filtered using a 0.2 μM sterile filter. The resulting filtrate was stored at −80° C.

LNP Formulation Procedure C:

The RNA cargo were prepared in 25 mM sodium citrate, 100 mM sodium chloride at pH 5 resulting in a concentration of RNA cargo of approximately 0.45 mg/mL. After mixing, the LNPs were collected in water at the ratio of 3:1. The LNPs were incubated for an hour at room temperature and Additional PCR was performed according to the manufacturer's protocols (Illumina) to add the necessary chemistry for sequencing. The amplicons were sequenced on an Illumina MiSeq instrument. The reads were aligned to the human reference genome (e.g., hg38) after eliminating those having low quality scores. The resulting files containing the reads were mapped to the reference genome (BAM files), where reads that overlapped the target region of interest were selected and the number of wild type reads versus the number of reads which contain an insertion, substitution, or deletion was calculated.

The editing percentage (e.g., the "editing efficiency" or "percent editing") is defined as the total number of sequence reads with insertions or deletions over the total number of sequence reads, including wild type.

G. LNP Delivery In Vivo

CD-1 female mice, ranging 6-10 weeks of age were used in each study. Animals were weighed and grouped according to body weight for preparing dosing solutions based on group average weight. LNPs were dosed via the lateral tail vein in a volume of 0.2 mL per animal (approximately 10 mL per kilogram body weight). The animals were observed at approximately 6 hours post dose for adverse effects. Body weight was measured at twenty-four hours post-administration, and animals were euthanized at various time points by exsanguination via cardiac puncture under isoflourane anesthesia. Blood was collected into serum separator tubes or into tubes containing buffered sodium citrate for plasma as described herein. For studies involving in vivo editing, liver tissue was collected from the median lobe from each animal for DNA extraction and analysis.

H. Cytokine Induction Analysis

For this analysis, approximately 50-100 µL of blood was collected by tail vein nick for serum cytokine measurements. Blood was allowed to clot at room temperature for approximately 2 hours, and then centrifuged at 1000×g for 10 minutes before collecting the serum. A Luminex based magnetic bead multiplex assay (Affymetrix ProcartaPlus, catalog number Exp040-00000-801) measuring IL-6, TNF-alpha, IFN-alpha, and MCP-1 was used for cytokine analysis in collected in samples. Kit reagents and standards were prepared as directed in the manufacturer's protocol. 25 µL of mouse serum was added to wells containing 25 µL of the diluted antibody coated magnetic beads. The plate was incubated for 2 hours at room temperature and then washed. Diluted biotin antibody (50 µL) was added to the beads and incubated for 1 hour at room temperature. The beads were washed again before adding 50 µL of diluted streptavidin-PE to each well, followed by incubation for 30 minutes. The beads were washed once again and then suspended in 100 µL of wash buffer and read on the Bio-Plex 200 instrument (Bio-Rad). The data was analyzed using Bioplex Manager ver. 6.1 analysis package with cytokine concentrations calculated off a standard curve using a five parameter logistic curve fit.

I. Genomic DNA Isolation

For the in vivo studies, genomic DNA was extracted from 10 mg of tissue using a bead based extraction kit, MagMAX-96 DNA Multi-Sample Kit (ThermoFisher, Cat #4413020) according to manufacturer's protocol, which includes homogenizing the tissue in lysis buffer (approximately 400 µL/10 mg tissue). All DNA samples were normalized to 100 ng/µL concentration for PCR and subsequent NGS analysis, as described herein.

J. Transthyretin (TTR) ELISA Analysis

Blood was collected and the serum was isolated as indicated. The total TTR serum levels were determined using a Mouse Prealbumin (Transthyretin) ELISA Kit (Aviva Systems Biology, Cat. OKIA00111). Kit reagents and standards were prepared according to the manufacture's protocol. Mouse serum was diluted to a final dilution of 10,000-fold with 1× assay diluent. This was done by carrying out two sequential 50-fold dilutions resulting in a 2500-fold dilution. A final 4-fold dilution step was carried out for a total sample dilution of 10,000-fold. Both standard curve dilutions (100 µL each) and diluted serum samples were added to each well of the ELISA plate pre-coated with capture antibody. The plate was incubated at room temperature for 30 minutes before washing. Enzyme-antibody conjugate (100 µL per well) was added for a 20-minute incubation. Unbound antibody conjugate was removed and the plate was washed again before the addition of the chromogenic substrate solution. The plate was incubated for 10 minutes before adding 100 µL of the stop solution, e.g., sulfuric acid (approximately 0.3 M). The plate was read on a SpectraMax M5 plate reader at an absorbance of 450 nm. Serum TTR levels were calculated by SoftMax Pro software ver. 6.4.2 using a four parameter logistic curve fit off the standard curve. Final serum values were adjusted for the assay dilution.

Example 2—Engineering Modified gRNA and In Vitro Testing

Modified gRNAs were designed in the dual guide format (dgRNA), as shown in Table 4. Accordingly, both modified crRNAs and trRNAs were designed and chemically synthesized to allow for the pairing of modified and unmodified components forming dgRNA. These pairings were transfected into Neuro2A cells at concentrations as indicated in the figures and editing efficiency (e.g., percent editing) was measured by NGS, as described in Example 1.

Figure 1:
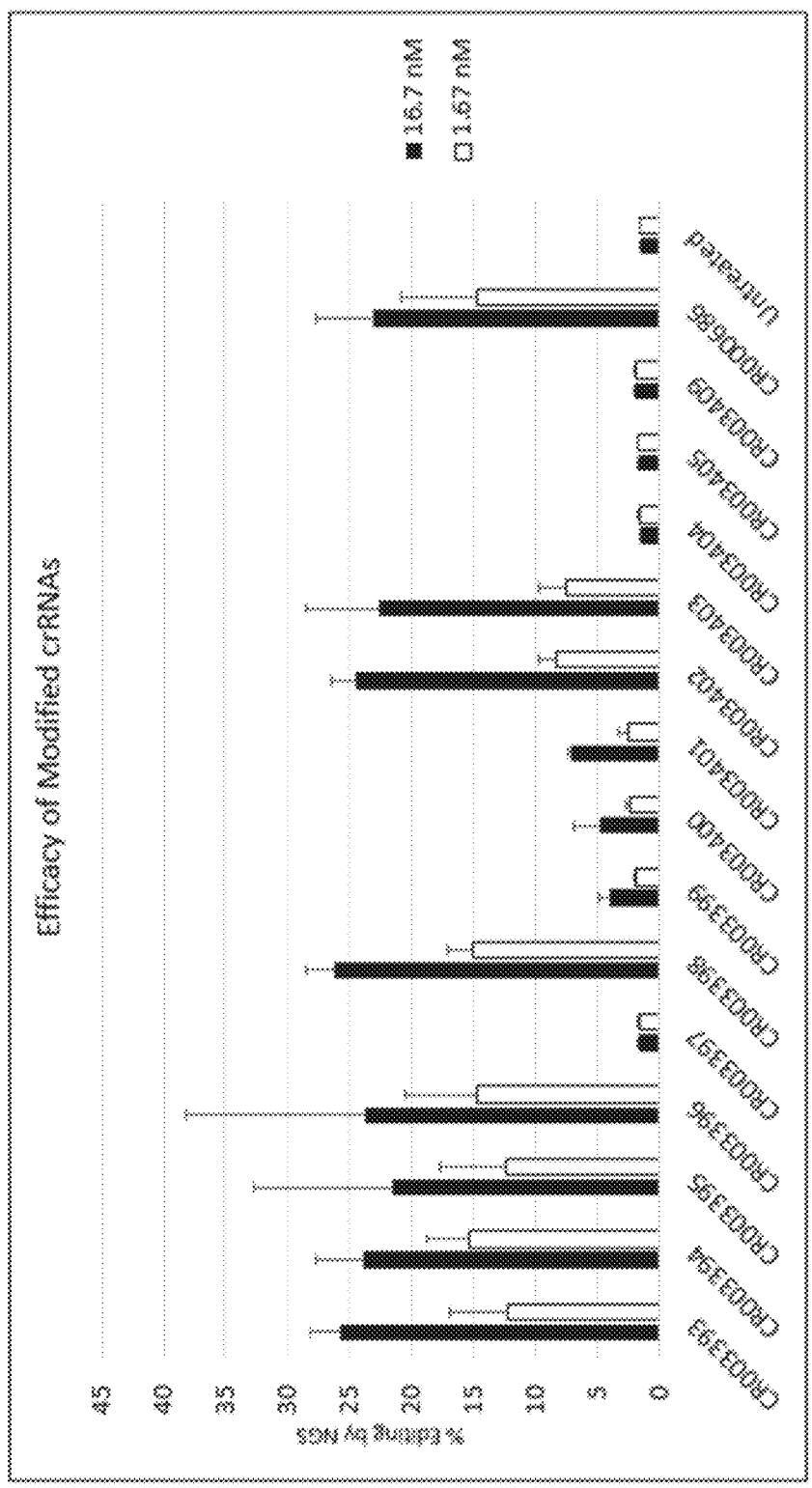
FIG. 1 shows percent editing as measured by next-generation sequence (NGS) of mouse transthyretin (TTR) gene following transfection of Neuro2A cells with modified crRNAs together with Cas9 mRNA and unmodified trRNA (TR000002).

Certain modified crRNAs from Table 4 targeting the mouse TTR gene were transfected with Cas9 mRNA and unmodified trRNA (TR000002). Tested guides included SEQ ID Nos: 1-18. As shown in FIG. 1, some of the modified crRNAs (together with unmodified trRNA) conferred similar or enhanced activity as compared to the unmodified control, while other modified crRNAs decreased activity.

Figure 2:
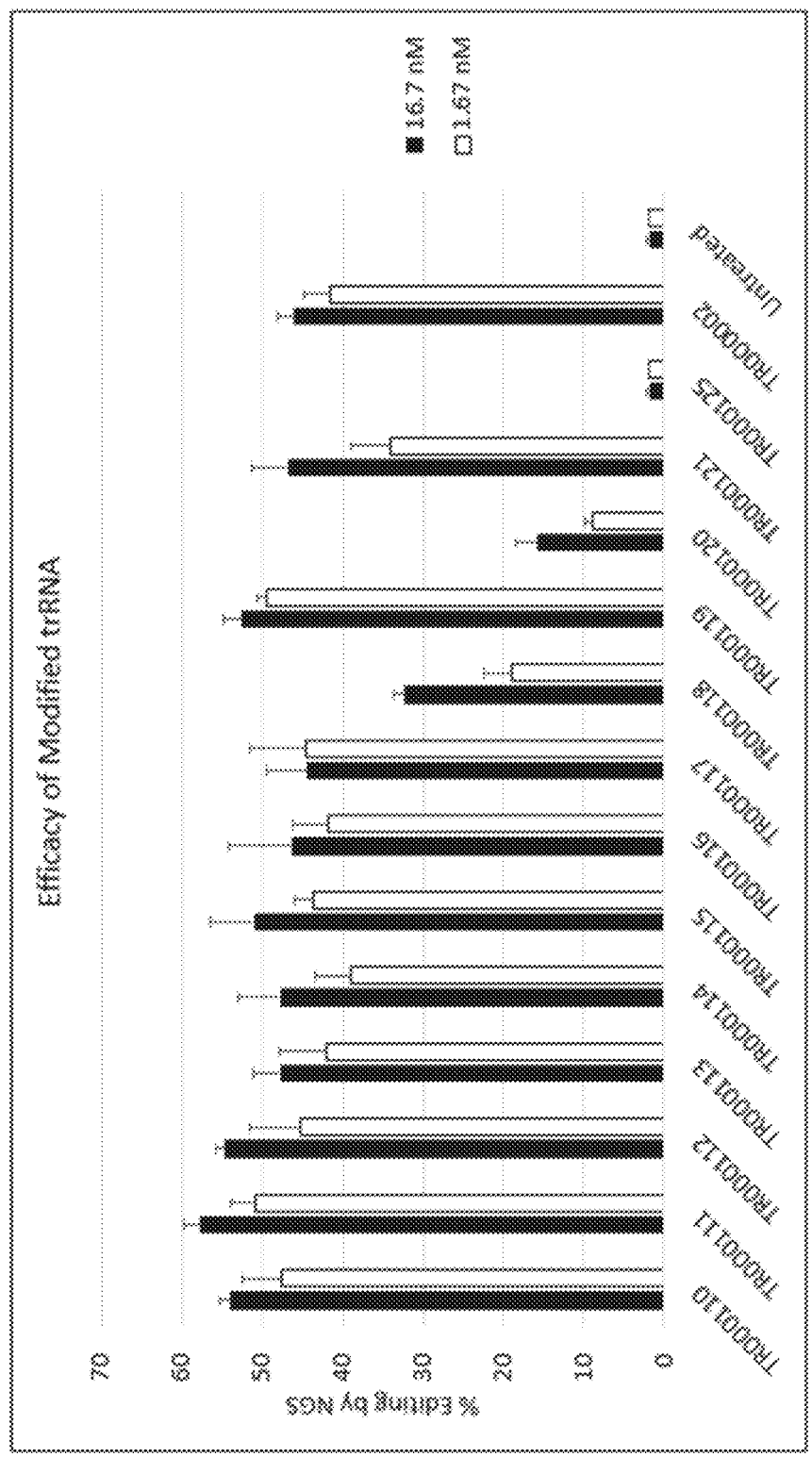
FIG. 2 shows percent editing as measured by NGS of mouse TTR gene following transfection of Neuro2A cells with modified trRNAs together with unmodified crRNA (CR000686) and Cas9 mRNA.

In parallel, modified trRNAs from Table 4 were transfected with Cas9 mRNA along with an unmodified crRNA (CR000686) targeting the same sequence of the mouse TTR gene. Tested guides included SEQ ID Nos: 188-200, and 204. As shown in FIG. 2, many of the modified trRNAs (together with unmodified crRNA) conferred similar or enhanced activity as compared to the unmodified control, while some of the modified trRNAs decreased activity.

Figure 3:
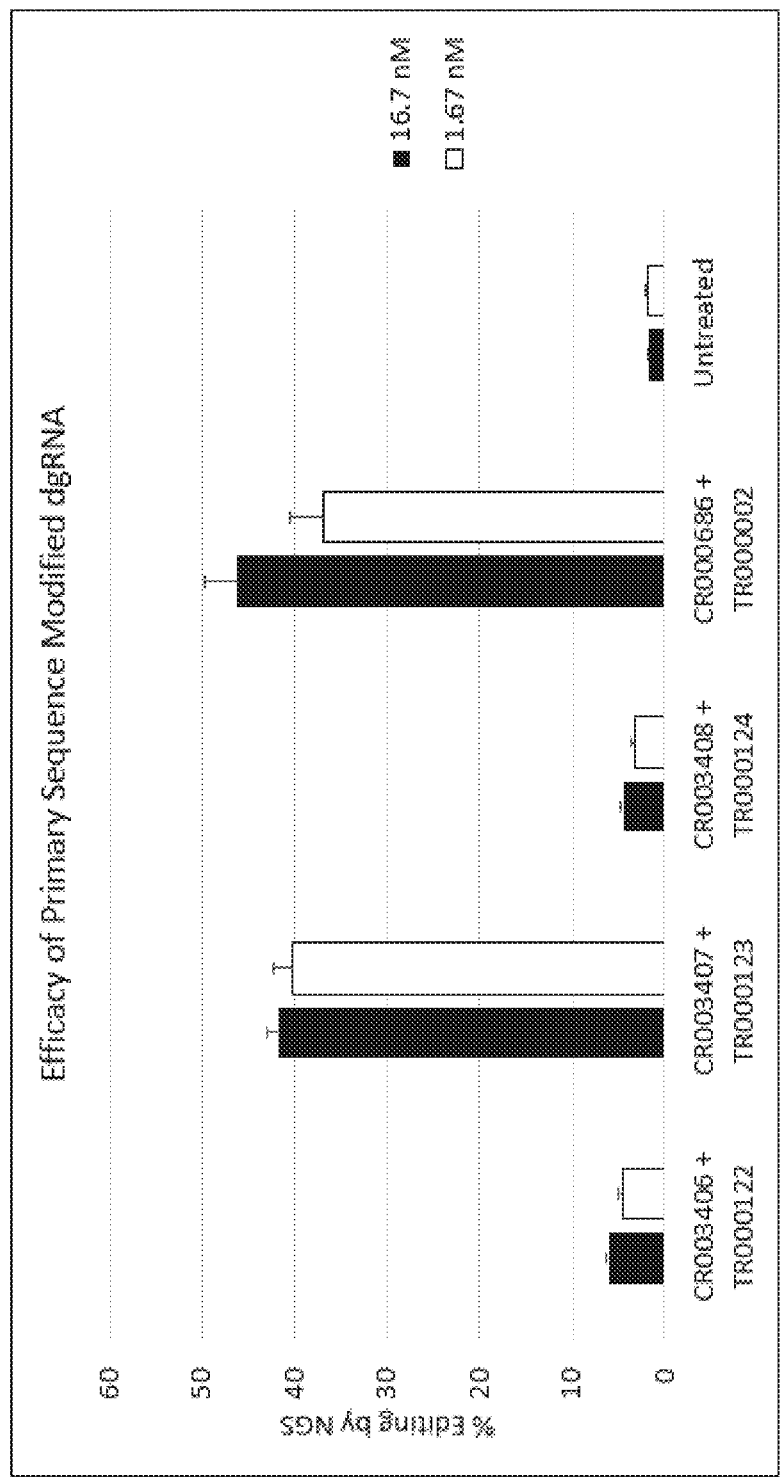
FIG. 3 shows percent editing as measured by NGS of mouse TTR gene following transfection of Neuro2A cells with Cas9 mRNA and crRNAs and trRNAs having G-C pairings not found in parental sequences.

In addition to substituting chemically modified nucleotides, some of the crRNA and trRNA pairings tested were also engineered with sequence substitutions, e.g., resulting in G-C pairings not found in the parental sequences. Tested guides included SEQ ID Nos: 15 and 201; 16 and 202; 1 and 188. As shown in FIG. 3, one such pairing (SEQ ID Nos: 16 and 202) resulted in similar or enhanced activity as compared to the unmodified control, while two of the pairings decreased activity.

Next, pairings of modified crRNAs and modified trRNAs from Table 4 were tested. As shown in FIG. 4, some of the pairings of modified crRNA with modified trRNA conferred similar or enhanced activity as compared to the unmodified controls, while some of the pairings decreased activity. In FIG. 4, the column headings depict different trRNA used in the experiment, and the row headings depict different crRNA used. To determine the combination used in the experiment, you match column to row. TR000002 and CR000686 are the unmodified controls (see lower right cells).

Figure 5:
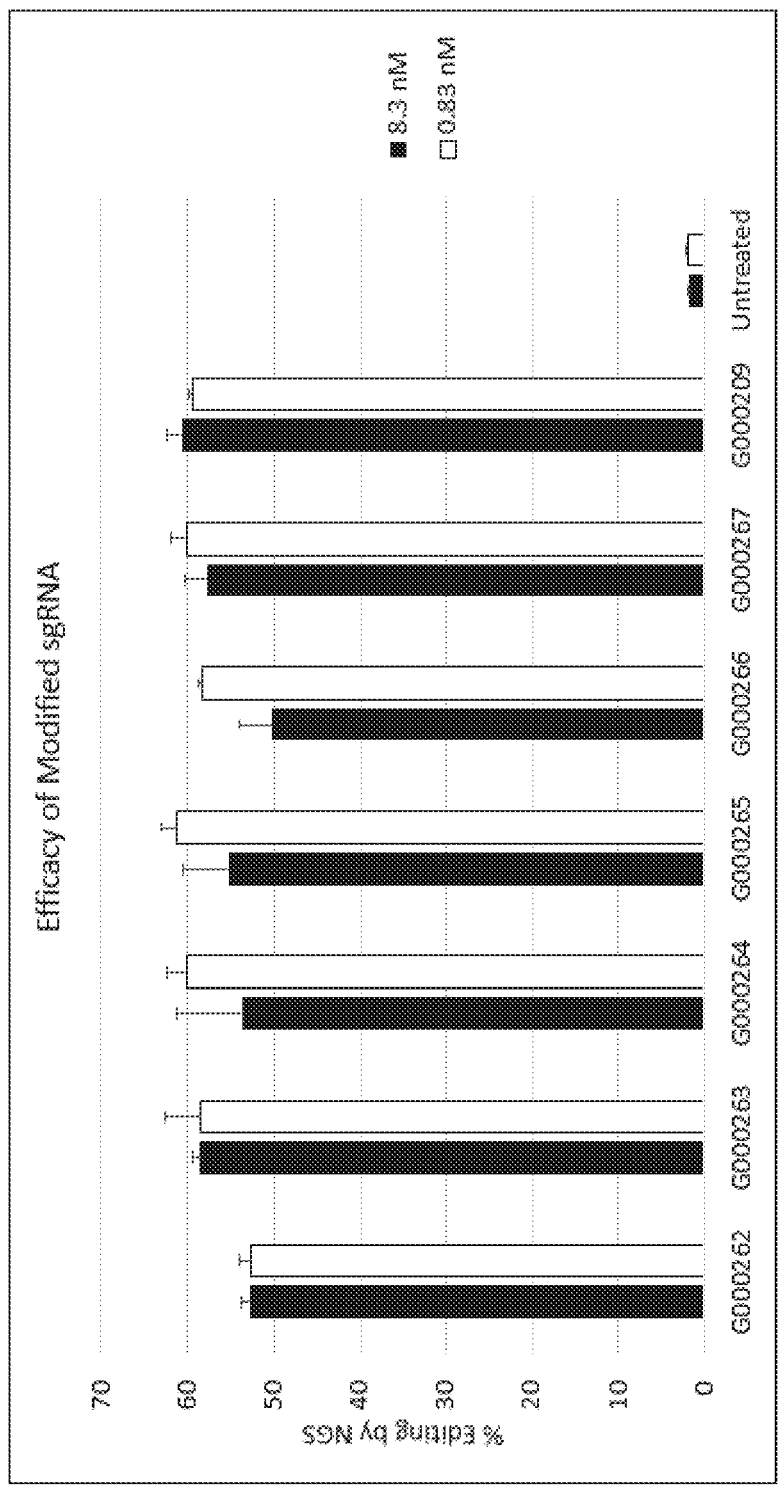
FIG. 5 shows percent editing as measured by NGS of mouse TTR gene following transfection of Neuro2A cells with modified sgRNAs together with Cas9 mRNA.

Based on the dgRNA designs, corresponding single guide RNAs (sgRNAs) were engineered featuring aspects of some of the modified crRNAs and trRNAs, as depicted in Table 4 and FIG. 15D. These sgRNAs, SEQ ID Nos: 228-234, were also tested in Neuro2A cells, and as shown in FIG. 5, each of the modified sgRNAs displayed activities comparable to the controls containing only 5' and 3' end modifications (G0000209; SEQ ID NO: 228).

A similar set of experiments were conducted for additional dgRNAs guides depicted in Table 4 and FIG. 6. Tested guides included SEQ ID Nos: 32-47, and 1. Modified crRNAs also targeting the mouse TTR gene were transfected with Cas9 mRNA and unmodified trRNA (TR000002). As shown in FIG. 6, some of the modified crRNAs (together with unmodified trRNA) conferred similar or enhanced activity as compared to the unmodified control (CR000686), while other modified crRNAs decreased activity.

In parallel, as shown in FIG. 7, modified trRNAs from Table 4 were transfected with Cas9 mRNA along with an unmodified crRNA (CR000686) targeting the same sequence of the mouse TTR gene. Tested guides included SEQ ID Nos: 205-222, and 1. As shown in FIG. 7, many of the modified trRNAs (together with unmodified crRNA)

conferred similar or enhanced activity as compared to the unmodified control (TR000002), while some of the modified trRNAs decreased activity.

In addition to substituting chemically modified nucleotides, some of the crRNA and trRNA pairings tested from Table 4 were also engineered with sequence substitutions, e.g., resulting in G-C pairings or G-U mismatches ("GU wobbles") not found in the parental sequences. As shown in FIG. 8, some of the modifications and pairings conferred similar or enhanced activity as compared to the unmodified control, while some (e.g., the "GU wobble" or mismatch pairings) decreased activity. FIG. 8 shows results using trRNA guides shown in SEQ ID Nos: 223-227 and 188 with crRNA guides shown in SEQ ID Nos: 48-52, and 1.

Next, select pairings of the modified crRNAs and modified trRNAs from Table 4 were tested as shown in FIG. 9. Some of the pairings of modified crRNA with modified trRNA conferred similar or enhanced activity as compared to the unmodified controls, while some of the pairings decreased activity. In FIG. 9, the column headings depict different trRNA used in the experiment, and the row headings depict different crRNA used. To determine the combination used in the experiment, you match column to row. Unmodified controls are TR000002, and CR000686.

Some of the modified gRNAs (dgRNAs and sgRNAs) from Table 4 were also tested in a purely biochemical assay (i.e., cell free cleavage assay). Interestingly, many of the modified gRNAs that were largely inactive in the Neuro2A cells were active in the biochemical assay, indicating that such biochemical assays may not be predictive of modified gRNA activity in cells (data not shown).

Example 3. Further Testing of Modified gRNAs to Other Targets

Having established that certain modifications affected gRNA activity, it was next tested whether these modifications would affect the activity when targeting (1) a separate sequence in the same gene or (2) a sequence in a different gene. Accordingly, gRNAs targeting another sequence in the mouse TTR gene as well as a sequence in the mouse Factor-VII (FVII) gene were engineered and synthesized having certain modification patterns tested in Example 2 (see Table 4). These gRNAs were transfected into Neuro2A cells at the concentrations indicated in the figures and editing efficiency (e.g., percent editing) was measured by NGS, as described in Example 1.

Modified crRNAs from Table 4 targeting either the mouse TTR gene (different sequence as targeted in Example 2) or the mouse FVII gene, were transfected with Cas9 mRNA and unmodified trRNA (TR000002). Tested guides included those shown in FIGS. 12A and 12B. Some of the modified crRNAs (together with unmodified trRNA) conferred similar or enhanced activity as compared to the unmodified controls, while other modified crRNAs decreased activity.

In parallel, modified trRNAs from Table 4 were transfected with Cas9 mRNA along with an unmodified crRNA targeting the same sequence of the mouse TTR gene (CR000705; different sequence as targeted in Example 2) or the same sequence as the mouse FVII gene (CR000657). As shown in FIGS. 13A and 13B, many of the modified trRNAs (together with unmodified crRNAs) conferred similar or enhanced activity as compared to the unmodified controls, while some of the modified trRNAs decreased activity. This data shows that certain modification patterns tended to have similar effects over the different sequences.

Based on the dgRNA designs described above, corresponding single guide RNAs (sgRNAs) were engineered featuring aspects of some of the modified crRNAs and trRNAs. See, Table 4. These sgRNAs were also tested in Neuro2A cells. Results are shown in FIG. 10 (mouse TTR) and FIG. 11 (mouse FVII). These experiments show that some modification patterns result in similar effects even when targeting different genes.

Example 4. Testing of Modified gRNA In Vivo

Following the in vitro testing, modified sgRNAs were delivered to animals in six separate studies in order to determine whether the modifications conferred any benefits for editing in vivo.

LNPs were formulated with IVT Cas9 mRNA together with chemically modified sgRNA (targeting TTR or FVII), as described in Example 1. The ratio of mRNA:sgRNA was approximately 1:1, by weight of the RNA components. Unless otherwise indicated, the Cas9 mRNA used in the studies described in this example had the sequence of SEQ ID NO: 360 and the LNPs were formulated using LNP Formulation Procedure A described above.

In one experiment, mice (n=5 per group) were administered a single dose of LNP at 2 mg/kg and blood was collected four hours post dose for serum cytokine analysis. 7 days post dose at necropsy, livers and blood were collected for NGS measurements of editing efficiency and serum TTR analysis, respectively. Each of the sgRNAs in this experiment targeted the same sequence in the TTR gene, the only difference between the sgRNAs being the modifications made to each (See FIGS. 14A-D and 15A-E; Table 4 SEQ ID Nos: 228-234). G000209 (two lots tested) served as the less modified control, having only 2'-O-methyl modifications and phosphorothioate linkages at and between the three terminal nucleotides at both the 5' and 3' termini of the sgRNA, respectively. (See FIG. 15D).

The results shown in FIGS. 14A-D, show that the more heavily modified sgRNAs tended to induce less of a response for each the cytokines assayed, as compared to the less modified G000209 controls. The more heavily modified sgRNAs also conferred larger editing efficiencies in the livers of treated animals, with percent editing reaching ~60% for two of the more heavily modified sgRNAs (e.g., G000263 and G000267) as compared to ~44-47% for the less modified controls (G000209 lots) (FIG. 15A). Importantly, the editing efficiencies correlated with phenotypic changes as serum knockdown of TTR levels were comparable or significantly greater than the less modified controls (See e.g., G000263 and G000267 vs G000209 lots in FIGS. 15A-15B). The differences between the end-modified 6000209 and highly-modified G000267 are summarized in FIGS. 15D and 15E (2'-O-Me modified nucleotides are shown in bold, and * represents phosphorothioate linkages).

In another in vivo study, three sgRNAs targeting a separate sequence in the mouse TTR gene were tested. Mice (n=5 per group) were administered a single dose of LNP at 2 mg/kg, 1 mg/kg, or 0.3 mg/kg. Blood was collected four hours post dose for serum cytokine analysis. 7 days post dose at necropsy, livers and blood were collected for NGS measurements of editing efficiency and serum TTR analysis, respectively. In this study, each of the sgRNAs targeted the same sequence in the TTR gene (a different sequence from what was targeted in the previous in vivo study) with one sgRNA being completely unmodified (G000201 (SEQ ID NO: 243)), another having only end modifications (G000211 (SEQ ID NO: 241)), with 2'-O-methyl modifications and phosphorothioate linkages at and between the three terminal nucleotides at both the 5' and 3' termini of the sgRNA, respectively), and a third sgRNA having the same modification pattern as G000267 in the previous in vivo study (G000282 (SEQ ID NO: 242)).

As shown in FIGS. 16A-16D, each of the sgRNAs resulted in similar responses in a dose dependent manner for each of the cytokines tested. For editing efficiency, the unmodified sgRNA (G000201(SEQ ID NO: 243)) conferred little in vivo editing, while the heavily modified sgRNA (G000282 (SEQ ID NO: 242)) conferred levels reaching ~60% with a dose of 2 mg/kg, which was significantly greater than the levels achieved with the less modified sgRNA (G000211 (SEQ ID NO: 241)) (FIGS. 17A and B). As with the previous in vivo study, the levels of editing correlated with the amount of serum TTR knockdown (FIGS. 17C and D).

A similar study as the second in vivo study was next conducted with another set of three sgRNAs targeting yet a different TTR sequence in the mouse TTR gene (targeting a different sequence then what was targeted in the two previous in vivo studies). Mice (n=5 per group) were administered a single dose of LNP at 2 mg/kg, 1 mg/kg, or 0.3 mg/kg. Blood was collected four hours post dose for serum cytokine analysis. 7 days post dose at necropsy, livers and blood were collected for NGS measurements of editing efficiency and serum TTR analysis, respectively. In this study, each of the sgRNAs targeted the same sequence in the TTR gene (a different sequence from what was targeted in the previous two in vivo studies) with one sgRNA being completely unmodified (G000285; (SEQ ID NO: 332)), another having only end modifications (G000269 (SEQ ID NO: 330)), with 2'-O-methyl modifications and phosphorothioate linkages at and between the three terminal nucleotides at both the 5' and 3' ends of the sgRNA, respectively), and a third sgRNA having the same modification pattern as G000267 and G000282 in the previous two in vivo studies (G000283 (SEQ ID NO: 331)).

In this study, the unmodified sgRNA (G000285 (SEQ ID NO: 332)) conferred little in vivo editing, while the heavily modified sgRNA (G000283 (SEQ ID NO: 331)) conferred levels reaching ~60% with a dose of 2 mg/kg, which was significantly greater than the levels achieved with the less modified sgRNA (G000269 (SEQ ID NO: 330)) (FIGS. 18A-18B). As with the previous in vivo studies, the levels of editing correlated with the amount of serum TTR knockdown (FIG. 18C).

In a fourth in vivo study, the effects of modifications to gRNAs was evaluated for another gene (FVII). For in-study comparison, two of the sgRNAs tested in the first in vivo study were included (G000209 and G000267). Mice (n=5 per group) were administered a single dose of LNP at 2 mg/kg, 1 mg/kg, or 0.3 mg/kg, and blood was collected four hours post dose for serum cytokine analysis. 6 days post dose at necropsy, livers were collected for NGS measurements of editing efficiency. In this study, each of the sgRNAs targeted the same sequence in the TTR or FVII genes, with one sgRNA for each having only end modifications (G000208 (SEQ ID NO: 286)) for FVII, G000209 for TTR, both having 2'-O-methyl modifications and phosphorothioate linkages at and between the three terminal nucleotides at both the 5' and 3' ends of the sgRNA, respectively), and a second sgRNA having the same modification patterns as G000267, G000282, and G000283 in the previous in vivo studies (G000373 (SEQ ID NO: 287) for FVII; G000267 (SEQ ID NO: 234) for TTR).

As shown in FIGS. 19A-19D, each of the sgRNAs resulted in similar responses in a dose dependent manner for each of the cytokines tested. For editing efficiency, the more heavily modified sgRNA targeting FVII (G000373 (SEQ ID NO: 287)) had an increase in editing efficiency as compared to the less modified version (G000208 (SEQ ID NO: 286)) across each of the doses tested (FIG. 18A). These results were also observed for the sgRNAs targeting TTR (FIGS. 20A-20B).

In another in vivo study, ten additional sgRNAs targeting the same sequence in the mouse TTR gene as G000282 were tested. 0000282 was also included in the study for comparative purposes. Mice (n=5 per group) were administered a single dose of LNP at 1 mg/kg or 0.5 mg/kg. The LNPs used in this study were formulated using LNP Formulation Procedure B described above. Seven (7) days post dose at necropsy, livers and blood were collected for NGS measurements of editing efficiency and serum TTR analysis, respectively. In this study, each of the sgRNAs targeted the same sequence in the TTR gene. The modification pattern of each sgRNA tested varied and included 2'-OMe, 2'-F, and PS modifications in the 5' terminus, 3' terminus, hairpin 1, hairpin 2, nexus, lower stem, bulge, and upper stem of the sgRNA. The results of this study are shown in FIGS. 22A-22C, including % editing (FIG. 22A), average editing and standard deviation (FIG. 22B), and serum TTR levels (FIG. 22C). These same sgRNAs were tested in primary mouse hepatocytes as per the methods described herein. The results of this dose response TTR editing study are shown in FIGS. 24A-24C, including % editing (FIG. 24A), dose response curves (FIG. 24B), and EC50 values (FIG. 24C).

In another in vivo study, thirteen sgRNAs targeting the same sequence in the mouse TTR gene as G000282 were tested. G000282 was also included in the study for comparative purposes. Mice (n=5 per group) were administered a single dose of LNP at 1 mg/kg. The LNPs used in this study were formulated using LNP Formulation Procedure C described above. The Cas9 mRNA used in this study had the sequence of SEQ ID NO: 359. Blood was collected four hours post dose for serum cytokine analysis. 7 days post dose at necropsy, livers and blood were collected for NGS measurements of editing efficiency and serum TTR analysis, respectively. In this study, each of the sgRNAs targeted the same sequence in the TTR gene. The sgRNAs tested include additional 2'-OMe and PS modifications in the 5' terminus, 3' terminus, hairpin 1, hairpin 2, and upper stem of the sgRNA. The results of this study are shown in FIGS. 23A-23C, including % editing (FIG. 23A), average % editing (FIG. 23B), and serum TTR levels (FIG. 23C).

We claim:

1. A single guide RNA (sgRNA) comprising
(i) an upper stem region and a hairpin region,
wherein (a) each nucleotide in the upper stem region is modified with 2'-O-Me;
(b) the hairpin region comprises a hairpin 1 region and a hairpin 2 region and each nucleotide in the hairpin 2 region is modified with 2'-O-Me; or both (a) and (b); and
(ii) a 5' end modification comprising at least two phosphorothioate (PS) linkages within the first seven nucleotides at the 5' end of the 5' terminus.

2. The sgRNA of claim 1, wherein
a. the sgRNA comprises one or more modifications in the upper stem region; and/or
b. the sgRNA comprises one or more modifications in the hairpin 1 region; and/or
c. the sgRNA comprises one or more modifications in the hairpin 2 region.

3. The sgRNA of claim 1, wherein the hairpin region comprises a hairpin 1 region and a hairpin 2 region, and the sgRNA comprises one or more modifications in each of the upper stem region, the hairpin 1 region, and the hairpin 2 region.

4. The sgRNA of claim 1, wherein the hairpin region comprises a hairpin 1 region and a hairpin 2 region, and the sgRNA comprises a modified nucleotide between the hairpin 1 and hairpin 2 regions.

5. The sgRNA of claim 1, further comprising a lower stem region comprising a modification.

6. The sgRNA of claim 1, further comprising a 3' terminus region comprising a modification.

7. The sgRNA of claim 6, further comprising a 3' end modification in the 3' terminus.

8. The sgRNA of claim 7, wherein at least two of the last four nucleotides at the 3' end of the 3' terminus are modified, optionally with 2'-O-Me, 2'-F, or 2'-O-moe.

9. The sgRNA of claim 7, further comprising phosphorothioate (PS) bonds between one or more of the last four nucleotides at the 3' end of the 3' terminus.

10. The sgRNA of claim 1, further comprising a bulge region comprising a modification and/or a *nexus* region comprising a modification.

11. The sgRNA of claim 1, wherein at least the first three nucleotides at the 5' end of the 5' terminus, and the last three nucleotides at the 3' end of the 3' terminus are modified.

12. The sgRNA of claim 1, wherein the first four nucleotides at the 5' end of the 5' terminus, and the last four nucleotides at the 3' end of the 3' terminus are linked with phosphorothioate (PS) bonds.

13. The sgRNA of claim 12, wherein the end modifications comprise 2'-O-Me or 2'-F.

14. The sgRNA of claim 1, wherein the first four nucleotides at the 5' end of the 5' terminus and the last four nucleotides at the 3' end of the 3' terminus are linked with a PS bond, and wherein the first three nucleotides at the 5' end of the 5' terminus and the last three or four nucleotides at the 3' end of the 3' terminus comprise 2'-O-Me modifications.

15. The sgRNA of claim 1, wherein the first four nucleotides at the 5' terminus and the last four nucleotides at the 3' terminus are linked with a PS bond, and wherein the first three nucleotides at the 5' terminus and the last three nucleotides at the 3' terminus comprise 2'-O-Me, 2'-F, and/or 2'-O-moe modifications.

16. The sgRNA of claim 1, wherein the lower stem region comprises nucleotides LS1 to LS12 from the 5' end to the 3' end thereof, and LS1, LS6, LS7, LS8, LS11, and/or LS12 are modified with 2'-O-Me and/or wherein the sgRNA comprises a bulge region and each nucleotide in the bulge region is modified with 2'-O-Me and/or wherein at least 50% of the nucleotides in the bulge region are modified with 2'-O-Me and/or wherein each nucleotide in the upper stem region is modified with 2'-O-Me and/or wherein the sgRNA further comprises a *nexus* region comprising nucleotides N1 through N18 from the 5' end to the 3' end thereof, and N16, N17, and/or N18 in the *nexus* region are modified with 2'-O-Me and/or wherein N15, N16, N17, and/or N18 in the *nexus* region are modified.

17. The sgRNA of claim 16, wherein the modifications in the *nexus* region are selected from 2'-O-Me and 2'F.

18. The sgRNA of claim 1, wherein each of the nucleotides in the hairpin 1 region and/or in the hairpin 2 region are modified with 2'-O-Me.

19. A composition comprising an sgRNA of claim 1, further comprising a lipid nanoparticle (LNP) and/or further comprising a nuclease or an mRNA which encodes the nuclease.

20. A pharmaceutical formulation comprising the sgRNA of claim 1 and a pharmaceutically acceptable carrier.

21. A method of modifying a target DNA comprising, delivering a Cas protein or a nucleic acid encoding a Cas protein, and the sgRNA of claim 1 to a cell.

22. The sgRNA of claim 1, wherein the upper stem region comprises US1 to US12 from the 5' end to the 3' end thereof, and the hairpin region comprises a hairpin 1 region and a hairpin 2 region, wherein the hairpin 1 region comprises H1-1 to H1-12 from the 5' end to the 3' end thereof and the hairpin 2 region comprises H2-1 to H2-15 from the 5' end to the 3' end thereof, and wherein the sgRNA is a sgRNA comprises 2'-O-Me modified nucleotides consisting of 2'-O-Me modified nucleotides at:
   a. the first three nucleotides at the 5' end of the 5' terminus;
   b. each of nucleotides US1, US2, US3, US4, US5, US6, US7, USB, US9, US10, US11 and US12;
   c. each of nucleotides H1-1, H1-2, H1-3, H1-4, H1-5, H1-6, H1-7, H1-8, H1-9, H1-10, H1-11, and H1-12;
   d. the nucleotide between hairpin 1 and hairpin 2;
   e. each of nucleotides H2-1, H2-2, H2-3, H2-4, H2-5, H2-6, H2-7, H2-8, H2-9, H2-10, H2-11, H2-12, H2-13, H2-14, and H2-15; and
   f. the last four nucleotides at the 3' end of the 3' terminus; and
three PS bonds linking the first four nucleotides at the 5' end of the 5' terminus and three PS bonds linking the last four nucleotides at the 3' end of the 3' terminus.

23. The sgRNA of claim 1, wherein the sgRNA comprises any of SEQ ID NOs: 235, 236, 240, 265-283, 309-327, or 331.

24. The sgRNA of claim 1, wherein the sgRNA comprises SEQ ID NO: 242 or 358.

25. The sgRNA of claim 1, wherein the sgRNA comprises 2'-O-Me modified nucleotides consisting of 2'-O-Me modified nucleotides at:
   a. the first three nucleotides at the 5' end of the 5' terminus;
   b. each nucleotide in the upper stem region;
   c. each nucleotide in the hairpin 1 region;
   d. the nucleotide between hairpin 1 and hairpin 2;
   e. each nucleotide in the hairpin 2 region; and
   f. the last four nucleotides at the 3' end of the 3' terminus.

26. The sgRNA of claim 1, wherein the first four nucleotides at the 5' end of the 5' terminus and the last four nucleotides at the 3' end of the 3'terminus are linked with a PS bond, and wherein the first three nucleotides at the 5' end of the 5' terminus and the last three nucleotides at the 3' end of the 3' terminus are modified with 2'-O-Me, and wherein each nucleotide in the upper stem region are modified with 2'-O-Me.

27. The sgRNA of claim 1, wherein the first four nucleotides at the 5' end of the 5' terminus and the last four nucleotides at the 3' end of the 3'terminus are linked with a PS bond, wherein the first three nucleotides at the 5' end of the 5' terminus and the last four nucleotides at the 3' end of the 3' terminus are modified with 2'-O-Me, and wherein each nucleotide in the upper stem region are modified with 2'-O-Me.

* * * * *

UNITED STATES PATENT AND TRADEMARK OFFICE
CERTIFICATE OF CORRECTION

PATENT NO. : 11,479,767 B2
APPLICATION NO. : 16/434512
DATED : October 25, 2022
INVENTOR(S) : Amy Madison Rhoden Smith, David V. Morrissey and Walter Strapps Page 1 of 1

It is certified that error appears in the above-identified patent and that said Letters Patent is hereby corrected as shown below:

In the Claims

Column 253, Line 20 Claim 22, "wherein the sgRNA is a sgRNA comprises 2'-O-Me modified nucleotides consisting of 2'-O-Me modified nucleotides at:" should read --wherein the sgRNA comprises 2'-O-Me modified nucleotides consisting of 2'-O-Me modified nucleotides at:--.

Signed and Sealed this
Sixth Day of August, 2024

Katherine Kelly Vidal
*Director of the United States Patent and Trademark Office*